(12) United States Patent
Du

(10) Patent No.: US 8,685,921 B2
(45) Date of Patent: Apr. 1, 2014

(54) INHIBITORS OF BETA INTEGRIN-G PROTEIN ALPHA SUBUNIT BINDING INTERACTIONS

(75) Inventor: Xiaoping Du, Willowbrook, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/621,064

(22) Filed: Sep. 15, 2012

(65) Prior Publication Data

US 2013/0072433 A1    Mar. 21, 2013

Related U.S. Application Data

(63) Continuation-in-part of application No. PCT/US2011/028567, filed on Mar. 15, 2011.

(60) Provisional application No. 61/433,037, filed on Jan. 14, 2011, provisional application No. 61/314,027, filed on Mar. 15, 2010.

(51) Int. Cl.
| | |
|---|---|
| *A61K 38/36* | (2006.01) |
| *C07K 7/06* | (2006.01) |
| *C07K 7/08* | (2006.01) |
| *A61K 38/08* | (2006.01) |
| *A61K 38/10* | (2006.01) |
| *C07K 14/745* | (2006.01) |
| *A61P 9/00* | (2006.01) |
| *A61P 7/02* | (2006.01) |

(52) U.S. Cl.
USPC .......... 514/13.8; 530/324; 530/325; 530/326; 530/327; 530/328; 530/329; 530/330

(58) Field of Classification Search
IPC .............. C07K 7/06,7/08, 14/745; A61K 38/36, A61K 38/08, 38/10; A61P 9/00, 7/02
See application file for complete search history.

(56) References Cited

U.S. PATENT DOCUMENTS

2008/0293628 A1 * 11/2008 Dai et al. ............ 514/12

FOREIGN PATENT DOCUMENTS

| WO | WO 92/09302 | 6/1992 | | |
|---|---|---|---|---|
| WO | WO 00/63236 | 10/2000 | | |
| WO | WO 02/072759 | 9/2002 | | |
| WO | WO 2004098627 A1 * | 11/2004 | ............ | A61K 38/08 |
| WO | WO 2008087216 A1 * | 7/2008 | ............ | A61K 38/10 |
| WO | WO2008102557 A1 * | 8/2008 | ............ | C07K 14/00 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Josef Vagner, Peptidomimetic, a synthetic tool of drug discovery, 2008, Curr Opin Chem Biol:12(3):292-296.*
Ngo et al, Computational Complexity, Protein Structure Protection, and the Levinthal Paradox, 1994, pp. 491-494.*
Voet et al, Biochemistry, John Wiley & Sons Inc., 1995, pp. 235-241.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Allison R. Nelson, Myristoyl-Based Transport of Peptides into living Cells, 2007, Biochemistry, 46(51):pp. 14771-14781.*
Xiaoping Du, Calpain Cleavage of the Cytoplasmic Domain of the Integrin B2 subunit, Journal of Biological Chemistry, 1995, 270:26146-26151.*
Anthis et al., Beta integrin tyrosine phosphorylation is a conserved mechanism for regulating talin-induced integrin activation, J. Biol. Chem., 284(52):36700-10 (2009).
Arias-Salgado et al., Src kinase activation by direct interaction with the integrin beta cytoplasmic domain, Proc. Natl. Acad. Sci. USA, 100(23): 13298-302 (2003).
Arthur et al., Integrin engagement suppresses RhoA activity via a c-Src-dependent mechanism, Curr. Biol., 10(12):719-22 (2000).
Brass et al., GTP-binding proteins and platelet activation, Prog. Hemost. Thromb., 10:127-74 (1991).
Calderwood et al., The Talin head domain binds to integrin beta subunit cytoplasmic tails and regulates integrin activation, J. Biol. Chem., 274(40):28071-4 (1999).
Cho et al., A critical role for extracellular protein disulfide isomerase during thrombus formation in mice, J. Clin. Invest., 118(3):1123-31 (2008).
Coller, Anti-GPIIb/IIIa drugs: current strategies and future directions, Thromb. Haemost., 86(1):427-43 (2001).
Coller, Interaction of normal, thrombasthenic, and Bernard-Soulier platelets with immobilized fibrinogen: defective platelet-fibrinogen interaction in thrombasthenia, Blood, 55(2):169-78 (1980).
Dai et al., A critical role for 14-3-3zeta protein in regulating the VWF binding function of platelet glycoprotein Ib-IX and its therapeutic implications, Blood, 106(6):1975-81 (2005).
Day et al., Murine thrombosis models, Thromb. Haemost., 92(3):486-94 (2004).
Du et al., Identification of a binding sequence for the 14-3-3 protein within the cytoplasmic domain of the adhesion receptor, platelet glycoprotein Ib alpha, J. Biol. Chem., 271(13):7362-7 (1996).
Du et al., Ligands "activate" integrin alpha IIb beta 3 (platelet GPIIb-IIIa), Cell, 65(3):409-16 (1991).
Dyke, Safety of glycoprotein IIb-IIIa inhibitors: A heart surgeon's perspective, Am. Heart J., 138(Pt. 2):307-16 (1999).
Edelstein et al., Computer control of microscopes using μManager, Unit 14.20.1-14.20.17 Current Protocols in Molecular Biology (Oct. 2010).
Falati et al., Real-time in vivo imaging of platelets, tissue factor and fibrin during arterial thrombus formation in the mouse, Nat. Med., 8(10):1175-81 (2002).

(Continued)

*Primary Examiner* — Julie Ha
*Assistant Examiner* — Erinne Dabkowski
(74) *Attorney, Agent, or Firm* — Marshall, Gerstein & Borun LLP

(57) ABSTRACT

Provided herein are compounds that inhibit a binding interaction between a β integrin and a G protein subunit, as well as compositions, e.g., pharmaceutical compositions, comprising the same, and related kits. In some embodiments, the compound is an antibody or antibody analog, and, in other embodiments, the compound is a peptide or peptide analog. Also provided are methods of using the compounds, including methods of treating or preventing a medical condition, such as stroke, heart attack, cancer, or inflammation.

26 Claims, 30 Drawing Sheets

(56) References Cited

OTHER PUBLICATIONS

Flevaris et al., A molecular switch that controls cell spreading and retraction, J. Cell Biol., 179(3):553-65 (2007).

Flevaris et al., Two distinct roles of mitogen-activated protein kinases in platelets and a novel Rac1-MAPK-dependent integrin outside-in retractile signaling pathway, Blood, 113(4):893-901 (2009).

Giannone et al., Talin1 is critical for force-dependent reinforcement of initial integrin-cytoskeleton bonds but not tyrosine kinase activation, J. Cell Biol., 163(2):409-19 (2003).

Ginsberg et al., Integrin regulation, Curr. Opin. Cell Biol., 17(5):509-16 (2005).

Goksoy et al., Structural basis for the autoinhibition of talin in regulating integrin activation, Mol. Cell, 31(1):124-33 (2008).

Gong et al., G protein subunit Galpha13 binds to integrin alphaIIb-beta3 and mediates integrin "outside-in" signaling, Science, 327(5963):340-3 (2010).

Gu et al., Analysis of the roles of 14-3-3 in the platelet glycoprotein Ib-IX-mediated activation of integrin alpha(IIb)beta(3) using a reconstituted mammalian cell expression model, J. Cell Biol., 147(5):1085-96 (1999).

Guanine nucleotide-binding protein subunit alpha-12 [*Homo sapiens*], NP_031379, (Dec. 23, 2012).

Guanine nucleotide-binding protein subunit alpha-13 [*Homo sapiens*], NP_006563.2 (Dec. 23, 2012).

Haling et al., Talin-dependent integrin activation is required for fibrin clot retraction by platelets, Blood, 117(5):1719-22 (2011).

Hart et al., Direct stimulation of the guanine nucleotide exchange activity of p115 RhoGEF by Galpha13, Science, 280(5372):2112-4 (1998).

Hayward et al., Platelet function analyzer (PFA)-100 closure time in the evaluation of platelet disorders and platelet function, J. Thromb. Haemost., 4(2):312-9 (2006).

Hu et al., Lsc activity is controlled by oligomerization and regulates integrin adhesion, Mol. Immunol., 45(7):1825-36 (2008).

Huang et al., Signaling through G(alpha)13 switch region I is essential for protease-activated receptor 1-mediated human platelet shape change, aggregation, and secretion, J. Biol. Chem., 282(14):10210-22 (2007).

Humphries et al., Vinculin controls focal adhesion formation by direct interactions with talin and actin, J. Cell Biol., 179(5):1043-57 (2007).

Hynes, Integrins: bidirectional, allosteric signaling machines, Cell, 110(6):673-87 (2002).

Integrin beta-1 isoform 1A precursor [*Homo sapiens*], NP_002202.2 (Dec. 30, 2012).

Integrin beta-1 isoform 1D precursor [*Homo sapiens*], NP_391988 (Dec. 30, 2012).

Integrin beta-3 precursor [*Homo sapiens*], NP_000203.2 (Dec. 9, 2012).

Integrin beta-6 precursor [*Homo sapiens*], NP_000879.2 (Dec. 9, 2012).

International Search Report and Written Opinion from corresponding international application No. PCT/US11/28567, mailing date Oct. 18, 2011.

Kataoka et al., Block copolymer micelles for drug delivery: design, characterization and biological significance, Adv. Drug Deliv. Rev., 47(1):113-31 (2001).

Klages et al., Activation of G12/G13 results in shape change and Rho/Rho-kinase-mediated myosin light chain phosphorylation in mouse platelets, J. Cell Biol., 144(4):745-54 (1999).

Kong et al., Regulation of integrin expression by G?12: An additional potential mechanism modulating cell attachment, Cell Adh. Migr., 4(3):372-6 (2010).

Kozasa et al., p115 RhoGEF, a GTPase activating protein for Galpha12 and Galpha13, Science, 280(5372):2109-11 (1998).

Krishnadas et al., Sterically stabilized phospholipid mixed micelles: in vitro evaluation as a novel carrier for water-insoluble drugs, Pharm. Res., 20(2):297-302 (2003).

Law et al., Integrin cytoplasmic tyrosine motif is required for outside-in alphaIIbbeta3 signalling and platelet function, Nature, 401(6755):808-11 (1999).

Li et al., A platelet secretion pathway mediated by cGMP-dependent protein kinase, J. Biol. Chem., 279(41):42469-75 (2004).

Li et al., A stimulatory role for cGMP-dependent protein kinase in platelet activation, Cell, 112(1):77-86 (2003).

Li et al., Sequential activation of p38 and ERK pathways by cGMP-dependent protein kinase leading to activation of the platelet integrin alphaIIb beta3, Blood, 107(3):965-72 (2006).

Li et al., Signaling during platelet adhesion and activation, Arterioscler. Thromb. Vasc. Biol., 30(12):2341-9 (2010).

Ma et al., Kindlin-2 (Mig-2): a co-activator of beta3 integrins, J. Cell Biol., 181(3):439-46 (2008).

Ma et al., Platelet integrin alpha(IIb)beta(3): activation mechanisms, J. Thromb. Haemost., 5(7):1345-52 (2007).

Marjanovic et al., Stimulatory roles of nitric-oxide synthase 3 and guanylyl cyclase in platelet activation, J. Biol. Chem., 280(45):37430-8 (2005).

Moers et al., G13 is an essential mediator of platelet activation in hemostasis and thrombosis, Nat. Med., 9(11):1418-22 (2003).

Moissoglu et al., Integrin signalling in directed cell migration, Biol. Cell, 98(9):547-55 (2006).

Montanez et al., Kindlin-2 controls bidirectional signaling of integrins, Genes Dev., 22(10):1325-30 (2008).

Moser et al., Kindlin-3 is essential for integrin activation and platelet aggregation, Nat. Med., 14(3):325-30 (2008).

Nayal et al., Talin: an emerging focal point of adhesion dynamics, Curr. Opin. Cell Biol., 16(1):94-8 (2004).

NCBI Reference Sequence: NP_000770.2, cytochrome P450 4B1 isoform b [*Homo sapiens*] (Jan. 6, 2013).

NCBI Reference Sequence: NP_002204.2, Integrin beta-5 precursor [*Homo sapiens*] (Jan. 13, 2013).

Nieves et al., The NPIY motif in the integrin beta1 tail dictates the requirement for talin-1 in outside-in signaling, J. Cell Sci., 123(Pt. 8):1216-26 (2010).

Niu et al., G Protein betagamma subunits stimulate p114RhoGEF, a guanine nucleotide exchange factor for RhoA and Rac1: regulation of cell shape and reactive oxygen species production, Circ. Res., 93(9):848-56 (2003).

O'Brien et al., An important role for Akt3 in platelet activation and thrombosis, Blood, 118(15):4215-23 (2011).

Obergfell et al., Coordinate interactions of Csk, Src, and Syk kinases with [alpha]IIb[beta]3 initiate integrin signaling to the cytoskeleton, J. Cell Biol., 157(2):265-75 (2002).

Patil et al., Identification of a talin-binding site in the integrin beta(3) subunit distinct from the NPLY regulatory motif of post-ligand binding functions. The talin n-terminal head domain interacts with the membrane-proximal region of the beta(3) cytoplasmic tail, J. Biol. Chem., 274(40):28575-83 (1999).

Petrich et al., Talin is required for integrin-mediated platelet function in hemostasis and thrombosis, J. Exp. Med., 204(13):3103-11 (2007).

Petrich et al., The antithrombotic potential of selective blockade of talin-dependent integrin alpha IIb beta 3 (platelet GPIIb-IIIa) activation, J. Clin. Invest., 117(8):2250-9 (2007).

Ren et al., Determination of GTP loading on Rho, Methods Enzymol., 325:264-72 (2000).

Ren et al., The platelet release reaction: just when you thought platelet secretion was simple, Curr. Opin. Hematol., 15(5):537-41 (2008).

Riobo et al., Receptors coupled to heterotrimeric G proteins of the G12 family, Trends Pharmacol. Sci., 26(3):146-54 (2005).

Roger et al., Executive summary: heart disease and stroke statistics—2012 update: a report from the American Heart Association, Circulation, 125(1):188-97 (2012).

Ruggeri, Platelets in atherothrombosis, Nat. Med., 8(11):1227-34 (2002).

Saab et al., Bleeding risk and safety profile related to the use of eptifibatide: a current review, Expert Opin. Drug Saf., 11(2):315-24 (2012).

(56) References Cited

OTHER PUBLICATIONS

Salsmann et al., A new functional role of the fibrinogen RGD motif as the molecular switch that selectively triggers integrin alphaIIbbeta3-dependent RhoA activation during cell spreading, J. Biol. Chem., 280(39):33610-9 (2005).

Senyuk et al., Consistent up-regulation of Stat3 Independently of Jak2 mutations in a new murine model of essential thrombocythemia, Cancer Res., 69(1):262-71 (2009).

Shattil et al., Integrin signaling: the platelet paradigm, Blood, 91(8):2645-57 (1998).

Shattil et al., Integrins: dynamic scaffolds for adhesion and signaling in platelets, Blood, 104(6):1606-15 (2004).

Shattil, Integrins and Src: dynamic duo of adhesion signaling, Trends Cell Biol., 15(8):399-403 (2005).

Su et al., RGT, a synthetic peptide corresponding to the integrin beta 3 cytoplasmic C-terminal sequence, selectively inhibits outside-in signaling in human platelets by disrupting the interaction of integrin alpha IIb beta 3 with Src kinase, Blood, 112(3):592-602 (2008).

Tadokoro et al., Talin binding to integrin beta tails: a final common step in integrin activation, Science, 302(5642):103-6 (2003).

Tanabe et al., Regulation of RGS-RhoGEFs by Galpha12 and Galpha13 proteins, Methods Enzymol., 390:285-94 (2004).

Ugarova et al., Conformational changes in fibrinogen elicited by its interaction with platelet membrane glycoprotein GPIIb-IIIa, J. Biol. Chem., 268(28):21080-7 (1993).

Vidal et al., Cdc42/Rac1-dependent activation of the p21-activated kinase (PAK) regulates human platelet lamellipodia spreading: implication of the cortical-actin binding protein cortactin, Blood, 100(13):4462-9 (2002).

Wang et al., Truncation of the cytoplasmic domain of beta3 in a variant form of Glanzmann thrombasthenia abrogates signaling through the integrin alpha(IIb)beta3 complex, J. Clin. Invest., 100(9):2393-403 (1997).

Wegener et al., Structural basis of integrin activation by talin, Cell, 128(1):171-82 (2007).

Xi et al., Critical roles for the COOH-terminal NITY and RGT sequences of the integrin beta3 cytoplasmic domain in inside-out and outside-in signaling, J. Cell Biol., 162(2):329-39 (2003).

Ye et al., Molecular mechanism of inside-out integrin regulation, J. Thromb. Haemost., 9 Suppl 1:20-5 (2011).

Yin et al., Src family tyrosine kinase Lyn mediates VWF/GPIb-IX-induced platelet activation via the cGMP signaling pathway, Blood, 112(4):1139-46 (2008).

Yin et al., The role of Akt in the signaling pathway of the glycoprotein Ib-IX induced platelet activation, Blood, 111(2):658-65 (2007).

Zhang et al., Talin depletion reveals independence of initial cell spreading from integrin activation and traction, Nat. Cell Biol., 10(9):1062-8 (2008).

Zuckermann et al., Efficient method for the preparation of peptoids { oligo(N-substituted glycines) } by sunmonomer solid-phase synthesis, J. Am. Chem. Soc., 114(26):10646-7 (1992).

Katz, Inhibition of inflammatory responses by leukcyte Ig-like receptors, Adv. Immunol., 91:251-72 (2006).

Kuchroo et al., TIM family of genes in immunity and tolerance, Adv. Immunol., 91:227-49 (2006).

* cited by examiner

FIG. 3A
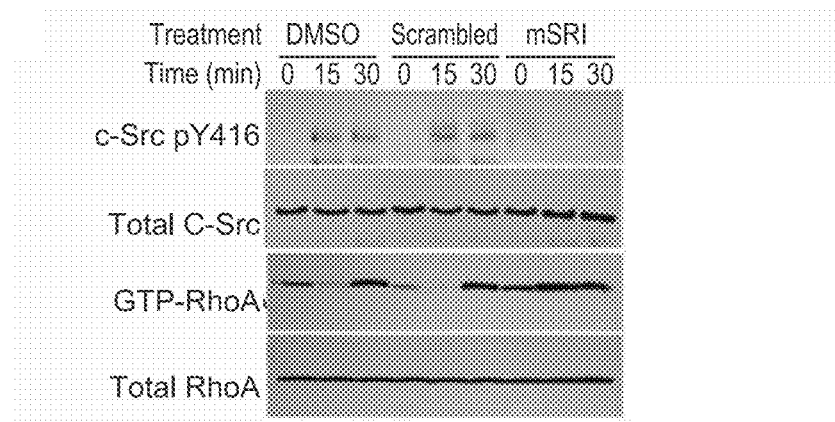
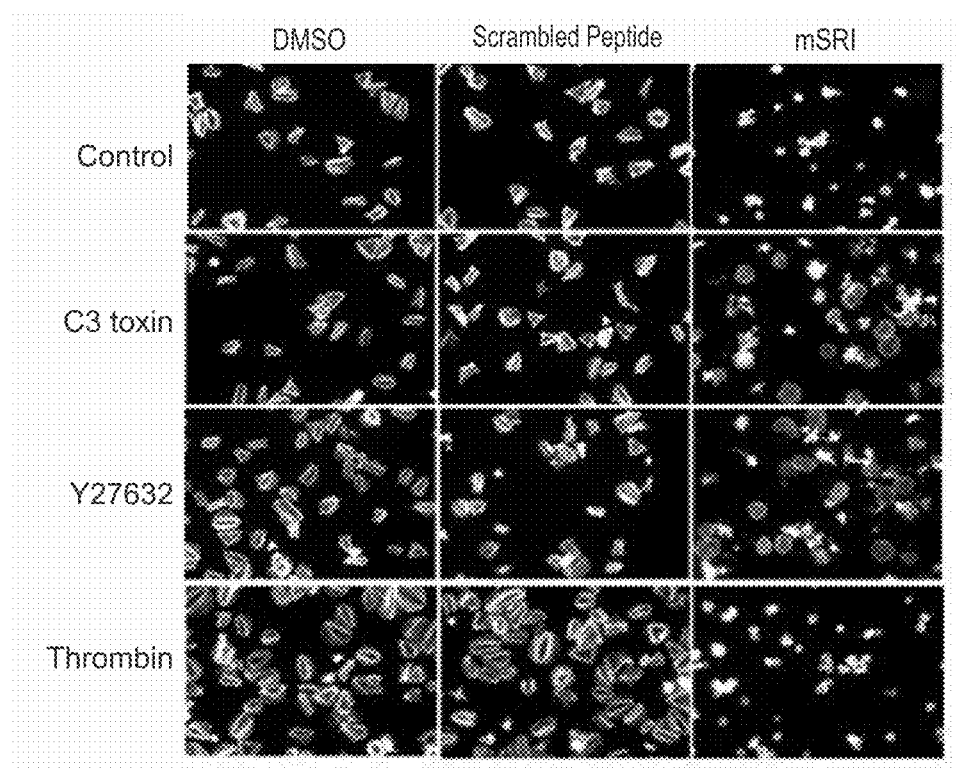
FIG. 3B

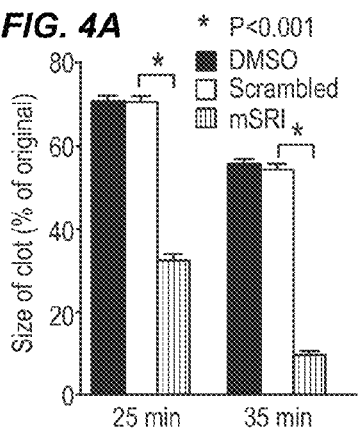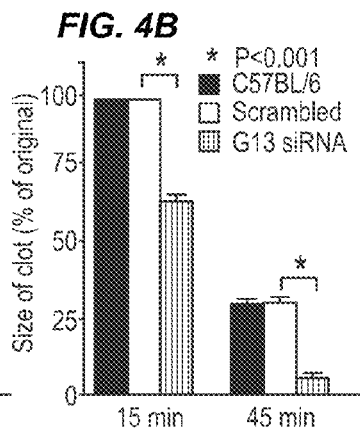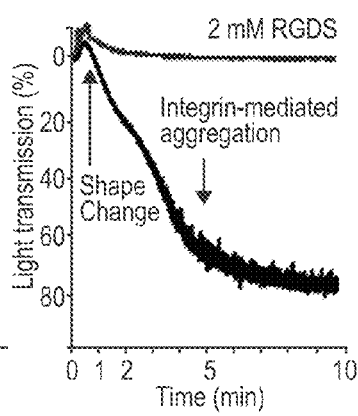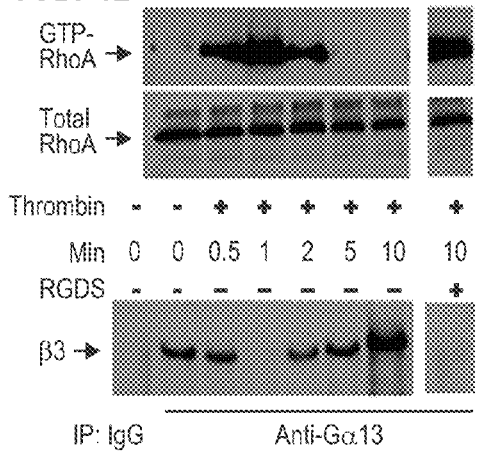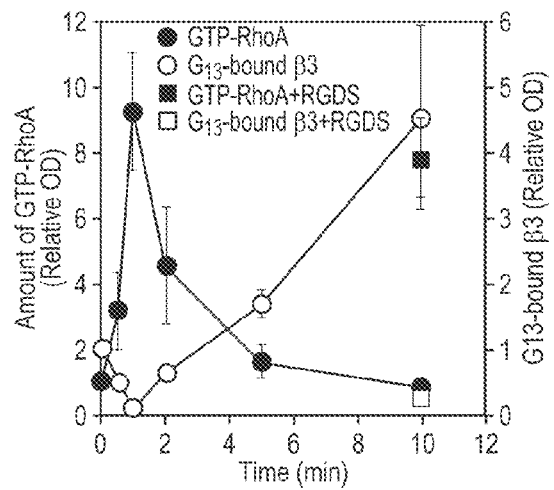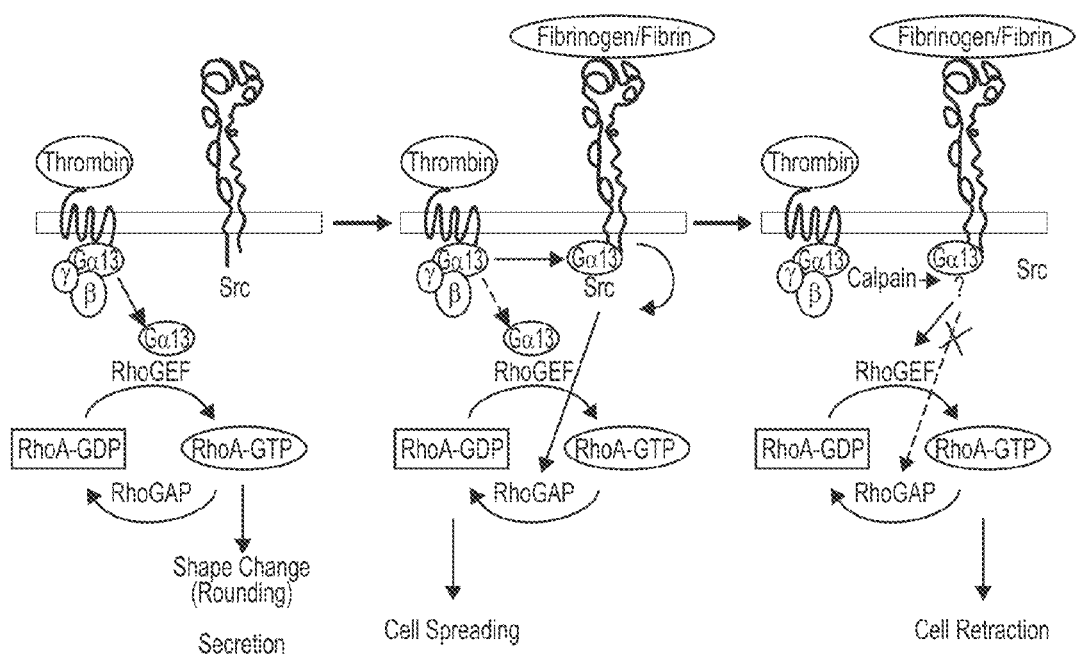
FIG. 4G

*FIG. 6A*
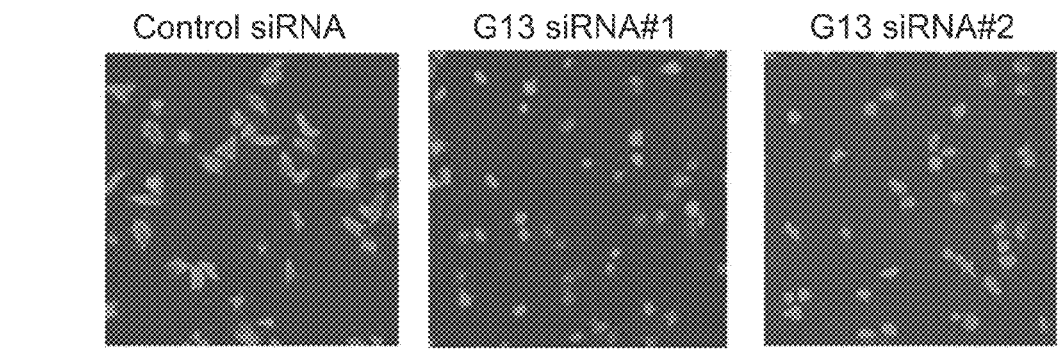
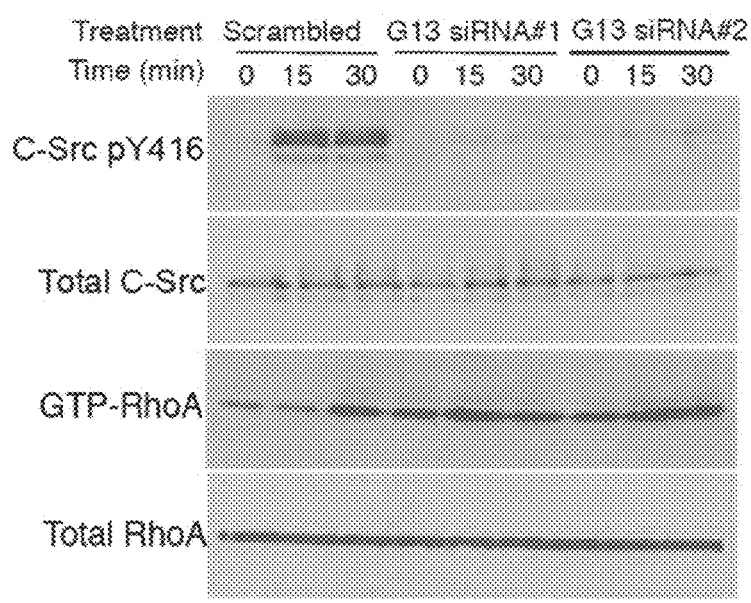
*FIG. 6B*
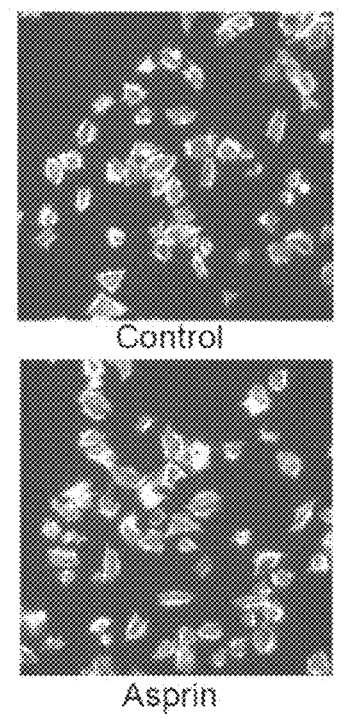
*FIG. 6C*

Scrambled siRNA     G13 siRNA#1     G13 siRNA#1 +Flag-G13-Mut1

FIG. 11A
Human Integrin β subunit cytoplasmic domain sequences
β1A  732KLLMIIHDRREFAKFEKEKMNAKWDTGENPIYKSAVTTVV--------NPKYEGK
β1D  732KLLMIIHDRREFAKFEKEKMNAKWDTGENPIYKSPINNFK--------NPNYGRKAGL
β2   702KALIHLSDLREYRRFEKEKLKSQWNND-NPLFKSATTTVM--------NPKFAES
β3   716KLLITIHDRKEFAKFEEERARAKWDTAN NPLYKEATSTFT--------NITYRGT
β5   720KLLVTIHDRREFAKFQSERSRARY EMASNPLYRKPISTHTVDFTFNKFNKSYNGTVD
β6   710KLLVSFHDRKEVAKFEAERSKAKWQTG TNPLYRGSTSTKF--------NVTYKHREKQKVDLSTDC
β7   728RLSVEIYDRREYSRFEKEQQQLNWKQDSNPLYKSAITTTI--------NPRFQEADSPTL Inhibitor peptides:  Myr-EEERA
                    Myr-KFEEERARAKWDT
           Myr-HDRKEFAKFEEERARAKWDT

FIG. 11B

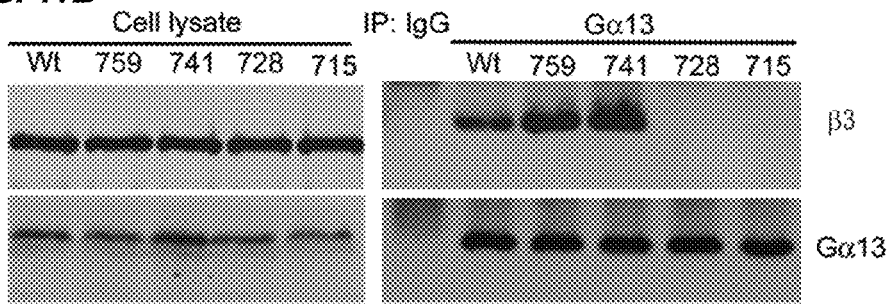

FIG. 11C

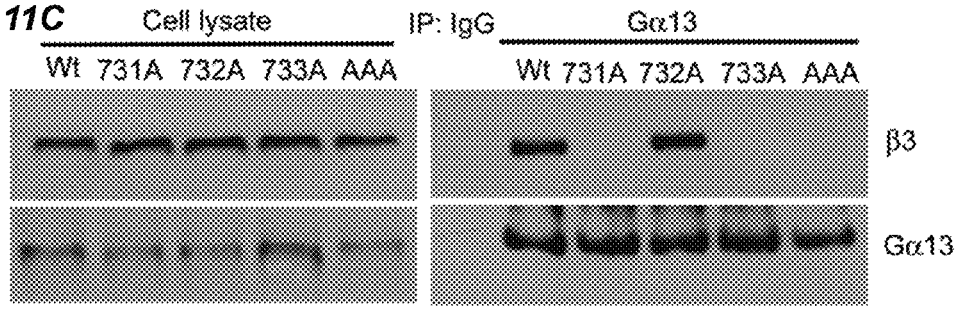

FIG. 11D

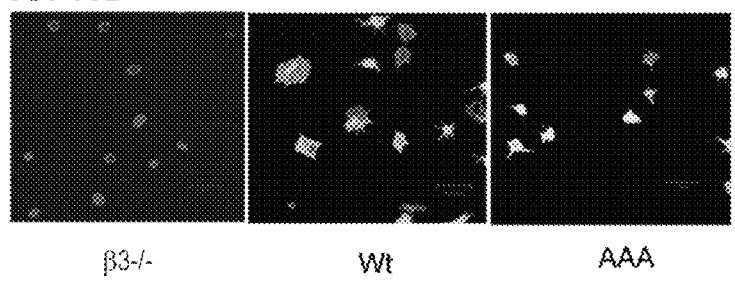

FIG. 11E

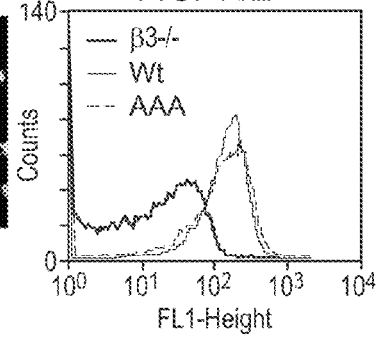

FIG. 15A

Human integrin β subunit cytoplasmic domain sequences

```
β1A  751WKLLM II HDRREFAKFEKEKMNAKWDTGENPIYKSAVTTVV--------NPKYEGK
β1D  751WKLLM II HDRREFAKFEKEKMNAKWDTGENPIYKSFINNFK--------NPNYGRKAGL
β2   723WKALI HLSDLREYRRFEKEKLKSQWNND-NPLFKSATTTVM--------NPKFAES
β3   741WKLLITIHDRKEFAKFEEERARAKWDTAN NPLYKEATSTFT--------NITYRGT
```

Inhibitor peptides:  Myr-EEERA
Myr-KFEEERARAKWDT
Myr-HDRKEFAKFEEERARAKWDT

FIG. 15B

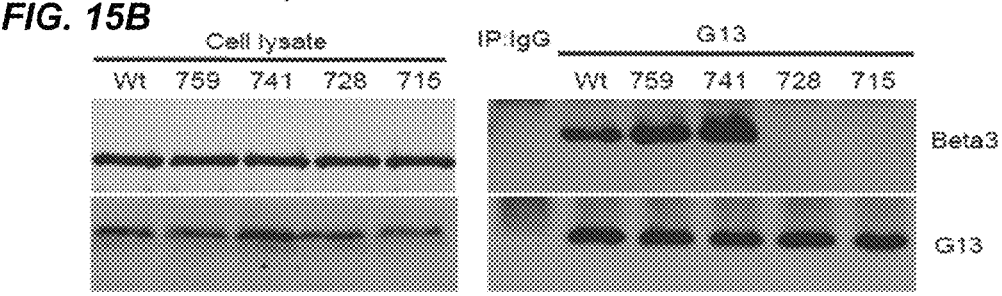

FIG. 15C

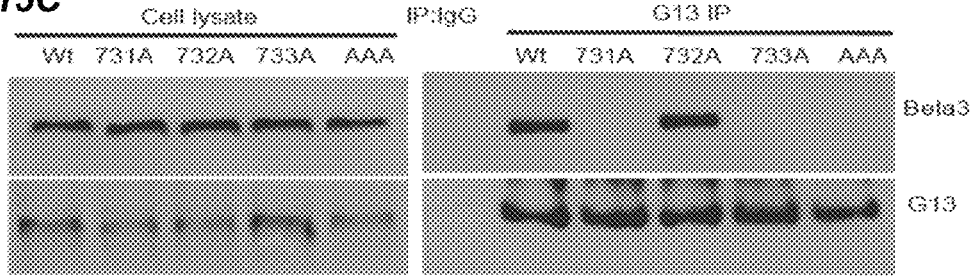

FIG. 15D

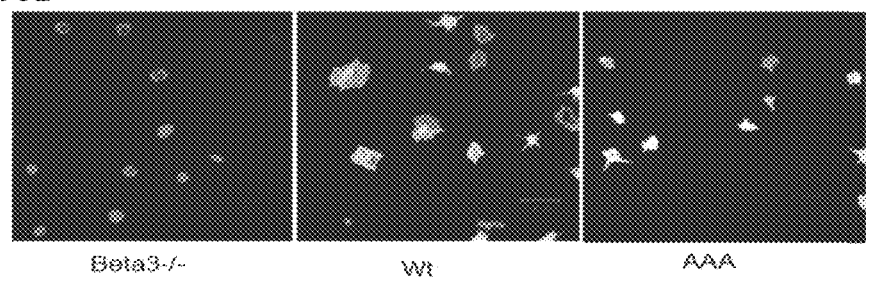

FIG. 15E

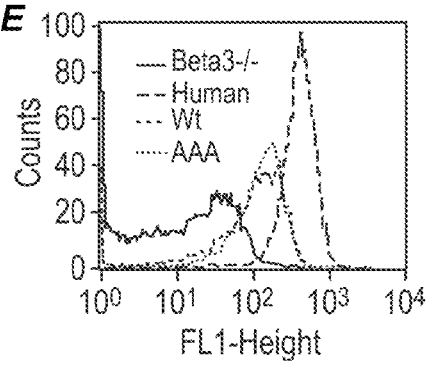

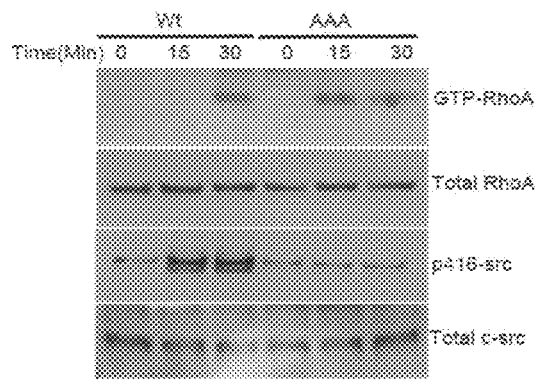
FIG. 16A
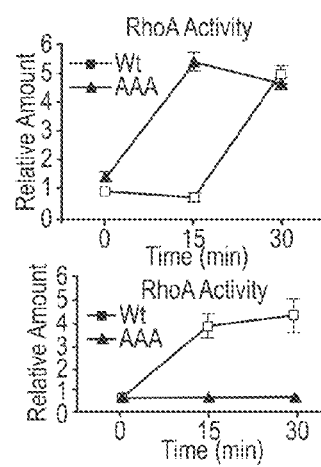
FIG. 16B
FIG. 16C
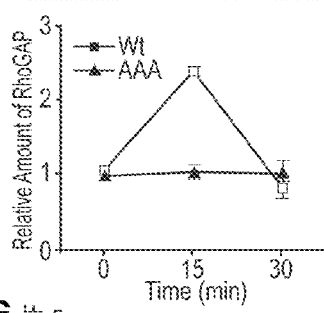
FIG. 16E
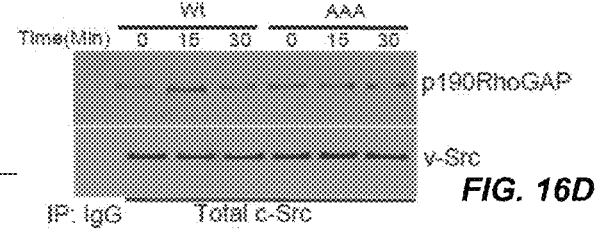
FIG. 16D
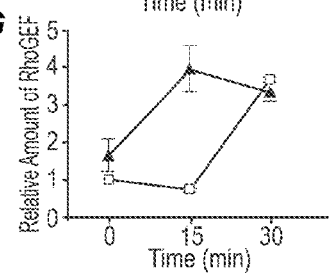
FIG. 16G
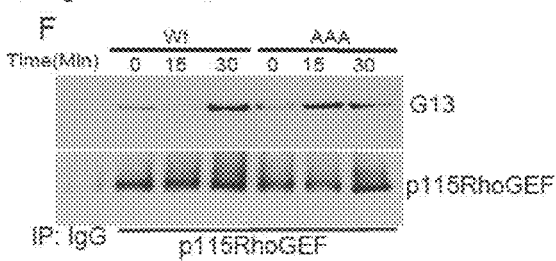
FIG. 16F
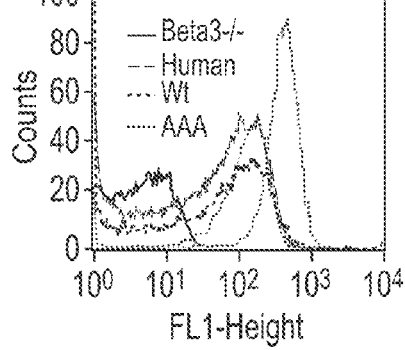
FIG. 16H

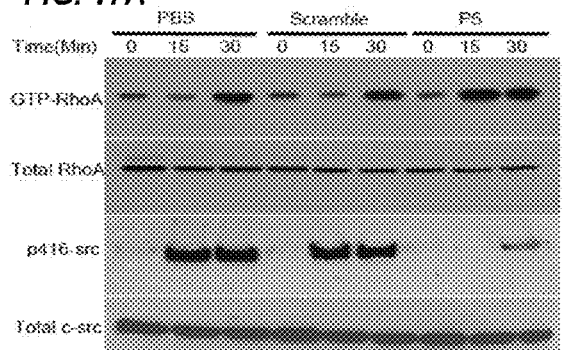
FIG. 17A
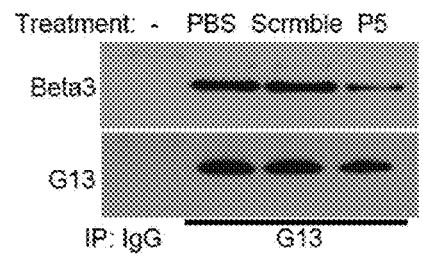
FIG. 17D
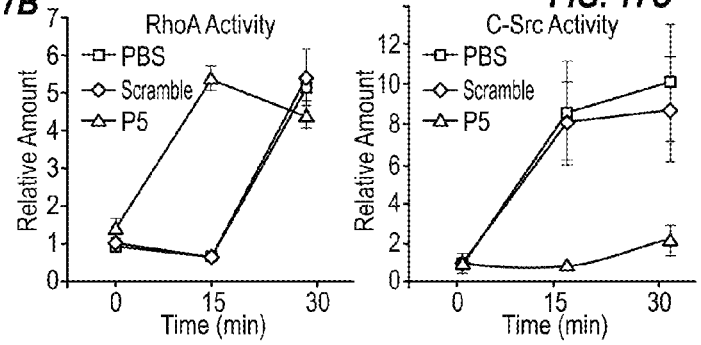
FIG. 17B FIG. 17C FIG. 17E
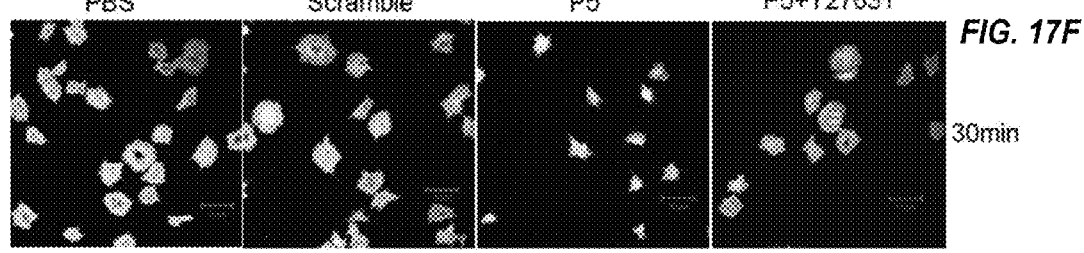
FIG. 17F
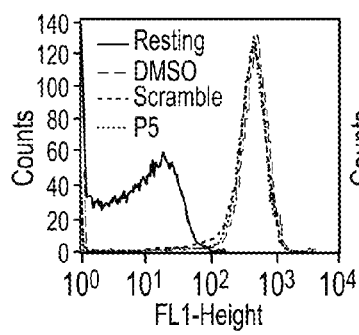
FIG. 17G
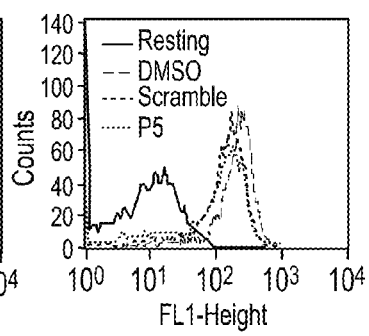
FIG. 17H
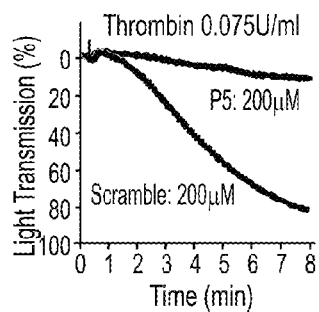
FIG. 17I

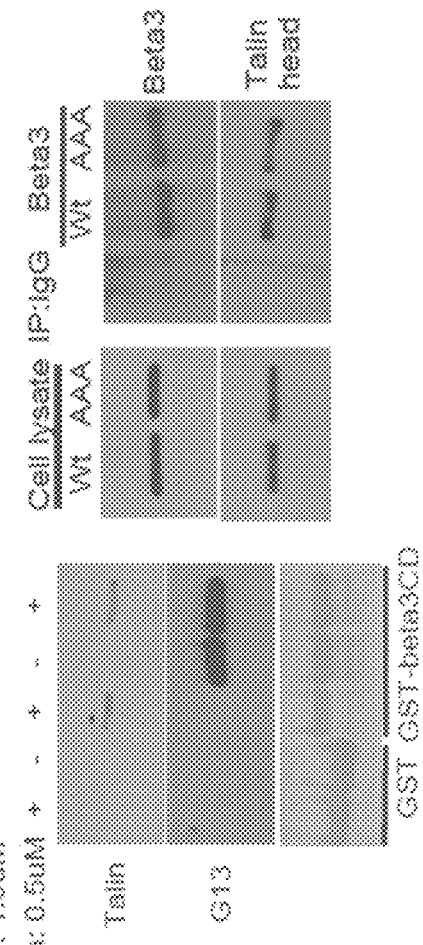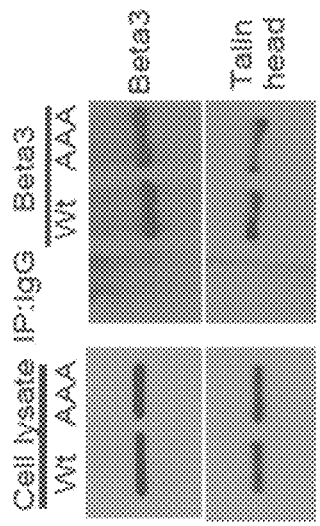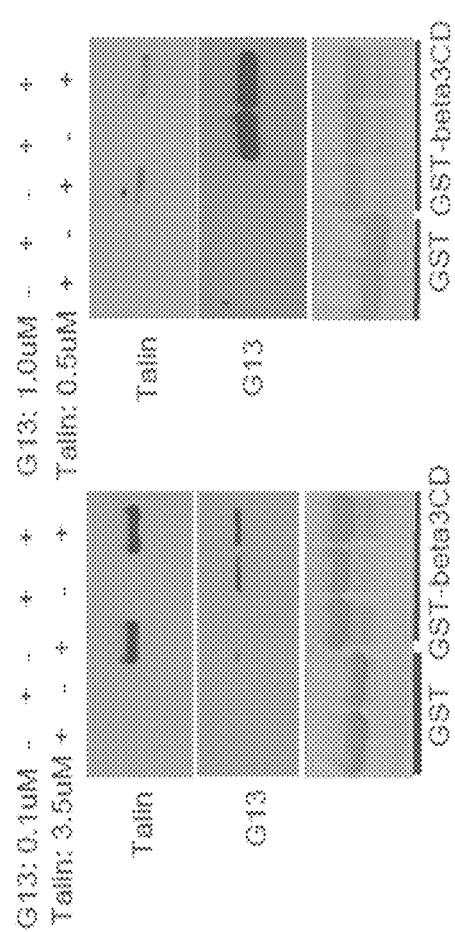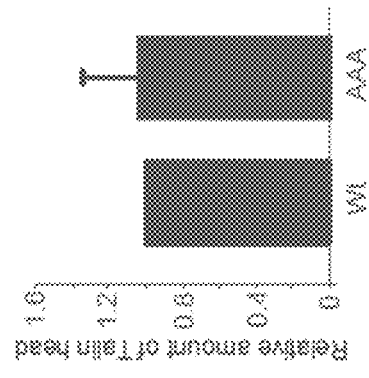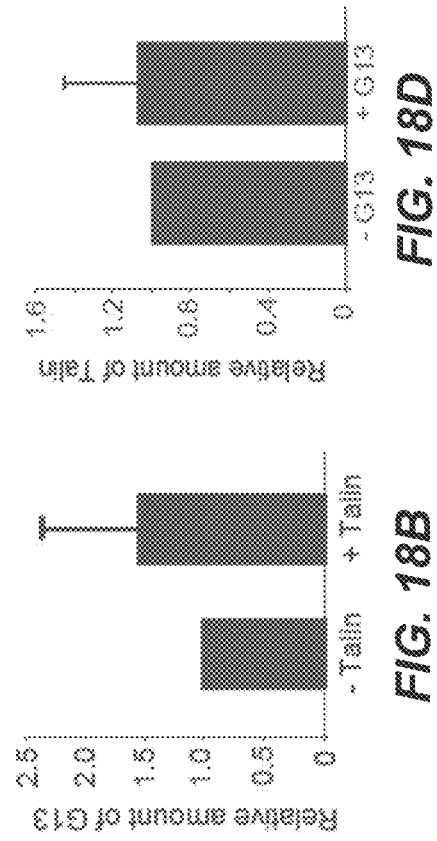
FIG. 18A  FIG. 18B  FIG. 18C  FIG. 18D  FIG. 18E  FIG. 18F

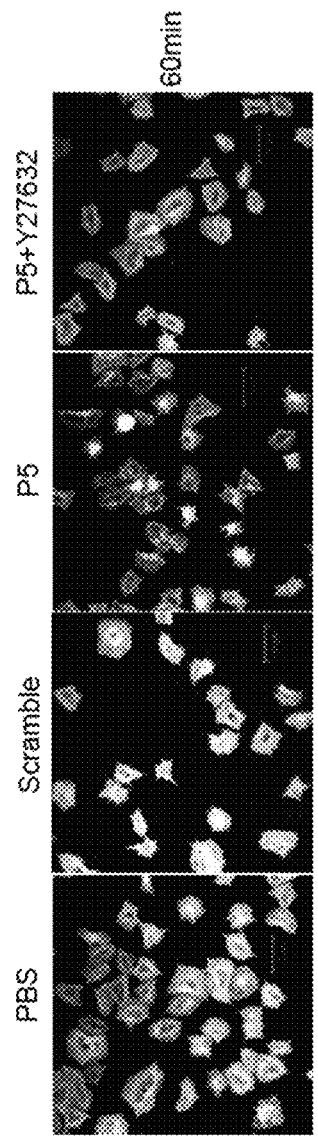
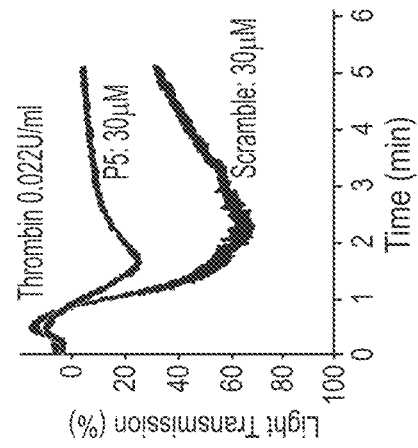
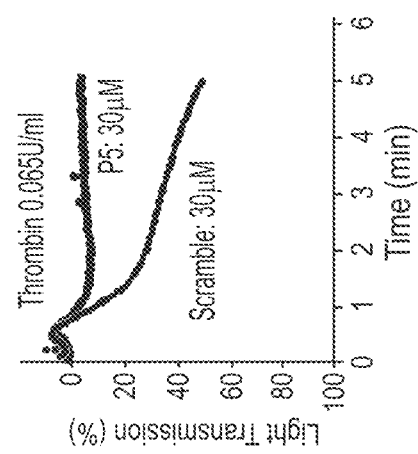

FIG. 29
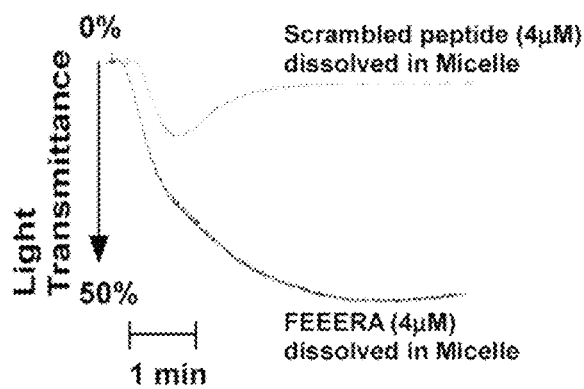
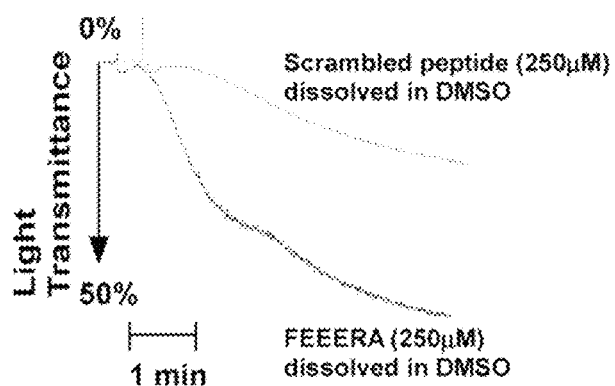

Comparison of the inhibitory effects of DMSO-solubilized EEERA and FEEERA on platelet aggregation

| Doses (µM) | EEERA (mP5) | FEEERA |
|---|---|---|
| 25 | - | ± |
| 50 | - | ± |
| 100 | - | + |
| 250 | ± | + |
| 500 | + | |

SEQUENCE LISTING

```
<160> NUMBER OF SEQ ID NOS: 412

<210> SEQ ID NO 1
<211> LENGTH: 377
<212> TYPE: PRT
<213> ORGANISM: Homo sapiens
<220> FEATURE:
<221> NAME/KEY: misc_feature
<223> OTHER INFORMATION: G Protein - Alpha 13
<300> PUBLICATION INFORMATION:
<308> DATABASE ACCESSION NUMBER: Genbank / AAH36756
<309> DATABASE ENTRY DATE: 2006-07-15
<313> RELEVANT RESIDUES IN SEQ ID NO: (1)..(377)

<400> SEQUENCE: 1

Met Ala Asp Phe Leu Pro Ser Arg Ser Val Leu Ser Val Cys Phe Pro
1               5                   10                  15

Gly Cys Leu Leu Thr Ser Gly Glu Ala Glu Gln Gln Arg Lys Ser Lys
                20                  25                  30

Glu Ile Asp Lys Cys Leu Ser Arg Glu Lys Thr Tyr Val Lys Arg Leu
            35                  40                  45

Val Lys Ile Leu Leu Leu Gly Ala Gly Glu Ser Gly Lys Ser Thr Phe
    50                  55                  60

Leu Lys Gln Met Arg Ile Ile His Gly Gln Asp Phe Asp Gln Arg Ala
65                  70                  75                  80

Arg Glu Glu Phe Arg Pro Thr Ile Tyr Ser Asn Val Ile Lys Gly Met
                85                  90                  95

Arg Val Leu Val Asp Ala Arg Glu Lys Leu His Ile Pro Trp Gly Asp
                100                 105                 110

Asn Ser Asn Gln Gln His Gly Asp Lys Met Met Ser Phe Asp Thr Arg
            115                 120                 125

Ala Pro Met Ala Ala Gln Gly Met Val Glu Thr Arg Val Phe Leu Gln
    130                 135                 140

Tyr Leu Pro Ala Ile Arg Ala Leu Trp Ala Asp Ser Gly Ile Gln Asn
145                 150                 155                 160

Ala Tyr Asp Arg Arg Arg Glu Phe Gln Leu Gly Glu Ser Val Lys Tyr
                165                 170                 175

Phe Leu Asp Asn Leu Asp Lys Leu Gly Glu Pro Asp Tyr Ile Pro Ser
            180                 185                 190

Gln Gln Asp Ile Leu Leu Ala Arg Arg Pro Thr Lys Gly Ile His Glu
        195                 200                 205
```

```
Tyr Asp Phe Glu Ile Lys Asn Val Pro Phe Lys Met Val Asp Val Gly
    210                 215                 220
Gly Gln Arg Ser Glu Arg Lys Arg Trp Phe Glu Cys Phe Asp Ser Val
225                 230                 235                 240
Thr Ser Ile Leu Phe Leu Val Ser Ser Glu Phe Asp Gln Val Leu
                245                 250                 255
Met Glu Asp Arg Leu Thr Asn Arg Leu Thr Glu Ser Leu Asn Ile Phe
            260                 265                 270
Glu Thr Ile Val Asn Asn Arg Val Phe Ser Asn Val Ser Ile Ile Leu
        275                 280                 285
Phe Leu Asn Lys Thr Asp Leu Leu Glu Glu Lys Val Gln Ile Val Ser
    290                 295                 300
Ile Lys Asp Tyr Phe Leu Glu Phe Glu Gly Asp Pro His Cys Leu Arg
305                 310                 315                 320
Asp Val Gln Lys Phe Leu Val Glu Cys Phe Arg Asn Lys Arg Arg Asp
                325                 330                 335
Gln Gln Gln Lys Pro Leu Tyr His His Phe Thr Thr Ala Ile Asn Thr
            340                 345                 350
Glu Asn Ile Arg Leu Val Phe Arg Asp Val Lys Asp Thr Ile Leu His
        355                 360                 365
Asp Asn Leu Lys Gln Leu Met Leu Gln
    370                 375

<210> SEQ ID NO 2
<211> LENGTH: 798
<212> TYPE: PRT
<213> ORGANISM: Homo sapiens
<220> FEATURE:
<221> NAME/KEY: misc_feature
<223> OTHER INFORMATION: Beta-1 integrin
<300> PUBLICATION INFORMATION:
<308> DATABASE ACCESSION NUMBER: Swiss Prot / P05556
<309> DATABASE ENTRY DATE: 2011-01-11
<313> RELEVANT RESIDUES IN SEQ ID NO: (1)..(798)

<400> SEQUENCE: 2

Met Asn Leu Gln Pro Ile Phe Trp Ile Gly Leu Ile Ser Ser Val Cys
1               5                   10                  15
Cys Val Phe Ala Gln Thr Asp Glu Asn Arg Cys Leu Lys Ala Asn Ala
                20                  25                  30
Lys Ser Cys Gly Glu Cys Ile Gln Ala Gly Pro Asn Cys Gly Trp Cys
            35                  40                  45
Thr Asn Ser Thr Phe Leu Gln Glu Gly Met Pro Thr Ser Ala Arg Cys
        50                  55                  60
Asp Asp Leu Glu Ala Leu Lys Lys Lys Gly Cys Pro Pro Asp Asp Ile
65                  70                  75                  80
Glu Asn Pro Arg Gly Ser Lys Asp Ile Lys Lys Asn Lys Asn Val Thr
                85                  90                  95
Asn Arg Ser Lys Gly Thr Ala Glu Lys Leu Lys Pro Glu Asp Ile Thr
            100                 105                 110
Gln Ile Gln Pro Gln Gln Leu Val Leu Arg Leu Arg Ser Gly Glu Pro
        115                 120                 125
Gln Thr Phe Thr Leu Lys Phe Lys Arg Ala Glu Asp Tyr Pro Ile Asp
    130                 135                 140
Leu Tyr Tyr Leu Met Asp Leu Ser Tyr Ser Met Lys Asp Asp Leu Glu
145                 150                 155                 160
Asn Val Lys Ser Leu Gly Thr Asp Leu Met Asn Glu Met Arg Arg Ile
                165                 170                 175
```

```
Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
            195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
            290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
            370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
            435                 440                 445

Gly Phe Thr Glu Glu Val Glu Val Ile Leu Gln Tyr Ile Cys Glu Cys
450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
            515                 520                 525

Gly Glu Cys Val Cys Gly Gln Cys Val Cys Arg Lys Arg Asp Asn Thr
            530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
```

```
              595                 600                 605
Gly Arg Gly Ile Cys Glu Cys Gly Val Cys Lys Cys Thr Asp Pro Lys
            610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
            675                 680                 685

Ser His Cys Lys Glu Lys Asp Val Asp Cys Trp Phe Tyr Phe Thr
            690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
            755                 760                 765

Glu Lys Met Asn Ala Lys Trp Asp Thr Gly Glu Asn Pro Ile Tyr Lys
770                 775                 780

Ser Ala Val Thr Thr Val Val Asn Pro Lys Tyr Glu Gly Lys
785                 790                 795

<210> SEQ ID NO 3
<211> LENGTH: 788
<212> TYPE: PRT
<213> ORGANISM: Homo sapiens
<220> FEATURE:
<221> NAME/KEY: misc_feature
<223> OTHER INFORMATION: Beta-3 integrin
<300> PUBLICATION INFORMATION:
<308> DATABASE ACCESSION NUMBER: Swiss Prot / P05106
<309> DATABASE ENTRY DATE: 2011-01-11
<313> RELEVANT RESIDUES IN SEQ ID NO: (1)..(788)

<400> SEQUENCE: 3

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140
```

```
Asp Leu Ser Tyr Ser Met Lys Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
        275                 280                 285

Ala Gly Ile Val Gln Pro Asn Asp Gly Gln Cys His Val Gly Ser Asp
290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
        355                 360                 365

Leu Ile Val Asp Ala Tyr Gly Lys Ile Arg Ser Lys Val Glu Leu Glu
370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
        435                 440                 445

Asp Ser Leu Ile Val Gln Val Thr Phe Asp Cys Asp Cys Ala Cys Gln
450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
        515                 520                 525

Cys Gly Gln Cys Val Cys His Ser Ser Asp Phe Gly Lys Ile Thr Gly
530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575
```

```
Ser Asp Trp Thr Gly Tyr Tyr Cys Asn Cys Thr Thr Arg Thr Asp Thr
            580                 585                 590
Cys Met Ser Ser Asn Gly Leu Leu Cys Ser Gly Arg Gly Lys Cys Glu
            595                 600                 605
Cys Gly Ser Cys Val Cys Ile Gln Pro Gly Ser Tyr Gly Asp Thr Cys
        610                 615                 620
Glu Lys Cys Pro Thr Cys Pro Asp Ala Cys Thr Phe Lys Lys Glu Cys
625                 630                 635                 640
Val Glu Cys Lys Lys Phe Asp Arg Gly Ala Leu His Asp Glu Asn Thr
                645                 650                 655
Cys Asn Arg Tyr Cys Arg Asp Glu Ile Glu Ser Val Lys Glu Leu Lys
            660                 665                 670
Asp Thr Gly Lys Asp Ala Val Asn Cys Thr Tyr Lys Asn Glu Asp Asp
            675                 680                 685
Cys Val Val Arg Phe Gln Tyr Tyr Glu Asp Ser Ser Gly Lys Ser Ile
        690                 695                 700
Leu Tyr Val Val Glu Glu Pro Glu Cys Pro Lys Gly Pro Asp Ile Leu
705                 710                 715                 720
Val Val Leu Leu Ser Val Met Gly Ala Ile Leu Leu Ile Gly Leu Ala
                725                 730                 735
Ala Leu Leu Ile Trp Lys Leu Leu Ile Thr Ile His Asp Arg Lys Glu
            740                 745                 750
Phe Ala Lys Phe Glu Glu Glu Arg Ala Arg Ala Lys Trp Asp Thr Ala
            755                 760                 765
Asn Asn Pro Leu Tyr Lys Glu Ala Thr Ser Thr Phe Thr Asn Ile Thr
        770                 775                 780
Tyr Arg Gly Thr
785

<210> SEQ ID NO 4
<211> LENGTH: 13
<212> TYPE: PRT
<213> ORGANISM: Homo sapiens
<220> FEATURE:
<221> NAME/KEY: misc_feature
<223> OTHER INFORMATION: amino acids 197-209 of G Protein - Alpha 13
<300> PUBLICATION INFORMATION:
<308> DATABASE ACCESSION NUMBER: Genbank / AAH36756
<309> DATABASE ENTRY DATE: 2006-07-15
<313> RELEVANT RESIDUES IN SEQ ID NO: (197)..(209)

<400> SEQUENCE: 4

Leu Leu Ala Arg Arg Pro Thr Lys Gly Ile His Glu Tyr
1               5                   10

<210> SEQ ID NO 5
<211> LENGTH: 47
<212> TYPE: PRT
<213> ORGANISM: Homo sapiens
<300> PUBLICATION INFORMATION:
<308> DATABASE ACCESSION NUMBER: Swiss Prot / P05556
<309> DATABASE ENTRY DATE: 2011-01-11
<313> RELEVANT RESIDUES IN SEQ ID NO: (752)..(798)

<400> SEQUENCE: 5

Lys Leu Leu Met Ile Ile His Asp Arg Arg Glu Phe Ala Lys Phe Glu
1               5                   10                  15
Lys Glu Lys Met Asn Ala Lys Trp Asp Thr Gly Glu Asn Pro Ile Tyr
            20                  25                  30
Lys Ser Ala Val Thr Thr Val Val Asn Pro Lys Tyr Glu Gly Lys
```

<210> SEQ ID NO 6
<211> LENGTH: 47
<212> TYPE: PRT
<213> ORGANISM: Homo sapiens
<220> FEATURE:
<221> NAME/KEY: misc_feature
<223> OTHER INFORMATION: Amino acids 716-762 of Beta-3 integrin
<300> PUBLICATION INFORMATION:
<308> DATABASE ACCESSION NUMBER: Swiss Prot / P05106
<309> DATABASE ENTRY DATE: 2011-01-11
<313> RELEVANT RESIDUES IN SEQ ID NO: (716)..(762)

<400> SEQUENCE: 6

```
Gly Pro Asp Ile Leu Val Val Leu Leu Ser Val Met Gly Ala Ile Leu
1               5                   10                  15

Leu Ile Gly Leu Ala Ala Leu Leu Ile Trp Lys Leu Leu Ile Thr Ile
            20                  25                  30

His Asp Arg Lys Glu Phe Ala Lys Phe Glu Glu Glu Arg Ala Arg
        35                  40                  45
```

<210> SEQ ID NO 7
<211> LENGTH: 19
<212> TYPE: DNA
<213> ORGANISM: Homo sapiens

<400> SEQUENCE: 7
gtccaccttc ctgaagcag                                           19

<210> SEQ ID NO 8
<211> LENGTH: 19
<212> TYPE: DNA
<213> ORGANISM: Homo sapiens

<400> SEQUENCE: 8
ggagatcgac aaatgcctg                                           19

<210> SEQ ID NO 9
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(12)
<223> OTHER INFORMATION: Xaa can be any naturally occurring amino acid

<400> SEQUENCE: 9

```
Xaa Xaa Xaa Xaa Xaa Xaa Xaa Xaa Xaa Xaa Xaa Xaa
1               5                   10
```

<210> SEQ ID NO 10
<211> LENGTH: 377
<212> TYPE: PRT
<213> ORGANISM: Homo sapiens
<220> FEATURE:
<221> NAME/KEY: MISC_FEATURE
<223> OTHER INFORMATION: G alpha 13 (GenBank Accession # NP_006563.2)

<400> SEQUENCE: 10

```
Met Ala Asp Phe Leu Pro Ser Arg Ser Val Leu Ser Val Cys Phe Pro
1               5                   10                  15

Gly Cys Leu Leu Thr Ser Gly Glu Ala Glu Gln Gln Arg Lys Ser Lys
            20                  25                  30
```

Glu Ile Asp Lys Cys Leu Ser Arg Glu Lys Thr Tyr Val Lys Arg Leu
             35                  40                  45

Val Lys Ile Leu Leu Leu Gly Ala Gly Glu Ser Gly Lys Ser Thr Phe
 50                  55                  60

Leu Lys Gln Met Arg Ile Ile His Gly Gln Asp Phe Asp Gln Arg Ala
 65                  70                  75                  80

Arg Glu Glu Phe Arg Pro Thr Ile Tyr Ser Asn Val Ile Lys Gly Met
                 85                  90                  95

Arg Val Leu Val Asp Ala Arg Glu Lys Leu His Ile Pro Trp Gly Asp
            100                 105                 110

Asn Ser Asn Gln Gln His Gly Asp Lys Met Met Ser Phe Asp Thr Arg
            115                 120                 125

Ala Pro Met Ala Ala Gln Gly Met Val Glu Thr Arg Val Phe Leu Gln
        130                 135                 140

Tyr Leu Pro Ala Ile Arg Ala Leu Trp Ala Asp Ser Gly Ile Gln Asn
145                 150                 155                 160

Ala Tyr Asp Arg Arg Arg Glu Phe Gln Leu Gly Glu Ser Val Lys Tyr
                165                 170                 175

Phe Leu Asp Asn Leu Asp Lys Leu Gly Glu Pro Asp Tyr Ile Pro Ser
            180                 185                 190

Gln Gln Asp Ile Leu Leu Ala Arg Arg Pro Thr Lys Gly Ile His Glu
        195                 200                 205

Tyr Asp Phe Glu Ile Lys Asn Val Pro Phe Lys Met Val Asp Val Gly
210                 215                 220

Gly Gln Arg Ser Glu Arg Lys Arg Trp Phe Glu Cys Phe Asp Ser Val
225                 230                 235                 240

Thr Ser Ile Leu Phe Leu Val Ser Ser Ser Glu Phe Asp Gln Val Leu
                245                 250                 255

Met Glu Asp Arg Leu Thr Asn Arg Leu Thr Glu Ser Leu Asn Ile Phe
            260                 265                 270

Glu Thr Ile Val Asn Asn Arg Val Phe Ser Asn Val Ser Ile Ile Leu
        275                 280                 285

Phe Leu Asn Lys Thr Asp Leu Leu Glu Glu Lys Val Gln Ile Val Ser
290                 295                 300

Ile Lys Asp Tyr Phe Leu Glu Phe Glu Gly Asp Pro His Cys Leu Arg
305                 310                 315                 320

Asp Val Gln Lys Phe Leu Val Glu Cys Phe Arg Asn Lys Arg Arg Asp
                325                 330                 335

Gln Gln Gln Lys Pro Leu Tyr His His Phe Thr Thr Ala Ile Asn Thr
            340                 345                 350

Glu Asn Ile Arg Leu Val Phe Arg Asp Val Lys Asp Thr Ile Leu His
        355                 360                 365

Asp Asn Leu Lys Gln Leu Met Leu Gln
370                 375

<210> SEQ ID NO 11
<211> LENGTH: 381
<212> TYPE: PRT
<213> ORGANISM: Homo sapiens
<220> FEATURE:
<221> NAME/KEY: MISC_FEATURE
<223> OTHER INFORMATION: G alpha 12 (GenBank Accession # NP_031379.2)

<400> SEQUENCE: 11

Met Ser Gly Val Val Arg Thr Leu Ser Arg Cys Leu Leu Pro Ala Glu
1               5                  10                  15

Ala Gly Gly Ala Arg Glu Arg Ala Gly Ser Gly Ala Arg Asp Ala
            20                  25                  30

Glu Arg Glu Ala Arg Arg Ser Arg Asp Ile Asp Ala Leu Leu Ala
        35                  40                  45

Arg Glu Arg Arg Ala Val Arg Arg Leu Val Lys Ile Leu Leu Gly
    50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                85                  90                  95

Ile Phe Asp Asn Ile Leu Lys Gly Ser Arg Val Leu Val Asp Ala Arg
            100                 105                 110

Asp Lys Leu Gly Ile Pro Trp Gln Tyr Ser Glu Asn Glu Lys His Gly
        115                 120                 125

Met Phe Leu Met Ala Phe Glu Asn Lys Ala Gly Leu Pro Val Glu Pro
    130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Ser Glu Phe Gln Leu Gly
                165                 170                 175

Glu Ser Val Lys Tyr Phe Leu Asp Asn Leu Asp Arg Ile Gly Gln Leu
            180                 185                 190

Asn Tyr Phe Pro Ser Lys Gln Asp Ile Leu Leu Ala Arg Lys Ala Thr
        195                 200                 205

Lys Gly Ile Val Glu His Asp Phe Val Ile Lys Ile Pro Phe Lys
    210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Glu
                245                 250                 255

Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
            340                 345                 350

Ala Ile Asp Thr Glu Asn Val Arg Phe Val Phe His Ala Val Lys Asp
        355                 360                 365

Thr Ile Leu Gln Glu Asn Leu Lys Asp Ile Met Leu Gln
    370                 375                 380

<210> SEQ ID NO 12
<211> LENGTH: 778
<212> TYPE: PRT
<213> ORGANISM: Homo sapiens
<220> FEATURE:
<221> NAME/KEY: MISC_FEATURE
<223> OTHER INFORMATION: Beta 1A integrin (GenBank Accession No.
      NP_002202)

<400> SEQUENCE: 12

```
Gln Thr Asp Glu Asn Arg Cys Leu Lys Ala Asn Ala Lys Ser Cys Gly
 1               5                  10                  15
Glu Cys Ile Gln Ala Gly Pro Asn Cys Gly Trp Cys Thr Asn Ser Thr
             20                  25                  30
Phe Leu Gln Glu Gly Met Pro Thr Ser Ala Arg Cys Asp Asp Leu Glu
         35                  40                  45
Ala Leu Lys Lys Lys Gly Cys Pro Pro Asp Asp Ile Glu Asn Pro Arg
 50                  55                  60
Gly Ser Lys Asp Ile Lys Lys Asn Lys Asn Val Thr Asn Arg Ser Lys
 65                  70                  75                  80
Gly Thr Ala Glu Lys Leu Lys Pro Glu Asp Ile Thr Gln Ile Gln Pro
             85                  90                  95
Gln Gln Leu Val Leu Arg Leu Arg Ser Gly Glu Pro Gln Thr Phe Thr
            100                 105                 110
Leu Lys Phe Lys Arg Ala Glu Asp Tyr Pro Ile Asp Leu Tyr Tyr Leu
        115                 120                 125
Met Asp Leu Ser Tyr Ser Met Lys Asp Asp Leu Glu Asn Val Lys Ser
    130                 135                 140
Leu Gly Thr Asp Leu Met Asn Glu Met Arg Arg Ile Thr Ser Asp Phe
145                 150                 155                 160
Arg Ile Gly Phe Gly Ser Phe Val Glu Lys Thr Val Met Pro Tyr Ile
                165                 170                 175
Ser Thr Thr Pro Ala Lys Leu Arg Asn Pro Cys Thr Ser Glu Gln Asn
            180                 185                 190
Cys Thr Ser Pro Phe Ser Tyr Lys Asn Val Leu Ser Leu Thr Asn Lys
        195                 200                 205
Gly Glu Val Phe Asn Glu Leu Val Gly Lys Gln Arg Ile Ser Gly Asn
    210                 215                 220
Leu Asp Ser Pro Glu Gly Gly Phe Asp Ala Ile Met Gln Val Ala Val
225                 230                 235                 240
Cys Gly Ser Leu Ile Gly Trp Arg Asn Val Thr Arg Leu Leu Val Phe
                245                 250                 255
Ser Thr Asp Ala Gly Phe His Phe Ala Gly Asp Gly Lys Leu Gly Gly
            260                 265                 270
Ile Val Leu Pro Asn Asp Gly Gln Cys His Leu Glu Asn Asn Met Tyr
        275                 280                 285
Thr Met Ser His Tyr Tyr Asp Tyr Pro Ser Ile Ala His Leu Val Gln
    290                 295                 300
Lys Leu Ser Glu Asn Asn Ile Gln Thr Ile Phe Ala Val Thr Glu Glu
305                 310                 315                 320
Phe Gln Pro Val Tyr Lys Glu Leu Lys Asn Leu Ile Pro Lys Ser Ala
                325                 330                 335
Val Gly Thr Leu Ser Ala Asn Ser Ser Asn Val Ile Gln Leu Ile Ile
            340                 345                 350
Asp Ala Tyr Asn Ser Leu Ser Ser Glu Val Ile Leu Glu Asn Gly Lys
        355                 360                 365
Leu Ser Glu Gly Val Thr Ile Ser Tyr Lys Ser Tyr Cys Lys Asn Gly
    370                 375                 380
Val Asn Gly Thr Gly Glu Asn Gly Arg Lys Cys Ser Asn Ile Ser Ile
385                 390                 395                 400
Gly Asp Glu Val Gln Phe Glu Ile Ser Ile Thr Ser Asn Lys Cys Pro
                405                 410                 415
Lys Lys Asp Ser Asp Ser Phe Lys Ile Arg Pro Leu Gly Phe Thr Glu
```

```
                    420             425             430
Glu Val Glu Val Ile Leu Gln Tyr Ile Cys Glu Cys Glu Cys Gln Ser
            435                 440                 445

Glu Gly Ile Pro Glu Ser Pro Lys Cys His Glu Gly Asn Gly Thr Phe
450                 455                 460

Glu Cys Gly Ala Cys Arg Cys Asn Glu Gly Arg Val Gly Arg His Cys
465                 470                 475                 480

Glu Cys Ser Thr Asp Glu Val Asn Ser Glu Asp Met Asp Ala Tyr Cys
                485                 490                 495

Arg Lys Glu Asn Ser Ser Glu Ile Cys Ser Asn Asn Gly Glu Cys Val
            500                 505                 510

Cys Gly Gln Cys Val Cys Arg Lys Arg Asp Asn Thr Asn Glu Ile Tyr
        515                 520                 525

Ser Gly Lys Phe Cys Glu Cys Asp Asn Phe Asn Cys Asp Arg Ser Asn
    530                 535                 540

Gly Leu Ile Cys Gly Gly Asn Gly Val Cys Lys Cys Arg Val Cys Glu
545                 550                 555                 560

Cys Asn Pro Asn Tyr Thr Gly Ser Ala Cys Asp Cys Ser Leu Asp Thr
                565                 570                 575

Ser Thr Cys Glu Ala Ser Asn Gly Gln Ile Cys Asn Gly Arg Gly Ile
            580                 585                 590

Cys Glu Cys Gly Val Cys Lys Cys Thr Asp Pro Lys Phe Gln Gly Gln
        595                 600                 605

Thr Cys Glu Met Cys Gln Thr Cys Leu Gly Val Cys Ala Glu His Lys
    610                 615                 620

Glu Cys Val Gln Cys Arg Ala Phe Asn Lys Gly Glu Lys Lys Asp Thr
625                 630                 635                 640

Cys Thr Gln Glu Cys Ser Tyr Phe Asn Ile Thr Lys Val Glu Ser Arg
                645                 650                 655

Asp Lys Leu Pro Gln Pro Val Gln Pro Asp Pro Val Ser His Cys Lys
            660                 665                 670

Glu Lys Asp Val Asp Asp Cys Trp Phe Tyr Phe Thr Tyr Ser Val Asn
        675                 680                 685

Gly Asn Asn Glu Val Met Val His Val Val Glu Asn Pro Glu Cys Pro
    690                 695                 700

Thr Gly Pro Asp Ile Ile Pro Ile Val Ala Gly Val Val Ala Gly Ile
705                 710                 715                 720

Val Leu Ile Gly Leu Ala Leu Leu Ile Trp Lys Leu Leu Met Ile
                725                 730                 735

Ile His Asp Arg Arg Glu Phe Ala Lys Phe Glu Lys Glu Lys Met Asn
            740                 745                 750

Ala Lys Trp Asp Thr Gly Glu Asn Pro Ile Tyr Lys Ser Ala Val Thr
        755                 760                 765

Thr Val Val Asn Pro Lys Tyr Glu Gly Lys
    770                 775

<210> SEQ ID NO 13
<211> LENGTH: 781
<212> TYPE: PRT
<213> ORGANISM: Homo sapiens
<220> FEATURE:
<221> NAME/KEY: MISC_FEATURE
<223> OTHER INFORMATION: Beta 1D integrin (GenBank Accession No.
      NP_391988)

<400> SEQUENCE: 13
```

```
Gln Thr Asp Glu Asn Arg Cys Leu Lys Ala Asn Ala Lys Ser Cys Gly
1               5                   10                  15

Glu Cys Ile Gln Ala Gly Pro Asn Cys Gly Trp Cys Thr Asn Ser Thr
            20                  25                  30

Phe Leu Gln Glu Gly Met Pro Thr Ser Ala Arg Cys Asp Asp Leu Glu
        35                  40                  45

Ala Leu Lys Lys Lys Gly Cys Pro Pro Asp Asp Ile Glu Asn Pro Arg
    50                  55                  60

Gly Ser Lys Asp Ile Lys Lys Asn Lys Asn Val Thr Asn Arg Ser Lys
65                  70                  75                  80

Gly Thr Ala Glu Lys Leu Lys Pro Glu Asp Ile Thr Gln Ile Gln Pro
                85                  90                  95

Gln Gln Leu Val Leu Arg Leu Arg Ser Gly Glu Pro Gln Thr Phe Thr
            100                 105                 110

Leu Lys Phe Lys Arg Ala Glu Asp Tyr Pro Ile Asp Leu Tyr Tyr Leu
        115                 120                 125

Met Asp Leu Ser Tyr Ser Met Lys Asp Asp Leu Glu Asn Val Lys Ser
    130                 135                 140

Leu Gly Thr Asp Leu Met Asn Glu Met Arg Arg Ile Thr Ser Asp Phe
145                 150                 155                 160

Arg Ile Gly Phe Gly Ser Phe Val Glu Lys Thr Val Met Pro Tyr Ile
                165                 170                 175

Ser Thr Thr Pro Ala Lys Leu Arg Asn Pro Cys Thr Ser Glu Gln Asn
            180                 185                 190

Cys Thr Ser Pro Phe Ser Tyr Lys Asn Val Leu Ser Leu Thr Asn Lys
    195                 200                 205

Gly Glu Val Phe Asn Glu Leu Val Gly Lys Gln Arg Ile Ser Gly Asn
210                 215                 220

Leu Asp Ser Pro Glu Gly Gly Phe Asp Ala Ile Met Gln Val Ala Val
225                 230                 235                 240

Cys Gly Ser Leu Ile Gly Trp Arg Asn Val Thr Arg Leu Leu Val Phe
                245                 250                 255

Ser Thr Asp Ala Gly Phe His Phe Ala Gly Asp Gly Lys Leu Gly Gly
            260                 265                 270

Ile Val Leu Pro Asn Asp Gly Gln Cys His Leu Glu Asn Asn Met Tyr
    275                 280                 285

Thr Met Ser His Tyr Tyr Asp Tyr Pro Ser Ile Ala His Leu Val Gln
290                 295                 300

Lys Leu Ser Glu Asn Asn Ile Gln Thr Ile Phe Ala Val Thr Glu Glu
305                 310                 315                 320

Phe Gln Pro Val Tyr Lys Glu Leu Lys Asn Leu Ile Pro Lys Ser Ala
                325                 330                 335

Val Gly Thr Leu Ser Ala Asn Ser Ser Asn Val Ile Gln Leu Ile Ile
            340                 345                 350

Asp Ala Tyr Asn Ser Leu Ser Ser Glu Val Ile Leu Glu Asn Gly Lys
    355                 360                 365

Leu Ser Glu Gly Val Thr Ile Ser Tyr Lys Ser Tyr Cys Lys Asn Gly
370                 375                 380

Val Asn Gly Thr Gly Glu Asn Gly Arg Lys Cys Ser Asn Ile Ser Ile
385                 390                 395                 400

Gly Asp Glu Val Gln Phe Glu Ile Ser Ile Thr Ser Asn Lys Cys Pro
                405                 410                 415

Lys Lys Asp Ser Asp Ser Phe Lys Ile Arg Pro Leu Gly Phe Thr Glu
            420                 425                 430
```

Glu Val Glu Val Ile Leu Gln Tyr Ile Cys Glu Cys Glu Cys Gln Ser
            435                 440                 445

Glu Gly Ile Pro Glu Ser Pro Lys Cys His Glu Gly Asn Gly Thr Phe
            450                 455                 460

Glu Cys Gly Ala Cys Arg Cys Asn Glu Gly Arg Val Gly Arg His Cys
465                 470                 475                 480

Glu Cys Ser Thr Asp Glu Val Asn Ser Glu Asp Met Asp Ala Tyr Cys
            485                 490                 495

Arg Lys Glu Asn Ser Ser Glu Ile Cys Ser Asn Asn Gly Glu Cys Val
            500                 505                 510

Cys Gly Gln Cys Val Cys Arg Lys Arg Asp Asn Thr Asn Glu Ile Tyr
            515                 520                 525

Ser Gly Lys Phe Cys Glu Cys Asp Asn Phe Asn Cys Asp Arg Ser Asn
            530                 535                 540

Gly Leu Ile Cys Gly Gly Asn Gly Val Cys Lys Cys Arg Val Cys Glu
545                 550                 555                 560

Cys Asn Pro Asn Tyr Thr Gly Ser Ala Cys Asp Cys Ser Leu Asp Thr
            565                 570                 575

Ser Thr Cys Glu Ala Ser Asn Gly Gln Ile Cys Asn Gly Arg Gly Ile
            580                 585                 590

Cys Glu Cys Gly Val Cys Lys Cys Thr Asp Pro Lys Phe Gln Gly Gln
            595                 600                 605

Thr Cys Glu Met Cys Gln Thr Cys Leu Gly Val Cys Ala Glu His Lys
            610                 615                 620

Glu Cys Val Gln Cys Arg Ala Phe Asn Lys Gly Glu Lys Lys Asp Thr
625                 630                 635                 640

Cys Thr Gln Glu Cys Ser Tyr Phe Asn Ile Thr Lys Val Glu Ser Arg
            645                 650                 655

Asp Lys Leu Pro Gln Pro Val Gln Pro Asp Pro Val Ser His Cys Lys
            660                 665                 670

Glu Lys Asp Val Asp Asp Cys Trp Phe Tyr Phe Thr Tyr Ser Val Asn
            675                 680                 685

Gly Asn Asn Glu Val Met Val His Val Val Glu Asn Pro Glu Cys Pro
            690                 695                 700

Thr Gly Pro Asp Ile Ile Pro Ile Val Ala Gly Val Val Ala Gly Ile
705                 710                 715                 720

Val Leu Ile Gly Leu Ala Leu Leu Ile Trp Lys Leu Leu Met Ile
            725                 730                 735

Ile His Asp Arg Arg Glu Phe Ala Lys Phe Glu Lys Glu Lys Met Asn
            740                 745                 750

Ala Lys Trp Asp Thr Gln Glu Asn Pro Ile Tyr Lys Ser Pro Ile Asn
            755                 760                 765

Asn Phe Lys Asn Pro Asn Tyr Gly Arg Lys Ala Gly Leu
            770                 775                 780

<210> SEQ ID NO 14
<211> LENGTH: 747
<212> TYPE: PRT
<213> ORGANISM: Homo sapiens
<220> FEATURE:
<221> NAME/KEY: MISC_FEATURE
<223> OTHER INFORMATION: Beta 2 integrin (GenBank Accession NP_000202)

<400> SEQUENCE: 14

Gln Glu Cys Thr Lys Phe Lys Val Ser Ser Cys Arg Glu Cys Ile Glu
1               5                   10                  15

```
Ser Gly Pro Gly Cys Thr Trp Cys Gln Lys Leu Asn Phe Thr Gly Pro
            20                  25                  30

Gly Asp Pro Asp Ser Ile Arg Cys Asp Thr Arg Pro Gln Leu Leu Met
        35                  40                  45

Arg Gly Cys Ala Ala Asp Asp Ile Met Asp Pro Thr Ser Leu Ala Glu
 50                  55                  60

Thr Gln Glu Asp His Asn Gly Gly Gln Lys Gln Leu Ser Pro Gln Lys
 65                  70                  75                  80

Val Thr Leu Tyr Leu Arg Pro Gly Gln Ala Ala Phe Asn Val Thr
                85                  90                  95

Phe Arg Arg Ala Lys Gly Tyr Pro Ile Asp Leu Tyr Tyr Leu Met Asp
                100                 105                 110

Leu Ser Tyr Ser Met Leu Asp Asp Leu Arg Asn Val Lys Lys Leu Gly
            115                 120                 125

Gly Asp Leu Leu Arg Ala Leu Asn Glu Ile Thr Glu Ser Gly Arg Ile
130                 135                 140

Gly Phe Gly Ser Phe Val Asp Lys Thr Val Leu Pro Phe Val Asn Thr
145                 150                 155                 160

His Pro Asp Lys Leu Arg Asn Pro Cys Pro Asn Lys Glu Lys Glu Cys
                165                 170                 175

Gln Pro Pro Phe Ala Phe Arg His Val Leu Lys Leu Thr Asn Asn Ser
            180                 185                 190

Asn Gln Phe Gln Thr Glu Val Gly Lys Gln Leu Ile Ser Gly Asn Leu
            195                 200                 205

Asp Ala Pro Glu Gly Gly Leu Asp Ala Met Met Gln Val Ala Ala Cys
        210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
                245                 250                 255

Leu Thr Pro Asn Asp Gly Arg Cys His Leu Glu Asp Asn Leu Tyr Lys
            260                 265                 270

Arg Ser Asn Glu Phe Asp Tyr Pro Ser Val Gly Gln Leu Ala His Lys
        275                 280                 285

Leu Ala Glu Asn Asn Ile Gln Pro Ile Phe Ala Val Thr Ser Arg Met
290                 295                 300

Val Lys Thr Tyr Glu Lys Leu Thr Glu Ile Ile Pro Lys Ser Ala Val
305                 310                 315                 320

Gly Glu Leu Ser Glu Asp Ser Ser Asn Val Val Gln Leu Ile Lys Asn
                325                 330                 335

Ala Tyr Asn Lys Leu Ser Ser Arg Val Phe Leu Asp His Asn Ala Leu
            340                 345                 350

Pro Asp Thr Leu Lys Val Thr Tyr Asp Ser Phe Cys Ser Asn Gly Val
        355                 360                 365

Thr His Arg Asn Gln Pro Arg Gly Asp Cys Asp Gly Val Gln Ile Asn
        370                 375                 380

Val Pro Ile Thr Phe Gln Val Lys Val Thr Ala Thr Glu Cys Ile Gln
385                 390                 395                 400

Glu Gln Ser Phe Val Ile Arg Ala Leu Gly Phe Thr Asp Ile Val Thr
                405                 410                 415

Val Gln Val Leu Pro Gln Cys Glu Cys Arg Cys Arg Asp Gln Ser Arg
            420                 425                 430

Asp Arg Ser Leu Cys His Gly Lys Gly Phe Leu Glu Cys Gly Ile Cys
```

```
                435                 440                 445
Arg Cys Asp Thr Gly Tyr Ile Gly Lys Asn Cys Glu Cys Gln Thr Gln
450                 455                 460

Gly Arg Ser Ser Gln Glu Leu Glu Gly Ser Cys Arg Lys Asp Asn Asn
465                 470                 475                 480

Ser Ile Ile Cys Ser Gly Leu Gly Asp Cys Val Cys Gly Gln Cys Leu
                485                 490                 495

Cys His Thr Ser Asp Val Pro Gly Lys Leu Ile Tyr Gly Gln Tyr Cys
                500                 505                 510

Glu Cys Asp Thr Ile Asn Cys Glu Arg Tyr Asn Gly Gln Val Cys Gly
                515                 520                 525

Gly Pro Gly Arg Gly Leu Cys Phe Cys Gly Lys Cys Arg Cys His Pro
530                 535                 540

Gly Phe Glu Gly Ser Ala Cys Gln Cys Glu Arg Thr Thr Glu Gly Cys
545                 550                 555                 560

Leu Asn Pro Arg Arg Val Glu Cys Ser Gly Arg Gly Arg Cys Arg Cys
                565                 570                 575

Asn Val Cys Glu Cys His Ser Gly Tyr Gln Leu Pro Leu Cys Gln Glu
                580                 585                 590

Cys Pro Gly Cys Pro Ser Pro Cys Gly Lys Tyr Ile Ser Cys Ala Glu
                595                 600                 605

Cys Leu Lys Phe Glu Lys Gly Pro Phe Gly Lys Asn Cys Ser Ala Ala
                610                 615                 620

Cys Pro Gly Leu Gln Leu Ser Asn Asn Pro Val Lys Gly Arg Thr Cys
625                 630                 635                 640

Lys Glu Arg Asp Ser Glu Gly Cys Trp Val Ala Tyr Thr Leu Glu Gln
                645                 650                 655

Gln Asp Gly Met Asp Arg Tyr Leu Ile Tyr Val Asp Glu Ser Arg Glu
                660                 665                 670

Cys Val Ala Gly Pro Asn Ile Ala Ala Ile Val Gly Gly Thr Val Ala
                675                 680                 685

Gly Ile Val Leu Ile Gly Ile Leu Leu Leu Val Ile Trp Lys Ala Leu
                690                 695                 700

Ile His Leu Ser Asp Leu Arg Glu Tyr Arg Arg Phe Glu Lys Glu Lys
705                 710                 715                 720

Leu Lys Ser Gln Trp Asn Asn Asp Asn Pro Leu Phe Lys Ser Ala Thr
                725                 730                 735

Thr Thr Val Met Asn Pro Lys Phe Ala Glu Ser
                740                 745

<210> SEQ ID NO 15
<211> LENGTH: 762
<212> TYPE: PRT
<213> ORGANISM: Homo sapiens
<220> FEATURE:
<221> NAME/KEY: MISC_FEATURE
<223> OTHER INFORMATION: Beta 3 integrin (GenBank Accession No.
      NP_000203)

<400> SEQUENCE: 15

Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
                20                  25                  30

Leu Gly Ser Pro Arg Cys Asp Leu Lys Glu Asn Leu Leu Lys Asp Asn
                35                  40                  45
```

```
Cys Ala Pro Glu Ser Ile Glu Phe Pro Val Ser Glu Ala Arg Val Leu
 50                  55                  60

Glu Asp Arg Pro Leu Ser Asp Lys Gly Ser Gly Asp Ser Ser Gln Val
 65                  70                  75                  80

Thr Gln Val Ser Pro Gln Arg Ile Ala Leu Arg Leu Arg Pro Asp Asp
                 85                  90                  95

Ser Lys Asn Phe Ser Ile Gln Val Arg Gln Val Glu Asp Tyr Pro Val
                100                 105                 110

Asp Ile Tyr Tyr Leu Met Asp Leu Ser Tyr Ser Met Lys Asp Asp Leu
            115                 120                 125

Trp Ser Ile Gln Asn Leu Gly Thr Lys Leu Ala Thr Gln Met Arg Lys
        130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Glu Ala Leu Glu Asn Pro
                165                 170                 175

Cys Tyr Asp Met Lys Thr Thr Cys Leu Pro Met Phe Gly Tyr Lys His
            180                 185                 190

Val Leu Thr Leu Thr Asp Gln Val Thr Arg Phe Asn Glu Glu Val Lys
        195                 200                 205

Lys Gln Ser Val Ser Arg Asn Arg Asp Ala Pro Glu Gly Gly Phe Asp
    210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Gln Pro Asn Asp Gly Gln
            260                 265                 270

Cys His Val Gly Ser Asp Asn His Tyr Ser Ala Ser Thr Thr Met Asp
        275                 280                 285

Tyr Pro Ser Leu Gly Leu Met Thr Glu Lys Leu Ser Gln Lys Asn Ile
    290                 295                 300

Asn Leu Ile Phe Ala Val Thr Glu Asn Val Val Asn Leu Tyr Gln Asn
305                 310                 315                 320

Tyr Ser Glu Leu Ile Pro Gly Thr Thr Val Gly Val Leu Ser Met Asp
                325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Glu Glu Leu Ser Leu
        355                 360                 365

Ser Phe Asn Ala Thr Cys Leu Asn Asn Glu Val Ile Pro Gly Leu Lys
    370                 375                 380

Ser Cys Met Gly Leu Lys Ile Gly Asp Thr Val Ser Phe Ser Ile Glu
385                 390                 395                 400

Ala Lys Val Arg Gly Cys Pro Gln Glu Lys Glu Lys Ser Phe Thr Ile
                405                 410                 415

Lys Pro Val Gly Phe Lys Asp Ser Leu Ile Val Gln Val Thr Phe Asp
            420                 425                 430

Cys Asp Cys Ala Cys Gln Ala Gln Ala Glu Pro Asn Ser His Arg Cys
        435                 440                 445

Asn Asn Gly Asn Gly Thr Phe Glu Cys Gly Val Cys Arg Cys Gly Pro
    450                 455                 460

Gly Trp Leu Gly Ser Gln Cys Glu Cys Ser Glu Glu Asp Tyr Arg Pro
465                 470                 475                 480
```

Ser Gln Gln Asp Glu Cys Ser Pro Arg Glu Gly Gln Pro Val Cys Ser
                485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Asp Phe Ser Cys
        515                 520                 525

Val Arg Tyr Lys Gly Glu Met Cys Ser Gly His Gly Gln Cys Ser Cys
    530                 535                 540

Gly Asp Cys Leu Cys Asp Ser Asp Trp Thr Gly Tyr Tyr Cys Asn Cys
545                 550                 555                 560

Thr Thr Arg Thr Asp Thr Cys Met Ser Ser Asn Gly Leu Leu Cys Ser
                565                 570                 575

Gly Arg Gly Lys Cys Glu Cys Gly Ser Cys Val Cys Ile Gln Pro Gly
            580                 585                 590

Ser Tyr Gly Asp Thr Cys Glu Lys Cys Pro Thr Cys Pro Asp Ala Cys
        595                 600                 605

Thr Phe Lys Lys Glu Cys Val Glu Cys Lys Lys Phe Asp Arg Gly Ala
    610                 615                 620

Leu His Asp Glu Asn Thr Cys Asn Arg Tyr Cys Arg Asp Glu Ile Glu
625                 630                 635                 640

Ser Val Lys Glu Leu Lys Asp Thr Gly Lys Asp Ala Val Asn Cys Thr
                645                 650                 655

Tyr Lys Asn Glu Asp Asp Cys Val Val Arg Phe Gln Tyr Tyr Glu Asp
            660                 665                 670

Ser Ser Gly Lys Ser Ile Leu Tyr Val Val Glu Glu Pro Glu Cys Pro
        675                 680                 685

Lys Gly Pro Asp Ile Leu Val Val Leu Leu Ser Val Met Gly Ala Ile
    690                 695                 700

Leu Leu Ile Gly Leu Ala Ala Leu Leu Ile Trp Lys Leu Leu Ile Thr
705                 710                 715                 720

Ile His Asp Arg Lys Glu Phe Ala Lys Phe Glu Glu Glu Arg Ala Arg
                725                 730                 735

Ala Lys Trp Asp Thr Ala Asn Asn Pro Leu Tyr Lys Glu Ala Thr Ser
            740                 745                 750

Thr Phe Thr Asn Ile Thr Tyr Arg Gly Thr
        755                 760

<210> SEQ ID NO 16
<211> LENGTH: 776
<212> TYPE: PRT
<213> ORGANISM: Homo sapiens
<220> FEATURE:
<221> NAME/KEY: MISC_FEATURE
<223> OTHER INFORMATION: Beta 5 integrin (GenBank Accession No.
    NP_002204.2)

<400> SEQUENCE: 16

Gly Leu Asn Ile Cys Thr Ser Gly Ser Ala Thr Ser Cys Glu Glu Cys
1               5                   10                  15

Leu Leu Ile His Pro Lys Cys Ala Trp Cys Ser Lys Glu Asp Phe Gly
                20                  25                  30

Ser Pro Arg Ser Ile Thr Ser Arg Cys Asp Leu Arg Ala Asn Leu Val
            35                  40                  45

Lys Asn Gly Cys Gly Gly Glu Ile Glu Ser Pro Ala Ser Ser Phe His
        50                  55                  60

Val Leu Arg Ser Leu Pro Leu Ser Ser Lys Gly Ser Gly Ser Ala Gly

```
                65                  70                  75                  80
Trp Asp Val Ile Gln Met Thr Pro Gln Glu Ile Ala Val Asn Leu Arg
                        85                  90                  95

Pro Gly Asp Lys Thr Thr Phe Gln Leu Gln Val Arg Gln Val Glu Asp
            100                 105                 110

Tyr Pro Val Asp Leu Tyr Tyr Leu Met Asp Leu Ser Leu Ser Met Lys
        115                 120                 125

Asp Asp Leu Asp Asn Ile Arg Ser Leu Gly Thr Lys Leu Ala Glu Glu
130                 135                 140

Met Arg Lys Leu Thr Ser Asn Phe Arg Leu Gly Phe Gly Ser Phe Val
145                 150                 155                 160

Asp Lys Asp Ile Ser Pro Phe Ser Tyr Thr Ala Pro Arg Tyr Gln Thr
                165                 170                 175

Asn Pro Cys Ile Gly Tyr Lys Leu Phe Pro Asn Cys Val Pro Ser Phe
            180                 185                 190

Gly Phe Arg His Leu Leu Pro Leu Thr Asp Arg Val Asp Ser Phe Asn
        195                 200                 205

Glu Glu Val Arg Lys Gln Arg Val Ser Arg Asn Arg Asp Ala Pro Glu
210                 215                 220

Gly Gly Phe Asp Ala Val Leu Gln Ala Ala Val Cys Lys Glu Lys Ile
225                 230                 235                 240

Gly Trp Arg Lys Asp Ala Leu His Leu Leu Val Phe Thr Thr Asp Asp
                245                 250                 255

Val Pro His Ile Ala Leu Asp Gly Lys Leu Gly Gly Leu Val Gln Pro
            260                 265                 270

His Asp Gly Gln Cys His Leu Asn Glu Ala Asn Glu Tyr Thr Ala Ser
        275                 280                 285

Asn Gln Met Asp Tyr Pro Ser Leu Ala Leu Leu Gly Glu Lys Leu Ala
290                 295                 300

Glu Asn Asn Ile Asn Leu Ile Phe Ala Val Thr Lys Asn His Tyr Met
305                 310                 315                 320

Leu Tyr Lys Asn Phe Thr Ala Leu Ile Pro Gly Thr Thr Val Glu Ile
                325                 330                 335

Leu Asp Gly Asp Ser Lys Asn Ile Ile Gln Leu Ile Ile Asn Ala Tyr
            340                 345                 350

Asn Ser Ile Arg Ser Lys Val Glu Leu Ser Val Trp Asp Gln Pro Glu
        355                 360                 365

Asp Leu Asn Leu Phe Phe Thr Ala Thr Cys Gln Asp Gly Val Ser Tyr
370                 375                 380

Pro Gly Gln Arg Lys Cys Glu Gly Leu Lys Ile Gly Asp Thr Ala Ser
385                 390                 395                 400

Phe Glu Val Ser Leu Glu Ala Arg Ser Cys Pro Ser Arg His Thr Glu
                405                 410                 415

His Val Phe Ala Leu Arg Pro Val Gly Phe Arg Asp Ser Leu Glu Val
            420                 425                 430

Gly Val Thr Tyr Asn Cys Thr Cys Gly Cys Ser Val Gly Leu Glu Pro
        435                 440                 445

Asn Ser Ala Arg Cys Asn Gly Ser Gly Thr Tyr Val Cys Gly Leu Cys
450                 455                 460

Glu Cys Ser Pro Gly Tyr Leu Gly Thr Arg Cys Glu Cys Gln Asp Gly
465                 470                 475                 480

Glu Asn Gln Ser Val Tyr Gln Asn Leu Cys Arg Glu Ala Glu Gly Lys
                485                 490                 495
```

```
Pro Leu Cys Ser Gly Arg Gly Asp Cys Ser Cys Asn Gln Cys Ser Cys
            500                 505                 510

Phe Glu Ser Glu Phe Gly Lys Ile Tyr Gly Pro Phe Cys Glu Cys Asp
        515                 520                 525

Asn Phe Ser Cys Ala Arg Asn Lys Gly Val Leu Cys Ser Gly His Gly
    530                 535                 540

Glu Cys His Cys Gly Glu Cys Lys Cys His Ala Gly Tyr Ile Gly Asp
545                 550                 555                 560

Asn Cys Asn Cys Ser Thr Asp Ile Ser Thr Cys Arg Gly Arg Asp Gly
                565                 570                 575

Gln Ile Cys Ser Glu Arg Gly His Cys Leu Cys Gly Gln Cys Gln Cys
            580                 585                 590

Thr Glu Pro Gly Ala Phe Gly Glu Met Cys Glu Lys Cys Pro Thr Cys
        595                 600                 605

Pro Asp Ala Cys Ser Thr Lys Arg Asp Cys Val Glu Cys Leu Leu Leu
    610                 615                 620

His Ser Gly Lys Pro Asp Asn Gln Thr Cys His Ser Leu Cys Arg Asp
625                 630                 635                 640

Glu Val Ile Thr Trp Val Asp Thr Ile Val Lys Asp Asp Gln Glu Ala
                645                 650                 655

Val Leu Cys Phe Tyr Lys Thr Ala Lys Asp Cys Val Met Met Phe Thr
            660                 665                 670

Tyr Val Glu Leu Pro Ser Gly Lys Ser Asn Leu Thr Val Leu Arg Glu
        675                 680                 685

Pro Glu Cys Gly Asn Thr Pro Asn Ala Met Thr Ile Leu Leu Ala Val
    690                 695                 700

Val Gly Ser Ile Leu Leu Val Gly Leu Ala Leu Leu Ala Ile Trp Lys
705                 710                 715                 720

Leu Leu Val Thr Ile His Asp Arg Arg Glu Phe Ala Lys Phe Gln Ser
                725                 730                 735

Glu Arg Ser Arg Ala Arg Tyr Glu Met Ala Ser Asn Pro Leu Tyr Arg
            740                 745                 750

Lys Pro Ile Ser Thr His Thr Val Asp Phe Thr Phe Asn Lys Phe Asn
        755                 760                 765

Lys Ser Tyr Asn Gly Thr Val Asp
    770                 775

<210> SEQ ID NO 17
<211> LENGTH: 767
<212> TYPE: PRT
<213> ORGANISM: Homo sapiens
<220> FEATURE:
<221> NAME/KEY: MISC_FEATURE
<223> OTHER INFORMATION: Beta 6 integrin (GenBank Accession No.
      NP_000879.2)

<400> SEQUENCE: 17

Gly Cys Ala Leu Gly Gly Ala Glu Thr Cys Glu Asp Cys Leu Leu Ile
1               5                   10                  15

Gly Pro Gln Cys Ala Trp Cys Ala Gln Glu Asn Phe Thr His Pro Ser
            20                  25                  30

Gly Val Gly Glu Arg Cys Asp Thr Pro Ala Asn Leu Leu Ala Lys Gly
        35                  40                  45

Cys Gln Leu Asn Phe Ile Glu Asn Pro Val Ser Gln Val Glu Ile Leu
    50                  55                  60

Lys Asn Lys Pro Leu Ser Val Gly Arg Gln Lys Asn Ser Ser Asp Ile
65                  70                  75                  80
```

-continued

```
Val Gln Ile Ala Pro Gln Ser Leu Ile Leu Lys Leu Arg Pro Gly Gly
                85                  90                  95
Ala Gln Thr Leu Gln Val His Val Arg Gln Thr Glu Asp Tyr Pro Val
            100                 105                 110
Asp Leu Tyr Tyr Leu Met Asp Leu Ser Ala Ser Met Asp Asp Asp Leu
            115                 120                 125
Asn Thr Ile Lys Glu Leu Gly Ser Arg Leu Ser Lys Glu Met Ser Lys
        130                 135                 140
Leu Thr Ser Asn Phe Arg Leu Gly Phe Gly Ser Phe Val Glu Lys Pro
145                 150                 155                 160
Val Ser Pro Phe Val Lys Thr Thr Pro Glu Glu Ile Ala Asn Pro Cys
                165                 170                 175
Ser Ser Ile Pro Tyr Phe Cys Leu Pro Thr Phe Gly Phe Lys His Ile
            180                 185                 190
Leu Pro Leu Thr Asn Asp Ala Glu Arg Phe Asn Glu Ile Val Lys Asn
            195                 200                 205
Gln Lys Ile Ser Ala Asn Ile Asp Thr Pro Glu Gly Gly Phe Asp Ala
        210                 215                 220
Ile Met Gln Ala Ala Val Cys Lys Glu Lys Ile Gly Trp Arg Asn Asp
225                 230                 235                 240
Ser Leu His Leu Leu Val Phe Val Ser Asp Ala Asp Ser His Phe Gly
                245                 250                 255
Met Asp Ser Lys Leu Ala Gly Ile Val Ile Pro Asn Asp Gly Leu Cys
            260                 265                 270
His Leu Asp Ser Lys Asn Glu Tyr Ser Met Ser Thr Val Leu Glu Tyr
            275                 280                 285
Pro Thr Ile Gly Gln Leu Ile Asp Lys Leu Val Gln Asn Asn Val Leu
        290                 295                 300
Leu Ile Phe Ala Val Thr Gln Glu Gln Val His Leu Tyr Glu Asn Tyr
305                 310                 315                 320
Ala Lys Leu Ile Pro Gly Ala Thr Val Gly Leu Leu Gln Lys Asp Ser
                325                 330                 335
Gly Asn Ile Leu Gln Leu Ile Ile Ser Ala Tyr Glu Glu Leu Arg Ser
            340                 345                 350
Glu Val Glu Leu Glu Val Leu Gly Asp Thr Glu Gly Leu Asn Leu Ser
            355                 360                 365
Phe Thr Ala Ile Cys Asn Asn Gly Thr Leu Phe Gln His Gln Lys Lys
        370                 375                 380
Cys Ser His Met Lys Val Gly Asp Thr Ala Ser Phe Ser Val Thr Val
385                 390                 395                 400
Asn Ile Pro His Cys Glu Arg Arg Ser Arg His Ile Ile Ile Lys Pro
                405                 410                 415
Val Gly Leu Gly Asp Ala Leu Glu Leu Leu Val Ser Pro Glu Cys Asn
            420                 425                 430
Cys Asp Cys Gln Lys Glu Val Glu Val Asn Ser Ser Lys Cys His His
            435                 440                 445
Gly Asn Gly Ser Phe Gln Cys Gly Val Cys Ala Cys His Pro Gly His
        450                 455                 460
Met Gly Pro Arg Cys Glu Cys Gly Glu Asp Met Leu Ser Thr Asp Ser
465                 470                 475                 480
Cys Lys Glu Ala Pro Asp His Pro Ser Cys Ser Gly Arg Gly Asp Cys
                485                 490                 495
Tyr Cys Gly Gln Cys Ile Cys His Leu Ser Pro Tyr Gly Asn Ile Tyr
```

-continued

```
                500                 505                 510
Gly Pro Tyr Cys Gln Cys Asp Asn Phe Ser Cys Val Arg His Lys Gly
            515                 520                 525

Leu Leu Cys Gly Gly Asn Gly Asp Cys Asp Cys Gly Glu Cys Val Cys
        530                 535                 540

Arg Ser Gly Trp Thr Gly Glu Tyr Cys Asn Cys Thr Thr Ser Thr Asp
545                 550                 555                 560

Ser Cys Val Ser Glu Asp Gly Val Leu Cys Ser Gly Arg Gly Asp Cys
            565                 570                 575

Val Cys Gly Lys Cys Val Cys Thr Asn Pro Gly Ala Ser Gly Pro Thr
            580                 585                 590

Cys Glu Arg Cys Pro Thr Cys Gly Asp Pro Cys Asn Ser Lys Arg Ser
            595                 600                 605

Cys Ile Glu Cys His Leu Ser Ala Ala Gly Gln Ala Arg Glu Glu Cys
            610                 615                 620

Val Asp Lys Cys Lys Leu Ala Gly Ala Thr Ile Ser Glu Glu Glu Asp
625                 630                 635                 640

Phe Ser Lys Asp Gly Ser Val Ser Cys Ser Leu Gln Gly Glu Asn Glu
            645                 650                 655

Cys Leu Ile Thr Phe Leu Ile Thr Thr Asp Asn Glu Gly Lys Thr Ile
            660                 665                 670

Ile His Ser Ile Asn Glu Lys Asp Cys Pro Lys Pro Pro Asn Ile Pro
            675                 680                 685

Met Ile Met Leu Gly Val Ser Leu Ala Ile Leu Leu Ile Gly Val Val
            690                 695                 700

Leu Leu Cys Ile Trp Lys Leu Leu Val Ser Phe His Asp Arg Lys Glu
705                 710                 715                 720

Val Ala Lys Phe Glu Ala Glu Arg Ser Lys Ala Lys Trp Gln Thr Gly
            725                 730                 735

Thr Asn Pro Leu Tyr Arg Gly Ser Thr Ser Thr Phe Lys Asn Val Thr
            740                 745                 750

Tyr Lys His Arg Glu Lys Gln Lys Val Asp Leu Ser Thr Asp Cys
            755                 760                 765

<210> SEQ ID NO 18
<211> LENGTH: 779
<212> TYPE: PRT
<213> ORGANISM: Homo sapiens
<220> FEATURE:
<221> NAME/KEY: MISC_FEATURE
<223> OTHER INFORMATION: Beta 7 integrin (GenBank Accession No.
      NP_000880.1)

<400> SEQUENCE: 18

Glu Leu Asp Ala Lys Ile Pro Ser Thr Gly Asp Ala Thr Glu Trp Arg
1               5                   10                  15

Asn Pro His Leu Ser Met Leu Gly Ser Cys Gln Pro Ala Pro Ser Cys
            20                  25                  30

Gln Lys Cys Ile Leu Ser His Pro Ser Cys Ala Trp Cys Lys Gln Leu
        35                  40                  45

Asn Phe Thr Ala Ser Gly Glu Ala Glu Ala Arg Arg Cys Ala Arg Arg
    50                  55                  60

Glu Glu Leu Leu Ala Arg Gly Cys Pro Leu Glu Glu Leu Glu Glu Pro
65                  70                  75                  80

Arg Gly Gln Gln Glu Val Leu Gln Asp Gln Pro Leu Ser Gln Gly Ala
            85                  90                  95
```

-continued

```
Arg Gly Glu Gly Ala Thr Gln Leu Ala Pro Gln Arg Val Arg Val Thr
            100                 105                 110

Leu Arg Pro Gly Glu Pro Gln Leu Gln Val Arg Phe Leu Arg Ala
        115                 120                 125

Glu Gly Tyr Pro Val Asp Leu Tyr Tyr Leu Met Asp Leu Ser Tyr Ser
        130                 135                 140

Met Lys Asp Asp Leu Glu Arg Val Arg Gln Leu Gly His Ala Leu Leu
145                 150                 155                 160

Val Arg Leu Gln Glu Val Thr His Ser Val Arg Ile Gly Phe Gly Ser
                165                 170                 175

Phe Val Asp Lys Thr Val Leu Pro Phe Val Ser Thr Val Pro Ser Lys
                180                 185                 190

Leu Arg His Pro Cys Pro Thr Arg Leu Glu Arg Cys Gln Ser Pro Phe
            195                 200                 205

Ser Phe His His Val Leu Ser Leu Thr Gly Asp Ala Gln Ala Phe Glu
        210                 215                 220

Arg Glu Val Gly Arg Gln Ser Val Ser Gly Asn Leu Asp Ser Pro Glu
225                 230                 235                 240

Gly Gly Phe Asp Ala Ile Leu Gln Ala Ala Leu Cys Gln Glu Gln Ile
                245                 250                 255

Gly Trp Arg Asn Val Ser Arg Leu Leu Val Phe Thr Ser Asp Asp Thr
            260                 265                 270

Phe His Thr Ala Gly Asp Gly Lys Leu Gly Gly Ile Phe Met Pro Ser
        275                 280                 285

Asp Gly His Cys His Leu Asp Ser Asn Gly Leu Tyr Ser Arg Ser Thr
        290                 295                 300

Glu Phe Asp Tyr Pro Ser Val Gly Gln Val Ala Gln Ala Leu Ser Ala
305                 310                 315                 320

Ala Asn Ile Gln Pro Ile Phe Ala Val Thr Ser Ala Ala Leu Pro Val
                325                 330                 335

Tyr Gln Glu Leu Ser Lys Leu Ile Pro Lys Ser Ala Val Gly Glu Leu
            340                 345                 350

Ser Glu Asp Ser Ser Asn Val Val Gln Leu Ile Met Asp Ala Tyr Asn
        355                 360                 365

Ser Leu Ser Ser Thr Val Thr Leu Glu His Ser Ser Leu Pro Pro Gly
        370                 375                 380

Val His Ile Ser Tyr Glu Ser Gln Cys Glu Gly Pro Glu Lys Arg Glu
385                 390                 395                 400

Gly Lys Ala Glu Asp Arg Gly Gln Cys Asn His Val Arg Ile Asn Gln
                405                 410                 415

Thr Val Thr Phe Trp Val Ser Leu Gln Ala Thr His Cys Leu Pro Glu
            420                 425                 430

Pro His Leu Leu Arg Leu Arg Ala Leu Gly Phe Ser Glu Glu Leu Ile
        435                 440                 445

Val Glu Leu His Thr Leu Cys Asp Cys Asn Cys Ser Asp Thr Gln Pro
        450                 455                 460

Gln Ala Pro His Cys Ser Asp Gly Gln Gly His Leu Gln Cys Gly Val
465                 470                 475                 480

Cys Ser Cys Ala Pro Gly Arg Leu Gly Arg Leu Cys Glu Cys Ser Val
                485                 490                 495

Ala Glu Leu Ser Ser Pro Asp Leu Glu Ser Gly Cys Arg Ala Pro Asn
            500                 505                 510

Gly Thr Gly Pro Leu Cys Ser Gly Lys Gly His Cys Gln Cys Gly Arg
        515                 520                 525
```

```
Cys Ser Cys Ser Gly Gln Ser Ser Gly His Leu Cys Glu Cys Asp Asp
        530                 535                 540
Ala Ser Cys Glu Arg His Glu Gly Ile Leu Cys Gly Gly Phe Gly Arg
545                 550                 555                 560
Cys Gln Cys Gly Val Cys His Cys His Ala Asn Arg Thr Gly Arg Ala
                565                 570                 575
Cys Glu Cys Ser Gly Asp Met Asp Ser Cys Ile Ser Pro Glu Gly Gly
                580                 585                 590
Leu Cys Ser Gly His Gly Arg Cys Lys Cys Asn Arg Cys Gln Cys Leu
            595                 600                 605
Asp Gly Tyr Tyr Gly Ala Leu Cys Asp Gln Cys Pro Gly Cys Lys Thr
        610                 615                 620
Pro Cys Glu Arg His Arg Asp Cys Ala Glu Cys Gly Ala Phe Arg Thr
625                 630                 635                 640
Gly Pro Leu Ala Thr Asn Cys Ser Thr Ala Cys Ala His Thr Asn Val
                645                 650                 655
Thr Leu Ala Leu Ala Pro Ile Leu Asp Asp Gly Trp Cys Lys Glu Arg
            660                 665                 670
Thr Leu Asp Asn Gln Leu Phe Phe Phe Leu Val Glu Asp Asp Ala Arg
        675                 680                 685
Gly Thr Val Val Leu Arg Val Arg Pro Gln Glu Lys Gly Ala Asp His
690                 695                 700
Thr Gln Ala Ile Val Leu Gly Cys Val Gly Gly Ile Val Ala Val Gly
705                 710                 715                 720
Leu Gly Leu Val Leu Ala Tyr Arg Leu Ser Val Glu Ile Tyr Asp Arg
                725                 730                 735
Arg Glu Tyr Ser Arg Phe Glu Lys Glu Gln Gln Gln Leu Asn Trp Lys
            740                 745                 750
Gln Asp Ser Asn Pro Leu Tyr Lys Ser Ala Ile Thr Thr Thr Ile Asn
        755                 760                 765
Pro Arg Phe Gln Glu Ala Asp Ser Pro Thr Leu
    770                 775

<210> SEQ ID NO 19
<211> LENGTH: 5
<212> TYPE: PRT
<213> ORGANISM: Artificial sequence
<220> FEATURE:
<223> OTHER INFORMATION: Synthetic peptide

<400> SEQUENCE: 19

Lys Phe Glu Glu Glu
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Lys Phe Glu Glu Glu Arg Ala
1               5

<210> SEQ ID NO 21
<211> LENGTH: 5
<212> TYPE: PRT
<213> ORGANISM: Artificial sequence
```

```
<220> FEATURE:
<223> OTHER INFORMATION: Synthetic peptide

<400> SEQUENCE: 21

Glu Glu Glu Arg Ala
1               5

<210> SEQ ID NO 22
<211> LENGTH: 13
<212> TYPE: PRT
<213> ORGANISM: Artificial sequence
<220> FEATURE:
<223> OTHER INFORMATION: Synthetic peptide

<400> SEQUENCE: 22

Lys Phe Glu Glu Glu Arg Ala Arg Ala Lys Trp Asp Thr
1               5                   10

<210> SEQ ID NO 23
<211> LENGTH: 5
<212> TYPE: PRT
<213> ORGANISM: Artificial sequence
<220> FEATURE:
<223> OTHER INFORMATION: Synthetic peptide

<400> SEQUENCE: 23

Lys Phe Glu Lys Glu
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic peptide

<400> SEQUENCE: 24

Arg Phe Glu Lys Glu
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic peptide

<400> SEQUENCE: 25

Lys Phe Glu Lys Glu Lys Met
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic peptide

<400> SEQUENCE: 26

Lys Phe Glu Lys Glu Lys Leu
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 27

Lys Phe Glu Lys Glu Gln Gln
1               5

<210> SEQ ID NO 28
<211> LENGTH: 7
<212> TYPE: PRT
<213> ORGANISM: Artificial sequence
<220> FEATURE:
<223> OTHER INFORMATION: Synthetic peptide

<400> SEQUENCE: 28

Arg Phe Glu Lys Glu Lys Met
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic peptide

<400> SEQUENCE: 29

Arg Lys Phe Glu Lys Glu Lys Leu
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic peptide

<400> SEQUENCE: 30

Arg Phe Glu Lys Glu Gln Gln
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic peptide

<400> SEQUENCE: 31

Glu Lys Glu Lys Met
1               5

<210> SEQ ID NO 32
<211> LENGTH: 5
<212> TYPE: PRT
<213> ORGANISM: Artificial sequence
<220> FEATURE:
<223> OTHER INFORMATION: Synthetic peptide

<400> SEQUENCE: 32

Glu Lys Glu Lys Leu
1               5

<210> SEQ ID NO 33
<211> LENGTH: 5
<212> TYPE: PRT
<213> ORGANISM: Artificial sequence
<220> FEATURE:
<223> OTHER INFORMATION: Synthetic peptide

<400> SEQUENCE: 33
```

```
Glu Lys Glu Gln Gln
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic peptide

<400> SEQUENCE: 34

Lys Phe Glu Ala Glu
1               5

<210> SEQ ID NO 35
<211> LENGTH: 7
<212> TYPE: PRT
<213> ORGANISM: Artificial sequence
<220> FEATURE:
<223> OTHER INFORMATION: Synthetic peptide

<400> SEQUENCE: 35

Lys Phe Glu Ala Glu Arg Ser
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic peptide

<400> SEQUENCE: 36

Glu Ala Glu Arg Ser
1               5

<210> SEQ ID NO 37
<211> LENGTH: 5
<212> TYPE: PRT
<213> ORGANISM: Artificial sequence
<220> FEATURE:
<223> OTHER INFORMATION: Synthetic peptide

<400> SEQUENCE: 37

Lys Phe Gln Ser Glu
1               5

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Lys Phe Gln Ser Glu Arg Ser
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic peptide

<400> SEQUENCE: 39

Gln Ser Glu Arg Ser
```

```
<210> SEQ ID NO 40
<211> LENGTH: 13
<212> TYPE: PRT
<213> ORGANISM: Artificial sequence
<220> FEATURE:
<223> OTHER INFORMATION: Synthetic peptide

<400> SEQUENCE: 40

Leu Leu Ala Arg Arg Pro Thr Lys Gly Ile His Glu Tyr
1               5                   10

<210> SEQ ID NO 41
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 41

Xaa Xaa Glu
1

<210> SEQ ID NO 42
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(4)
<223> OTHER INFORMATION: Xaa can be any naturally occurring amino acid

<400> SEQUENCE: 42

Xaa Xaa Xaa Xaa Glu
1               5

<210> SEQ ID NO 43
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 43

Xaa Xaa Glu Xaa Xaa
1               5

<210> SEQ ID NO 44
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(7)
```

```
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid

<400> SEQUENCE: 44

Xaa Xaa Xaa Xaa Xaa Xaa Xaa Lys Xaa Xaa Xaa Xaa
1               5                   10

<210> SEQ ID NO 45
<211> LENGTH: 13
<212> TYPE: PRT
<213> ORGANISM: Artificial sequence
<220> FEATURE:
<223> OTHER INFORMATION: Synthetic peptide

<400> SEQUENCE: 45

Leu Leu Ala Arg Arg Pro Thr Lys Gly Ile His Glu Tyr
1               5                   10

<210> SEQ ID NO 46
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 46

Leu Leu Ala Arg Arg Pro Thr Lys Gly Ile His Glu Tyr
1               5                   10

<210> SEQ ID NO 47
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 47

Leu Ile Arg Tyr Ala Leu His Arg Pro Thr Lys Glu Gly
1               5                   10

<210> SEQ ID NO 48
<211> LENGTH: 34
<212> TYPE: DNA
<213> ORGANISM: Artificial sequence
<220> FEATURE:
<223> OTHER INFORMATION: Synthetic primer

<400> SEQUENCE: 48
cgtggatcca aactcctcat caccatccac gacc                              34

<210> SEQ ID NO 49
<211> LENGTH: 34
<212> TYPE: DNA
<213> ORGANISM: Artificial sequence
<220> FEATURE:
<223> OTHER INFORMATION: Synthetic primer

<400> SEQUENCE: 49
```

-continued

```
gcgctcgagt taagtgcccc ggtacgtgat attg                          34
```

<210> SEQ ID NO 50
<211> LENGTH: 32
<212> TYPE: DNA
<213> ORGANISM: Artificial sequence
<220> FEATURE:
<223> OTHER INFORMATION: Synthetic primer

<400> SEQUENCE: 50

```
gcgaattcaa gcttttaatg ataattcatg ac                            32
```

<210> SEQ ID NO 51
<211> LENGTH: 33
<212> TYPE: DNA
<213> ORGANISM: Artificial sequence
<220> FEATURE:
<223> OTHER INFORMATION: Synthetic primer

<400> SEQUENCE: 51

```
gcgctcgagt cattttccct catacttcgg att                           33
```

<210> SEQ ID NO 52
<211> LENGTH: 65
<212> TYPE: DNA
<213> ORGANISM: Artificial sequence
<220> FEATURE:
<223> OTHER INFORMATION: Synthetic primer

<400> SEQUENCE: 52

```
gcgggtaccg ccatggacta caaggacgac gatgacaagg cggacttcct gccgtcgcgg    60
tccgt                                                              65
```

<210> SEQ ID NO 53
<211> LENGTH: 40
<212> TYPE: DNA
<213> ORGANISM: Artificial sequence
<220> FEATURE:
<223> OTHER INFORMATION: Synthetic primer

<400> SEQUENCE: 53

```
ggccggcggc cgctcactgt agcataagct gcttgaggtt                    40
```

<210> SEQ ID NO 54
<211> LENGTH: 65
<212> TYPE: PRT
<213> ORGANISM: Artificial sequence
<220> FEATURE:
<223> OTHER INFORMATION: Synthetic primer

<400> SEQUENCE: 54

Gly Gly Cys Cys Gly Gly Cys Gly Gly Cys Cys Gly Cys Thr Cys Ala
1               5                   10                  15
Ala Ala Thr Ala Thr Cys Thr Thr Gly Thr Thr Gly Thr Gly Ala Thr
                20                  25                  30
Gly Gly Ala Ala Thr Ala Thr Ala Ala Thr Cys Thr Gly Gly Thr Thr
            35                  40                  45
Cys Thr Cys Cys Ala Ala Gly Thr Thr Ala Thr Cys Cys Ala Ala
        50                  55                  60
Gly
65

<210> SEQ ID NO 55
<211> LENGTH: 40
```

```
<212> TYPE: DNA
<213> ORGANISM: Artificial sequence
<220> FEATURE:
<223> OTHER INFORMATION: Synthetic primer

<400> SEQUENCE: 55
ggccggcggc cgctcattca aagtcgtatt catggatgcc                        40

<210> SEQ ID NO 56
<211> LENGTH: 19
<212> TYPE: DNA
<213> ORGANISM: Artificial sequence
<220> FEATURE:
<223> OTHER INFORMATION: Synthetic primer

<400> SEQUENCE: 56
gtccaccttc ctgaagcag                                               19

<210> SEQ ID NO 57
<211> LENGTH: 19
<212> TYPE: DNA
<213> ORGANISM: Artificial sequence
<220> FEATURE:
<223> OTHER INFORMATION: Synthetic primer

<400> SEQUENCE: 57
ggagatcgac aaatgcctg                                               19

<210> SEQ ID NO 58
<211> LENGTH: 19
<212> TYPE: DNA
<213> ORGANISM: Artificial sequence
<220> FEATURE:
<223> OTHER INFORMATION: Synthetic primer

<400> SEQUENCE: 58
gaggagccga cgcttaata                                               19

<210> SEQ ID NO 59
<211> LENGTH: 19
<212> TYPE: DNA
<213> ORGANISM: Artificial sequence
<220> FEATURE:
<223> OTHER INFORMATION: Synthetic primer

<400> SEQUENCE: 59 gtccacctttt ttaaagcag                                              19

<210> SEQ ID NO 60
<211> LENGTH: 19
<212> TYPE: DNA
<213> ORGANISM: Artificial sequence
<220> FEATURE:
<223> OTHER INFORMATION: Synthetic primer

<400> SEQUENCE: 60
ggagatcgat aagtgcctg                                               19

<210> SEQ ID NO 61
<211> LENGTH: 64
<212> TYPE: DNA
<213> ORGANISM: Artificial sequence
<220> FEATURE:
<223> OTHER INFORMATION: Synthetic primer

<400> SEQUENCE: 61
cggaattcgc catggactac aaggacgacg atgacaaggc ggacttcctg ccgtcgcggt   60
``` ccgt                                                                64

<210> SEQ ID NO 62
<211> LENGTH: 36
<212> TYPE: DNA
<213> ORGANISM: Artificial sequence
<220> FEATURE:
<223> OTHER INFORMATION: Synthetic primer

<400> SEQUENCE: 62
gccgtcgact cactgtagca taagctgctt gaggtt                              36

<210> SEQ ID NO 63
<211> LENGTH: 34
<212> TYPE: PRT
<213> ORGANISM: Artificial sequence
<220> FEATURE:
<223> OTHER INFORMATION: Synthetic primer

<400> SEQUENCE: 63

Gly Thr Cys Cys Ala Ala Gly Gly Ala Gly Ala Thr Cys Gly Ala Thr
1               5                   10                  15

Ala Ala Gly Thr Gly Cys Cys Thr Gly Thr Cys Thr Cys Gly Gly Gly
            20                  25                  30

Ala Ala

<210> SEQ ID NO 64
<211> LENGTH: 34
<212> TYPE: DNA
<213> ORGANISM: Artificial sequence
<220> FEATURE:
<223> OTHER INFORMATION: Synthetic primer

<400> SEQUENCE: 64
ttcccgagac aggcacttat cgatctcctt ggac                                34

<210> SEQ ID NO 65
<211> LENGTH: 34
<212> TYPE: DNA
<213> ORGANISM: Artificial sequence
<220> FEATURE:
<223> OTHER INFORMATION: Synthetic primer

<400> SEQUENCE: 65
cggcaagtcc acctttttaa agcagatgcg gatc                                34

<210> SEQ ID NO 66
<211> LENGTH: 34
<212> TYPE: DNA
<213> ORGANISM: Artificial sequence
<220> FEATURE:
<223> OTHER INFORMATION: Synthetic primer

<400> SEQUENCE: 66
gatccgcatc tgctttaaaa aggtggactt gccg                                34

<210> SEQ ID NO 67
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 67

Lys Phe Glu Glu Glu Arg Ala Arg Ala Lys Trp Asp Thr
1               5                   10

<210> SEQ ID NO 68
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 68

Lys Phe Glu Glu Glu Arg Ala
1               5

<210> SEQ ID NO 69
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 69

Glu Glu Ala Arg Glu Arg Lys Asp Trp Ala Lys Phe Thr
1               5                   10

<210> SEQ ID NO 70
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 70

Glu Ala Arg Glu Lys Phe Glu
1               5

<210> SEQ ID NO 71
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: amino acid at position 1 is myristoylated

<400> SEQUENCE: 71

Glu Glu Ala Arg Glu
1               5

<210> SEQ ID NO 72
<211> LENGTH: 49
<212> TYPE: DNA
<213> ORGANISM: Artificial sequence
<220> FEATURE:

```
<223> OTHER INFORMATION: Synthetic peptide

<400> SEQUENCE: 72
gcgaagcttg ccgccatgga ccgagcgcgg ccgcggcccc ggccgctct         49

<210> SEQ ID NO 73
<211> LENGTH: 45
<212> TYPE: DNA
<213> ORGANISM: Artificial sequence
<220> FEATURE:
<223> OTHER INFORMATION: Synthetic peptide

<400> SEQUENCE: 73
gcgctcgagt caagcgaatt cttttcggtc gtggatggtg atgag             45

<210> SEQ ID NO 74
<211> LENGTH: 45
<212> TYPE: DNA
<213> ORGANISM: Artificial sequence
<220> FEATURE:
<223> OTHER INFORMATION: Synthetic peptide

<400> SEQUENCE: 74
gcgctcgagt caccagatga gcagggcggc aaggccaatg agcag             45

<210> SEQ ID NO 75
<211> LENGTH: 39
<212> TYPE: DNA
<213> ORGANISM: Artificial sequence
<220> FEATURE:
<223> OTHER INFORMATION: Synthetic primer

<400> SEQUENCE: 75
aagaattcgc taaatttgca gaagaacgcg ccagagcaa                    39

<210> SEQ ID NO 76
<211> LENGTH: 39
<212> TYPE: DNA
<213> ORGANISM: Artificial sequence
<220> FEATURE:
<223> OTHER INFORMATION: Synthetic peptide

<400> SEQUENCE: 76
aagaattcgc taaatttgag gcagaacgcg ccagagcaa                    39

<210> SEQ ID NO 77
<211> LENGTH: 39
<212> TYPE: DNA
<213> ORGANISM: Artificial sequence
<220> FEATURE:
<223> OTHER INFORMATION: Synthetic peptide

<400> SEQUENCE: 77
aagaattcgc taaatttgag gaagcacgcg ccagagcaa                    39

<210> SEQ ID NO 78
<211> LENGTH: 39
<212> TYPE: DNA
<213> ORGANISM: Artificial sequence
<220> FEATURE:
<223> OTHER INFORMATION: Synthetic peptide

<400> SEQUENCE: 78
aagaattcgc taaatttgca gcagcacgcg ccagagcaa                    39

<210> SEQ ID NO 79
```

```
<211> LENGTH: 49
<212> TYPE: DNA
<213> ORGANISM: Artificial sequence
<220> FEATURE:
<223> OTHER INFORMATION: Synthetic peptide

<400> SEQUENCE: 79
ccgcaattgg ccgccatgga ccgagcgcgg ccgcggcccc ggccgctct            49

<210> SEQ ID NO 80
<211> LENGTH: 34
<212> TYPE: DNA
<213> ORGANISM: Artificial sequence
<220> FEATURE:
<223> OTHER INFORMATION: Synthetic primer

<400> SEQUENCE: 80
gcgctcgagt taagtgcccc ggtacgtgat attg                            34

<210> SEQ ID NO 81
<211> LENGTH: 33
<212> TYPE: DNA
<213> ORGANISM: Artificial sequence
<220> FEATURE:
<223> OTHER INFORMATION: Synthetic peptide

<400> SEQUENCE: 81
cgtggatcca ttagacaggt gatactacaa tgg                             33

<210> SEQ ID NO 82
<211> LENGTH: 33
<212> TYPE: DNA
<213> ORGANISM: Artificial sequence
<220> FEATURE:
<223> OTHER INFORMATION: Synthetic peptide

<400> SEQUENCE: 82
gcgctcgagt tagaagttgc acctgaaagt ttc                             33

<210> SEQ ID NO 83
<211> LENGTH: 20
<212> TYPE: PRT
<213> ORGANISM: Artificial sequence
<220> FEATURE:
<223> OTHER INFORMATION: Synthetic peptide

<400> SEQUENCE: 83

His Asp Arg Lys Glu Phe Ala Lys Phe Glu Glu Glu Arg Ala Arg Ala
1               5                   10                  15

Lys Trp Asp Thr
            20

<210> SEQ ID NO 84
<211> LENGTH: 5
<212> TYPE: PRT
<213> ORGANISM: Artificial Sequence
<220> FEATURE:
<223> OTHER INFORMATION: Synthetic peptide

<400> SEQUENCE: 84

Phe Glu Glu Glu Arg
1               5

<210> SEQ ID NO 85
<211> LENGTH: 6
<212> TYPE: PRT
<213> ORGANISM: Artificial Sequence
```

```
<220> FEATURE:
<223> OTHER INFORMATION: Synthetic peptide

<400> SEQUENCE: 85

Ala Lys Phe Glu Glu Glu
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide

<400> SEQUENCE: 86

Lys Phe Glu Glu Glu Arg
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic peptide

<400> SEQUENCE: 87

Phe Glu Glu Glu Arg Ala
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide

<400> SEQUENCE: 88

Glu Glu Glu Arg Ala Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide

<400> SEQUENCE: 89

Glu Glu Glu Arg Ala Arg Ala
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic peptide

<400> SEQUENCE: 90

Glu Glu Glu Arg Ala Arg Ala Lys
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic peptide
```

<400> SEQUENCE: 91

Glu Arg Ala Phe Glu Glu
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic peptide

<400> SEQUENCE: 92

Arg Gly Asp Ser
1

<210> SEQ ID NO 93
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 93

Glu Xaa Glu
1

<210> SEQ ID NO 94
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any amino acid

<400> SEQUENCE: 94

Phe Glu Xaa Glu
1

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Lys Arg or Gln

<400> SEQUENCE: 95

Phe Glu Xaa Glu Xaa
1               5

<210> SEQ ID NO 96
<211> LENGTH: 4
<212> TYPE: PRT
<213> ORGANISM: Artificial Sequence
<220> FEATURE:

<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Lys, Arg or Gln

<400> SEQUENCE: 96

Glu Xaa Glu Xaa
1

<210> SEQ ID NO 97
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid

<400> SEQUENCE: 97

Xaa Phe Glu Xaa Glu
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

<400> SEQUENCE: 98

Xaa Phe Glu Xaa Glu Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

```
<220> FEATURE:
<221> NAME/KEY: MISC_FEATURE
<222> LOCATION: (7)..(7)
<223> OTHER INFORMATION: Xaa is any amino acid - optionally Met, Ala,
      Leu, Ser or Gln

<400> SEQUENCE: 99

Xaa Phe Glu Xaa Glu Xaa Xaa
1               5

<210> SEQ ID NO 100
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 100

Lys Phe Glu Xaa Glu
1               5

<210> SEQ ID NO 101
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 101

Lys Phe Glu Xaa Glu Arg Ala
1               5

<210> SEQ ID NO 102
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 102

Glu Xaa Glu Arg Ala
1               5

<210> SEQ ID NO 103
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 103

Lys Phe Glu Xaa Glu Arg Ala Arg Ala Lys Trp Asp Thr
1               5                   10
```

```
<210> SEQ ID NO 104
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amimo acid

<400> SEQUENCE: 104

Arg Phe Glu Xaa Glu
1               5

<210> SEQ ID NO 105
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 105

Lys Phe Glu Xaa Glu Lys Met
1               5

<210> SEQ ID NO 106
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 106

Lys Phe Glu Xaa Glu Lys Leu
1               5

<210> SEQ ID NO 107
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 107

Lys Phe Glu Xaa Glu Gln Gln
1               5

<210> SEQ ID NO 108
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 108
```

Arg Phe Glu Xaa Glu Lys Met
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid

<400> SEQUENCE: 109

Arg Lys Phe Glu Xaa Glu Lys Leu
1               5

<210> SEQ ID NO 110
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 110

Arg Phe Glu Xaa Glu Gln Gln
1               5

<210> SEQ ID NO 111
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 111

Glu Xaa Glu Lys Met
1               5

<210> SEQ ID NO 112
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 112

Glu Xaa Glu Lys Leu
1               5

<210> SEQ ID NO 113
<211> LENGTH: 5
<212> TYPE: PRT
<213> ORGANISM: Artificial sequence
<220> FEATURE:
<223> OTHER INFORMATION: Synthetic peptide
<220> FEATURE:

```
<221> NAME/KEY: MISC_FEATURE
<222> LOCATION: (2)..(2)
<223> OTHER INFORMATION: Xaa is any amino acid

<400> SEQUENCE: 113

Glu Xaa Glu Gln Gln
1               5

<210> SEQ ID NO 114
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 114

Lys Phe Glu Xaa Glu Arg Ser
1               5

<210> SEQ ID NO 115
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 115

Glu Xaa Glu Arg Ser
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any amino acid

<400> SEQUENCE: 116

Phe Glu Xaa Glu Arg
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid

<400> SEQUENCE: 117

Ala Lys Phe Glu Xaa Glu
1               5

<210> SEQ ID NO 118
<211> LENGTH: 6
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 118

Lys Phe Glu Xaa Glu Arg
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any amino acid

<400> SEQUENCE: 119

Phe Glu Xaa Glu Arg Ala
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 120

Glu Xaa Glu Arg Ala Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 121

Glu Xaa Glu Arg Ala Arg Ala
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 122

Glu Xaa Glu Arg Ala Arg Ala Lys
```

```
1               5

<210> SEQ ID NO 123
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 123

Lys Phe Glu Glu Glu
1               5

<210> SEQ ID NO 124
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 124

Lys Phe Glu Glu Glu Arg Ala
1               5

<210> SEQ ID NO 125
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 125

Glu Glu Glu Arg Ala
1               5

<210> SEQ ID NO 126
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 126

Lys Phe Glu Glu Glu Arg Ala Arg Ala Lys Trp Asp Thr
1               5                   10

<210> SEQ ID NO 127
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: Covalently bound to a fatty acid

<400> SEQUENCE: 127

Lys Phe Glu Lys Glu
1               5

<210> SEQ ID NO 128
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 128

Arg Phe Glu Lys Glu
1               5

<210> SEQ ID NO 129
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 129

Lys Phe Glu Lys Glu Lys Met
1               5

<210> SEQ ID NO 130
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 130

Lys Phe Glu Lys Glu Lys Leu
1               5

<210> SEQ ID NO 131
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 131

Lys Phe Glu Lys Glu Gln Gln
1               5

<210> SEQ ID NO 132
<211> LENGTH: 7
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 132

Arg Phe Glu Lys Glu Lys Met
1               5

<210> SEQ ID NO 133
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 133

Arg Lys Phe Glu Lys Glu Lys Leu
1               5

<210> SEQ ID NO 134
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 134

Arg Phe Glu Lys Glu Gln Gln
1               5

<210> SEQ ID NO 135
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 135

Glu Lys Glu Lys Met
1               5

<210> SEQ ID NO 136
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 136

Glu Lys Glu Lys Leu
1               5
```

```
<210> SEQ ID NO 137
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 137

Glu Lys Glu Gln Gln
1               5

<210> SEQ ID NO 138
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 138

Lys Phe Glu Ala Glu
1               5

<210> SEQ ID NO 139
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 139

Lys Phe Glu Ala Glu Arg Ser
1               5

<210> SEQ ID NO 140
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 140

Glu Ala Glu Arg Ser
1               5

<210> SEQ ID NO 141
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
```

-continued

```
<400> SEQUENCE: 141

Lys Phe Gln Ser Glu
1               5

<210> SEQ ID NO 142
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 142

Lys Phe Gln Ser Glu Arg Ser
1               5

<210> SEQ ID NO 143
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 143

Gln Ser Glu Arg Ser
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 144

Phe Glu Glu Glu Arg
1               5

<210> SEQ ID NO 145
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 145

Ala Lys Phe Glu Glu Glu
1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic peptide
```

```
-continued

<220> FEATURE:
<221> NAME/KEY: MISC_FEATURE
<222> LOCATION: (1)..(1)
<223> OTHER INFORMATION: Covalently bound to a fatty acid

<400> SEQUENCE: 146

Lys Phe Glu Glu Glu Arg
1               5

<210> SEQ ID NO 147
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 147

Phe Glu Glu Glu Arg Ala
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 148

Glu Glu Glu Arg Ala Arg
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 149

Glu Glu Glu Arg Ala Arg Ala
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid

<400> SEQUENCE: 150

Glu Glu Glu Arg Ala Arg Ala Lys
1               5

<210> SEQ ID NO 151
```

```
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 151

Glu Xaa Glu
1

<210> SEQ ID NO 152
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 152

Phe Glu Xaa Glu
1

<210> SEQ ID NO 153
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Lys Arg or Gln

<400> SEQUENCE: 153

Phe Glu Xaa Glu Xaa
1               5

<210> SEQ ID NO 154
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid
```

```
<220> FEATURE:
<221> NAME/KEY: MISC_FEATURE
<222> LOCATION: (4)..(4)
<223> OTHER INFORMATION: Xaa is Lys, Arg or Gln

<400> SEQUENCE: 154

Glu Xaa Glu Xaa
1

<210> SEQ ID NO 155
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid

<400> SEQUENCE: 155

Xaa Phe Glu Xaa Glu
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

<400> SEQUENCE: 156

Xaa Phe Glu Xaa Glu Xaa
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
```

```
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln
<220> FEATURE:
<221> NAME/KEY: MISC_FEATURE
<222> LOCATION: (7)..(7)
<223> OTHER INFORMATION: Xaa is any amino acid - optionally Met, Ala,
      Leu, Ser or Gln

<400> SEQUENCE: 157

Xaa Phe Glu Xaa Glu Xaa Xaa
1               5

<210> SEQ ID NO 158
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 158

Lys Phe Glu Xaa Glu
1               5

<210> SEQ ID NO 159
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 159

Lys Phe Glu Xaa Glu Arg Ala
1               5

<210> SEQ ID NO 160
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 160

Glu Xaa Glu Arg Ala
1               5
```

<210> SEQ ID NO 161
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 161

Lys Phe Glu Xaa Glu Arg Ala Arg Ala Lys Trp Asp Thr
1               5                   10

<210> SEQ ID NO 162
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 162

Arg Phe Glu Xaa Glu
1               5

<210> SEQ ID NO 163
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 163

Lys Phe Glu Xaa Glu Lys Met
1               5

<210> SEQ ID NO 164
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

```
<400> SEQUENCE: 164

Lys Phe Glu Xaa Glu Lys Leu
1               5

<210> SEQ ID NO 165
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 165

Lys Phe Glu Xaa Glu Gln Gln
1               5

<210> SEQ ID NO 166
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 166

Arg Phe Glu Xaa Glu Lys Met
1               5

<210> SEQ ID NO 167
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 167

Arg Lys Phe Glu Xaa Glu Lys Leu
1               5

<210> SEQ ID NO 168
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
```

```
<221> NAME/KEY: MISC_FEATURE
<222> LOCATION: (4)..(4)
<223> OTHER INFORMATION: Xaa is any amino acid

<400> SEQUENCE: 168

Arg Phe Glu Xaa Glu Gln Gln
1               5

<210> SEQ ID NO 169
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 169

Glu Xaa Glu Lys Met
1               5

<210> SEQ ID NO 170
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 170

Glu Xaa Glu Lys Leu
1               5

<210> SEQ ID NO 171
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 171

Glu Xaa Glu Gln Gln
1               5

<210> SEQ ID NO 172
<211> LENGTH: 7
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 172

Lys Phe Glu Xaa Glu Arg Ser
1               5

<210> SEQ ID NO 173
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 173

Glu Xaa Glu Arg Ser
1               5

<210> SEQ ID NO 174
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 174

Phe Glu Xaa Glu Arg
1               5

<210> SEQ ID NO 175
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 175

Ala Lys Phe Glu Xaa Glu
1               5

<210> SEQ ID NO 176
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 176

Lys Phe Glu Xaa Glu Arg
1               5

<210> SEQ ID NO 177
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 177

Phe Glu Xaa Glu Arg Ala
1               5

<210> SEQ ID NO 178
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 178

Glu Xaa Glu Arg Ala Arg
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 179

Glu Xaa Glu Arg Ala Arg Ala
1               5
```

```
<210> SEQ ID NO 180
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 180

Glu Xaa Glu Arg Ala Arg Ala Lys
1               5

<210> SEQ ID NO 181
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 181

Lys Phe Glu Glu Glu
1               5

<210> SEQ ID NO 182
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 182

Lys Phe Glu Glu Glu Arg Ala
1               5

<210> SEQ ID NO 183
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 183

Glu Glu Glu Arg Ala
1               5

<210> SEQ ID NO 184
<211> LENGTH: 13
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Covalently bound to a C4-C30 fatty acid

<400> SEQUENCE: 184

Lys Phe Glu Glu Glu Arg Ala Arg Ala Lys Trp Asp Thr
1               5                   10

<210> SEQ ID NO 185
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 185

Lys Phe Glu Lys Glu
1               5

<210> SEQ ID NO 186
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 186

Arg Phe Glu Lys Glu
1               5

<210> SEQ ID NO 187
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 187

Lys Phe Glu Lys Glu Lys Met
1               5

<210> SEQ ID NO 188
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 188

Lys Phe Glu Lys Glu Lys Leu
1               5

<210> SEQ ID NO 189
<211> LENGTH: 7
```

```
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 189

Lys Phe Glu Lys Glu Gln Gln
1               5

<210> SEQ ID NO 190
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 190

Arg Phe Glu Lys Glu Lys Met
1               5

<210> SEQ ID NO 191
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 191

Arg Lys Phe Glu Lys Glu Lys Leu
1               5

<210> SEQ ID NO 192
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 192

Arg Phe Glu Lys Glu Gln Gln
1               5

<210> SEQ ID NO 193
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 193

Glu Lys Glu Lys Met
```

-continued

<210> SEQ ID NO 194
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 194

Glu Lys Glu Lys Leu
1               5

<210> SEQ ID NO 195
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 195

Glu Lys Glu Gln Gln
1               5

<210> SEQ ID NO 196
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 196

Lys Phe Glu Ala Glu
1               5

<210> SEQ ID NO 197
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 197

Lys Phe Glu Ala Glu Arg Ser
1               5

<210> SEQ ID NO 198
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)

```
<223> OTHER INFORMATION: Covalently bound to a C4-C30 fatty acid

<400> SEQUENCE: 198

Glu Ala Glu Arg Ser
1               5

<210> SEQ ID NO 199
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 199

Lys Phe Gln Ser Glu
1               5

<210> SEQ ID NO 200
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 200

Lys Phe Gln Ser Glu Arg Ser
1               5

<210> SEQ ID NO 201
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 201

Gln Ser Glu Arg Ser
1               5

<210> SEQ ID NO 202
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 202

Phe Glu Glu Glu Arg
1               5

<210> SEQ ID NO 203
<211> LENGTH: 6
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 203

Ala Lys Phe Glu Glu Glu
1               5

<210> SEQ ID NO 204
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 204

Lys Phe Glu Glu Glu Arg
1               5

<210> SEQ ID NO 205
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 205

Phe Glu Glu Glu Arg Ala
1               5

<210> SEQ ID NO 206
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 206

Glu Glu Glu Arg Ala Arg
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 207

Glu Glu Glu Arg Ala Arg Ala
1               5
```

```
<210> SEQ ID NO 208
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid

<400> SEQUENCE: 208

Glu Glu Glu Arg Ala Arg Ala Lys
1               5

<210> SEQ ID NO 209
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 209

Glu Xaa Glu
1

<210> SEQ ID NO 210
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 210

Phe Glu Xaa Glu
1

<210> SEQ ID NO 211
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Lys Arg or Gln

<400> SEQUENCE: 211
```

```
Phe Glu Xaa Glu Xaa
1               5

<210> SEQ ID NO 212
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Lys, Arg or Gln

<400> SEQUENCE: 212

Glu Xaa Glu Xaa
1

<210> SEQ ID NO 213
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid

<400> SEQUENCE: 213

Xaa Phe Glu Xaa Glu
1               5

<210> SEQ ID NO 214
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

<400> SEQUENCE: 214
```

```
Xaa Phe Glu Xaa Glu Xaa
1               5

<210> SEQ ID NO 215
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln
<220> FEATURE:
<221> NAME/KEY: MISC_FEATURE
<222> LOCATION: (7)..(7)
<223> OTHER INFORMATION: Xaa is any amino acid - optionally Met, Ala,
      Leu, Ser or Gln

<400> SEQUENCE: 215

Xaa Phe Glu Xaa Glu Xaa Xaa
1               5

<210> SEQ ID NO 216
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 216

Lys Phe Glu Xaa Glu
1               5

<210> SEQ ID NO 217
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 217

Lys Phe Glu Xaa Glu Arg Ala
1               5
```

```
<210> SEQ ID NO 218
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 218

Glu Xaa Glu Arg Ala
1               5

<210> SEQ ID NO 219
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 219

Lys Phe Glu Xaa Glu Arg Ala Arg Ala Lys Trp Asp Thr
1               5                   10

<210> SEQ ID NO 220
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 220

Arg Phe Glu Xaa Glu
1               5

<210> SEQ ID NO 221
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 221
```

```
Lys Phe Glu Xaa Glu Lys Met
1               5

<210> SEQ ID NO 222
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 222

Lys Phe Glu Xaa Glu Lys Leu
1               5

<210> SEQ ID NO 223
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 223

Lys Phe Glu Xaa Glu Gln Gln
1               5

<210> SEQ ID NO 224
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 224

Arg Phe Glu Xaa Glu Lys Met
1               5

<210> SEQ ID NO 225
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (5)..(5)
```

<223> OTHER INFORMATION: Xaa is any amino acid

<400> SEQUENCE: 225

Arg Lys Phe Glu Xaa Glu Lys Leu
1               5

<210> SEQ ID NO 226
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 226

Arg Phe Glu Xaa Glu Gln Gln
1               5

<210> SEQ ID NO 227
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 227

Glu Xaa Glu Lys Met
1               5

<210> SEQ ID NO 228
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 228

Glu Xaa Glu Lys Leu
1               5

<210> SEQ ID NO 229
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)

```
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 229

Glu Xaa Glu Gln Gln
1               5

<210> SEQ ID NO 230
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 230

Lys Phe Glu Xaa Glu Arg Ser
1               5

<210> SEQ ID NO 231
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 231

Glu Xaa Glu Arg Ser
1               5

<210> SEQ ID NO 232
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 232

Phe Glu Xaa Glu Arg
1               5

<210> SEQ ID NO 233
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 233

Ala Lys Phe Glu Xaa Glu
1               5

<210> SEQ ID NO 234
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 234

Lys Phe Glu Xaa Glu Arg
1               5

<210> SEQ ID NO 235
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 235

Phe Glu Xaa Glu Arg Ala
1               5

<210> SEQ ID NO 236
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 236

Glu Xaa Glu Arg Ala Arg
1               5

<210> SEQ ID NO 237
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 237

Glu Xaa Glu Arg Ala Arg Ala
1               5

<210> SEQ ID NO 238
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 238

Glu Xaa Glu Arg Ala Arg Ala Lys
1               5

<210> SEQ ID NO 239
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 239

Lys Phe Glu Glu Glu
1               5

<210> SEQ ID NO 240
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 240

Lys Phe Glu Glu Glu Arg Ala
1               5

<210> SEQ ID NO 241
<211> LENGTH: 5
<212> TYPE: PRT
<213> ORGANISM: Artificial sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 241

Glu Glu Glu Arg Ala
1               5

<210> SEQ ID NO 242
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 242

Lys Phe Glu Glu Glu Arg Ala Arg Ala Lys Trp Asp Thr
1               5                  10

<210> SEQ ID NO 243
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 243

Lys Phe Glu Lys Glu
1               5

<210> SEQ ID NO 244
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 244

Arg Phe Glu Lys Glu
1               5

<210> SEQ ID NO 245
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 245

Lys Phe Glu Lys Glu Lys Met
1               5
```

```
<210> SEQ ID NO 246
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 246

Lys Phe Glu Lys Glu Lys Leu
1               5

<210> SEQ ID NO 247
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 247

Lys Phe Glu Lys Glu Gln Gln
1               5

<210> SEQ ID NO 248
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 248

Arg Phe Glu Lys Glu Lys Met
1               5

<210> SEQ ID NO 249
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 249

Arg Lys Phe Glu Lys Glu Lys Leu
1               5

<210> SEQ ID NO 250
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 250
```

```
Arg Phe Glu Lys Glu Gln Gln
1               5

<210> SEQ ID NO 251
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 251

Glu Lys Glu Lys Met
1               5

<210> SEQ ID NO 252
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 252

Glu Lys Glu Lys Leu
1               5

<210> SEQ ID NO 253
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 253

Glu Lys Glu Gln Gln
1               5

<210> SEQ ID NO 254
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 254

Lys Phe Glu Ala Glu
1               5

<210> SEQ ID NO 255
<211> LENGTH: 7
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Covalently bound to a C12-C18 fatty acid

<400> SEQUENCE: 255

Lys Phe Glu Ala Glu Arg Ser
1               5

<210> SEQ ID NO 256
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 256

Glu Ala Glu Arg Ser
1               5

<210> SEQ ID NO 257
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 257

Lys Phe Gln Ser Glu
1               5

<210> SEQ ID NO 258
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 258

Lys Phe Gln Ser Glu Arg Ser
1               5

<210> SEQ ID NO 259
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 259

Gln Ser Glu Arg Ser
1               5

<210> SEQ ID NO 260
<211> LENGTH: 5
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 260

Phe Glu Glu Glu Arg
1               5

<210> SEQ ID NO 261
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 261

Ala Lys Phe Glu Glu Glu
1               5

<210> SEQ ID NO 262
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 262

Lys Phe Glu Glu Glu Arg
1               5

<210> SEQ ID NO 263
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 263

Phe Glu Glu Glu Arg Ala
1               5

<210> SEQ ID NO 264
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 264

Glu Glu Glu Arg Ala Arg
```

```
<210> SEQ ID NO 265
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 265

Glu Glu Glu Arg Ala Arg Ala
1               5

<210> SEQ ID NO 266
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid

<400> SEQUENCE: 266

Glu Glu Glu Arg Ala Arg Ala Lys
1               5

<210> SEQ ID NO 267
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 267

Glu Xaa Glu
1

<210> SEQ ID NO 268
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 268

Phe Glu Xaa Glu
1

<210> SEQ ID NO 269
```

```
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Lys Arg or Gln

<400> SEQUENCE: 269

Phe Glu Xaa Glu Xaa
1               5

<210> SEQ ID NO 270
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Lys, Arg or Gln

<400> SEQUENCE: 270

Glu Xaa Glu Xaa
1

<210> SEQ ID NO 271
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid

<400> SEQUENCE: 271

Xaa Phe Glu Xaa Glu
1               5

<210> SEQ ID NO 272
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

<400> SEQUENCE: 272

Xaa Phe Glu Xaa Glu Xaa
1               5

<210> SEQ ID NO 273
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln
<220> FEATURE:
<221> NAME/KEY: MISC_FEATURE
<222> LOCATION: (7)..(7)
<223> OTHER INFORMATION: Xaa is any amino acid - optionally Met, Ala,
      Leu, Ser or Gln

<400> SEQUENCE: 273

Xaa Phe Glu Xaa Glu Xaa Xaa
1               5

<210> SEQ ID NO 274
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 274

Lys Phe Glu Xaa Glu
1               5

<210> SEQ ID NO 275
<211> LENGTH: 7
```

```
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 275

Lys Phe Glu Xaa Glu Arg Ala
1               5

<210> SEQ ID NO 276
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 276

Glu Xaa Glu Arg Ala
1               5

<210> SEQ ID NO 277
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 277

Lys Phe Glu Xaa Glu Arg Ala Arg Ala Lys Trp Asp Thr
1               5                   10

<210> SEQ ID NO 278
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 278

Arg Phe Glu Xaa Glu
1               5
```

```
<210> SEQ ID NO 279
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 279

Lys Phe Glu Xaa Glu Lys Met
1               5

<210> SEQ ID NO 280
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 280

Lys Phe Glu Xaa Glu Lys Leu
1               5

<210> SEQ ID NO 281
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 281

Lys Phe Glu Xaa Glu Gln Gln
1               5

<210> SEQ ID NO 282
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid
```

-continued

```
<400> SEQUENCE: 282

Arg Phe Glu Xaa Glu Lys Met
1               5

<210> SEQ ID NO 283
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 283

Arg Lys Phe Glu Xaa Glu Lys Leu
1               5

<210> SEQ ID NO 284
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 284

Arg Phe Glu Xaa Glu Gln Gln
1               5

<210> SEQ ID NO 285
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 285

Glu Xaa Glu Lys Met
1               5

<210> SEQ ID NO 286
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
```

-continued

```
<221> NAME/KEY: MISC_FEATURE
<222> LOCATION: (2)..(2)
<223> OTHER INFORMATION: Xaa is any amino acid

<400> SEQUENCE: 286

Glu Xaa Glu Lys Leu
1               5

<210> SEQ ID NO 287
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 287

Glu Xaa Glu Gln Gln
1               5

<210> SEQ ID NO 288
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 288

Lys Phe Glu Xaa Glu Arg Ser
1               5

<210> SEQ ID NO 289
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 289

Glu Xaa Glu Arg Ser
1               5

<210> SEQ ID NO 290
<211> LENGTH: 5
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 290

Phe Glu Xaa Glu Arg
1               5

<210> SEQ ID NO 291
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 291

Ala Lys Phe Glu Xaa Glu
1               5

<210> SEQ ID NO 292
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 292

Lys Phe Glu Xaa Glu Arg
1               5

<210> SEQ ID NO 293
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 293

Phe Glu Xaa Glu Arg Ala
1               5

<210> SEQ ID NO 294
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 294

Glu Xaa Glu Arg Ala Arg
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 295

Glu Xaa Glu Arg Ala Arg Ala
1               5

<210> SEQ ID NO 296
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C12-C18 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 296

Glu Xaa Glu Arg Ala Arg Ala Lys
1               5

<210> SEQ ID NO 297
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 297

Lys Phe Glu Glu Glu
1               5

<210> SEQ ID NO 298
<211> LENGTH: 7
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 298

Lys Phe Glu Glu Glu Arg Ala
1               5

<210> SEQ ID NO 299
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 299

Glu Glu Glu Arg Ala
1               5

<210> SEQ ID NO 300
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 300

Lys Phe Glu Glu Glu Arg Ala Arg Ala Lys Trp Asp Thr
1               5                   10

<210> SEQ ID NO 301
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 301

Lys Phe Glu Lys Glu
1               5

<210> SEQ ID NO 302
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 302

Arg Phe Glu Lys Glu
1               5
```

```
<210> SEQ ID NO 303
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 303

Lys Phe Glu Lys Glu Lys Met
1               5

<210> SEQ ID NO 304
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 304

Lys Phe Glu Lys Glu Lys Leu
1               5

<210> SEQ ID NO 305
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 305

Lys Phe Glu Lys Glu Gln Gln
1               5

<210> SEQ ID NO 306
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 306

Arg Phe Glu Lys Glu Lys Met
1               5

<210> SEQ ID NO 307
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
```

```
<400> SEQUENCE: 307

Arg Lys Phe Glu Lys Glu Lys Leu
1               5

<210> SEQ ID NO 308
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 308

Arg Phe Glu Lys Glu Gln Gln
1               5

<210> SEQ ID NO 309
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 309

Glu Lys Glu Lys Met
1               5

<210> SEQ ID NO 310
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 310

Glu Lys Glu Lys Leu
1               5

<210> SEQ ID NO 311
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 311

Glu Lys Glu Gln Gln
1               5

<210> SEQ ID NO 312
<211> LENGTH: 5
<212> TYPE: PRT
<213> ORGANISM: Artificial sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 312

Lys Phe Glu Ala Glu
1               5

<210> SEQ ID NO 313
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 313

Lys Phe Glu Ala Glu Arg Ser
1               5

<210> SEQ ID NO 314
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 314

Glu Ala Glu Arg Ser
1               5

<210> SEQ ID NO 315
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 315

Lys Phe Gln Ser Glu
1               5

<210> SEQ ID NO 316
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 316

Lys Phe Gln Ser Glu Arg Ser
1               5
```

```
<210> SEQ ID NO 317
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 317

Gln Ser Glu Arg Ser
1               5

<210> SEQ ID NO 318
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 318

Phe Glu Glu Glu Arg
1               5

<210> SEQ ID NO 319
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 319

Ala Lys Phe Glu Glu Glu
1               5

<210> SEQ ID NO 320
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 320

Lys Phe Glu Glu Glu Arg
1               5

<210> SEQ ID NO 321
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 321
```

```
Phe Glu Glu Glu Arg Ala
1               5

<210> SEQ ID NO 322
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 322

Glu Glu Glu Arg Ala Arg
1               5

<210> SEQ ID NO 323
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 323

Glu Glu Glu Arg Ala Arg Ala
1               5

<210> SEQ ID NO 324
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid

<400> SEQUENCE: 324

Glu Glu Glu Arg Ala Arg Ala Lys
1               5

<210> SEQ ID NO 325
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 325

Glu Xaa Glu
1

<210> SEQ ID NO 326
<211> LENGTH: 4
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 326

Phe Glu Xaa Glu
1

<210> SEQ ID NO 327
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Lys Arg or Gln

<400> SEQUENCE: 327

Phe Glu Xaa Glu Xaa
1               5

<210> SEQ ID NO 328
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Lys, Arg or Gln

<400> SEQUENCE: 328

Glu Xaa Glu Xaa
1

<210> SEQ ID NO 329
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
```

```
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid

<400> SEQUENCE: 329

Xaa Phe Glu Xaa Glu
1               5

<210> SEQ ID NO 330
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

<400> SEQUENCE: 330

Xaa Phe Glu Xaa Glu Xaa
1               5

<210> SEQ ID NO 331
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln
<220> FEATURE:
<221> NAME/KEY: MISC_FEATURE
<222> LOCATION: (7)..(7)
<223> OTHER INFORMATION: Xaa is any amino acid - optionally Met, Ala,
      Leu, Ser or Gln

<400> SEQUENCE: 331

Xaa Phe Glu Xaa Glu Xaa Xaa
1               5

<210> SEQ ID NO 332
<211> LENGTH: 5
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 332

Lys Phe Glu Xaa Glu
1               5

<210> SEQ ID NO 333
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 333

Lys Phe Glu Xaa Glu Arg Ala
1               5

<210> SEQ ID NO 334
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 334

Glu Xaa Glu Arg Ala
1               5

<210> SEQ ID NO 335
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 335

Lys Phe Glu Xaa Glu Arg Ala Arg Ala Lys Trp Asp Thr
1               5                   10
```

```
<210> SEQ ID NO 336
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 336

Arg Phe Glu Xaa Glu
1               5

<210> SEQ ID NO 337
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 337

Lys Phe Glu Xaa Glu Lys Met
1               5

<210> SEQ ID NO 338
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 338

Lys Phe Glu Xaa Glu Lys Leu
1               5

<210> SEQ ID NO 339
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 339
```

```
Lys Phe Glu Xaa Glu Gln Gln
1               5
```

<210> SEQ ID NO 340
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 340

```
Arg Phe Glu Xaa Glu Lys Met
1               5
```

<210> SEQ ID NO 341
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 341

```
Arg Lys Phe Glu Xaa Glu Lys Leu
1               5
```

<210> SEQ ID NO 342
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 342

```
Arg Phe Glu Xaa Glu Gln Gln
1               5
```

<210> SEQ ID NO 343
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)

```
<223> OTHER INFORMATION: Xaa is any amino acid

<400> SEQUENCE: 343

Glu Xaa Glu Lys Met
1               5

<210> SEQ ID NO 344
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 344

Glu Xaa Glu Lys Leu
1               5

<210> SEQ ID NO 345
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 345

Glu Xaa Glu Gln Gln
1               5

<210> SEQ ID NO 346
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 346

Lys Phe Glu Xaa Glu Arg Ser
1               5

<210> SEQ ID NO 347
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 347

Glu Xaa Glu Arg Ser
1               5

<210> SEQ ID NO 348
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 348

Phe Glu Xaa Glu Arg
1               5

<210> SEQ ID NO 349
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 349

Ala Lys Phe Glu Xaa Glu
1               5

<210> SEQ ID NO 350
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 350

Lys Phe Glu Xaa Glu Arg
1               5

<210> SEQ ID NO 351
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 351

Phe Glu Xaa Glu Arg Ala
1               5

<210> SEQ ID NO 352
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 352

Glu Xaa Glu Arg Ala Arg
1               5

<210> SEQ ID NO 353
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 353

Glu Xaa Glu Arg Ala Arg Ala
1               5

<210> SEQ ID NO 354
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Covalently bound to a C16 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 354

Glu Xaa Glu Arg Ala Arg Ala Lys
1               5

<210> SEQ ID NO 355
```

```
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 355

Lys Phe Glu Glu Glu
1               5

<210> SEQ ID NO 356
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 356

Lys Phe Glu Glu Glu Arg Ala
1               5

<210> SEQ ID NO 357
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 357

Glu Glu Glu Arg Ala
1               5

<210> SEQ ID NO 358
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 358

Lys Phe Glu Glu Glu Arg Ala Arg Ala Lys Trp Asp Thr
1               5                   10

<210> SEQ ID NO 359
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 359

Lys Phe Glu Lys Glu
1               5

<210> SEQ ID NO 360
```

```
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 360

Arg Phe Glu Lys Glu
1               5

<210> SEQ ID NO 361
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 361

Lys Phe Glu Lys Glu Lys Met
1               5

<210> SEQ ID NO 362
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 362

Lys Phe Glu Lys Glu Lys Leu
1               5

<210> SEQ ID NO 363
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 363

Lys Phe Glu Lys Glu Gln Gln
1               5

<210> SEQ ID NO 364
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 364

Arg Phe Glu Lys Glu Lys Met
1               5

<210> SEQ ID NO 365
```

```
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 365

Arg Lys Phe Glu Lys Glu Lys Leu
1               5

<210> SEQ ID NO 366
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 366

Arg Phe Glu Lys Glu Gln Gln
1               5

<210> SEQ ID NO 367
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 367

Glu Lys Glu Lys Met
1               5

<210> SEQ ID NO 368
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 368

Glu Lys Glu Lys Leu
1               5

<210> SEQ ID NO 369
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 369

Glu Lys Glu Gln Gln
1               5

<210> SEQ ID NO 370
```

```
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 370

Lys Phe Glu Ala Glu
 1               5

<210> SEQ ID NO 371
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 371

Lys Phe Glu Ala Glu Arg Ser
 1               5

<210> SEQ ID NO 372
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 372

Glu Ala Glu Arg Ser
 1               5

<210> SEQ ID NO 373
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 373

Lys Phe Gln Ser Glu
 1               5

<210> SEQ ID NO 374
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 374

Lys Phe Gln Ser Glu Arg Ser
 1               5

<210> SEQ ID NO 375
```

```
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 375

Gln Ser Glu Arg Ser
1               5

<210> SEQ ID NO 376
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 376

Phe Glu Glu Glu Arg
1               5

<210> SEQ ID NO 377
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 377

Ala Lys Phe Glu Glu Glu
1               5

<210> SEQ ID NO 378
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 378

Lys Phe Glu Glu Glu Arg
1               5

<210> SEQ ID NO 379
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 379

Phe Glu Glu Glu Arg Ala
1               5

<210> SEQ ID NO 380
```

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 380

Glu Glu Glu Arg Ala Arg
1               5

<210> SEQ ID NO 381
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 381

Glu Glu Glu Arg Ala Arg Ala
1               5

<210> SEQ ID NO 382
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid

<400> SEQUENCE: 382

Glu Glu Glu Arg Ala Arg Ala Lys
1               5

<210> SEQ ID NO 383
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 383

Glu Xaa Glu
1

<210> SEQ ID NO 384
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid
```

```
<400> SEQUENCE: 384

Phe Glu Xaa Glu
1

<210> SEQ ID NO 385
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Lys Arg or Gln

<400> SEQUENCE: 385

Phe Glu Xaa Glu Xaa
1               5

<210> SEQ ID NO 386
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Lys, Arg or Gln

<400> SEQUENCE: 386

Glu Xaa Glu Xaa
1

<210> SEQ ID NO 387
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid

<400> SEQUENCE: 387

Xaa Phe Glu Xaa Glu
1               5

<210> SEQ ID NO 388
```

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln

<400> SEQUENCE: 388

Xaa Phe Glu Xaa Glu Xaa
1               5

<210> SEQ ID NO 389
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys, Arg or Gln
<220> FEATURE:
<221> NAME/KEY: MISC_FEATURE
<222> LOCATION: (7)..(7)
<223> OTHER INFORMATION: Xaa is any amino acid - optionally Met, Ala,
      Leu, Ser or Gln

<400> SEQUENCE: 389

Xaa Phe Glu Xaa Glu Xaa Xaa
1               5

<210> SEQ ID NO 390
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 390

Lys Phe Glu Xaa Glu
1               5
```

```
<210> SEQ ID NO 391
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 391

Lys Phe Glu Xaa Glu Arg Ala
1               5

<210> SEQ ID NO 392
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 392

Glu Xaa Glu Arg Ala
1               5

<210> SEQ ID NO 393
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 393

Lys Phe Glu Xaa Glu Arg Ala Arg Ala Lys Trp Asp Thr
1               5                   10

<210> SEQ ID NO 394
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 394

Arg Phe Glu Xaa Glu
1               5
```

```
<210> SEQ ID NO 395
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 395

Lys Phe Glu Xaa Glu Lys Met
1               5

<210> SEQ ID NO 396
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 396

Lys Phe Glu Xaa Glu Lys Leu
1               5

<210> SEQ ID NO 397
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 397

Lys Phe Glu Xaa Glu Gln Gln
1               5

<210> SEQ ID NO 398
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 398

Arg Phe Glu Xaa Glu Lys Met
1               5
```

```
<210> SEQ ID NO 399
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 399

Arg Lys Phe Glu Xaa Glu Lys Leu
1               5

<210> SEQ ID NO 400
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 400

Arg Phe Glu Xaa Glu Gln Gln
1               5

<210> SEQ ID NO 401
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 401

Glu Xaa Glu Lys Met
1               5

<210> SEQ ID NO 402
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 402

Glu Xaa Glu Lys Leu
1               5
```

```
<210> SEQ ID NO 403
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 403

Glu Xaa Glu Gln Gln
1               5

<210> SEQ ID NO 404
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 404

Lys Phe Glu Xaa Glu Arg Ser
1               5

<210> SEQ ID NO 405
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 405

Glu Xaa Glu Arg Ser
1               5

<210> SEQ ID NO 406
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 406

Phe Glu Xaa Glu Arg
1               5
```

```
<210> SEQ ID NO 407
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (5)..(5)
<223> OTHER INFORMATION: Xaa is any amino acid

<400> SEQUENCE: 407

Ala Lys Phe Glu Xaa Glu
1               5

<210> SEQ ID NO 408
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (4)..(4)
<223> OTHER INFORMATION: Xaa is any amino acid

<400> SEQUENCE: 408

Lys Phe Glu Xaa Glu Arg
1               5

<210> SEQ ID NO 409
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (3)..(3)
<223> OTHER INFORMATION: Xaa is any amino acid

<400> SEQUENCE: 409

Phe Glu Xaa Glu Arg Ala
1               5

<210> SEQ ID NO 410
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 410

Glu Xaa Glu Arg Ala Arg
1               5
```

```
<210> SEQ ID NO 411
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 411

Glu Xaa Glu Arg Ala Arg Ala
1               5

<210> SEQ ID NO 412
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Covalently bound to a C4-C30 fatty acid
<220> FEATURE:
<221> NAME/KEY: MISC_FEATURE
<222> LOCATION: (2)..(2)
<223> OTHER INFORMATION: Xaa is any amino acid

<400> SEQUENCE: 412

Glu Xaa Glu Arg Ala Arg Ala Lys
1               5
```

INHIBITORS OF BETA INTEGRIN-G PROTEIN ALPHA SUBUNIT BINDING INTERACTIONS

CROSS-REFERENCE TO RELATED APPLICATIONS

This application claims priority to International Patent Application No. PCT/US2011/028567, filed Mar. 15, 2011, which claims priority to U.S. Provisional Patent Application No. 61/314,027, filed on Mar. 15, 2010, and U.S. Provisional Patent Application No. 61/433,037, filed on Jan. 14, 2011; each application of which is incorporated by reference in their entirety.

GRANT FUNDING

This invention was made with government support under Grant Nos. HL080264, HL062350, HL068819, awarded by the National Heart, Lung, and Blood Institute. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 89 kilobytes ACII (Text) file named "45326B_SeqListing," created on Sep. 14, 2012.

BACKGROUND

Integrins are heterodimer transmembrane receptors for the extracellular matrix and are composed of an alpha and beta subunit. Naturally-occurring integrin ligands include laminin, fibronectin, and vitronectin, and also include fibrinogen and fibrin, thrombospondin, and von Willebrand factor, and fibroblast growth factor 2. Integrins bind ligands by recognizing short amino acid stretches on exposed loops, particularly the arginine-glycine-aspartic acid (RGD) or like sequences. Upon ligation, integrins mediate cell adhesion, and initiate complex signaling events, alone or in combination with other types of receptors (such as growth factor receptors), and regulate cell spreading, retraction, adhesion, proliferation, survival, and migration. Integrin signaling is bi-directional. Intracellular signals mediates so-called "inside-out" signaling, which induces activation of the ligand binding functions of integrins. Integrin ligation activate "outside-in" signaling pathways, including, for example Src family kinases (SFK), the phosphoinositide 3-kinase, protein kinase B (PKB/Akt), mitogen-activated protein kinase (MAPK), and Rac. See, e.g., Li Z, Delaney M K, O'Brien K A, Du X., Arterioscler Thromb Vasc Biol. 30(12):2341-2349, 2010.

Integrins are expressed and serve as major adhesion receptors on the surface of blood platelets, a type of blood cells that are critical in thrombosis and hemostasis. The major integrin expressed on platelet surface is the integrin αIIbβ3, also called glycoprotein IIb-IIIa (GPIIa-IIIa). Upon exposure to the site of vascular injury, platelets adhere to and spread on the injured or stimulated vascular endothelial cells or extracellular matrix, becomes activated and aggregate to from primary thrombus. Integrin αIIbβ3 mediates stable platelet adhesion, spreading and aggregation. This process normally serves to stop bleeding and prevent loss of blood (that is called hemostasis). Under certain conditions, such as at sites of atherosclerosis, platelets form a occlusive thrombus that block blood vessels, leading to ischemia of organs and tissues, causing such as heart attack and thrombotic stroke etc (Li Z, Delaney M K, O'Brien K A, Du X., Arterioscler Thromb Vasc Biol. 30(12):2341-2349, 2010.). Thus, inhibitors of integrin function are clinically used to prevent and treat thrombotic diseases. Integrins are also important in other physiological and pathological processes such as immunity, inflammation, angiogenesis and tumor progression and metastasis.

Three classes of integrin inhibitors are currently in clinical use or development: monoclonal antibodies targeting the extracellular ligand binding domain of the heterodimer (eg, Reopro, Eli Lilly, Indiapolis, Vitaxin; Medlmmune, Gaithersburg, Md.), synthetic peptides containing an RGD or KGD sequences (eg, Integrillin, Millennium Pharmaceuticals; cilengitide; Merck KGaA, Darmstadt, Germany), and peptidomimetics (eg, aggrestat (Tirofiban), Merck, White House Station, N.J.; 5247; Pfizer, St Louis, Mo.).

The first integrin-specific drugs targeted the integrin $\alpha_{IIb}\beta_3$, which is central to hemostasis and plays an important role in platelet adhesion and thrombus formation. $\alpha_{IIb1 \beta3}$ also functions in the inflammatory response. The first FDA-approved $\alpha_{IIb}\beta_3$ antagonists have proven benefit for indications, including acute coronary syndromes and prevention of myocardial infarction. However, the use of some of these drugs are limited due to their pharmacokinetic profiles—some drugs demonstrate rapid plasma clearance, rapid metabolism, poor oral bioavailability, and/or large variation in plasma levels. Also, some antagonists of $\alpha_{IIb}\beta_3$ integrin induced thrombocytopenia. See, e.g., *Advances in Immunology*, Volume 91, Elsevier Academic Press (San Diego, Calif.), 2006. A common and potentially life-threatening adverse effect of integrin inhibitor is bleeding (this is because intergrin is impotant in hemosrsis).

SUMMARY

The invention provides a compound that inhibits a binding interaction between a β integrin and a G protein α subunit. As further discussed herein, in exemplary embodiments, the compound takes form of an antibody, or antibody analog, a peptide, or peptide analog. Accordingly, the invention provides, antibodies, antibody analogs, peptides, and peptide analogs.

Also provided by the invention is a composition, e.g., a pharmaceutical composition, comprising a compound that inhibits a binding interaction between a β integrin and a G protein α subunit. Kits comprising one or more compounds of the are also provided herein.

Methods of using the compounds and compositions of the invention are further provided. For example, the invention provides a method of inhibiting a binding interaction between an integrin and a G protein subunit in a cell. The method comprises the step of contacting the cell with a compound or composition of the invention in an amount effective to inhibit the binding interaction.

The invention further provides a method of inhibiting integrin-dependent Src activation in a cell. The method comprises the step of contacting the cells with a compound or composition of the invention in an amount effective to inhibiting the Src activation.

A method of activating a GTPase is furthermore provided by the invention. The method comprises the step of contacting a G protein subunit with a compound or composition in an amount effective to activate a GTPase.

The invention moreover provides a method of inhibiting spreading or migration of a cell. The method comprises the step of contacting the cell with a compound or composition of the invention in an amount effective to inhibit spreading and migration.

Also provided by the invention is a method of inhibiting platelet adhesion. The method comprises the step of contacting a platelet with a compound or composition of the invention in an amount effective to inhibit platelet adhesion. The invention further provides a method of inhibiting platelet granule secretion and platelet aggregation. The method comprises the step of contacting a platelet with a compound or composition of the invention in an amount effective to inhibit granule secretion and aggregation.

The compounds and compositions of the invention are additionally contemplated for therapeutic purposes. For example, the compounds and compositions of the invention may be used to enhance blood clot retraction or inhibit thrombosis in a subject in need thereof. Accordingly, the invention provides a method of enhancing blood clot retraction in a subject in need thereof. The method comprises the step of administering to the subject a compound or composition of the invention in an amount effective to enhance blood clot retraction. Also provided is a method of inhibiting thrombosis in a subject in need thereof. The method comprises the step of administering to the subject a compound or composition of the invention in an amount effective to inhibit thrombosis.

Because thrombosis play a role in stroke and heart attack, the invention furthermore provides a method of treating or preventing a stroke or a heart attack in a subject in need thereof. The method comprises the step of administering to the subject a compound or composition of the invention in an amount effective to treat or prevent stroke or heart attack.

Because the compounds and compositions provided herein relate to the coordinated cell spreading-retraction process, which in turn, is important in cell migration, the invention also provides a method of inhibiting metastasis of a tumor cell. The method comprises the step of contacting a tumor cell with a compound or composition of the invention in an amount effective to inhibit metastasis. The compounds and compositions are also contemplated for use in inhibiting angiogenesis. Accordingly, the invention provides a method of inhibiting angiogenesis in a subject in need thereof. The method comprises the step of administering to the subject a compound or composition of the invention in an amount effective to inhibit angiogenesis.

Since metastasis and angiogenesis are important aspects of cancer, the invention moreover provides a method of treating or preventing cancer in a subject in need thereof. The method comprises the step of administering to the subject a compound or composition of the invention in an amount effective to treat or prevent cancer.

The compounds and compositions provided herein also may be used for affecting leukocyte function. The invention accordingly provides a method of inhibiting leukocyte adhesion, spreading, migration, or chemotaxis. The method comprises the step of contacting a leukocyte with a compound or composition of the invention in an amount effective to inhibit leukocyte adhesion, spreading, migration, or chemotaxis. Since these leukocyte functions are related to inflammation, the invention additionally provides a method of inhibiting or treating inflammation in a subject in need thereof. The method comprises the step of administering to the subject a compound or composition of the invention in an amount effective to inhibit or treat inflammation.

BRIEF DESCRIPTION OF THE DRAWINGS

FIG. 1 demonstrates a role of $G\alpha_{13}$ in integrin outside-in signaling.

FIG. 2 demonstrates the binding of $G\alpha_{13}$ to $\beta_3$ and the inhibitory effect of mSRI peptide.

FIG. 3 demonstrates the effects of mSRI on integrin-induced c-Src phosphorylation, RhoA activity and platelet spreading. (FIG. 3A) Washed human platelets pre-treated with DMSO, mSRI, or scrambled control peptide were allowed to adhere to fibrinogen and then solubilized at indicated time points. Proteins from lysates were immunoblotted with antibodies to c-Src phosphorylated at $Tyr^{416}$, c-Src, or RhoA. GTP-bound RhoA was measured by association with GST-RBD beads (25). See Fig. S4 for quantitative data. (FIG. 3B) Spreading of platelets treated with 0.1% DMSO, scrambled control peptide, or mSRI, in the absence or presence of C3 toxin, Y27632, or 0.01 U/ml thrombin. Platelets were stained with Alexa Fluor 546-conjugated phalloidin.

FIG. 4 demonstrates a role of $G\alpha_{13}$ in clot retraction and dynamic RhoA regulation. (FIG. 4A) Effect of 250 µM mSRI peptide on clot retraction of human platelet-rich plasma compared with DMSO and scrambled peptide. Clot sizes were quantified using Image J (mean±SD, n=3, t-test). (FIG. 4B) Comparison of clot retraction (mean±SD, n=3, t-test) mediated by control siRNA platelets and $G\alpha_{13}$-depleted platelets. (FIG. 4C, FIG. 4D, FIG. 4E, FIG. 4F) Platelets were stimulated with thrombin with or without 2 mM RGDS, and monitored for turbidity changes of platelet suspension caused by shape change and aggregation (FIG. 4C). The platelets were then solubilized at indicated time points and analyzed for amount of $\beta_3$ coimmunoprecipitated with $G\alpha_{13}$ (FIG. 4D) and amount of GTP-RhoA bound to GST-RBD beads (FIG. 4E) by immunoblot. (FIG. 4F) quantitative data (mean±SD) from 3 experiments. (FIG. 4G) A schematic illustrating $G\alpha_{13}$-dependent dynamic regulation of RhoA and crosstalk between GPCR and integrin signaling.

FIG. 6 demonstrates the similar effects of two different Gα13 siRNA on platelet spreading, c-Src activation and RhoA activity, and the effect of aspirin on platelet spreading. (FIG. 6A) Confocal microscopy images of spreading mouse platelets transfected with scrambled siRNA, $G\alpha_{13}$ siRNA #1- and $G\alpha_{13}$ siRNA #2 on immobilized fibrinogen. Merged EGFP green fluorescence and Alexa Fluor 546-conjugated phalloidin red fluorescence. (FIG. 6B) Scrambled siRNA, $G\alpha_{13}$ siRNA#1- and $G\alpha_{13}$ siRNA#2-transfected platelets were allowed to adhere to immobilized fibrinogen for the indicated time, and analyzed for c-Src activation and RhoA activity. Note that two different siRNA similarly inhibited platelet spreading and c-Src activation, and accelerated activation of RhoA. (FIG. 6C) Mouse platelets were pre-incubated with or without 1 mM aspirin for 30 minutes at room temperature, and then allowed to spread on immobilized fibrinogen.

FIG. 7 demonstrates the inhibitory effects of $G\alpha_{13}$ siRNA on cell spreading and c-Src phosphorylation in CHO cells expressing integrin $\alpha_{IIb}\beta_3$ and its rescue by an siRNA resistant mutant of $G\alpha_{13}$. Stable CHO cell line expressing integrin $\alpha_{IIb}\beta_3$ (123 cells) were transfected with cDNA constructs encoding EGFP and scrambled control siRNA or $G\alpha_{13}$ siRNA with or without co-transfection of Flag-tagged siRNA-resistant mutants of $G\alpha_{13}$ cDNA constructs (Flag-G13-Mut1).

FIG. 8 provides quantitative data from experiments shown in FIGS. 2 and 3.

FIG. 10 provides typical images of clot retraction showing the effects of mSRI and $G\alpha_{13}$-knockdown on platelet-mediated clot retraction.

FIG. 11 demonstrates the $G\alpha_{13}$ binding site in the integrin $\beta_3$ cytoplasmic domain. (FIG. 11A) Amino acid sequence alignment of the cytoplasmic domains of various human integrins $\beta$ subunits. Key sequences critical in Gα13 binding is marked as red. Synthetic peptides corresponding to the Ga13 binding region of β3 were synthesized (FIG. 11B) Lysates from CHO cells expressing a similar level of wild type and truncated integrin $\beta_3$ were immunoprecipitated with anti-$G\alpha_{13}$ antibody or equal amount of control rabbit IgG. Lysates and immunoprecipitates were immunoblotted with anti-$G\alpha_{13}$ or anti-$\beta_3$ (MAb15) antibody. (FIG. 11C) Lysates from CHO cells expressing wild type or mutant $\beta_3$ were immunoprecipitated with anti-$G\alpha_{13}$ antibody or equal amount of control rabbit IgG. Immunoprecipitates were immunoblotted with anti-$G\alpha_{13}$ or anti-$\beta_3$ (MAb 15) monoclonal antibodies. (FIG. 11D) Confocal microscopy images of $\beta_3^{-/-}$ platelets, and $\beta_3^{-/-}$ platelets expressing wild type or AAA-mutant integrin $\beta_3$ spreading on fibrinogen. Merged anti-integrin $\beta_3$ (MAb15) fluorescence (green) and Alexa Fluor 546-conjugated phalloidin fluorescence (red). (FIG. 11E) Flow cytometry analysis of $\beta_3$ expression levels in $\beta_3^{-/-}$ mouse platelets transfected with wild type and AAA ($E^{731-733}$ to alanine) mutant integrin $\beta_3$ in complex with wild type $\alpha_{IIb}$. $\beta_3^{-/-}$ platelets serve as negative control. (b)

FIG. 13 demonstrates the identification of a $G\alpha_{13}$ binding motif in integrins.

FIG. 14 demonstrates the inhibition of integrin outside-in and inside-out signalling by mP$_{13}$ peptide.

FIG. 15 demonstrates that the EEE motif of integrin β3-CD is important for Gα13 binding and cell spreading. (FIG. 15A) Human integrin cytoplasmic domain sequences were aligned manually. The conserved ExE motifs are highlighted in red. The conserved NxxY and HDR[R/K] motifs are highlighted in bold. Residues are numbered according to the National Center for Biotechnology Information (NCBI) sequence. The sequences of the peptide inhibitors developed in this study are shown below the corresponding β$_3$ cytoplasmic domain sequences. (FIG. 15B) Lysates from truncated integrin β3-stable expression 123 cells were precipitated with anti-Gα13 antibody or equal amount of normal rabbit IgG as control. Immunoprecipitates were immunoblotted with anti-Gα13 or anti-β$_3$ (M15) antibody. (FIG. 15C) Lysates from E to A mutant integrin β3-stable expression 123 cells were precipitated with anti-Gα13 antibody or equal amount of normal rabbit IgG as control. Immunoprecipitates were immunoblotted with anti-Gα13 or anti-β3 (M15) antibody. (FIG. 15D) Confocal microscopy images of spreading β3−/− control platelets or platelets express wide type or AAA-mutant integrin β3 on fibrinogen. Merged integrin β3 (green) fluorescence and Alex Fluor 546-conjugated phalloidin (Red) fluorescence. (FIG. 15E) Flow cytometry analysis of wide type and AAA-mutant integrin β3 expression level. Human platelets and β3−/− platelets serve as positive and negative control.

FIG. 16 demonstrates that the AAA mutation is responsible for increased RhoA activity and decreased c-Src activity without affecting integrin inside-out signaling. (FIG. 16A) Wide type or AAA-mutant123 cells were allowed to adhere to immobilized fibrinogen, solubilized and analyzed for RhoA activation and c-Src Tyr416 phosphorylation. (FIG. 16B) Quantitation of RhoA activity for A. (FIG. 16C) Quantitation of c-Src Tyr416 phosphorylation for A. (FIG. 16D) Lysates from wide type or AAA-mutant integrin β3-stable expression 123 cells were precipitated with anti-c-Src antibody or equal amount of normal rabbit IgG as control. Immunoprecipitates were immunoblotted with anti-v-Src or anti-p190RhoGAP antibody. (FIG. 16E) Quantitation of c-Src bound p190RhoGAP for D. (FIG. 16F) Lysates from wide type or AAA-mutant integrin β3-stable expression 123 cells were precipitated with anti-p115RhoGEF antibody or equal amount of normal mouse IgG as control. Immunoprecipitates were immunoblotted with anti-Gα13 or anti-p115RhoGEF antibody. (FIG. 16G) Quantitation of p115RhoGEF bound Gα13 for F. (FIG. 16H) Flow cytometry analysis of wide type and AAA-mutant integrin β3-expression platelets fibrinogen binding ability induced by Par4-. Human platelets and β3−/− platelets serve as positive and negative control.

FIG. 17 demonstrates that the Myr-P5 peptide inhibited platelets aggregation and spreading due to increased RhoA activity and decreased c-Src activity without affecting integrin inside-out signaling. (FIG. 17A) Human platelets treated with DMSO, Myr-Scramble or Myr-P5 peptide were allowed to adhere to immobilized fibrinogen, solubilized and analyzed for RhoA activation and c-Src Tyr416 phosphorylation. (FIG. 17B) Quantitation of RhoA activity for A. (FIG. 17C) Quantitation of c-Src Tyr416 phosphorylation for A. (FIG. 17D) Lysates form DMSO, Myr-Scramble or Myr-P5 peptide treated platelets were precipitated with anti-Gα13 antibody or equal amount of normal rabbit IgG as control. Immunoprecipitates were immunoblotted with anti-Gα13 or anti-β3 (M15) antibody. (FIG. 17E) Quantitation of Gα13-bound integrin β3 for D. (FIG. 17F) Confocal microscopy images of DMSO, Myr-Scramble or Myr-P5 peptide treated platelets spreading on fibrinogen for 30 minutes, without or with Y27632. Merged integrin β3 (green) fluorescence and Alex Fluor 546-conjugated phalloidin (Red) fluorescence. (FIG. 17G, FIG. 17H) Flow cytometry analysis of DMSO, Myr-Scramble or Myr-P5 peptide treated platelets fibrinogen binding ability induced by Par4. Peptide concentration was 150 μM for G, 250 μM for H. (FIG. 17I) 200 μM Myr-P5 peptide inhibited platelets aggregation induced by thrombin.

FIG. 18 demonstrates that Talin head could not rescue AAA-mutant 123 cells spreading-deficiency on fibrinogen. (FIG. 18A, FIG. 18C) Purified GST-β3-CD bound to glutathione beads was mixed with purified Gα13 with or without purified talin. Bound proteins were immunoblotted with anti-Gα13 or anti-talin antibody. Quantitative data are shown as mean±SD and p value (ttest). (FIG. 18B, FIG. 18D) Quantitation of GST-β3-CD bound Gα13 or talin for A and C. (FIG. 18E) Lysates from 123 or AAA cells transfected with talin head were precipitated with anti-β3 rabbit serum (8053) or eqival amount of pre-immune serum. Immunoprecipitates were immunoblotted with anti-Gα13 or anti-β3 antibody. (FIG. 18F) Quantitation of integrin β3-bound talin for E.

FIG. 19 demonstrates that the EEE motif of integrin β3 is important for mediating cell spreading on immobilized fibrinogen.

FIG. 20 demonstrates that the effect of P5 peptide on platelets spreading and aggregation. (FIG. 20A) Confocal microscopy images of DMSO, Myr-Scramble or Myr-P5 peptide treated platelets spreading on fibrinogen for 60 minutes, without or with Y27632. Merged integrin β3 (green) fluorescence and Alex Fluor 546-conjugated phalloidin (Red) fluorescence. (FIG. 20B, FIG. 20C) 30 μM Myr-P5 peptide inhibited both human (FIG. 20B) and mouse (FIG. 20C) platelets aggregation induced by thrombin.

FIG. 29 represents a graph of turbidometric measurement of platelet aggregation showing the doses of the EXE motif peptide FEEERA (SEQ ID NO: 87) required for inhibition of platelet aggregation among the peptide in micellar form vs. the peptide dissolved in DMSO.

DETAILED DESCRIPTION

Figure 1A:
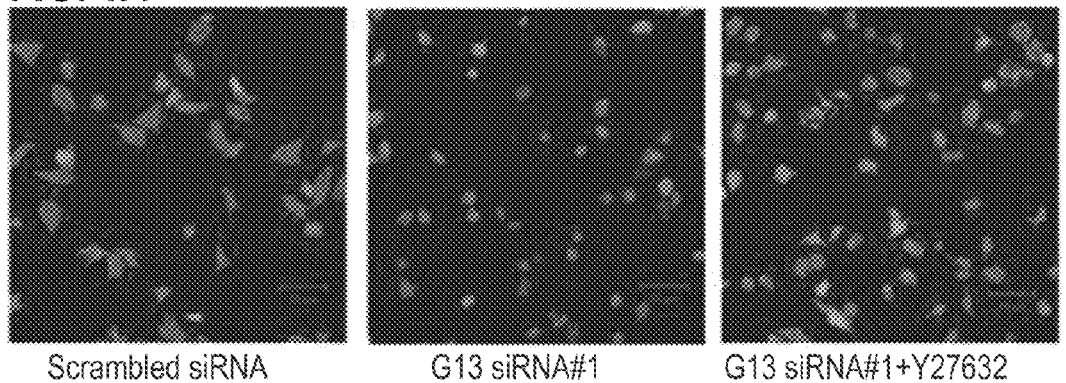
(FIG. 1A) Confocal microscopy images of spreading scrambled siRNA control platelets or $G\alpha_{13}$-depleted platelets ($G\alpha_{13}$-siRNA) on fibrinogen, without or with Y27632. Merged EGFP (green) fluorescence and Alex Fluor 546-conjugated phalloidin (Red) fluorescence.

Inhibitors of Binding Interactions Between a β Integrin and a G Protein a Subunit Provided herein are compounds that inhibit a protein-protein binding interaction between a β integrin and a G protein α subunit. The compounds of the invention may be considered as inhibitors of a β integrin binding to a G protein α subunit and/or inhibitors of a G protein α subunit binding to a β integrin. In some embodiments, the compounds are competitive binding inhibitors. In certain aspects, the compounds bind to the site of a β integrin to which a G protein α subunit binds. In certain aspects, the compounds bind to the site of a G protein α subunit to which a β integrin binds. In alternative embodiments, the compounds are non-competitive binding inhibitors. In certain aspects, the compounds inhibit the binding interaction between a α integrin and a G protein α subunit, yet the compounds bind to a site of β integrin other than the site to which G protein α subunit binds or the compounds bind to a site of a G protein α subunit other than the site to which β integrin binds.

The inhibition provided by the compounds of the invention may not be a 100% or complete inhibition or abrogation of the binding interaction between the β integrin and G protein α subunit. Rather, there are varying degrees of inhibition of which one of ordinary skill in the art recognizes as having a potential benefit or therapeutic effect. In this respect, the compounds of the invention may inhibit the binding interaction between a β integrin and a G protein α subunit to any amount or level. In exemplary embodiments, the compound provides at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition) of the binding between a β integrin and G protein α subunit. In some embodiments, the compound completely abrogates the binding interaction between the β integrin and the G protein α subunit, such that no β integrin-G protein α subunit binding complexes are detectable in a sample obtained from a subject, as measured by, for example, immunoprecipitation, Western blotting, immunohistochemistry, and the like.

In some embodiments of the invention, the compounds inhibit the binding interaction between a wild-type human β integrin and a wild-type human G protein α subunit. In exemplary aspects, the wild-type human G protein α subunit is a wild-type human $Gα_{12}$ or a wild-type human $Gα_{13}$. In exemplary aspects, the wild-type human β integrin is a wildtype human $β_{1A}$ integrin, wild-type human $β_{1D}$ integrin, wild-type human $β_2$ integrin, wildtype human $β_3$ integrin, wildtype human $β_5$ integrin, wildtype human $β_6$ integrin, or wildtype human $β_7$ integrin. The amino acid sequences of these wild-type human proteins are known in the art and are available in the Protein database of the National Center for Biotechnology Information (NCBI) website as NCBI Reference Sequence Nos. NP_006563.2 ($Gα_{13}$), NP_031379.2 ($Gα_{12}$), NP_002202 ($β_{1A}$ integrin), NP_391988 ($β_{1D}$ integrin), NP_000202 ($β_2$ integrin), NP_000203 ($β_3$ integrin), NP_002204.2 ($β_5$ integrin), NP_000879.2 ($β_6$ integrin), and NP_000770.1 ($β_7$ integrin). The amino acid sequences also are provided herein as SEQ ID NOs: 1-4 and 10-18.

In other exemplary embodiments, the compounds inhibit the binding interaction between a β integrin and a G protein α subunit, wherein one or both of the β integrin and the G protein α subunit is/are not-wild-type, e.g., mutant. For example, the amino acid sequence of the mutant β integrin differs at one or more (e.g., 1, 2, 3, 4, 5, 6, 7, 8, 9, 10, 15, 20, 25, 30, 35, 40, or more) positions from the amino acid sequence of a wild-type human β integrin recognized in the art (e.g., $β_{1A}$ integrin, $β_{1D}$ integrin, $β_2$ integrin, $β_3$ integrin, $β_5$ integrin, $β_6$ integrin, $β_7$ integrin). The amino acid sequence of the mutant β integrin in exemplary aspects is about 98% or less (e.g., about 95% or less, about 90% or less, about 85% or less, about 80% or less, about 75% or less, about 70% or less, about 65% or less, about 60% or less, about 55% or less, about 50% or less) identical to that of a wild-type β integrin. Also, for example, the amino acid sequence of the mutant G protein α subunit differs at one or more (e.g., 1, 2, 3, 4, 5, 6, 7, 8, 9, 10, 15, 20, 25, 30, 35, 40, or more) positions from the amino acid sequence of a wild-type human G protein α subunit recognized in the art (e.g., $Gα_{12}$, $Gα_{13}$). The amino acid sequence of the mutant G protein α subunit in exemplary aspects is about 98% or less (e.g., about 95% or less, about 90% or less, about 85% or less, about 80% or less, about 75% or less, about 70% or less, about 65% or less, about 60% or less, about 55% or less, about 50% or less) identical to that of a wild-type G protein α subunit.

In exemplary aspects, the compound is an antibody, an antibody analog, a peptide, a peptide analog (e.g., peptoid, peptidomimetic), a nucleic acid molecule encoding any of the antibodies or peptides, or analogs thereof, or a small molecule compound (e.g., small molecule compound rationally designed based on any of the antibodies or peptides described herein).

Antibodies and Analogs Thereof

In some embodiments of the invention, the compound that inhibits a binding interaction between a β integrin and a G protein α subunit comprises an antibody, or antigen binding fragment thereof. In some embodiments of the invention, the compound that inhibits a binding interaction between a β integrin and a G protein α subunit is an antibody, or antigen binding fragment thereof. The antibody may be any type of immunoglobulin known in the art. In exemplary embodiments, the antibody is an antibody of isotype IgA, IgD, IgE, IgG, or IgM. Also, the antibody in some embodiments is a monoclonal antibody. In other embodiments, the antibody is a polyclonal antibody.

In some embodiments, the antibody is a naturally-occurring antibody, e.g., an antibody isolated and/or purified from a mammal, e.g., mouse, rabbit, goat, horse, chicken, hamster, human, and the like. In this regard, the antibody may be considered as a mammalian antibody, e.g., a mouse antibody, rabbit antibody, goat antibody, horse antibody, chicken antibody, hamster antibody, human antibody, and the like. Methods of producing naturally-occurring antibodies are known in the art, some of which are described further herein under the section entitled "Methods of Antibody Production."

In some embodiments, the antibody is a genetically-engineered antibody, e.g., a single chain antibody, a humanized antibody, a chimeric antibody, a CDR-grafted antibody, an antibody which includes portions of CDR sequences specific for a β integrin or a G protein α subunit, a humaneered antibody, a bispecific antibody, a trispecific antibody, and the like. Genetic engineering techniques also provide the ability to make fully human antibodies in a non-human source.

In some aspects, the genetically-engineered antibody is a single chain antibody (SCA) specific for a β integrin or a G protein α subunit. In particular aspects, the SCA binds to the site of a β integrin to which G protein α subunit binds or the SCA binds to the site of a G protein α subunit to which a β integrin binds. In exemplary aspects, the SCA binds to an epitope as further described herein under the section entitled "Epitopes." Methods of making SCAs are known in the art. See, for example, Davis et al., *Nature Biotechnology* 9: 165-169 (1991).

In some aspects, the antibody is a chimeric antibody. The term "chimeric antibody" is used herein to refer to an antibody containing constant domains from one species and the variable domains from a second, or more generally, containing stretches of amino acid sequence from at least two species. In particular aspects, the chimeric antibody binds to the site of a β integrin to which a G protein α subunit binds or the chimeric antibody binds to the site of a G protein α subunit to which a β integrin binds. In exemplary aspects, the chimeric antibody binds to an epitope as further described herein under the section entitled "Epitopes."

In some aspects, the antibody is a humanized antibody. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence. In particular aspects, the humanized antibody binds to the site of a β integrin to which a G protein α subunit binds or the humanized antibody binds to the site of a G protein α subunit to which a β integrin binds. In exemplary aspects, the humanized antibody binds to an epitope as further described herein under the section entitled "Epitopes."

Use of the terms "chimeric or humanized" herein is not meant to be mutually exclusive, and rather, is meant to encompass chimeric antibodies, humanized antibodies, and chimeric antibodies that have been further humanized. Except where context otherwise indicates, statements about (properties of, uses of, testing of, and so on) chimeric antibodies of the invention apply to humanized antibodies of the invention, and statements about humanized antibodies of the invention pertain also to chimeric antibodies. Likewise, except where context dictates, such statements also should be understood to be applicable to antibodies and antigen binding fragments of such antibodies of the invention.

In some aspects, the antibody is a CDR-grafted antibody specific for a β integrin or a G protein α subunit. In particular aspects, the CDR-grafted antibody binds to the site of a β integrin to which a G protein α subunit binds or the CDR-grafted antibody binds to the site of a G protein α subunit to which a β integrin binds. In exemplary aspects, the CDR-grafted antibody binds to an epitope as further described herein under the section entitled "Epitopes." Methods of making CDR-grafted antibodies are known in the art. See, for example, Lo, Benny, *Antibody Engineering: Methods and Protocols*, Volume 248 (2004), which is incorporated by reference in its entirety.

In some aspects, the antibody is a bispecific or trispecific antibody specific for a β integrin or a G protein α subunit. In particular aspects, the bispecific or trispecific antibody binds to the site of a β integrin to which a G protein α subunit binds or the bispecific or trispecific antibody binds to the site of a G protein α subunit to which a β integrin binds. In exemplary aspects, the bispecific or trispecific antibody binds to an epitope as further described herein under the section entitled "Epitopes." Methods of making bispecific or trispecific antibodies are known in the art. See, for example, Marvin and Zhu, *Acta Pharmacologica Sinica* 26: 649-658 (2005) and U.S. Pat. No. 6,551,592.

In some aspects, the antibody is a Humaneered™ antibody. Humaneering technology is a proprietary method of Kalo-Bios Pharmaceuticals, Inc. (San Francisco, Calif.) for converting non human antibodies into engineered human antibodies. Humaneered™ antibodies are high affinity, and highly similar to human germline antibody sequences.

In some embodiments, the antibody has a level of affinity or avidity for the β integrin which is sufficient to prevent the G protein α subunit from binding to the β integrin. In some embodiments, the antibody has a level of affinity or avidity for the G protein α subunit which is sufficient to prevent a β integrin from binding G protein α subunit. Therefore in some embodiments, the affinity constant, $K_a$, (which is the inverted dissocation constant, $K_d$) of the antibody of the invention for the a β integrin is greater than the $K_a$ of G protein α subunit for the β integrin. Alternatively, in some embodiments, the $K_a$ of the antibody of the invention for the G protein α subunit is greater than that of the β integrin for the G protein α subunit. Binding constants, including dissociation constants, may be determined by methods known in the art, including, for example, methods which utilize the principles of surface plasmon resonance, e.g., methods utilizing a Biacore™ system.

In some embodiments, the antibody is in monomeric form, while in other embodiments, the antibody is conjugated to one or more antibodies (e.g., each of which recognize the same epitope of the first antibody). Accordingly, in some aspects, the antibody is in polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

Antigen Binding Fragments

In some aspects of the invention, the compound which inhibits a binding interaction between an α β integrin and a G protein α subunit is an antigen binding fragment of an antibody. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, F(ab')$_2$, dsFv, sFv, diabodies, triabodies, bis-scFvs, fragments expressed by a Fab expression library, domain antibodies, VhH domains, V-NAR domains, VH domains, VL domains, and the like. Antibody fragments of the invention, however, are not limited to these exemplary types of antibody fragments.

A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth of a full antibody. Domain antibodies may be derived from full antibodies such as those described herein. The antigen binding fragments in some embodiments are monomeric or polymeric, bispecific or trispecific, bivalent or trivalent.

Antibody fragments that contain the antigen binding, or idiotype, of the antibody molecule may be generated by techniques known in the art. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab' fragments which may be generated by treating the antibody molecule with papain and a reducing agent.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., *Biomol Eng.* 2001 18:95-108, (2001) and Todorovska et al., *J Immunol Methods.* 248:47-66, (2001).

Bispecific antibodies (bscAb) are molecules comprising two single-chain Fv fragments joined via a glycine-serine linker using recombinant methods. The V light-chain ($V_L$) and V heavy-chain ($V_H$) domains of two antibodies of interest in exemplary embodiments are isolated using standard PCR methods. The $V_L$ and $V_H$ cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both applications of which are incorporated herein by reference in their entirety.

Methods of Antibody or Antigen Binding Fragment Production

Suitable methods of making antibodies are known in the art. For instance, standard hybridoma methods are described in, e.g., Harlow and Lane (eds.), Antibodies: A Laboratory Manual, CSH Press (1988), and C A. Janeway et al. (eds.), Immunobiology, $5^{th}$ Ed., Garland Publishing, New York, N.Y. (2001)).

Briefly, a polyclonal antibody is prepared by immunizing an animal with an immunogen comprising a polypeptide of the present invention and collecting antisera from that immunized animal. A wide range of animal species can be used for the production of antisera. In some aspects, an animal used for production of anti-antisera is a non-human animal including rabbits, mice, rats, hamsters, goat, sheep, pigs or horses. Because of the relatively large blood volume of rabbits, a rabbit is a preferred choice for production of polyclonal antibodies. In an exemplary method for generating a polyclonal antisera immunoreactive with the chosen β integrin epitope, 50 μg of β integrin antigen is emulsified in Freund's Complete Adjuvant for immunization of rabbits. At intervals of, for example, 21 days, 50 μg of epitope are emulsified in Freund's Incomplete Adjuvant for boosts. Polyclonal antisera may be obtained, after allowing time for antibody generation, simply by bleeding the animal and preparing serum samples from the whole blood.

Monoclonal antibodies for use in the invention may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

Briefly, in exemplary embodiments, to generate monoclonal antibodies, a mouse is injected periodically with recombinant β integrin against which the antibody is to be raised (e.g., 10-20 μg emulsified in Freund's Complete Adjuvant). The mouse is given a final pre-fusion boost of an β integrin polypeptide in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice.

Spleen cells ($1\times10^8$) are combined with $2.0\times10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5 \times 10^6$ splenocytes/ml and plated into 10 Corning flat-bottom 96-well tissue culture plates (Corning, Corning N.Y.).

On days 2, 4, and 6, after the fusion, 100 µl of medium is removed from the wells of the fusion plates and replaced with fresh medium. On day 8, the fusion is screened by ELISA, testing for the presence of mouse IgG binding to β integrin as follows. Immulon 4 plates (Dynatech, Cambridge, Mass.) are coated for 2 hours at 37° C. with 100 ng/well of β integrin diluted in 25 mM Tris, pH 7.5. The coating solution is aspirated and 200 µl/well of blocking solution (0.5% fish skin gelatin (Sigma) diluted in CMF-PBS) is added and incubated for 30 min. at 37° C. Plates are washed three times with PBS with 0.05% Tween 20 (PBST) and 50 µl culture supernatant is added. After incubation at 37° C. for 30 minutes, and washing as above, 50 µl of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 µl substrate, consisting of 1 mg/ml o-phenylene diamine (Sigma) and 0.1 µl/ml 30% $H_2O_2$ in 100 mM Citrate, pH 4.5, are added. The color reaction is stopped after 5 minutes with the addition of 50 µl of 15% $H_2SO_4$. $A_{490}$ is read on a plate reader (Dynatech).

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/15XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated to be novel compositions of the invention.

Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Antibodies may also be produced by inducing in vivo production in the lymphocyte population or by screening recombinant immunoglobulin libraries or panels of highly specific binding reagents as disclosed in Orlandi et al (Proc Natl Acad Sci 86: 3833-3837; 1989), and Winter G and Milstein C (Nature 349: 293-299, 1991).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, $3^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. No. 5,403,484; U.S. Pat. No. 5,571,698; U.S. Pat. No. 5,837,500; U.S. Pat. No. 5,702,892. The techniques described in U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; U.S. Pat. No. 6,225,447, Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol, 235, 959-973 (1994).

Techniques developed for the production of "chimeric antibodies", the splicing of mouse antibody genes to human antibody genes to obtain a molecule with appropriate antigen specificity and biological activity, can be used (Morrison et al., Proc Natl Acad Sci 81: 6851-6855, 1984; Neuberger et al., Nature 312: 604-608, 1984; Takeda et al., Nature 314: 452-454; 1985). Alternatively, techniques described for the production of single chain antibodies (U.S. Pat. No. 4,946,778) can be adapted to produce β integrin- or G protein α subunit-specific single chain antibodies.

A preferred chimeric or humanized antibody has a human constant region, while the variable region, or at least a CDR, of the antibody is derived from a non-human species. Methods for humanizing non-human antibodies are well known in the art. (see U.S. Pat. Nos. 5,585,089, and 5,693,762). Generally, a humanized antibody has one or more amino acid residues introduced into its framework region from a source which is non-human. Humanization can be performed, for example, using methods described in Jones et al. (*Nature* 321: 522-525, 1986), Riechmann et al., (*Nature*, 332: 323-327, 1988) and Verhoeyen et al. (*Science* 239:1534-1536, 1988), by substituting at least a portion of a rodent complementarity-determining region (CDRs) for the corresponding regions of a human antibody. Numerous techniques for preparing engineered antibodies are described, e.g., in Owens and Young, *J. Immunol. Meth.*, 168:149-165 (1994). Further changes can then be introduced into the antibody framework to modulate affinity or immunogenicity.

Likewise, using techniques known in the art to isolate CDRs, compositions comprising CDRs are generated. Complementarity determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions (Janeway and Travers, *Immunobiology*, $2^{nd}$ Edition, Garland Publishing, New York, (1996)). The murine CDR also are found at approximately these amino acid residues. It is understood in the art that CDR regions may be found within several amino acids of these approximated residues set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. Techniques for cloning and expressing nucleotide and polypeptide sequences are well-established in the art (see e.g. Sambrook et al., *Molecular Cloning: A Laboratory Manual*, $2^{nd}$ Edition, Cold Spring Harbor, N.Y. (1989)). The amplified CDR sequences are ligated into an appropriate plasmid. The plasmid comprising one, two, three, four, five and/or six cloned CDRs optionally contains additional polypeptide encoding regions linked to the CDR.

Framework regions (FR) of a murine antibody are humanized by substituting compatible human framework regions chosen from a large database of human antibody variable sequences, including over twelve hundred human $V_H$ sequences and over one thousand $V_L$ sequences. The database of antibody sequences used for comparison is downloaded from Andrew C. R. Martin's KabatMan web page (http://www.rubic.rdg.ac.uk/abs/). The Kabat method for identifying CDR provides a means for delineating the approximate CDR and framework regions from any human antibody and comparing the sequence of a murine antibody for similarity to determine the CDRs and FRs. Best matched human $V_H$ and $V_L$ sequences are chosen on the basis of high overall framework matching, similar CDR length, and minimal mismatching of canonical and $V_H/V_L$ contact residues. Human framework regions most similar to the murine sequence are inserted between the murine CDR. Alternatively, the murine framework region may be modified by making amino acid substitutions of all or part of the native framework region that more closely resemble a framework region of a human antibody.

Additionally, another useful technique for generating antibodies for use in the present invention may be one which uses a rational design type approach. The goal of rational design is to produce structural analogs of biologically active polypeptides or compounds with which they interact (agonists, antagonists, inhibitors, peptidomimetics, binding partners, etc.). In one approach, one would generate a three-dimensional structure for the antibodies or an epitope binding fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to solve the crystal structure of the specific antibodies. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate additional antibodies from banks of chemically- or biologically-produced peptides.

Chemically constructed bispecific antibodies may be prepared by chemically crosslinking heterologous Fab or $F(ab')_2$ fragments by means of chemicals such as heterobifunctional reagent succinimidyl-3-(2-pyridyldithiol)-propionate (SPDP, Pierce Chemicals, Rockford, Ill.). The Fab and $F(ab')_2$ fragments can be obtained from intact antibody by digesting it with papain or pepsin, respectively (Karpovsky et al., J. Exp. Med. 160:1686-701, 1984; Titus et al., J. Immunol., 138:4018-22, 1987).

Methods of testing antibodies for the ability to bind to the epitope of the β integrin regardless of how the antibodies are produced are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Aptamers

In some embodiments, the compound that inhibits a binding interaction between β integrin and G protein α subunit is an analog of an antibody. In some aspects, the compound is an aptamer. Recent advances in the field of combinatorial sciences have identified short polymer sequences (e.g., oligonucleic acid or peptide molecules) with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the invention, molecular evolution techniques can be used to isolate compounds specific for the β integrins or G protein α subunits described herein that inhibit the binding interaction between β integrin and G protein α subunit. For more on aptamers, see, generally, Gold, L., Singer, B., He, Y. Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

Epitopes

By "epitope" as used herein is meant the region of or within the β integrin or G protein α subunit which is bound by the compound, e.g., the antibody, the antigen binding fragment, the aptamer. In some embodiments, the epitope is a linear epitope. By "linear epitope" as used herein refers to the region of or within the β integrin or G protein α subunit which is bound by the compound, which region is composed of contiguous amino acids of the amino acid sequence of the β integrin or G protein α subunit. The amino acids of a linear epitope are located in close promity to each other in the primary structure of the antigen and the secondary and/or tertiary structure(s) of the antigen. For example, when the antigen, e.g., β integrin or G protein α subunit, is in its properly folded state (e.g., its native conformation), the contiguous amino acids of the linear epitope are located in close proximity to one another.

In other aspects, the epitope of the binding construct is a conformational epitope. By "conformational epitope" is meant an epitope which is composed of amino acids which are located in close proximity to one another only when the β integrin or G protein α subunit is in its properly folded state, but are not contiguous amino acids of the amino acid sequence of the β integrin or G protein α subunit.

In exemplary embodiments of the invention, the compound that inhibits a binding interaction between a β integrin and a G protein α subunit binds to an epitope of a β integrin. In some aspects, the epitope to which the compound binds is within the cytoplasmic domain of a β integrin. In exemplary aspects, the epitope to which the compound binds is within the cytoplasmic domain of a $β_{1A}$ integrin, $β_{1D}$ integrin, $β_2$ integrin, $β_3$ integrin, $β_5$ integrin, $β_6$ integrin, or $β_7$ integrin. In exemplary aspects, the epitope to which the compound binds is within amino acids 738-777 of a $β_{1A}$ integrin (SEQ ID NO: 12) or amino acids 732-778 of a $β_{1A}$ integrin (SEQ ID NO: 12). In exemplary aspects, the epitope to which the compound binds is within amino acids 738-776 of a $β_{1D}$ integrin (SEQ ID NO: 13) or amino acids 732-781 of a $β_{1D}$ integrin (SEQ ID NO: 13). In exemplary aspects, the epitope to which the compound binds is within amino acids 702-746 of a $β_2$ integrin (SEQ ID NO: 14) or amino acids 702-747 of a $β_2$ integrin (SEQ ID NO: 14). In exemplary aspects, the epitope to which the compound binds is within amino acids 722-761 of a $β_3$ integrin (SEQ ID NO: 15) or amino acids 716-762 of a $β_3$ integrin (SEQ ID NO: 15). In exemplary aspects, the epitope to which the compound binds is within amino acids 720-765 of a $β_5$ integrin (SEQ ID NO: 16) or amino acids 720-776 of a $β_5$ integrin (SEQ ID NO: 16). In exemplary aspects, the epitope to which the compound binds is within amino acids 710-755 of a $β_6$ integrin (SEQ ID NO: 17) or amino acids 710-767 of a $β_6$ integrin (SEQ ID NO: 17). In exemplary aspects, the epitope to which the compound binds is within amino acids 728-773 of a $β_7$ integrin (SEQ ID NO: 18) or amino acids 728-779 of a $β_7$ integrin (SEQ ID NO: 18).

In exemplary embodiments of the invention, the compound that inhibits a binding interaction between a β integrin and a G protein α subunit binds to an epitope of the G protein α subunit. In some aspects, the epitope to which the compound binds is within the Switch Region I of a G protein α subunit. In exemplary aspects, the epitope to which the compound binds is within the Switch Region I of G protein α subunit $Gα_{12}$ or $Gα_{13}$. In exemplary aspects, the compound binds to an epitope within amino acids 201-216 of $Gα_{12}$ (SEQ ID NO: 11) or amino acids 197-212 of $Gα_{13}$ (SEQ ID NO: 10). In exemplary aspects, the compound binds to an epitope within amino acids 197-209 of $Gα_{13}$ (SEQ ID NO: 10) or amino acids 198-206 of $Gα_{13}$ (SEQ ID NO: 10). In exemplary aspects, the compound binds to an epitope within amino acids 203-211 of $Gα_{12}$ (SEQ ID NO: 11).

In yet other embodiments, the compound that inhibits the binding interaction between a β integrin and a G protein α subunit binds to an epitope comprising the amino acid sequence of any of the peptides or peptide analogs described herein. See, e.g., the section entitled "Fragments of β Integrin or G protein α Subunit and Derivatives Thereof." In exemplary aspects, the compound that inhibits the binding interaction between a β integrin and a G protein α subunit binds to an epitope comprising an amino acid sequence of any of SEQ ID NOs: 19-40.

Peptides

In some embodiments of the invention, the compound that inhibits a binding interaction between a β integrin and a G protein α subunit is a peptide comprising at least four amino acids connected via peptide bonds. Accordingly, the invention provides a peptide. In some aspects, the peptide is about 4 to about 50 amino acids in length. In some aspects, the compound is about 5 to about 25 amino acids in length. In some aspects, the compound is about 5 to 20 amino acids in length. In some aspects, the peptide is 5-15 amino acids in length. In some aspects, the peptide is 5-9 or 5-8 or 5-7 amino acids in length. In some embodiments, the peptide is a 5-mer, 6-mer, 7-mer, 8-mer, 9-mer-10-mer, 11-mer, 12-mer, 13-mer, 14-mer, 15-mer, 16-mer, 17-mer, 18-mer, 19-mer, or 20-mer.

Fragments of β Integrin or G protein α Subunit and Derivatives Thereof

In some embodiments, the peptide that inhibits a binding interaction between a β integrin and a G protein α subunit comprises a fragment or is a fragment of a human wild-type β integrin, e.g., any of those disclosed herein. As used herein, the term "fragment" does not encompass a full length β integrin or a full length G protein α subunit. In some aspects, the compound comprises or is a fragment of a $β_{1A}$ integrin, $β_{1D}$ integrin, $β_2$ integrin, $β_3$ integrin, $β_5$ integrin, $β_6$ integrin, or $β_7$ integrin. In specific aspects, the compound comprises 4 to 50 (e.g., 5 to 25) consecutive amino acids of a cytoplasmic domain of a β integrin.

In exemplary embodiments of the invention, the compound that inhibits a binding interaction between a β integrin and a G protein α subunit comprises 4 to 50 (e.g., 5 to 25) consecutive amino acids of the cytoplasmic domain of a $β_{1A}$ integrin, $β_{1D}$ integrin, $β_2$ integrin, $β_3$ integrin, $β_5$ integrin, $β_6$ integrin, or $β_7$ integrin. In exemplary aspects, the compound comprises 4 to 50 (e.g., 5 to 25) consecutive amino acids of amino acids 738-777 of a $β_{1A}$ integrin (SEQ ID NO: 12) or amino acids 732-778 of a $β_{1A}$ integrin (SEQ ID NO: 12). In exemplary aspects, the compound comprises 4 to 50 (e.g., 5 to 25) consecutive amino acids of amino acids 738-776 of a $β_{1D}$ integrin (SEQ ID NO: 13) or amino acids 732-781 of a $β_{1D}$ integrin (SEQ ID NO: 13). In exemplary aspects, the compound comprises 4 to 50 (e.g., 5 to 25) consecutive amino acids of amino acids 702-746 of a $β_2$ integrin (SEQ ID NO: 14) or amino acids 702-747 of a $β_2$ integrin (SEQ ID NO: 14). In exemplary aspects, the compound comprises 4 to 50 (e.g., 5 to 25) consecutive amino acids of amino acids 722-761 of a $β_3$ integrin (SEQ ID NO: 15) or amino acids 716-762 of a $β_3$ integrin (SEQ ID NO: 15). In exemplary aspects, the compound comprises 4 to 50 (e.g., 5 to 25) consecutive amino acids of amino acids 720-765 of a $β_5$ integrin (SEQ ID NO: 16) or amino acids 720-776 of a $β_5$ integrin (SEQ ID NO: 16). In exemplary aspects, the compound comprises 4 to 50 (e.g., 5 to 25) consecutive amino acids of amino acids 710-755 of a $β_6$ integrin (SEQ ID NO: 17) or amino acids 710-767 of a $β_6$ integrin (SEQ ID NO: 17). In exemplary aspects, the compound comprises 4 to 50 (e.g., 5 to 25) consecutive amino acids of amino acids 728-773 of a $\beta_7$ integrin (SEQ ID NO: 18) or amino acids 728-779 of a $\beta_7$ integrin (SEQ ID NO: 18).

In exemplary embodiments of the invention, the compound that inhibits a binding interaction between a $\beta$ integrin and a G protein $\alpha$ subunit the compound comprises 4 to 50 (e.g., 5 to 25) consecutive amino acids of the G protein $\alpha$ subunit. In some aspects, the compound comprises 4 to 50 (e.g., 5 to 25) consecutive amino acids of the Switch Region I of a G protein $\alpha$ subunit. In exemplary aspects, the compound comprises 4 to 50 (e.g., 5 to 25) consecutive amino acids of the Switch Region I of G protein $\alpha$ subunit $G\alpha_{12}$ or $G\alpha_{13}$. In exemplary aspects, the compound comprises 4 to 50 (e.g., 5 to 25) consecutive amino acids of amino acids 201-216 of $G\alpha_{12}$ (SEQ ID NO: 11) or amino acids 197-212 of $G\alpha_{13}$ (SEQ ID NO: 10). In exemplary aspects, the compound comprises 4 to 50 (e.g., 5 to 25) consecutive amino acids of amino acids 197-209 of $G\alpha_{13}$ (SEQ ID NO: 10) or amino acids 198-206 of $G\alpha_{13}$ (SEQ ID NO: 10). In exemplary aspects, the compound comprises 4 to 50 (e.g., 5 to 25) consecutive amino acids of amino acids 203-211 of $G\alpha_{12}$ (SEQ ID NO: 11).

In exemplary aspects, the compound comprises a core sequence of three amino acids which is a portion or fragment of a cytoplasmic domain of the $\beta$ integrin. For example, the compound comprises a core sequence identical to amino acids 731 to 733 of the amino acid sequence of $\beta_3$ integrin (SEQ ID NO: 15), which is EEE. In exemplary aspects, the compound comprises a core sequence identical to amino acids 747-749 of the amino acid sequence of $\beta_{1A}$ integrin (SEQ ID NO: 12) or $\beta_{1D}$ integrin (SEQ ID NO: 13), amino acids 717-719 of the amino acid sequence of $\beta_2$ integrin (SEQ ID NO: 14), or amino acids 743-745 of the amino acid sequence of $\beta_7$ integrin (SEQ ID NO: 18), each of which is EKE. In exemplary aspects, the compound comprises a core sequence identical amino acids 725-727 of the amino acid sequence of $\beta_6$ integrin (SEQ ID NO: 17), which is EAE. In exemplary aspects, the compound comprises a core sequence identical amino acids 735-737 of the amino acid sequence of $\beta_5$ integrin (SEQ ID NO: 16), which is QSE.

In exemplary embodiments, the compound comprises additional amino acids N-terminal and/or C-terminal to the core sequence. The additional amino acids, e.g., the non-core sequence(s), may represent amino acids which are N-terminal and/or C-terminal to the core sequence of the amino acid sequence of the $\beta$ integrin. For example, the compound may comprise a core sequence of EEE (amino acids 731 to 733 of the amino acid sequence of $\beta_3$ integrin (SEQ ID NO: 15) and may additionally comprise an N-terminal non-core sequence comprising KF (Lys-Phe) and/or a C-terminal non-core sequence comprising RA (Arg-Ala). Accordingly, the compound in exemplary aspects comprises the amino acid sequence of KFEEE (SEQ ID NO: 19), KFEEERA (SEQ ID NO: 20), EEERA (SEQ ID NO: 21). In exemplary aspects, the compound comprises an amino acid sequence of KFEEER-ARAKWDT (SEQ ID NO: 22).

In exemplary aspects, the compound comprises a core sequence of EKE and comprises a N-terminal non-core sequence comprising KF (Lys-Phe) or RF (Arg-Phe) and/or a C-terminal non-core sequence comprising KM (Lys-Met), KL (Lys-Leu), or QQ (Gln-Gln). Accordingly, the compound in exemplary aspects comprises the amino acid sequence of KFEKE (SEQ ID NO: 23), RFEKE (SEQ ID NO: 24), KFEKEKM (SEQ ID NO: 25), KFEKEKL (SEQ ID NO: 26), KFEKEQQ (SEQ ID NO: 27), RFEKEKM (SEQ ID NO: 28), RKFEKEKL (SEQ ID NO: 29), RFEKEQQ (SEQ ID NO: 30), EKEKM (SEQ ID NO: 31), EKEKL (SEQ ID NO: 32), or EKEQQ (SEQ ID NO: 33).

In exemplary aspects, the compound comprises a core sequence of EAE and comprises a N-terminal non-core sequence comprising KF (Lys-Phe) and/or a C-terminal non-core sequence comprising RS (Arg-Ser). Accordingly, the compound in exemplary aspects comprises the amino acid sequence of KFEAE (SEQ ID NO: 34), KFEAERS (SEQ ID NO: 35), or EAERS (SEQ ID NO: 36).

In exemplary aspects, the compound comprises a core sequence of QSE and comprises a N-terminal non-core sequence comprising KF (Lys-Phe) and/or a C-terminal non-core sequence comprising RS (Arg-Ser). Accordingly, the compound in exemplary aspects comprises the amino acid sequence of KFQSE (SEQ ID NO: 37), KFQSERS (SEQ ID NO: 38), or QSERS (SEQ ID NO: 39).

In alternative or additional embodiments, the compound comprises a non-core sequence which is not based on the wild-type sequence of the $\beta$ integrin. In exemplary aspects, the compound may comprise a core sequence of EEE (amino acids 731 to 733 of the amino acid sequence of $\beta_3$ integrin (SEQ ID NO: 15) and may additionally comprise a N-terminal non-core sequence other than KF (Lys-Phe) and/or a C-terminal non-core sequence other than RA (Arg-Ala).

In exemplary embodiments, the peptide that inhibits a binding interaction between a $\beta$ integrin and a G protein $\alpha$ subunit comprises a fragment or is a fragment of a human wild-type G protein $\alpha$ subunit, e.g., $G\alpha_{12}$, $G\alpha_{13}$. In some aspects, the compound comprises or is a fragment of $G\alpha_{12}$ or $G\alpha_{13}$. In specific aspects, the compound comprises 4 to 50 (e.g., 5 to 25) consecutive amino acids of the Switch Region I of the G protein $\alpha$ subunit.

In exemplary aspects, the compound comprises 4 to 50 (e.g., 5 to 25) consecutive amino acids of the Switch Region I of G protein $\alpha$ subunit $G\alpha_{12}$ or $G\alpha_{13}$. In exemplary aspects, the compound comprises 4 to 50 (e.g., 5 to 25) consecutive amino acids of amino acids 201-216 of $G\alpha_{12}$ (SEQ ID NO: 11) or amino acids 197-212 of $G\alpha_{13}$ (SEQ ID NO: 10). In exemplary aspects, the compound comprises 4 to 50 (e.g., 5 to 25) consecutive amino acids of amino acids 197-209 of $G\alpha_{13}$ (SEQ ID NO: 10) or amino acids 198-206 of $G\alpha_{13}$ (SEQ ID NO: 10). In exemplary aspects, the compound comprises 4 to 50 (e.g., 5 to 25) consecutive amino acids of amino acids 203-211 of $G\alpha_{12}$ (SEQ ID NO: 11). In some aspects, the compound comprises an amino acid sequence of LLARRPT-KGIHEY (SEQ ID NO: 40).

In some embodiments, the peptide that inhibits a binding interaction between a $\beta$ integrin and a G protein $\alpha$ subunit comprises an amino acid sequence which is based on the amino acid sequence of a human wild-type $\beta$ integrin, or a fragment thereof, but differs at one or more (e.g., two, three, four, five, six, seven, eight, nine, ten, or more) amino acid positions, when aligned with the human wild-type $\beta$ integrin sequence, or fragment thereof.

In some embodiments, the peptide that inhibits a binding interaction between an a $\beta$ integrin and a G protein $\alpha$ subunit comprises an amino acid sequence which has at least 25% sequence identity to the amino acid sequence of a human wild-type $\beta$ integrin, e.g., SEQ ID NO: 15, or a fragment thereof (e.g., a fragment of about 4 to about 50 contiguous amino acids of SEQ ID NO: 15). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to SEQ ID NO: 15, or a fragment thereof (e.g., a fragment of about 4 to about 25 contiguous amino acids of SEQ ID NO: 15). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to any of SEQ ID NOs: 12-18, or a fragment thereof (e.g., a fragment of about 4 to about 25 contiguous amino acids of any one of SEQ ID NOs:12-18). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to any one of SEQ ID NOs: 19-39.

In some embodiments, the peptide that inhibits a binding interaction between a β integrin and a G protein α subunit comprises an amino acid sequence which is based on the amino acid sequence of a human wild-type G protein α subunit, or a fragment thereof, but differs at one or more (e.g., two, three, four, five, six, seven, eight, nine, ten, or more) amino acid positions, when aligned with the human wild-type G protein α subunit sequence, or fragment thereof. In some embodiments, the peptide that inhibits a binding interaction between an a β integrin and a G protein α subunit comprises an amino acid sequence which has at least 25% sequence identity to the amino acid sequence of a human wild-type G protein α subunit, e.g., SEQ ID NO: 10 or 11 or a fragment thereof (e.g., a fragment of about 4 to about 15 contiguous amino acids of SEQ ID NO: 10 or 11). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to SEQ ID NO: 10 or 11 or a fragment thereof (e.g., a fragment of about 4 to about 10 contiguous amino acids of SEQ ID NO: 10 or 11). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to amino acids 201-216 of $G\alpha_{12}$ (SEQ ID NO: 11) or amino acids 197-212 of $G\alpha_{13}$ (SEQ ID NO: 10), amino acids 197-209 of $G\alpha_{13}$ (SEQ ID NO: 10) or amino acids 198-206 of $G\alpha_{13}$ (SEQ ID NO: 10), amino acids 203-211 of $G\alpha_{12}$ (SEQ ID NO: 11). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to SEQ ID NOs: 40.

In exemplary embodiments, the compound comprises an amino acid sequence:

$Xaa_1Xaa_2Glu$, wherein $Xaa_1$ is Glu or Gln and $Xaa_2$ is Glu, Lys, Ser, or Ala. In exemplary aspects, (i) $Xaa_1$ is Glu and $Xaa_2$ is Glu, Lys, or Ala or (ii) $Xaa_1$ is Gln and $Xaa_2$ is Ser. In exemplary aspects, each of $Xaa_1$ and $Xaa_2$ is Glu. In exemplary aspects, the peptide comprises Phe N-terminal to $Xaa_1$ $Xaa_2$ Glu. In exemplary aspects, the peptide comprises Arg C-terminal to $Xaa_1$ $Xaa_2$ Glu. In exemplary aspects, the peptide comprises Phe N-terminal to $Xaa_1$ $Xaa_2$ Glu and Arg C-terminal to $Xaa_1$ $Xaa_2$ Glu. In exemplary aspects, the compound comprises an extension of two amino acids, $Xaa_1$ $Xaa_0$ N-terminal to $Xaa_1$ $Xaa_2$ Glu. In exemplary aspects, $Xaa_1$ of the N-terminal extension is Lys or Arg. In exemplary aspects, $Xaa_0$ of the N-terminal extension is Phe. In exemplary aspects, the compound comprises an extension of two amino acids $Xaa_3$ $Xaa_4$ C terminal to $Xaa_1$ $Xaa_2$ Glu. In exemplary aspects, $Xaa_3$ of the C-terminal extension is Lys, Arg, or Gln. In exemplary aspects, $Xaa_4$ of the C-terminal extension is Met, Leu, Ala, Ser, or Gln. In exemplary aspects, $Xaa_3$ is Arg and $Xaa_4$ is Ala.

Accordingly, in exemplary aspects of the invention the compound comprises a sequence selected from the group consisting of: HDRKEFAKFEEERARAKWDT (SEQ ID NO: 83) KFEEERARAKWDT (SEQ ID NO: 22); KFEEERA (SEQ ID NO: 20); and EEERA (SEQ ID NO: 21). In exemplary aspects, the peptide comprises, consists essentially of, or consists of FEEERA (SEQ ID NO: 87). In exemplary aspects, the peptide comprises a sequence of KFEEE (SEQ ID NO: 19), FEEER (SEQ ID NO: 84), AKFEEE (SEQ ID NO: 85), KFEEER (SEQ ID NO: 86), FEEERA (SEQ ID NO: 87), EEERAR (SEQ ID NO: 88), EEERARA (SEQ ID NO: 89), or EEERARAK (SEQ ID NO: 90).

In exemplary aspects, the peptide comprises a core of EXE (SEQ ID NO: 93), wherein X is any amino acid. In exemplary aspects, X is Glu, Lys, Ser, or Ala. In exemplary aspects, X is Ala, Gly, Val, Leu, or Ile. In exemplary aspects, X is Glu or Asp. In exemplary aspects, X is Ser or Thr. In exemplary aspects, X is Lys or ornithine or Arg. In exemplary aspects, X is Pro, Phe, Tyr, Trp, Asn, Gln, His, Cys, or Met.

In exemplary aspects, the peptide comprises FEXE (SEQ ID NO: 94, wherein X is any amino acid. In exemplary aspect, X is Glu or Asp. In exemplary aspects, X is Ala, Gly, Val, Leu, or Ile. In exemplary aspects, X is Glu or Asp. In exemplary aspects, X is Ser or Thr. In exemplary aspects, X is Lys or ornithine or Arg. In exemplary aspects, X is Pro, Phe, Tyr, Trp, Asn, Gln, His, Cys, or Met.

In exemplary aspects, the peptide comprises $FEX_1EX_2$ wherein each of X1 and X2 is independently any amino acid. In exemplary aspects, the peptide comprises $FEX_1EX_2$ (SEQ ID NO: 95), wherein X1 is any amino acid and X2 is Lys, Arg, or Gln. In exemplary aspect, X1 is Glu or Asp. In exemplary aspects, X1 is Ala, Gly, Val, Leu, or Ile. In exemplary aspects, X1 is Glu or Asp. In exemplary aspects, X1 is Ser or Thr. In exemplary aspects, X1 is Lys or ornithine or Arg. In exemplary aspects, X1 is Pro, Phe, Tyr, Trp, Asn, Gln, His, Cys, or Met.

In exemplary aspects, the peptide comprises EX1EX2 wherein each of X1 and X2 is independently any amino acid. In exemplary aspects, the peptide comprises EX1EX2 (SEQ ID NO: 96), wherein X1 is any amino acid and X2 is Lys, Arg, or Gln. In exemplary aspect, X1 is Glu or Asp. In exemplary aspects, X1 is Ala, Gly, Val, Leu, or Ile. In exemplary aspects, X1 is Glu or Asp. In exemplary aspects, X1 is Ser or Thr. In exemplary aspects, X1 is Lys or ornithine or Arg. In exemplary aspects, X1 is Pro, Phe, Tyr, Trp, Asn, Gln, His, Cys, or Met.

In exemplary aspects, the peptide comprises X1FEX2E wherein each of X1 and X2 is independently any amino acid. In exemplary aspects, the peptide comprises X1FEX2E (SEQ ID NO: 97), wherein X1 is Lys or Arg and X2 is any amino acid. In exemplary aspect, X2 is Glu or Asp. In exemplary aspects, X2 is Ala, Gly, Val, Leu, or Ile. In exemplary aspects, X2 is Glu or Asp. In exemplary aspects, X2 is Ser or Thr. In exemplary aspects, X2 is Lys or ornithine or Arg. In exemplary aspects, X2 is Pro, Phe, Tyr, Trp, Asn, Gln, His, Cys, or Met.

In exemplary aspects, the peptide comprises X1FEX2EX3 wherein each of X1, X2, and X3 is independently any amino acid. In exemplary aspects, the peptide comprises X1FEX2EX3 (SEQ ID NO: 98), wherein X1 is Lys or Arg, wherein X2 is any amino acid, and X3 is Lys, Arg, or Gln. In exemplary aspect, X2 is Glu or Asp. In exemplary aspects, X2 is Ala, Gly, Val, Leu, or Ile. In exemplary aspects, X2 is Glu or Asp. In exemplary aspects, X2 is Ser or Thr. In exemplary aspects, X2 is Lys or ornithine or Arg. In exemplary aspects, X2 is Pro, Phe, Tyr, Trp, Asn, Gln, His, Cys, or Met.

In exemplary aspects, the peptide comprises X1FEX2EX3X4 wherein each of X1, X2, X3, and X4 is independently any amino acid. In exemplary aspects, the peptide comprises X1FEX2EX3X4 (SEQ ID NO: 99), wherein X1 is Lys or Arg, X2 is any amino acid, X3 is Lys, Arg, or Gln, and X4 is any amino acid, optionally, Met, Ala, Leu, Ser, or Gln. In exemplary aspect, X2 is Glu or Asp. In exemplary aspects, X2 is Ala, Gly, Val, Leu, or Ile. In exemplary aspects, X2 is Glu or Asp. In exemplary aspects, X2 is Ser or Thr. In exemplary aspects, X2 is Lys or ornithine or Arg. In exemplary aspects, X2 is Pro, Phe, Tyr, Trp, Asn, Gln, His, Cys, or Met.

In exemplary aspects, the peptide comprises any of SEQ ID NOs: 100-122.

In exemplary embodiments of the invention, the compound comprises the amino acid sequence $X_1X_2X_3X_4X_5X_6X_7KX_8X_9X_{10}X_{11}X_{12}$ (SEQ ID NO: 44). In exemplary aspects, each of $X_1$, $X_2$, $X_3$, $X_8$, and $X_9$ is independently an aliphatic amino acid. In exemplary aspects, each of $X_4$, $X_5$, and $X_{10}$ is independently a basic amino acid. In exemplary aspects, $X_6$ is Pro. In exemplary aspects, $X_7$ and $X_{12}$ is independently a hydroxyl-containing amino acid. In exemplary aspects, $X_{11}$ is an acidic amino acid. In exemplary aspects, each of $X_1$, $X_2$, $X_3$, $X_8$, and $X_9$ is independently selected from the group consisting of L, A, G, and I. In exemplary aspects, each of $X_4$, $X_5$, and $X_{10}$ is independently selected from the group consisting of R and H. In exemplary aspects, $X_7$ and $X_{12}$ is independently a T or Y. In exemplary aspects, $X_{11}$ is an E or D. Accordingly, in exemplary aspects, the compound comprises the amino acid sequence of LLAR-RPTKGIHEY (SEQ ID NO: 45).

Additional Peptide Modifications

In alternative or additional embodiments of the invention, the peptide is lipidated (e.g., myritoylated, palmitoylated), glycosylated, amidated, carboxylated, phosphorylated, esterified, acylated, acetylated, cyclized, or converted into an acid addition salt and/or optionally dimerized or polymerized, or conjugated, as further described herein.

Lipidation

In exemplary aspects, the peptide is lipidated, or otherwise, attached to a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In exemplary aspects, the peptide is covalently attached to a fatty acid. In some specific embodiments, the fatty acid is a C4 to C30 fatty acid. The fatty acid in exemplary aspects is any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the fatty acid is a C8 to C20 fatty acid, a C12 to C29 fatty acid, or a C14 to C18 fatty acid, e.g., a C14 fatty acid or a C16 fatty acid.

In exemplary aspects, the peptide is covalently attached to a fatty acid and the fatty acid is attached to the N-terminal amino acid or the C-terminal amino acid. In alternative aspects, the peptide is covalently attached to a fatty acid and the fatty acid is attached to an internal amino acid of the peptide, e.g., via a functional group off of a side chain of the internal amino acid. For example, the fatty acid may be attached to an amine, hydroxyl, or thiol of a side chain of an internal amino acid. In exemplary aspects, the peptide is covalently attached to a fatty acid and the fatty acid is attached to the second third, fourth, fifth, sixth, seventh, eighth, ninth, tenth, eleventh, or twelvth amino acid.

In exemplary aspects, the peptide comprises the amino acid sequence of any one of SEQ ID NOs: 19-39, 84-90, and 93-122 and the peptide is covalently attached to a C4-C30 fatty acid. In exemplary aspects, the peptide is any one of SEQ ID NOs: 355-412.

In some aspects, the first amino acid of the peptide is myristoylated at the N-terminus in which the N-terminal alpha —NH$_2$ group of an unmodified peptide is attached to a fatty acid. In exemplary aspects, the peptide is any one of SEQ ID NOs: 123-180.

In some aspects, the first amino acid of the peptide is myristoylated at the N-terminus in which the N-terminal alpha —NH$_2$ group of an unmodified peptide is attached to a C4-C30 fatty acid. In exemplary aspects, the peptide is any one of SEQ ID NOs: 181-238.

In some aspects, the first amino acid of the peptide is myristoylated at the N-terminus in which the N-terminal alpha —NH$_2$ group of an unmodified peptide is attached to a C12-C18 fatty acid. In exemplary aspects, the peptide is any one of SEQ ID NOs: 239-296.

In some aspects, the first amino acid of the peptide is myristoylated at the N-terminus in which the N-terminal alpha —NH$_2$ group of an unmodified peptide is attached to a myristate. In exemplary aspects, the peptide is any one of SEQ ID NOs: 297-354.

In exemplary aspects, the peptide comprises a my

In exemplary aspects, the lipid attached to the peptide facilitates micelle formation of the peptide. For further descriptions of micellar forms of peptides, see the descriptions below under "Micelles."

Cyclization

In exemplary aspects, the peptide is cyclized. For example, the peptide may comprise two Cys residues, the sulfur atoms of which participate in the formation of a disulfide bridge. In exemplary aspects, the peptide comprises a Cys residue as the terminal residues. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

The alpha helix of the analog can alternatively be stabilized through other means of peptide cyclizing, which means are reviewed in Davies, J. Peptide. Sci. 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

Peptide Analogs

In some embodiments, the compound is a peptide analog having a structure based on one of the peptides disclosed herein (the "parent peptide") but differs from the parent peptide in one or more respects. Accordingly, as appreciated by one of ordinary skill in the art the teachings of the parent peptides provided herein may also be applicable the peptide analogs.

In some aspects, the peptide analog comprises the structure of a parent peptide, except that the peptide analog comprises one or more non-peptide bonds in place of peptide bond(s). In exemplary aspects, the peptide analog comprises in place of a peptide bond, an ester bond, an ether bond, a thioether bond, an amide bond, and the like. In some aspects, the peptide analog is a depsipeptide comprising an ester linkage in place of a peptide bond.

In some aspects, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met (O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe (4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyro sine, O-Phosphotyro sine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain aspects, the peptide analog comprising one or more non-conservative amino acid substitutions inhibits the binding interaction between β integrin and G protein α subunit to an extent better than the parent peptide.

In some embodiments, and/or one or more amino acid insertions or deletions, in reference to the parent peptide described herein. In some embodiments, the peptide analog comprises an insertion of one or more amino acids at the N- or C-terminus in reference to the parent peptide. In some embodiments, the peptide analog comprises a deletion of one or more amino acids at the N- or C-terminus in reference to the parent peptide. In these aspects, the peptide analog still functions to a similar extent, the same extent, or an improved extent as the parent peptide to inhibit the binding interaction between β integrin and G protein α subunit.

In some aspects, the peptide analog is a peptidomimetic. Peptidomimetics as well as methods of making the same are known in the art. See, for example, *Advances in Amino Acid Mimetics and Peptidomimetics*, Volumes 1 and 2, ed., Abell, A., JAI Press Inc., Greenwich, Conn., 2006. In some aspects, the peptidomimetic is a D-peptide peptidomimetic comprising D-isomer amino acids. In some aspects, the peptidomimetic is a peptoid in which the side chain of an amino acid is connected to the alpha nitrogen atom of the peptide backbone. Methods of making peptoids are known in the art. See, e.g., Zuckermann et al., *JACS* 114(26): 10646-10647 (1992) and *Design, Synthesis, and Evaluation of Novel Peptoids*, Fowler, Sarah, University of Wisconsin-Madison, 2008. In some aspects, the peptidomimetic is a β-peptide comprising β amino acids which have their amino group bonded to the β-cargon rather than the alpha carbon. Methods of making β-peptides are known in the art. See, for example, Seebach et al., *Helvetica Chimica Acta* 79(4): 913-941 (1996).

Pharmaceutically Acceptable Salts

With regard to the invention, the compounds that inhibit a binding interaction between a β integrin and a G protein α subunit, (which compounds are collectively referred to hereinafter as "active agents") in some aspects is in the form of a salt, e.g., a pharmaceutically acceptable salt. Such salts can be prepared in situ during the final isolation and purification of the active agent or separately prepared by reacting a free base function with a suitable acid. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate.

Basic addition salts also can be prepared in situ during the final isolation and purification of the active agent, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like.

Further, basic nitrogen-containing groups can be quaternized with such active agents as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Isolated and Purified

The compounds of the invention that inhibit a binding interaction between a β integrin and a G protein α subunit can be isolated and/or purified. The term "isolated" as used herein means having been removed from its natural environment. The term "purified" as used herein means having been increased in purity, wherein "purity" is a relative term, and not to be necessarily construed as absolute purity. In exemplary aspects, the purity of the compound (e.g., in the composition) is at least or about 50%, at least or about 60%, at least or about 70%, at least or about 80%, at least or about 90%, at least or about 95%, or at least or about 98% or is about 100%.

Methods of Making Peptides

The peptides of the present disclosure may be obtained by methods known in the art. Suitable methods of de novo synthesizing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Additional exemplary methods of making the peptides of the invention are set forth herein.

In some embodiments, the peptides described herein are commercially synthesized by companies, such as Synpep (Dublin, Calif.), Peptide Technologies Corp. (Gaithersburg, Md.), Multiple Peptide Systems (San Diego, Calif.), Peptide 2.0 Inc. (Chantilly, Va.), and American Peptide Co. (Sunnyvale, Calif.). In this respect, the peptides can be synthetic, recombinant, isolated, and/or purified.

Also, in some aspects, the peptides are recombinantly produced using a nucleic acid encoding the amino acid sequence of the peptide using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994.

Nucleic Acids

In exemplary embodiments of the invention, the compound that inhibits a binding interaction between a β integrin and a G protein α subunit comprises or is a nucleic acid comprising a nucleotide sequence encoding any of the antibodies or peptides described herein (including analogs thereof). The nucleic acid can comprise any nucleotide sequence which encodes any of the antibodies, peptides, or analogs thereof.

In exemplary embodiments of the invention, the compound is a nucleic acid which inhibits expression of the β integrin or the G protein α subunit. In exemplary aspects, the compound is an antisense molecule, a microRNA (miRNA), small hairpin (shRNA), and the like. In exemplary embodiments of the invention, the compound is a nucleic acid which inhibits expression of any of the β integrins or G protein α subunits described herein. In exemplary aspects, the compound is a small interfering RNA molecule (siRNA). In some aspects, the siRNA inhibits the expression $G\alpha_{13}$. For example, the siRNA comprises the sequence of SEQ ID NO: 7 or 8.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. In other embodiments, the nucleic acid comprises one or more insertions, deletions, inversions, and/or substitutions.

In some aspects, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids in some aspects are constructed based on chemical synthesis and/or enzymatic ligation reactions using procedures known in the art. See, for example, Sambrook et al., supra; and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridme, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

Recombinant Expression Vector

The nucleic acids of the invention in some aspects are incorporated into a recombinant expression vector. In this regard, the invention provides recombinant expression vectors comprising any of the presently disclosed nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The presently disclosed recombinant expression vectors may comprise any type of nucleotides, including, but not limited to DNA and RNA, which may be single-stranded or double-stranded, synthesized or obtained in part from natural sources, and which can contain natural, non-natural or altered nucleotides. The recombinant expression vectors may comprise naturally-occurring or non-naturally-occurring internucleotide linkages, or both types of linkages. In some aspects, the altered nucleotides or non-naturally occurring internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGT1 1, λZapII (Stratagene), λEMBL4, and λNMl 149, also can be used. Examples of plant expression vectors include pBIOl, pBI101.2, pBIl01.3, pBIl21 and pBIN19 (Clontech). Examples of animal expression vectors include pEUK-Cl, pMAM and pMAMneo (Clontech). In some aspects, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from CoIEl, 2μ plasmid, λ, SV40, bovine papilloma virus, and the like.

In some aspects, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector may include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the presently disclosed expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The presently disclosed recombinant expression vectors may be designed for either transient expression, for stable expression, or for both. Also, the recombinant expression vectors may be made for constitutive expression or for inducible expression. Further, the recombinant expression vectors may be made to include a suicide gene.

As used herein, the term "suicide gene" refers to a gene that causes the cell expressing the suicide gene to die. The suicide gene in some aspects is a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews. Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Host Cells

In exemplary embodiments, the compound is a cell expressing the nucleic acid of the invention, optionally, wherein the nucleic acid is pary of a recombinant expression vector. As used herein, the term "host cell" refers to any type of cell that can contain the presently disclosed recombinant expression vector. The host cell in some aspects is a eukaryotic cell, e.g., plant, animal, fungi, or algae, or can be a prokaryotic cell, e.g., bacteria or protozoa. The host cell in some aspects is a cultured cell or a primary cell, i.e., isolated directly from an organism, e.g., a human. The host cell in some aspects is an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is in some aspects is a prokaryotic cell, e.g., a DH5α cell. For purposes of producing a recombinant polypeptide the host cell is in some aspects a mammalian cell, e.g., a human cell. The host cell may be of any cell type, can originate from any type of tissue, and can be of any developmental stage.

Also provided by the invention is a population of cells comprising at least one host cell described herein. The population of cells in some aspects is a heterogeneous population comprising the host cell comprising any of the recombinant expression vectors described, in addition to at least one other cell, which does not comprise any of the recombinant expression vectors. Alternatively, in some aspects, the population of cells is a substantially homogeneous population, in which the population comprises mainly of host cells (e.g., consisting essentially of) comprising the recombinant expression vector. The population in some aspects is a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

Conjugates

In some embodiments, the compounds of the invention are attached or linked or conjugated to a second moiety (e.g., a heterologous moiety, a conjugate moiety). As used herein, the term "heterologous moiety" is synonomous with "conjugate moiety" and refers to any molecule (chemical or biochemical, naturally-occurring or non-coded) which is different from the compounds of the invention. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent.

In some embodiments, the compounds are chemically modified with various substituents. In some embodiments, the chemical modifications impart additional desirable characteristics as discussed herein. Chemical modifications in some aspects take a number of different forms such as heterologous peptides, polysaccharides, lipids, radioisotopes, nonstandard amino acid resides and nucleic acids, metal chelates, and various cytotoxic agents.

In some embodiments, the compounds are fused to heterologous peptides to confer various properties, e.g., increased solubility and/or stability and/or half-life, resistance to proteolytic cleavage, modulation of clearance, targeting to particular cell or tissue types. In some embodiments, the compound is linked to a Fc domain of IgG or other immunoglobulin. In some embodiments, the compound is fused to alkaline phosphatase (AP). Methods for making Fc or AP fusion constructs are found in WO 02/060950. By fusing the compound with protein domains that have specific properties (e.g. half life, bioavailability) it is possible to confer these properties to the compound of the invention.

When the compounds are peptides, they can be modified, for instance, by glycosylation, amidation, carboxylation, or phosphorylation, or by the creation of acid addition salts, amides, esters, in particular C-terminal esters, and N-acyl derivatives, as discussed above. The peptides also can be modified to create peptide derivatives by forming covalent or noncovalent complexes with other moieties. Covalently bound complexes can be prepared by linking the chemical moieties to functional groups on the side chains of amino acids comprising the peptides, or at the N- or C-terminus.

Peptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin). Examples of analogs are described in WO 98/28621 and in Olofsson, et al, Proc. Nat'l. Acad. Sci. USA, 95:11709-11714 (1998), U.S. Pat. Nos. 5,512,545, and 5,474,982; U.S. Patent Application Nos. 20020164687 and 20020164710.

Cysteinyl residues most commonly are reacted with haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-.beta.(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R1) such as 1-cyclohexyl-3-(2-morpholinyl-(4-ethyl)carbodiimide or 1-ethyl-3(4 azonia 4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking the binding construct to water-insoluble support matrixes. Such derivation may also provide the linker that may connect adjacent binding elements in a binding construct, or a binding elements to a heterologous peptide, e.g., a Fc fragment. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiiobis(succinimidyl-propioonate), and bifunctional maleimides such as bis-N-maleimido-1,8-octane. Derivatizing agents such as methyl-3-[(p-azidophenyl)dithio]propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecule Properties, W. H. Freeman & Co., San Francisco, pp. 79-86,1983), acetylation of the N-terminal amine, and, in some instances, amidation of the C-terminal carboxyl groups. Such derivatives are chemically modified polypeptide compositions in which the binding construct polypeptide is linked to a polymer.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the binding construct becomes attached to one or more polymer molecules, and (b) obtaining the reaction product(s). The optimal reaction conditions will be determined based on known parameters and the desired result. For example, the larger the ratio of polymer molecules:protein, the greater the amount of attached polymer molecule. In some embodiments, the compound may have a single polymer molecule moiety at the amino terminus. (See, e.g., U.S. Pat. No. 5,234,784).

Derivatized binding constructs disclosed herein may have additional activities, enhanced or reduced biological activity, or other characteristics, such as increased or decreased half-life, as compared to the non-derivatized molecules.

In some embodiments, the compound is directly joined to a conjugate moiety in the absence of a linker. In alternative aspects, the compound is indirectly connected to the conjugate moiety via one or more linkers. Whether directly joined together or indirectly joined together through a linker, the compound may be connected through covalent bonds (e.g., a peptide, ester, amide, or sulfhydryl bond) or non-covalent bonds (e.g., via hydrophobic interaction, hydrogen bond, van der Waals bond, electrostatic or ionic interaction), or a combination thereof. The compound of the invention and conjugate moiety may be connected via any means known in the art, including, but not limited to, via a linker of any of the invention. See, for example, the section herein entitled "Linkers."

Conjugates: Fc Fusions

For substituents such as an Fc region of human IgG, the fusion can be fused directly to a compound of the invention or fused through an intervening sequence. For example, a human IgG hinge, CH2 and CH3 region may be fused at either the N-terminus or C-terminus of a binding construct to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation. As noted above, in some embodiments, the compounds are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Heterologous Moieties: Polymers, Carbohydrates, and Lipids

In some embodiments, the heterologous moiety is a polymer. The polymer may be branched or unbranched. The polymer may be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa.

In some embodiments, the polymer is modified to have a single reactive group, such as an active ester for acylation or an aldehyde for alkylation, so that the degree of polymerization may be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer.

In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C 10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers.

A particularly preferred water-soluble polymer for use herein is polyethylene glycol (PEG). As used herein, polyethylene glycol is meant to encompass any of the forms of PEG that can be used to derivatize other proteins, such as mono-(C1-C10)alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., Poly(Ethylene Glycol) Chemistry-Biotechnical and Biomedical Applications, 127-36, 1992, incorporated herein by reference. These phenomena are due to the exclusion properties of PEG in preventing recognition by the immune system. In addition, PEG has been widely used in surface modification procedures to decrease protein adsorption and improve blood compatibility. S. W. Kim et al., Ann. N.Y. Acad. Sci. 516: 116-30 1987; Jacobs et al., Artif. Organs 12: 500-501, 1988; Park et al., J. Poly. Sci, Part A 29:1725-31, 1991, incorporated herein by reference. Hydrophobic polymer surfaces, such as polyurethanes and polystyrene can be modified by the grafting of PEG (MW 3,400) and employed as nonthrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG.

PEG (MW 3,400) was determined as an optimal size in surface immobilization studies, Park et al., J. Biomed. Mat. Res. 26:739-45, 1992, while PEG (MW 5,000) was most beneficial in decreasing protein antigenicity. (F. M. Veronese et al., In J. M. Harris, et al., Poly(Ethylene Glycol) Chemistry-Biotechnical and Biomedical Applications, 127-36.)

Methods for preparing pegylated compounds may comprise the steps of (a) reacting the compound with polyethylene glycol (such as a reactive ester or aldehyde derivative of PEG) under conditions whereby the compound becomes attached to one or more PEG groups, and (b) obtaining the reaction product(s). In general, the optimal reaction conditions for the acylation reactions will be determined based on known parameters and the desired result. For example, the larger the ratio of PEG: compound, the greater the percentage of poly-pegylated product. In some embodiments, the compound will have a single PEG moiety at the N-terminus. See U.S. Pat. No. 8,234,784, herein incorporated by reference.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Heterologous Moieties: Therapeutic Agents

In some embodiments, the heterologous moiety is a therapeutic agent. The therapeutic agent may be any of those known in the art. Examples of therapeutic agents that are contemplated herein include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-$HT_4$ partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-$A_2$ inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopeptides, lincosamides, macrolies, oxazolidinones, penicillins, streptogramins, sulfonamides, trimethoprim and derivatives, tetracyclines, anthelmintics, amebicies, biguanides, cinchona alkaloids, folic acid antagonists, quinoline derivatives, *Pneumocystis carinii* therapy, hydrazides, imidazoles, triazoles, nitroimidzao les, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opoid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

The compounds of the invention may be conjugated to one or more cytokines and growth factors that are effective in inhibiting tumor metastasis, and wherein the cytokine or growth factor has been shown to have an antiproliferative effect on at least one cell population. Such cytokines, lymphokines, growth factors, or other hematopoietic factors include, but are not limited to: M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors for use herein include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epithelial-derived neutrophil attractant, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, and chimeric proteins and biologically or immunologically active fragments thereof.

In some embodiments, the conjugate comprises a compound as described herein and a cytotoxic agent. The cytotoxic agent is any molecule (chemical or biochemical) which is toxic to a cell. In some aspects, when a cytotoxic agent is conjugated to a compound of the invention, the results obtained are synergistic. That is to say, the effectiveness of the combination therapy of a compound and the cytotoxic agent is synergistic, i.e., the effectiveness is greater than the effectiveness expected from the additive individual effects of each. Therefore, the dosage of the cytotoxic agent can be reduced and thus, the risk of the toxicity problems and other side effects is concomitantly reduced. In some embodiments, the cytotoxic agent is a chemotherapeutic agent. Chemotherapeutic agents are known in the art and include, but not limited to, platinum coordination compounds, topoisomerase inhibitors, antibiotics, antimitotic alkaloids and difluoronucleosides, as described in U.S. Pat. No. 6,630,124.

In some embodiments, the chemotherapeutic agent is a platinum coordination compound. The term "platinum coordination compound" refers to any tumor cell growth inhibiting platinum coordination compound that provides the platinum in the form of an ion. In some embodiments, the platinum coordination compound is cis-diamminediaquoplatinum(II)ion; chloro(diethylenetriamine)-platinum(II) chloride; dichloro(ethylenediamine)-platinum(II), diammine (1,1-cyclobutanedicarboxylato)platinum(II) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(II); (1,2-diaminocyclohexane)oxalatoplatinum(II); ormaplatin; and tetraplatin.

In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

In some aspects, the topoisomerase inhibitor is camptothecin or a camptothecin analog. Camptothecin is a water-insoluble, cytotoxic alkaloid produced by Camptotheca accuminata trees indigenous to China and Nothapodytes foetida trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to; topotecan, irinotecan and 9-aminocamptothecin.

In additional embodiments, the cytotoxic agent is any tumor cell growth inhibiting camptothecin analog claimed or described in: U.S. Pat. No. 5,004,758, issued on Apr. 2, 1991 and European Patent Application Number 88311366.4, published on Jun. 21, 1989 as 20' Publication Number EP 0 321 122; U.S. Pat. No. 4,604,463, issued on Aug. 5, 1986 and European Patent Application Publication Number EP 0 137 145, published on Apr. 17, 1985; U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983; European Patent Application Publication Number EP 0 088 642, published on Sep. 14, 1983; Wani et al., J. Med. Chem., 29, 2358-2363 (1986); Nitta et al., Proc. 14th International Congr. Chemotherapy, Kyoto, 1985, Tokyo Press, Anticancer Section 1, p. 28-30, especially a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776, issued on Aug. 3, 1982; U.S. Pat. No. 581,916, filed on Sep. 13, 1990 and European Patent Application Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399, 276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

The preparation of numerous compounds of the camptothecin analog class (including pharmaceutically acceptable salts, hydrates and solvates thereof) as well as the preparation of oral and parenteral pharmaceutical compositions comprising such a compounds of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet other embodiments of the invention, the chemotherapeutic agent is an antibiotic compound. Suitable antibiotic include, but are not limited to, doxorubicin, mitomycin, bleomycin, daunorubicin and streptozocin.

In some embodiments, the chemotherapeutic agent is an antimitotic alkaloid. In general, antimitotic alkaloids can be extracted from Cantharanthus roseus, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620,985). In a preferred aspect of the present invention, the antimitotic alkaloid is vinorelbine.

In other embodiments of the invention, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. In certain specific aspects, the 2'-deoxy-2',2'-difluoronucleoside used in the compositions and methods of the present invention is 2'-deoxy-2',2'-difluorocytidine hydrochloride, also known as gemcitabine hydrochloride. Gemcitabine is commercially available or can be synthesized in a multi-step process as disclosed and taught in U.S. Pat. Nos. 4,526,988, 4,808,614 and 5,223,608, the teachings of which are incorporated herein by reference.

Conjugates: Targeted Forms

One of ordinary skill in the art will readily appreciate that the compounds of the present disclosure can be modified in any number of ways, such that the therapeutic or prophylactic efficacy of the compound of the invention is increased through the modification. For instance, the compound of the present disclosure can be conjugated either directly or indirectly through a linker to a targeting moiety. The practice of conjugating compounds to targeting moieties is known in the art. See, for instance, Wadhwa et al., *J Drug Targeting*, 3, 111-127 (1995) and U.S. Pat. No. 5,087,616. The term "targeting moiety" as used herein, refers to any molecule or agent that specifically recognizes and binds to a cell-surface receptor, such that the targeting moiety directs the delivery of the compound of the invention to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups. The term "linker" in some embodiments refers to any agent or molecule that bridges the compound of the invention to the targeting moiety. The linker may be any of those described herein under the section entitled "Linkers." One of ordinary skill in the art recognizes that sites on the compound of the invention, which are not necessary for the function of the compound, are ideal sites for attaching a linker and/or a targeting moiety, provided that the linker and/or targeting moiety, once attached to the compound, do(es) not interfere with the function of the compound, i.e., the ability to inhibit the binding interaction between β integrin and G protein α subunit, as described herein.

Linkers

In some embodiments, the conjugate comprises a linker that joins the compound of the invention to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. In some embodiments, the linker is an amino acid or a peptidyl linker. Such peptidyl linkers may be any length. Exemplary linkers are from about 1 to 50 amino acids in length, 5 to 50, 3 to 5, 5 to 10, 5 to 15, or 10 to 30 amino acids in length.

Dimers & Multimers

In some embodiments, the compound is provided as a dimer or a multimer in which more than one compound of the invention are linked together. The dimer in some aspects is a homodimer comprising two compounds of the same type (e.g., same structure) linked together. In alternative aspects, the dimer is a heterodimer comprising two compounds of the invention, wherein the two compounds are structurally distinct from each other. The multimer in some aspects is a homomultimer comprising more than one compound of the invention and each compound are of the same type (e.g., same structure). In alternative aspects, the multimer is a heteromultimer comprising more than one compound of the invention and wherein at least two compounds of the heteromultimer are structurally distinct from the other. Two or more of the compounds can be linked together using standard linking agents and procedures known to those skilled in the art. In certain embodiments, the linker connecting the two (or more) compounds is a linker as described in the section entitled "Linkers." In some embodiments, the linker is a disulfide bond. For example, each monomer of the dimer may comprise a sulfhydryl and the sulfur atom of each participates in the formation of the disulfide bond.

Compositions

The invention further provide compositions comprising a compound that inhibits a binding interaction between a β integrin and a G protein α subunit, e.g., an antibody, antigen binding fragment, aptamer, peptide, peptide analog, pharmaceutically acceptable salt, conjugate, multimer, dimer, as described herein. The compositions in some aspects comprise the compounds in isolated and/or purified form. In some aspects, the composition comprises a single type (e.g., structure) of a compound of the invention or comprises a combination of two or more compounds of the invention, wherein the combination comprises two or more compounds of different types (e.g., structures).

In some aspects, the composition comprises agents which enhance the chemico-physico features of the compound, e.g., via stabilizing the compound at certain temperatures, e.g., room temperature, increasing shelf life, reducing degradation, e.g., oxidation protease mediated degradation, increasing half-life of the compound, etc. In some aspects, the composition comprises any of the agents disclosed herein as a heterologous moiety or conjugate moiety, optionally in admixture with the compounds of the invention or conjugated to the compounds.

In certain aspects, the composition comprises a delivery agent which aids in localizing the compound of the invention to the appropriate place. In exemplary embodiments, the composition comprises a vehicle which aids in getting the compound of the invention inside a cell. In exemplary aspects, the vehicle is covalently attached to the compound. In alternative aspects, the composition comprises a vehicle in admixture with the compound. In exemplary aspects, the vehicle comprises or is any of the heterologous moieties described herein with regard to conjugates. For example, the vehicle may be a polymer, e.g., water soluble polymer, which may be linear or branched. In exemplary aspects, the water soluble polymer is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch or a starch derivative, dextran, carboxymethyl-dextran, polyalkylene oxide (PAO), polyalkylene glycol (PAG), polypropylene glycol (PPG), polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC).

In exemplary embodiments, the vehicle comprises a carbohydrate, such as any of those described herein. In exemplary aspects, the vehicle comprises a polysaccharide.

In exemplary aspects, the vehicle comprises a lipophilic moiety. In exemplary aspects, the vehicle comprises a fatty acid. The fatty acid may be a C4 to C30 fatty acid, e.g., C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In exemplary aspects, the fatty acid is a C12 to C30 fatty acid. In exemplary aspects, the fatty acid is a myristoyl group or a palmitoyl group. In exemplary aspects, the compound is a peptide or peptide analog and the fatty acid is covalently attached to the peptide or peptide analog. For example, the fatty acid is covalently attached to the peptide or peptide analog at the N-terminus or C-terminus or via a side chain of a non-terminal amino acid of the peptide or peptide analog.

In exemplary aspects, the vehicle comprises a polypeptide, which when in the composition improves the ability of the composition to enter a cell compared to the ability of the composition in the absence of the polypeptide. In certain aspects, the composition comprises a compound of the invention (e.g., a peptide that inhibits a binding interaction between a β integrin and a G protein α subunit) and a peptide delivery agent. In some aspects, the peptide delivery agent is a cell penetrating peptide (CPP). In particular aspects, the composition comprises a CPP fused to the compound, e.g., the composition comprises a fusion peptide product comprising a peptide of the invention that inhibits a binding interaction between a β integrin and a G protein α subunit fused to a CPP.

Pharmaceutical Compositions and Formulations

In yet other aspects of the invention, the composition comprises a compound that inhibits a binding interaction between a β integrin and a G protein α subunit and additionally comprises a pharmaceutically acceptable carrier, diluents, or excipient. In some embodiments, the compound of the invention, the pharmaceutically acceptable salt, the conjugate, the dimer or multimer, of the invention (hereinafter referred to as "active agents") is formulated into a pharmaceutical composition comprising the active agent, along with a pharmaceutically acceptable carrier, diluent, or excipient. In this regard, the invention further provides pharmaceutical compositions comprising an active agent that inhibits a binding interaction between a β integrin and a G protein α subunit which is intended for administration to a subject, e.g., a mammal.

In some embodiments, the active agent is present in the pharmaceutical composition at a purity level suitable for administration to a patient. In some embodiments, the active agent has a purity level of at least about 90%, about 91%, about 92%, about 93%, about 94%, about 95%, about 96%, about 97%, about 98% or about 99%, and a pharmaceutically acceptable diluent, carrier or excipient. The pharmaceutical composition in some aspects comprises the active agent of the present disclosure at a concentration of at least A, wherein A is about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the active agent at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an active agent at a concentration range of A to B mg/ml, for example, about 0.001 to about 30.0 mg/ml.

Depending on the route of administration, the particular active agent intended for use, as well as other factors, the pharmaceutical composition may comprise additional pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

Accordingly, in some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC) chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edentate, disodium edentate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclo dextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capabale of buffering at the desired pH such as, for example, phosphate buffers (e.g., PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

Routes of Administration

With regard to the invention, the active agent, pharmaceutical composition comprising the same, may be administered to the subject via any suitable route of administration. The following discussion on routes of administration is merely provided to illustrate exemplary embodiments and should not be construed as limiting the scope in any way.

Formulations suitable for oral administration can consist of (a) liquid solutions, such as an effective amount of the active agent of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the active agent of the present disclosure in a flavor, usually sucrose and acacia or tragacanth, as well as pastilles comprising the active agent of the present disclosure in an inert base, such as gelatin and glycerin, or sucrose and acacia, emulsions, gels, and the like containing, in addition to, such excipients as are known in the art.

The active agents of the present disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the active agent is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-l53-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the active agent of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the active agent of the invention can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the active agent of the disclosure can be formulated as inclusion complexes, such as cyclodextrin inclusion complexes, or liposomes.

Dosages

The active agents of the disclosure are believed to be useful in methods of inhibiting a binding interaction between β integrin and G protein α subunit, as well as other methods, as further described herein, including methods of treating or preventing stroke, heart attack, cancer, or inflammation. For purposes of the disclosure, the amount or dose of the active agent administered should be sufficient to effect, e.g., a therapeutic or prophylactic response, in the subject or animal over a reasonable time frame. For example, the dose of the active agent of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which cancer is treated upon administration of a given dose of the active agent of the present disclosure to a mammal among a set of mammals, each set of which is given a different dose of the active agent, could be used to determine a starting dose to be administered to a mammal. The extent to which cancer is treated upon administration of a certain dose can be represented by, for example, the cytotoxicity of the active agent or the extent of tumor regression achieved with the active agent in a mouse xenograft model. Methods of measuring cytotoxicity of compounds and methods of assaying tumor regression are known in the art, including, for instance, the methods described in the EXAMPLES set forth below.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the invention, the dose of the active agent of the present disclosure can be about 0.0001 to about 1 g/kg body weight of the subject being treated/day, from about 0.0001 to about 0.001 g/kg body weight/day, or about 0.01 mg to about 1 g/kg body weight/day.

Controlled Release Formulations

In some embodiments, the active agents described herein can be modified into a depot form, such that the manner in which the active agent of the invention is released into the body to which it is administered is controlled with respect to time and location within the body (see, for example, U.S. Pat. No. 4,450,150). Depot forms of active agents of the invention can be, for example, an implantable composition comprising the active agents and a porous or non-porous material, such as a polymer, wherein the active agent is encapsulated by or diffused throughout the material and/or degradation of the non-porous material. The depot is then implanted into the desired location within the body of the subject and the active agent is released from the implant at a predetermined rate.

The pharmaceutical composition comprising the active agent in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions may further comprise, for example, micelles or liposomes, or some other encapsulated form, or may be administered in an extended release form to provide a prolonged storage and/or delivery effect.

Micelles

The invention also provides a micelle comprising a peptide or peptide analog of the invention and at least one lipid, optionally, wherein the lipid is covalently attached to a water soluble polymer. In exemplary aspects, the peptide or peptide analog of the micelle is covalently attached to a fatty acid or other lipid moiety. In exemplary aspects, the peptide of the micelle consists of FEEERA (SEQ ID NO: 87), wherein the Phe at position 1 is covalently attached to a C16 fatty acid. In exemplary aspects, the micelle comprises a lipid covalently attached to a water soluble polymer and a lipid free of a water soluble polymer. Suitable lipids for use in micelle synthesis is known in the art. See, e.g., Banerjee and Onyuksel, Peptide Delivery Using Phospholipid Micelles, WIREs Nanomed Nanobiotechnol 4:562-574 (2012). In exemplary aspects, the lipid that is covalently attached to a water soluble polymer is 1,2-distearoyl-sn-glycero-3-phosphoethanolamine-N-[amino(polyethylene glycol)-2000] and the lipid that is free of a water soluble polymer is phophatidylcholine.

The invention further comprises a composition comprising any of the micelles described herein and an aqueous solution.

Timing of Administration

The disclosed pharmaceutical compositions and formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing can be fine-tuned based on dose-response studies, efficacy, and toxicity data, and initially guaged based on timing used for other antibody therapeutics.

Combinations

In some embodiments, the active agents described herein are administered alone, and in alternative embodiments, the active agents described herein are administered in combination with another therapeutic agent, e.g., another active agent of the invention of different type (e.g., structure), or another therapeutic which does not inhibit a binding interaction between β integrin and G protein α subunit. In some aspects, the other therapeutic aims to treat or prevent cancer. In specific aspects, the other therapeutic is one listed under the section entitled "Heterologous Moieties: Therapeutic Agents." In some embodiments, the other therapeutic is a chemotherapeutic agent. In some embodiments, the other therapeutic is an agent used in radiation therapy for the treatment of cancer.

In exemplary aspects, the active agents described herein are administered or packaged in combination with an anti-thrombotic agent. In exemplary embodiments, the anti-thrombotic agent is an anticoagulant, e.g., fondaparinux and bivalirudin. In exemplary embodiments, the anti-thrombotic agent is an anti-platelet agent, e.g., aspirin, clopidogrel, dipyridamole, and abciximab.

In exemplary aspects, the active agent described herein is administered or packaged in combination with an anti-platelet drug. In exemplary aspects, the antiplatelet drug is an irreversible cyclooxygenase inhibitor (e.g., aspirin), an adenosine diphosphate (ADP) receptor inhibitor (e.g., clopidogrel, prasugrel, ticagrelor, ticlopidine), a phosphodiesterase inhibitor (e.g., cilostazol), a glycoprotein IIb/IIIa inhibitor (e.g., abciximab, eptifibatide), tirofiban), an adenosine reuptake inhibitor (e.g., dipyridamole), or a thromboxane inhibitor (e.g., a thromboxane synthase inhibitor, a thromboxane receptor antagonist (e.g., terutroban). In exemplary aspects, the anti-platelet drug is aspirin, a thienopyridine, a cylooxygenase inhibitor or a P2Y12 inhibitor.

In exemplary aspects, the active agent described herein is administered or packaged in combination with an integrin antagonist or integrin inhibitor. The integrin inhibitor in exemplary aspects is eptifibatide In exemplary embodiments, the active agent is administered simultaneously as the other therapeutic. In alternative embodiments, the active agent is administered either before or after the other therapeutic.

Methods of Use

Given the importance of the biological roles of a β integrin and a G protein α subunit, individually, and, as shown herein, in combination with one another, the active agents of the invention are useful for a number of applications in a variety of settings. For example and most simplistically, the active agents of the invention are useful for inhibiting a binding interaction between a β integrin and a G protein α subunit in a cell. In this regard, the invention provide a method of inhibiting a binding interaction between a β integrin and a G protein α subunit in a cell. The method comprises contacting the cell with a compound or composition of the invention, in an amount effective to inhibit the binding interaction. In some aspects, the cell is part of an in vitro or ex vivo cell culture or in vitro or ex vivo tissue sample. In some aspects, the cell is an in vivo cell. In certain embodiments, the method is intended for research purposes, and, in other embodiments, the method is intended for therapeutic purposes.

The invention also provides a method of inhibiting integrin-dependent Src activation in a cell. The method comprises the step of contacting the cells with a compound or composition of the invention in an amount effective to inhibiting the Src activation. Methods of measuring integrin-dependent Src activation are known in the art, and include, for example, those set forth herein in EXAMPLES and use of the ProFluor® Src-Family Kinase Assay (Promega, Madison, Wis.) or one of the Src activity assay kits available from Millipore (Billerica, Mass.).

A method of activating a small GTPase is furthermore provided by the invention. The method comprises the step of contacting a G protein subunit with a compound or composition in an amount effective to activate the small GTPase. In exemplary aspects, the small GTPase of the method of the invention is RhoA. Methods of measuring GTPase activity are known in the art, and include, for example, those set forth herein in EXAMPLES. Additionally, the GTPase activity levels may be measured using commercially available kits (Thermo Fisher Scientific, Inc. (Rockford, Ill.), Innova Biosciences (Cambridge, UK), Cell Biolabs, Inc. (San Diego, Calif.).

The invention moreover provides a method of inhibiting spreading or migration of a cell. The method comprises the step of contacting the cell with a compound or composition of the invention in an amount effective to inhibit spreading and migration. The cell may be any cell that undergoes integrin-dependent adhesion, spreading, retraction, or migration, or any cell that undergoes anchorage-dependent survival and proliferation. In exemplary aspects, the cell is a platelet, leukocyte, endothelial cell, fibroblast, epithelial cell. Methods of measuring cell spreading or cell migration are known in the art. See, for example, the methods described herein in EXAMPLES.

Also provided by the invention is a method of inhibiting platelet adhesion. The method comprises the step of contacting a platelet with a compound or composition of the invention in an amount effective to inhibit platelet adhesion. The invention further provides a method of inhibiting platelet granule secretion and platelet aggregation. The method comprises the step of contacting a platelet with a compound or composition of the invention in an amount effective to inhibit granule secretion and aggregation. Methods of measuring platelet granule secretion or platelet aggregation are known in the art. For example, platelet aggregation may be measured in platelet rich-plasma (PRP) using a turbidomatric platelet aggregometer to analyze washed platelets. Aggregation may be indicated by an increase in light transmission through PRP or platelet suspension. Platelet aggregation also may be measured in whole blood using a whole blood platelet aggregometer, in which platelet aggregation is indicated by an increase in electric resistance of electrodes. See, for example, the methods described herein in EXAMPLES.

The compounds and compositions of the invention are additionally contemplated for therapeutic purposes. For example, the compounds and compositions of the invention may be used to enhance blood clot retraction or inhibit thrombosis in a subject in need thereof. Accordingly, the invention provides a method of enhancing blood clot retraction in a subject in need thereof. The method comprises the step of administering to the subject a compound or composition of the invention in an amount effective to enhance blood clot retraction. Also provided is a method of inhibiting thrombosis in a subject in need thereof. The method comprises the step of administering to the subject a compound or composition of the invention in an amount effective to inhibit thrombosis.

Because blood clotting and thrombosis play a role in stroke and heart attack, the invention furthermore provides a method of treating or preventing a stroke or a heart attack in a subject in need thereof. The method comprises the step of administering to the subject a compound or composition of the invention in an amount effective to treat or prevent stroke or heart attack. Because the compounds and compositions provided herein relate to the coordinated cell spreading-retraction process, which in turn, is important in cell migration, the invention also provides a method of inhibiting metastasis of a tumor cell. The method comprises the step of contacting a tumor cell with a compound or composition of the invention in an amount effective to inhibit metastasis. The compounds and compositions are also contemplated for use in inhibiting angiogenesis. Accordingly, the invention provides a method of inhibiting angiogenesis in a subject in need thereof. The method comprises the step of administering to the subject a compound or composition of the invention in an amount effective to inhibit angiogenesis.

Promotion of clot and cell retraction by the compounds of the invention can also facilitate wound healing. Accordingly, the invention provides a method of facilitating wound healing in a subject in need of thereof. The method comprises the step of administrating to the subject of a compound or composition of the invention in an amount effective to facilitate the wound healing. In exemplary aspects, the compound or composition is administered to the subject topically near or at the wound site. In exemplary embodiments, the rate of wound healing is increased by at least 10%, 25%, 50%, 75%, 90% or more, as compared to the time at which the wound would heal without administration of the compound or composition of the invention.

Since metastasis and angiogenesis are important aspects of cancer, the invention moreover provides a method of treating or preventing cancer in a subject in need thereof. The method comprises the step of administering to the subject a compound or composition of the invention in an amount effective to treat or prevent cancer. In exemplary aspects, the subject has a solid tumor and the compound or composition of the invention is administered near or at the tumor site. In exemplary aspects, the compound or composition of the invention is administered via injection at the tumor site.

The compounds and compositions provided herein also may be used for affecting leukocyte function. The invention accordingly provides a method of inhibiting leukocyte adhesion, spreading, migration, or chemotaxis. The method comprises the step of contacting a leukocyte with a compound or composition of the invention in an amount effective to inhibit leukocyte adhesion, spreading, migration, or chemotaxis. Since these leukocyte functions are related to inflammation, the invention additionally provides a method of inhibiting or treating inflammation in a subject in need thereof. The method comprises the step of administering to the subject a compound or composition of the invention in an amount effective to inhibit or treat inflammation. In exemplary embodiments, the compound or composition is administered to the subject systemically, e.g., parenterally (e.g., via intravenous injection).

Treatment, Prevention, and Inhibition

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a stroke or a heart attack or cancer or inflammation of the invention can provide any amount or any level of treatment. Furthermore, the treatment provided by the method of the invention may include treatment of one or more conditions or symptoms or signs of the stroke, heart attack, cancer or inflammation, being treated. Also, the treatment provided by the methods of the invention may encompass slowing the progression of the stroke, heart attack, cancer or inflammation. For example, the methods can treat cancer by virtue of reducing tumor or cancer growth, reducing metastasis of tumor cells, increasing cell death of tumor or cancer cells, and the like.

As used herein, the term "prevent" and words stemming therefrom encompasses delaying the onset of the medical condition being prevented. In exemplary aspects, the method delays the onset of the medical condition by 1 day, 2 days, 4 days, 6 days, 8 days, 10 days, 15 days, 30 days, two months, 4 months, 6 months, 1 year, 2 years, 4 years, or more. As used herein, the term "prevent" and words stemming therefrom encompasses reducing the risk of the medical condition being prevented. In exemplary aspects, the method reduces the risk of SCD 2-fold, 5-fold, 10-fold, 20-fold, 50-fold, 100-fold, or more.

As used herein, the term "inhibit" and words stemming therefrom may not be a 100% or complete inhibition or abrogation. Rather, there are varying degrees of inhibition of which one of ordinary skill in the art recognizes as having a potential benefit or therapeutic effect. In this respect, the compounds of the invention may inhibit the binding interaction between a β integrin and a G protein α subunit to any amount or level. In exemplary embodiments, the inhibition provided by the methods of the invention is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition).

Cancer

The cancer treatable by the methods disclosed herein may be any cancer, e.g., any malignant growth or tumor caused by abnormal and uncontrolled cell division that may spread to other parts of the body through the lymphatic system or the blood stream. In some embodiments, the cancer is a cancer in which an integrin and a G protein α subunit are expressed on the surface of the cells.

The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma.

Subjects

In some embodiments of the invention, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human. In some aspects, the human is an adult aged 18 years or older. In some aspects, the human is a child aged 17 years or less.

In exemplary aspects, the subject has a medical history of taking an integrin antagonist or an anti-platelet drug, or the subject has been prescribed an integrin antagonist or an anti-platelet drug. In exemplary aspects, the subject has a medical history of coronary heart disease, heart attack, angina, stroke, transient ischemic attack, peripheral artery disease, myocardial infarction, atrial fibrillation, and/or ischaemic stroke. In exemplary aspects, the subject has a medical history comprising angioplasty, stent placement, and/or heart bypass or valve replacement surgery. In exemplary aspects, the subject suffers from acute coronary syndrome, unstable angin, or non-ST-segment elevation myocardial infarction.

Kits

In some embodiments, the composition comprising a compound of the invention, a pharmaceutically acceptable salt thereof, a conjugate comprising the compound, or a multimer or dimer comprising the compound, is provided as a kit or package or unit dose. "Unit dose" is a discrete amount of a therapeutic composition dispersed in a suitable carrier. Accordingly, provided herein are kits comprising a compound of the invention, a pharmaceutically acceptable salt thereof, a conjugate comprising the compound, or a multimer or dimer comprising the compound.

In some embodiments, the components of the kit/unit dose are packaged with instructions for administration to a patient. In some embodiments, the kit comprises one or more devices for administration to a patient, e.g., a needle and syringe, a dropper, a measuring spoon or cup or like device, an inhaler, and the like. In some aspects, the compound of the invention, a pharmaceutically acceptable salt thereof, a conjugate comprising the compound, or a multimer or dimer comprising the compound, is pre-packaged in a ready to use form, e.g., a syringe, an intravenous bag, an inhaler, a tablet, capsule, etc. In some aspects, the kit further comprises other therapeutic or diagnostic agents or pharmaceutically acceptable carriers (e.g., solvents, buffers, diluents, etc.), including any of those described herein. In particular aspects, the kit comprises a compound of the invention, a pharmaceutically acceptable salt thereof, a conjugate comprising the compound, or a multimer or dimer comprising the compound, along with an agent, e.g., a therapeutic agent, used in chemotherapy or radiation therapy.

The following examples are given merely to illustrate the present invention and not in any way to limit its scope.

EXAMPLES

Example 1

The following materials and methods were used in the studies described in Example 2.

Reagents

Myristoylated $G\alpha_{13}$ SRI peptide, Myr-LLARRPTKGI-HEY (mSRI; SEQ ID NO: 46), and myristoylated-scrambled peptide (Myr-LIRYALHRPTKEG; SEQ ID NO: 47) were synthesized and purified at the Research Resource Center at University of Illinois, Chicago (S1). Expression and purification of recombinant $G\alpha_{13}$ was described previously (S2). Anti-RhoA antibody and cell permeable C3 transferase (C3 toxin) were purchased from Cytoskeleton, Inc.; anti-$G\alpha_{13}$ (SC410), anti-c-Src (sc-18) and anti-mouse integrin $\beta_3$ (sc-6627) antibodies were from Santa Cruz Biotechnology, Inc; anti-phospho-Src $Y^{416}$ antibody was obtained from Cell Signaling; anti-human integrin $\beta_3$ antibody, MAb 15 and anti-$\alpha_{IIb}\beta_3$ antibody, D57, were kindly provided by Dr. Mark Ginsberg (University of California, San Diego, La Jolla, Calif.); anti-GPIb monoclonal antibody LJP3 was kindly provided by Dr. Zaverio Ruggeri, the Scripps Research Institute, La, Jolla, Calif.); anti-tubulin and anti-flag antibodies were purchased from Sigma-Aldrich; lipofectamine 2000, viraPower lentivirus expression system, Alexa Fluor 546-conjugated phalloidin, Alexa Fluor 633-conjugated phalloidin, and Alexa Fluor 546-conjugated anti-mouse IgG antibody were from Invitrogen; Y27632 was purchased from Calbiochem.

Platelets Preparation, Platelet Spreading and Clot Retraction.

Studies using human platelets were approved by the Institutional Review Board of University of Illinois at Chicago. Human washed platelets were prepared from freshly drawn blood of healthy volunteers and resuspended in modified Tyrode's buffer (12 mM $NaHCO_3$, 138 mM NaCl, 5.5 mM glucose, 2.9 mM KCl, 2 mM $MgCl_2$, 0.42 mM $NaH_2PO_4$, 10 mM HEPES, (pH 7.4) (S3, S4). Animal studies were approved by the institutional Animal Care Committee of University of Illinois at Chicago. Blood was freshly drawn from the inferior vena cava in isoflurane-anethetized mice. Mouse platelets were isolated and washed using methods previously described (S4, S5). For analyzing platelet spreading on integrin ligand fibrinogen, washed platelets were allowed to spread on 100 µg/ml fibrinogen-coated coverslips at 37° C. for 90 minutes, stained and viewed with a Leica RMI RB microscope or Zeiss LSM510 META confocal microscope as previously described (S5). Clot retraction was analyzed with the previously described method (S6, S7). Briefly, mouse platelets ($6\times10^8$/ml) were resuspended in platelet-depleted human plasma, and 0.4 U/ml α-thrombin was added to initiate coagulation. The clots were photographed at various time points. Sizes of retracted clots on photographs were quantified using NIH Image J software. Statistical significance was determined using t-test.

Co-immunoprecipitation and Binding Assays

Human platelets or CHO cells expressing recombinant integrin $\alpha_{IIb}\beta_3$ were solubilized in modified RIPA Buffer (50 mM Tris, pH 7.4, 10 mM $MgCl_2$, 150 mM NaCl, 1% NP-40, 1 mM sodium orthovanadate, 1 mM NaF), or RIPA buffer (25 mM Tris, pH 7.6, 150 mM NaCl, 1% NP-40, 1% sodium deoxycholate, 0.1% SDS) and complete protease inhibitor cocktail tablets (1 tablet/5 ml buffer, Roche). As previously described (S7), cell lysates were incubated with 2 µg/ml of D57 (antibody to integrin $\alpha_{IIb}\beta_3$), LJP3 (antibody against GPIb), or mouse IgG, and further incubated with protein G-conjugated Sepharose beads. Cell lysates were also incubated with rabbit anti-$G\alpha_{13}$ IgG antibody (1.5 µg/ml) or an equal amount of rabbit IgG and further incubated with protein A-conjugated Sepharose beads. After 3-6 washes with lysis buffer, immunoprecipitates were analyzed by SDS-polyacrylamide gel electrophoresis and Western blots with antibodies against $\beta_3$ (MAb15), GPIb (anti-Ib$\alpha$C (S8)) or $G\alpha_{13}$. In some experiments, 1 µM GDP, 1 µM GTPγS or 30 [tM $AlF_4^-$ were added to the reaction to assess the effect of $G\alpha_{13}$ activation on integrin binding. In other experiments, 250 µM mSRI or scrambled control peptide was incubated with platelet lysates prior to immunoprecipitation. GST bead pull down analysis was previously described (S7). Purified $G\alpha_{13}$ was incubated with glutathione beads-bound to GST, GST-$\beta_1$CD or GST-$\beta_3$CD at 4° C. overnight. Bead-bound proteins were analyzed by immunoblotting. For GST-$\beta_3$CD cDNA construction, integrin-$\beta_3$ cytoplasmic domain (716-762) cDNA was generated by PCR and cloned into pGEX-4T2 vector using Bam HI and Xho I restriction sites. The forward primer is 5'-CGTGGATCCAAACTCCTCATCACCATCCACGACC-3' (SEQ ID NO: 48); the reverse primer is 5'-GCGCTCGAGTTAAGTGCCCCGGTACGTGATATTG-3' (SEQ ID NO: 49). For GST-I31CD cDNA construction, $\beta_1$ cytoplasmic domain (752-798) cDNA was amplified by PCR and cloned into pGEX-4T1 vector using EcoRI and Xho I restriction sites. The primer sequences are: (1) forward: 5'-GCGAATTCAAGCTTTTAATGATAATTCATGAC-3' (SEQ ID NO: 50); (2) reverse: GCGCTCGAGTCATTTTCCCTCATACTTCGGATT-3' (SEQ ID NO: 51). GST, GST-$\beta_1$CD and GST-$\beta_3$CD were purified from BL21 (DE3) *E. coli* using glutathione-conjugated beads.

Expression of Wild Type $G\alpha_{13}$ and Truncation Mutants for $\beta_3$ Binding Human $G\alpha_{13}$ cDNA (S9) was tagged with Flag-epitope at N-tenninus using PCR with the Flag cDNA sequence incorporated into the forward primer, and then subcloned into pCDEF3 vector using Kpn I and Not I restriction sites. The forward primer sequence is 5'-GCGGGTACCGCCATGGACTACAAGGACGACGATGACAAGGCGGACTTCCTGCCGTCGCGGTCCGT-3' (SEQ ID NO: 52). The reverse primer sequence is 5'-GGCCGGCGGCCGCTCACTGTAGCATAAGCTGCTTGAGGTT-3' (SEQ ID NO: 53). Truncation mutants of $G\alpha_{13}$ were generated using PCR with reverse primer sequences 5'-GGCCGGCGGCCGCTCAAATATCTTGTTGTGATGGAAT-ATAATCTGGTTCTCCAAGTTTATCCAAG-3' (SEQ ID NO: 54). for mutant 1-196; and 5'-GGCCGGCGGCCGCTCATTCAAAGTCGTATTCATGGATGCC-3' (SEQ ID NO: 55). for mutant 1-212.

cDNA encoding Flag-tagged wild type $G\alpha_{13}$ or $G\alpha_{13}$ mutants were transfected into 293FT cells using lipofectamine 2000. Cell lysates were prepared 48 hours after transfection. Flag-tagged wild type or mutant $G\alpha_{13}$ in 293FT cell lysates were incubated with glutathione bead-bound GST or GST-$\beta_3$CD at 4° C. overnight. After centrifugation and washing, bead-bound proteins were immunoblotted with anti-Flag antibody.

RhoA Activity Assay.

Platelets in modified Tyrode's buffer or adherent on immobilized fibrinogen were lysed quickly in 0.8 ml lysis buffer (50 mM Tris, pH 7.4, 10 mM $MgCl_2$, 500 mM NaCl, 1% Triton X-100, 0.1% SDS, 0.5% deoxycholate, 10 µg/ml each of aprotinin and leupeptin, 1 mM phenylmethylsulfonyl fluoride, and 200 µM sodium vanadate). Lysates were cleared by centrifugation at 18,000 g for 2 minutes at 4° C., and the supernatant was incubated for 1 hour with 30 µg purified GST-Rhotekin RhoA-binding domain fusion protein (GST-RBD) bound to glutathione-Sepharose beads (S10). Samples were washed three times using washing buffer (50 mM Tris, pH 7.4, 10 mM $MgCl_2$, 150 mM NaCl, 1% Triton X-100) and then immunoblotted with an anti-RhoA monoclonal antibody. Cell lysates were also immunoblotted with anti-RhoA as loading control.

Interference of $G\alpha_{13}$ Expression with siRNA, Rescue with siRNA-Resistant $G\alpha_{13}$, and Bone Marrow Transplantation.

Two different $G\alpha_{13}$ siRNA target sequences were used: siRNA #1, 5'-GTCCACCTTCCTGAAGCAG (SEQ ID NO: 56); siRNAi #2, 5'-GGAGATCGACAAATGCCTG (SEQ ID NO: 57). Scrambled siRNA sequence is: 5'-GAGGAGC-CGACGCTTAATA-3' (SEQ ID NO: 58). These sequences are conserved in hamsters and mice. Lentivirus was prepared by co-transfection of pLL3.7-scrambled siRNA or pLL3.7-$G\alpha_{13}$ siRNA (#1 and #2) with pLP1, pLP2 and pLP/VSVG plasmids (Invitrogen) into ~90% confluent 293FT cells using Lipofectamine 2000. 48 hours after transfection, cell culture medium containing virus was filtered, titered and stored at −80° C. Bone manow cells from 6-8 week old healthy C57/BL mice were isolated aseptically from femurs and tibias. Stem cells were negatively selected by MACS Lineage cell depletion kit (Miltenyi Biotec) and cultured in RPMI 1640 complete medium with 10 ng/ml interleukin-3, 10 ng/ml interleukin-6, 10 ng/ml granulocyte-macrophage colony stimulating factor (GM-CSF), and 100 ng/ml stem cell factor (SCF). 50 multiplicity of infection (MOI) lenti-virus was used to infect mice bone marrow stem cells twice with 6 μg/ml polybrene. 48 hours after infection, $5 \times 10^6$ stem cells resuspended in PBS were transplanted by retrobulbar injection into lethally irradiated (10.5Gy) C57/BL mice one day after irradiation (S11). The siRNA-resistant mutants of $G\alpha_{13}$ were generated by PCR.

These mutants changed the $G\alpha_{13}$ siRNA #1 target sequence to 5'-GTCCACCTTttTaAAGCAG-3' (SEQ ID NO: 59). or siRNA #2 target sequence to 5'-GGAGATC-GAtAAgTGCCTG-3' (SEQ ID NO: 60). without changing the amino acid sequence of $G\alpha_{13}$. The mutants were subcloned into pLenti6/V5-Dest vector using EcoR I and Sal I restriction sites in PCR fragments and EcoRI and Xho I restriction sites in the vector. The primer sequences are as follows: (1) Flag tagged forward primer: 5'-CGGAATTCG-CCATGGACTACAAGGACGACGATGA-CAAGGCGGACTTCCTGCCGTCGCGGTCCGT-3' (SEQ ID NO: 61); (2) reverse primer: 5'-GCCGTCGACTCACTG-TAGCATAAGCTGCTTGAGGTT-3' (SEQ ID NO: 62); (3) mutation site forward primer for resistance to siRNA#1: 5'-GTCCAAGGAGATCGATAAGTGCCT-GTCTCGGGAA-3' (SEQ ID NO: 63); (4) mutation site reverse primer for resistance to siRNA #1: 5'-TTCCCGAGA-CAGGCACTTATCGATCTCCTTGGAC-3' (SEQ ID NO: 64); (5) mutation site forward primer for resistance to siRNA#2: 5'-CGGCAAGTCCACCTTTTTAAAGCAGAT-GCGGATC-3' (SEQ ID NO: 65); (6): mutation site reverse primer for resistance to siRNA#2: 5'-GATCCGCATCT-GCTTTAAAAAGGTGGACTTGCCG-3' (SEQ ID NO: 66).

CHO cells expressing human $\alpha_{IIb}\beta_3$ cells (123 cells) were transfected with $G\alpha_{13}$ siRNA construct with or without cotransfection of Flag-tagged siRNA resistant-$G\alpha_{13}$ plasmid using lipofectamine 2000. After 30 hours, the cells were detached by 0.53 mM EDTA in phosphate-buffered saline, and allowed to spread on 100 μg/ml fibrinogen. For c-Src phosphorylation, cells were solubilized in SDS-sample buffer and immunoblotted with anti c-Src pY416 antibody. For immuno-staining experiments, 123 cells co-transfected with $G\alpha_{13}$ siRNA plasmid and siRNA-resistant $G\alpha_{13}$ plasmid were allowed to adhere to 100 μg/ml fibrinogen for 1 hour, fixed by 4% paraformaldehyde, and stained by anti-flag antibody and Alexa Fluor 546-conjugated secondary antibody, and Alexa Fluor 633-conjugated phalloidin. Images were obtained using a Zeiss LSM510META confocal microscope.

Quantitation and Statistics

Western blot bands were scanned, and analyzed for uncalibrated optical density using NIH Image J software. Student t-test was used to determine statistical significance.

Example 2

Integrins mediate cell adhesion and transmit signals within the cell that lead to cell spreading, retraction, migration, and proliferation (1). Thus, integrins have pivotal roles in biological processes such as development, immunity, cancer, wound healing, hemostasis and thrombosis. The platelet integrin, $\alpha_{IIb}\beta_3$, typically displays bidirectional signaling function (2, 3). Signals from within the cell activate binding of $\alpha_{IIb}\beta_3$ to extracellular ligands, which in turn triggers signaling within the cell initiated by the occupied receptor (so-called "outside-in" signaling). A major early consequence of integrin "outside-in" signaling is cell spreading, which requires activation of the protein kinase c-Src and c-Src-mediated inhibition of the small guanosine triphosphatase (GTPase) RhoA (4-7). Subsequent cleavage of the c-Src binding site in $\beta_3$ by calpain allows activation of RhoA, which stimulates cell retraction (7, 8). The molecular mechanism coupling ligand-bound $\alpha_{IIb}\beta_3$ to these signaling events has been unclear.

Figure 1B:
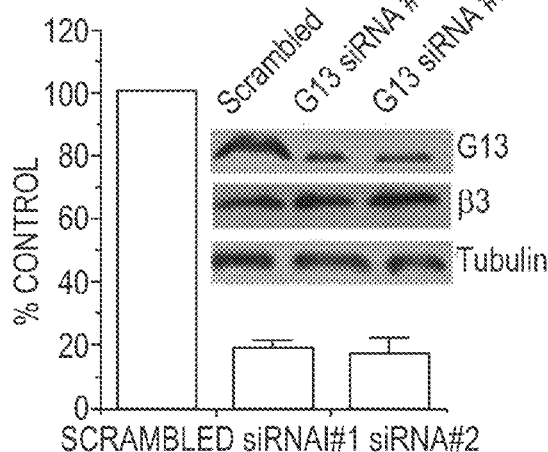
(FIG. 1B) Western blot comparison of $G\alpha_{13}$ abundance in platelets from mice innoculated with control siRNA- or $G\alpha_{13}$-siRNA-transfected bone marrow stem cells.
Figure 5:
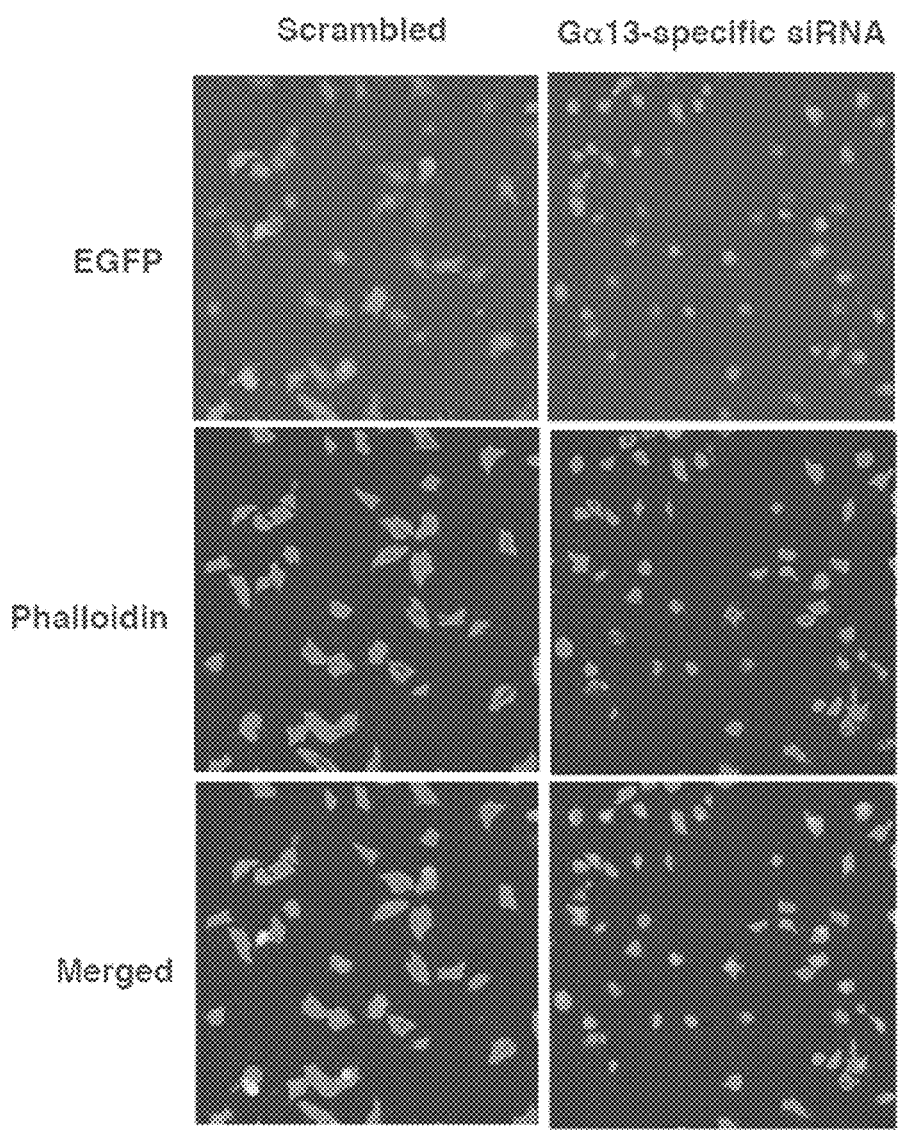
FIG. 5 demonstrates the efficiency of platelet replacement by irradiation and transplantation of lentivirus-infected bone marrow stem cells. Five weeks after high dose irradiation and transplantation of bone marrow stem cells infected with scrambled siRNA- or $G\alpha_{13}$-specific siRNA#1-encoding lentivirus, platelets were isolated from recipient mice, and allowed to adhere to immobilized fibrinogen. Platelets were imaged using a Zeiss LSM 510 META confocal microscope. Green: EGFP fluorescence indicating that platelets are derived from transplanted stem cells. Red: Alexa Fluor 546-conjugated phalloidin staining indicating total platelets.
Figure 7A:
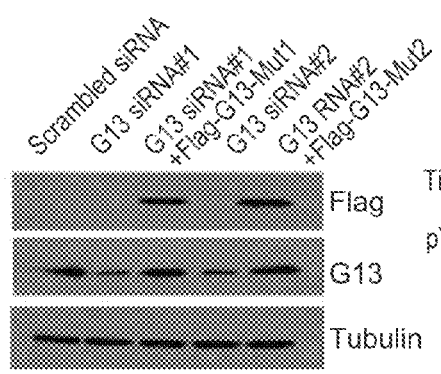
(FIG. 7A) Cells were solubilized and immunoblotted with anti-$G\alpha_{13}$ antibody, anti-Flag (for detecting Flag-tagged $G\alpha_{13}$) and an antibody to tubulin (loading control).
Figure 7B:
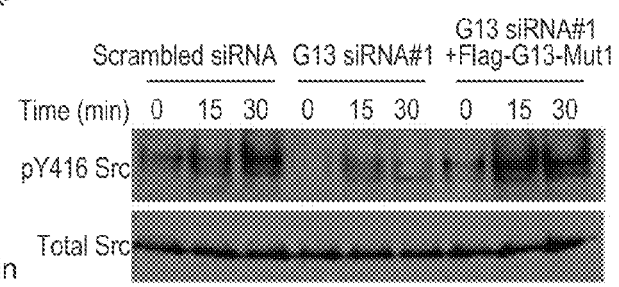
(FIG. 7B) Cells were plated on fibrinogen-coated surfaces for various lengths of time, solubilized, and lysates were immunoblotted for c-Src phosphorylation at Y416 to indicate c-Src activation, or total amount of c-Src.
Figure 7C:
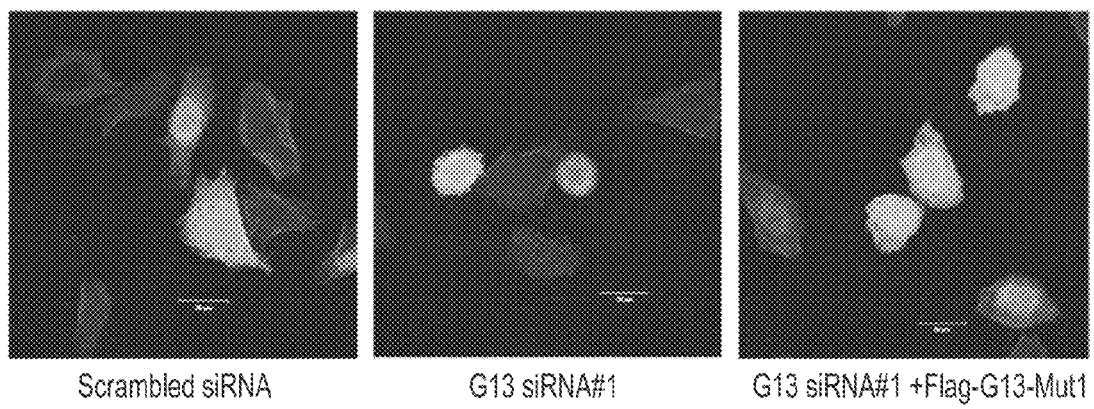
(FIG. 7C) Cells adherent to fibrinogen were stained with Alexa Fluor 633-labeled phalloidin (artificial blue color) and Alexa Fluor 546-conjugated anti-Flag antibody (Red), and imaged using a Zeiss LSM 510 META confocal microscope. Cells that were successfully transfected with siRNA constructs express EGFP and thus show green fluorescence. Note that $G\alpha_{13}$ siRNA inhibited integrin-dependent c-Src activation and cell spreading on fibrinogen, which was rescued by expressing Flag-G13-Mut1.
Figure 8A:
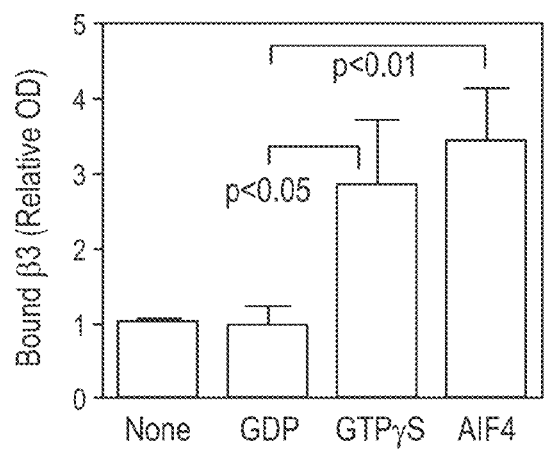
(FIG. 8A) Quantitative data for FIG. 2A, showing that co-immunoprecipitation of $\beta_3$ with $G\alpha_{13}$ was enhanced by GTP and AlF4⁻.
Figure 8B:
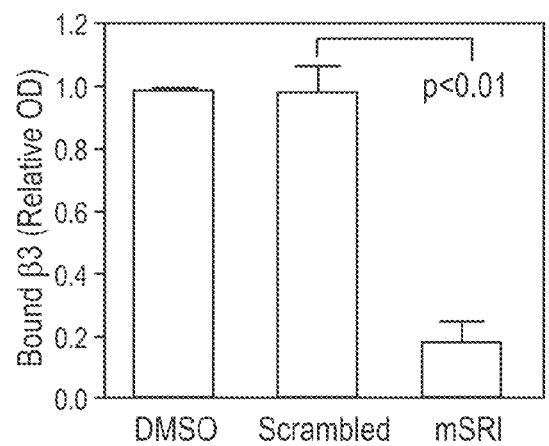
(FIG. 8B) Quantitative data for FIG. 2G, showing mSRI inhibited co-immunoprecipitation of $\beta_3$ with $G\alpha_{13}$.
Figure 8C:
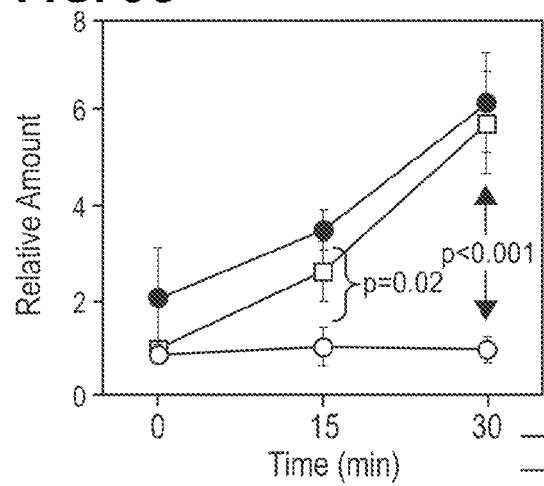
(FIG. 8C and FIG. 8D) Quantitative data from FIG. 3A showing that mSRI inhibited c-Src activation (FIG. 8C) and accelerated RhoA activation (FIG. 8D). All data are expressed as mean±SD from 3 experiments. Statistical significance was determined using Student t-test.
Figure 8D:
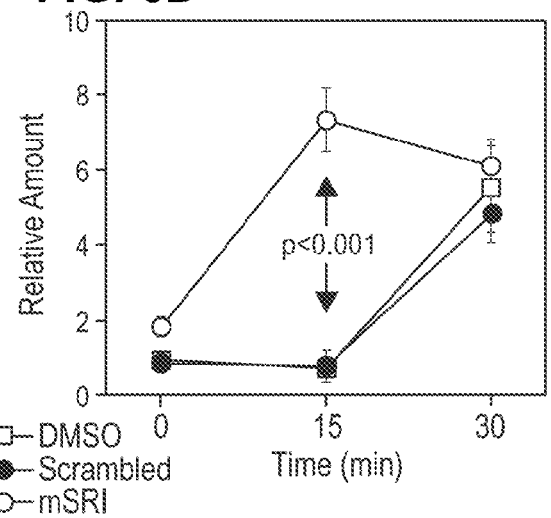

Heterotrimeric guanine nucleotide-binding proteins (G proteins) consist of $G\alpha$, $G\beta$ and $G\gamma$ subunits (9). G proteins bind to the intracellular side of G-protein coupled receptors (GPCR) and transmit signals that are important in many intracellular events (9-11). $G\alpha_{13}$, when activated by GPCRs, interacts with Rho guanine-nucleotide exchange factors (RhoGEF) and thus activates RhoA (11-14), facilitating contractility and rounding of discoid platelets (shape change). To determine whether $G\alpha_{13}$ functions in signaling from ligand-occupied integrin, we investigated whether inhibition of $G\alpha_{13}$ expression with small interfering RNA (siRNA) affected $\alpha_{IIb}\beta_3$-dependent spreading of platelets on fibrinogen, which is an integrin ligand. We isolated mouse bone marrow stem cells and transfected them with lentivirus encoding $G\alpha_{13}$ siRNA. The transfected stem cells were transplanted into irradiated C57/BL6 mice (15). Four to six weeks after transplantation, nearly all platelets isolated from recipient mice were derived from transplanted stem cells as indicated by the enhanced green fluorescent protein (EGFP) encoded in lentivirus vector (FIG. 5, FIG. 1A). Platelets from $G\alpha_{13}$ siRNA-transfected stem cell recipient mice showed >80% decrease in $G\alpha_{13}$ expression (FIG. 1B). When platelets were allowed to adhere to immobilized fibrinogen [$\alpha_{IIb}\beta_3$ binding to immobilized fibrinogen does not require prior "inside-out" signaling activation (16)], platelets depleted of $G\alpha_{13}$ spread poorly as compared with control platelets (FIG. 1A, FIG. 6). The inhibitory effect of $G\alpha_{13}$ deficiency is unlikely to be caused by its effect on GPCR-stimulated $G\alpha_{13}$ signaling because (i) washed resting platelets were used and no GPCR agonists were added, and (ii) prior treatment with 1 mM aspirin [which abolishes thromboxane $A_2$ ($TXA_2$) generation (17)] did not affect platelet spreading on fibrinogen (FIG. 6), making it unlikely the endogenous $TXA_2$-mediated stimulation of $G\alpha_{13}$. Furthermore, $G\alpha_{13}$ siRNA inhibited spreading of Chinese hamster ovary (CHO) cells expressing human $\alpha_{IIb}\beta_3$ (123 cells) (18), which was rescued by an siRNA-resistant $G\alpha_{13}$ (FIG. 7). Thus, $G\alpha_{13}$ appears to be important in integrin "outside-in" signaling leading to cell spreading.

Figure 1C:
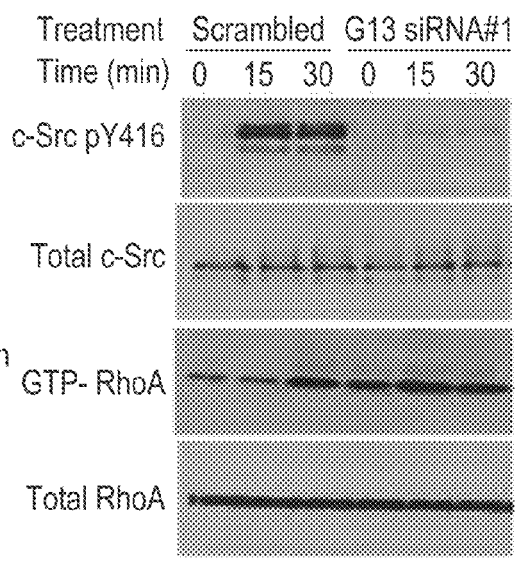
(FIG. 1C, FIG. 1D, FIG. 1E) Mouse platelets from scrambled siRNA—or $G\alpha_{13}$ siRNA-transfected stem cells were allowed to adhere to immobilized fibrinogen, solubilized and analyzed for c-Src $Tyr^{416}$ phosphorylation and RhoA activation.
Figure 1D:
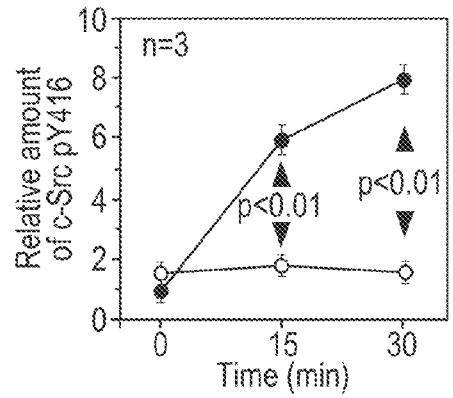
Figure 1E:
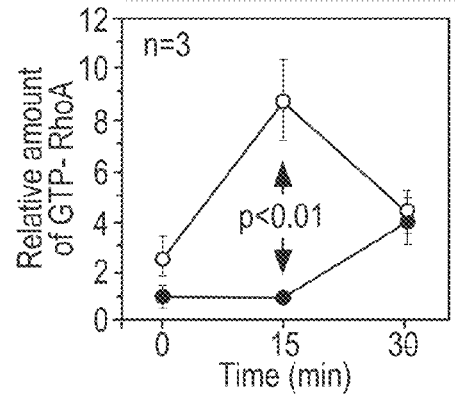

To determine whether $G\alpha_{13}$ serves as an early signaling mechanism that mediates integrin-induced activation of c-Src, we measured phosphorylation of c-Src at $Tyr^{416}$ (which indicates activation of c-Src) in control and fibrinogen-bound cells. Depletion of $G\alpha_{13}$ in mouse platelets or 123 cells abolished phosphorylation of c-Src $Tyr^{416}$ (FIG. 1C, FIG. 7), indicating that $G\alpha_{13}$ may link integrin $\alpha_{IIb}\beta_3$ and c-Src activation. Because c-Src inhibits RhoA (7, 19), we also tested the role of $G\alpha_{13}$ in regulating activation of RhoA. RhoA activity was suppressed to baseline 15 minutes after platelet adhesion, and became activated at 30 minutes (FIG. 1C), which is consistent with transient inhibition of RhoA by c-Src (7). The integrin-dependent delayed activation of RhoA was not inhibited by depletion of $G\alpha_{13}$, indicating its independence of the GPCR-$G\alpha_{13}$-RhoGEF pathway (FIG. 1C). In contrast, depletion of $G\alpha_{13}$ accelerated RhoA activation (FIG. 1C). Thus, $G\alpha_{13}$ appears to mediate inhibition of RhoA. The inhibitory effect of $G\alpha_{13}$ depletion on platelet spreading was reversed by Rho-kinase inhibitor Y27632 (FIG. 1A), suggesting that $G\alpha_{13}$-mediated inhibition of RhoA is important in stimulating platelet spreading. These data are consistent with $G\alpha_{13}$ mediating integrin "outside-in signaling" inducing c-Src activation, RhoA inhibition, and cell spreading.

Figure 2A:
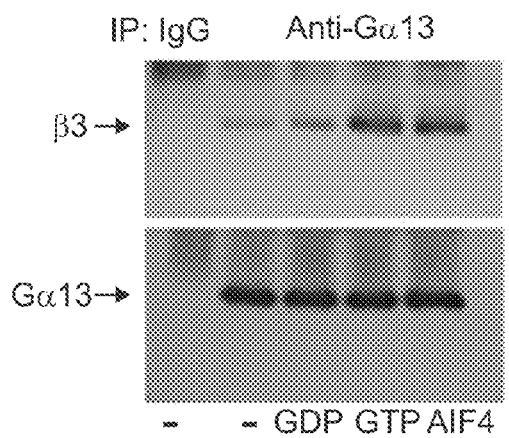
(FIG. 2A) Proteins from platelet lysates were immunoprecipitated with control IgG or antibody to $G\alpha_{13}$ with or without 1 µM GDP, 1 µM GTP or 30 µM $AlF_4^-$. Immunoprecipitates were immunoblotted with anti-$G\alpha_{13}$ or anti-$\beta_3$ (MAb15). See Fig. S4 for quantitation.
Figure 2B:
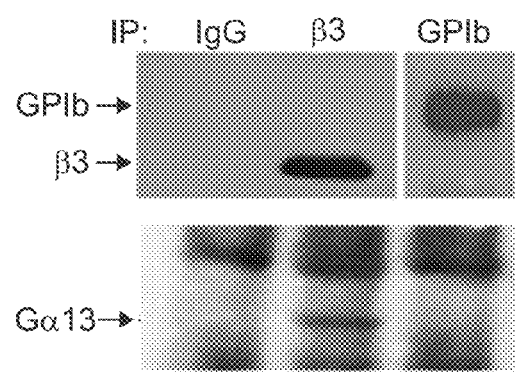
(FIG. 2B) Proteins from platelet lysates were immunoprecipitated with control mouse IgG, anti-$\alpha_{IIb}\beta_3$ (D57 (24)) or an antibody to the glycoprotein Ibα (GPIb). Immunoprecipitates were immunoblotted with anti-$G\alpha_{13}$, anti-$\beta_3$, or anti-GPIb antibodies.
Figure 2C:
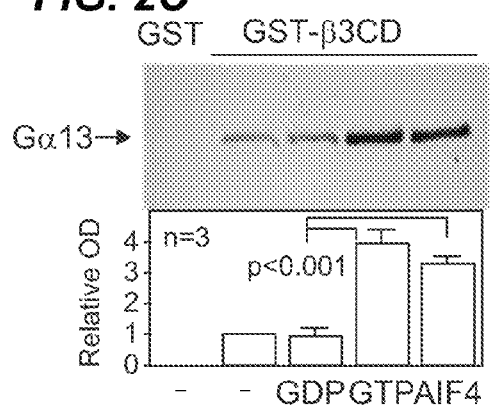
(FIG. 2C, FIG. 2D) Purified GST-$\beta$3CD (FIG. 2C) or GST-$\beta$1CD (D) bound to glutathione beads was mixed with purified $G\alpha_{13}$ with or without 1 µM GDP, 1 µM GTPγS or 30 µM $AlF_4^-$. Bound proteins were immunoblotted with anti-$G\alpha_{13}$. Quantitative data are shown as mean±SD and p value (t-test).
Figure 2D:
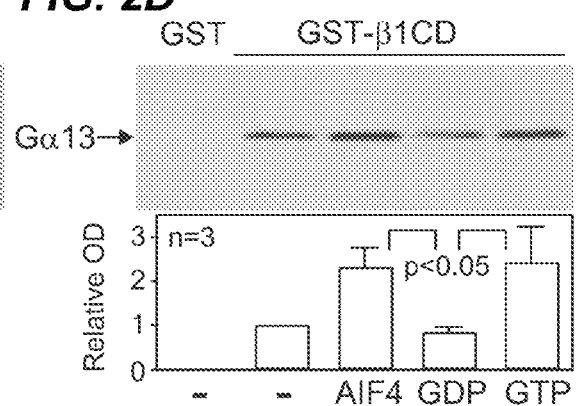
Figure 2E:
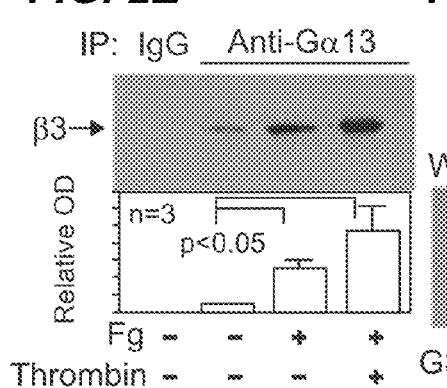
(FIG. 2E) Lysates of control platelets or platelets adherent to fibrinogen in the absence or presence of 0.025 U/ml thrombin were immunoprecipitated with anti-$G\alpha_{13}$, and then immunoblotted with MAb15. Quantitative data are shown as mean±SD and p value (t-test).

The integrin $\alpha_{IIb}\beta_3$ was co-immunoprecipitated by anti-$G\alpha_{13}$ antibody, but not control IgG, from platelet lysates (FIG. 2A). Conversely, an antibody to $\beta_3$ immunoprecipitated $G\alpha_{13}$ with $\beta_3$ (FIG. 2B). Co-immunoprecipitation of $\beta_3$ with $G\alpha_{13}$ was enhanced by GTP-γS or $AlF_4^-$ (FIG. 2A, FIG. 8). Thus, $\beta_3$ is present in a complex with $G\alpha_{13}$, preferably the active GTP-bound $G\alpha_{13}$. To determine whether $G\alpha_{13}$ directly binds to the integrin cytoplasmic domain, we incubated purified recombinant $G\alpha_{13}$ (20) with agarose beads conjugated with glutathione S-transferase (GST), or a GST-$\beta_3$ cytoplasmic domain fusion protein (GST-$\beta_3$CD). Purified $G\alpha_{13}$ bound to GST-$\beta_3$CD, but not to GST (FIG. 2C). Purified $G\alpha_{13}$ also bound to the $\beta_1$ integrin cytoplasmic domain fused with GST (GST-$\beta_1$CD) (FIG. 2D). The binding of $G\alpha_{13}$ to GST-$\beta_3$CD and GST-$\beta_1$CD was detected with GDP-loaded $G\alpha_{13}$, but enhanced by GTP-γS and $AlF_4^-$ (FIGS. 2C, 2D), indicating that the cytoplasmic domains of $\beta_3$ and $\beta_1$ can directly interact with $G\alpha_{13}$, and GTP enhances the interaction. The $G\alpha_{13}$-$\beta_3$ interaction was enhanced in platelets adherent to fibrinogen, and by thrombin, which stimulates GTP binding to $G\alpha_{13}$ via GPCR (FIG. 2E). Hence, the interaction is regulated by both integrin occupancy and GPCR signaling.

Figure 2F:
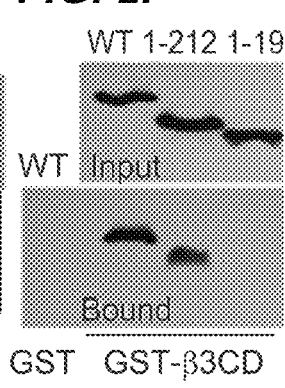
(FIG. 2F) Lysates from 293FT cells transfected with Flag-tagged wild type $G\alpha_{13}$ or indicated truncation mutants (see Fig. S5) were precipitated with GST-$\beta_3$CD- or GST-bound glutathione beads. Bead-bound proteins were immunoblotted with anti-Flag (Bound). Flag-tagged protein amounts in lysates are shown by anti-Flag immunoblot (Input).
Figure 2G:
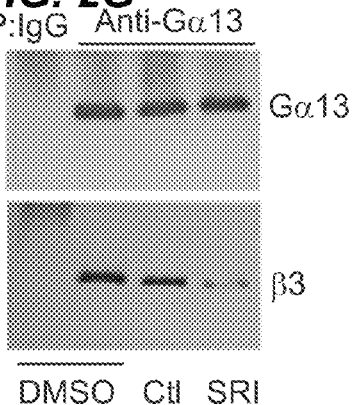
(FIG. 2G) Protein from platelet lysates treated with 0.1% DMSO, 250 µM scrambled control peptide (Ctrl) or mSRI were immunoprecipitated with anti-$G\alpha_{13}$. Immunoprecipitates were immunoblotted with anti-$G\alpha_{13}$ or anti-$\beta_3$. See Fig. S4 for quantitation.
Figure 9:
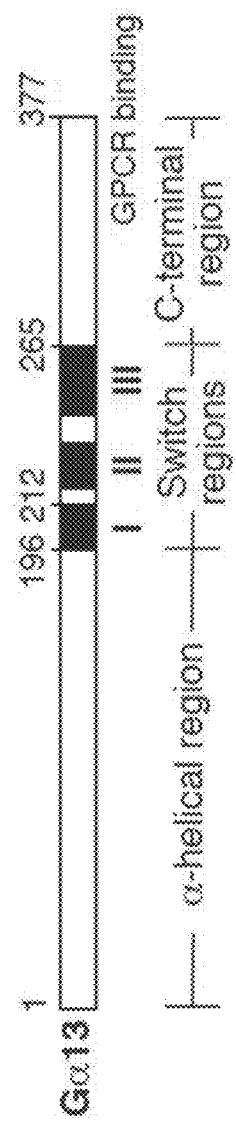
FIG. 9 represents a schematic of Gα13 with switch regions indicated. Two $G\alpha_{13}$ truncation mutants were developed to map the $\beta_3$ binding site (See FIG. 2F): (1) the mutant encoding a $G\alpha_{13}$ fragment containing residues 1-196 lacking switch region I, and (2) the mutant encoding a $G\alpha_{13}$ fragment (residues 1-212) containing switch region I.

To map the $\beta_3$ binding site in $G\alpha_{13}$, we incubated cell lysates containing Flag-tagged wild type or truncation mutants of $G\alpha_{13}$ (FIG. 9) with GST-$\beta_3$CD beads. GST-$\beta_3$CD associated with wild type $G\alpha_{13}$ and the $G\alpha_{13}$ 1-212 fragment containing α helical region and switch region I (SRI), but not with the $G\alpha_{13}$ fragment containing residues 1-196 lacking SRI (FIG. 2F). Thus, SRI appears to be critical for $\beta_3$ binding. To further determine the importance of SRI, $G\alpha_{13}$-$\beta_3$ binding was assessed in the presence of a myristoylated synthetic peptide, Myr-LLARRPTKGIHEY (mSRI; SEQ ID NO: 45), corresponding to the SRI sequence of $G\alpha_{13}$ (197-209) (21). The mSRI peptide, but not a myristoylated scrambled peptide, inhibited $G\alpha_{13}$ binding to $\beta_3$ (FIG. 2G), indicating that mSRI is an effective inhibitor of $\beta_3$-$G\alpha_{13}$ interaction. Therefore, we further examined whether mSRI might inhibit integrin signaling. Treatment of platelets with mSRI inhibited integrin-dependent phosphorylation of c-Src Tyr[416] and accelerated RhoA activation (FIG. 3A). The effect of mSRI is unlikely to result from its inhibitory effect on the binding of RhoGEFs to $G\alpha_{13}$ SRI because $G\alpha_{13}$ binding to RhoGEFs stimulates RhoA activation, which should be inhibited rather than promoted by mSRI (21). Thus, these data suggest that $\beta_3$-$G\alpha_{13}$ interaction mediates activation of c-Src and inhibition of RhoA. Furthermore, mSRI inhibited integrin-mediated platelet spreading (FIG. 3B), and this inhibitory effect was reversed by C3 toxin (which catalyzes the ADP ribosylation of RhoA) or Y27632, confirming the importance of $G\alpha_{13}$-dependent inhibition of RhoA in platelet spreading. Thrombin promotes platelet spreading, which requires cdc42/Rac pathways (22). However, thrombin-promoted platelet spreading was also abolished by mSRI (FIG. 3B), indicating the importance of $G\alpha_{13}$-$\beta_3$ interaction. Thus, $G\alpha_{13}$-integrin interaction appears to be a mechanism that mediates integrin signaling to c-Src and RhoA, thus regulating cell spreading.

Figure 10A:
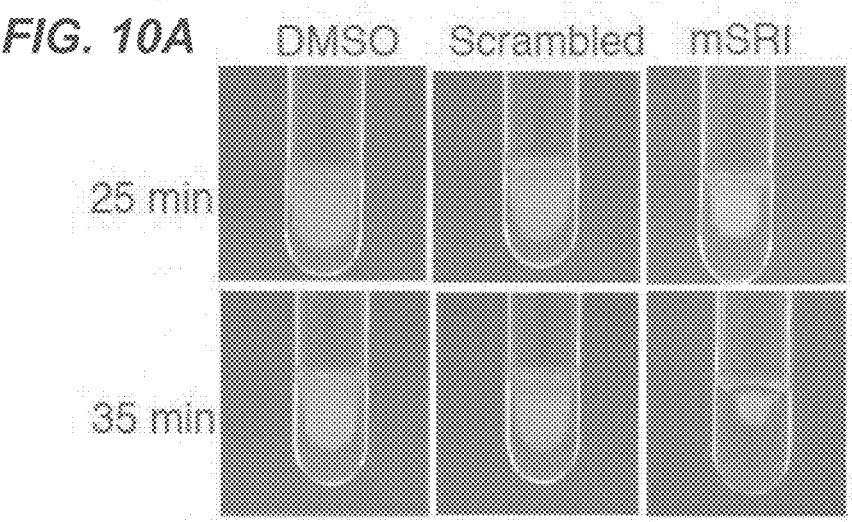
(FIG. 10A) Effect of 250 μM mSRI peptide on clot retraction of human platelet-rich plasma compared with DMSO and scrambled peptide. Quantitative data are shown in FIG. 4A.
Figure 10B:
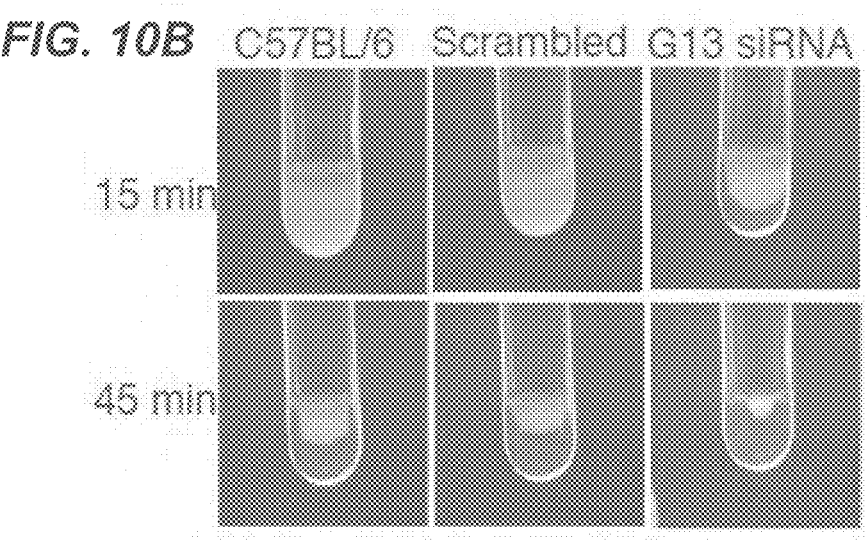
(FIG. 10B) Comparison of clot retraction mediated by control siRNA platelets and $G\alpha_{13}$-knockdown platelets. Quantitative data are shown in FIG. 4B.

To further determine whether $G\alpha_{13}$ mediates inhibition of integrin-induced RhoA-dependent contractile signaling, we investigated the effects of mSRI and depletion of $G\alpha_{13}$ on platelet-dependent clot retraction (shrinking and consolidation of a blood clot requires integrin-dependent retraction of platelets from within) (7, 8). Clot retraction was accelerated by mSRI and depletion of $G\alpha_{13}$ (FIGS. 4, A and B, FIG. 10), indicating that $G\alpha_{13}$ negatively regulates RhoA-dependent platelet retraction and coordinates cell spreading and retraction. The coordinated cell spreading-retraction process is also important in wound healing, cell migration and proliferation (23).

The function of $G\alpha_{13}$ in mediating the integrin-dependent inhibition of RhoA contrasts with the traditional role of $G\alpha_{13}$, which is to mediate GPCR-induced activation of RhoA. However, GPCR-mediated activation of RhoA is transient, peaking at 1 minute after exposure of platelets to thrombin, indicating the presence of a negative regulatory signal (FIGS. 4, D and F). Furthermore, thrombin-stimulated activation of RhoA occurs during platelet shape change before substantial ligand binding to integrins (FIGS. 4, C, D and F). In contrast, following thrombin stimulation, $\beta_3$ binding to $G\alpha_{13}$ was diminished at 1 minute when $G\alpha_{13}$-dependent activation of RhoA occurs, but increased after the occurrence of integrin-dependent platelet aggregation (FIGS. 4, E and F). Thrombin-stimulated binding of $G\alpha_{13}$ to $\alpha_{IIb}\beta_3$ and simultaneous RhoA inhibition both require ligand occupancy of $\alpha_{IIb}\beta_3$, and are inhibited by the integrin inhibitor RGDS (FIGS. 4, D-F). Thus, our study demonstrates not only a function of integrin $\alpha_{IIb}\beta_3$ as a non-canonical $G\alpha_{13}$-coupled receptor but also a new concept of $G\alpha_{13}$-dependent dynamic regulation of RhoA, in which $G\alpha_{13}$ mediates initial GPCR-induced RhoA activation and subsequent integrin-dependent RhoA inhibition (FIG. 4G). These findings are important for our understanding on how cells spread, retract, migrate, and proliferate, which is fundamental to development, cancer, immunity, wound healing, hemostasis and thrombosis.

Example 3

The following materials and methods were carried out and the results of some are described in Example 4.

Animals and Reagents

Integrin $\beta_3^{-/-}$ mice were obtained from the Jackson Laboratory. Myristoylated peptides were synthesized and purified at the Research Resource Center at University of Illinois. These peptides include: $mP_{13}$ (Myr-KFEEERARAKWDT; SEQ ID NO: 67), $mP_7$ (Myr-KFEEERA) and $mP_5$ (Myr-EEERA; SEQ ID NO: 68) and myristoylated scrambled peptide for $mP_{13}$ (Myr-EEARERKDWAKFT; SEQ ID NO: 69); myristoylated scrambled peptide for $mP_7$ (Myr-EAREKFE; SEQ ID NO: 70) and myristoylated scrambled peptide for $mP_5$ (Myr-EEAARE; SEQ ID NO: 71). Human integrin $\beta_3$ cDNA was cloned into pcDNA3.1 vector following digestion with Hind III and Xho I, or pLenti6-V5/Dest vector following digestion with EcoR I, Mfe I, and Xho I. Truncation mutants and integrin E to A mutants were either previously reported[23] or generated using PCR and cloned into pcDNA3.1 vector by Bam HI and Xho I. The primer sequences used are: (1): $ITGB_3$-UP: 5'-GCGAAGCTTGCCGCCATGGAC-CGAGCGCGGCCGCGGCCCCGGCCGCTCT-3' (SEQ ID NO: 72); (2): $ITGB_3$-728DN: 5'-GCGCTCGAGTCAAGC-GAATTCTTTTCGGTCGTGGATGGTGATGAG-3' (SEQ ID NO: 73); (3): $ITGB_3$-715DN: 5'-GCGCTCGAGTCAC- CAGATGAGCAGGGCGGCAAGGCCAATGAGCAG-3' (SEQ ID NO: 74); (4): Itgb$_3$-E731A-up: 5'-AAGAAT-TCGCTAAATTTGCAGAAGAACGCGCCAGAGCAA-3' (SEQ ID NO: 75); (5): Itgb$_3$-E732A-up: 5'-AAGAAT-TCGCTAAATTTGAGGCAGAACGCGCCAGAGCAA-3' (SEQ ID NO: 76); (6): Itgb$_3$-E733A-up: 5'-AAGAAT-TCGCTAAATTTGAGGAAGCACGCGCCAGAGCAA-3' (SEQ ID NO: 77); (7): Itgb$_3$-E731-733A-up: 5'-AAGAAT-TCGCTAAATTTGCAGCAGCACGCGCCAGAGCAA-3' (SEQ ID NO: 78); (8): Mfe-ITGB$_3$-Up: 5'-CCGCAATTG-GCCGCCATGGACCGAGCGCGGCCGCGGC-CCCGGCCGCTCT-3' (SEQ ID NO: 79); (9): Xho I-ITGB$_3$-DN: 5'-GCGCTCGAGTTAAGTGCCCCGGTACGTGATATTG-3' (SEQ ID NO: 80). Human integrin β$_8$-CD cDNA was cloned into pGEX4T-1 vector following digestion with Bam HI and Xho I. Primer sequences used are: (1): ITGB$_8$-UP: 5'-CGTGGATCC ATTAGACAGGTGATACTACAATGG-3' (SEQ ID NO: 81); (2): ITGB$_8$-Dn: 5'-GCGCTCGAGTTAGA AGTTGCACCTGAAAGTTTC-3' (SEQ ID NO: 82). GST-β$_3$CD and recombinant Gα$_{13}$ purification was described previously[8]. Human talin head domain cDNA corresponds to N-terminal talin amino acid residues 1-433, which was cloned into pcDNA3.1 vector and pMal-C2 vector between EcoR I and Xho I sites. Anti-RhoA antibody was purchased from Cytoskeleton, Inc.; anti-Gα$_{13}$(sc410), anti-total c-Src (scl8), anti-talin (sc7534), and anti-integrin β$_3$ (sc6627) antibodies were from Santa Cruz Biotechnology, Inc; anti-Gα$_{13}$ (26004) was from NewEast; anti-phospho-Src Y$^{416}$ antibody was obtained from Cell Signaling; anti-talin (TA205) was from Millipore; anti-human integrin β$_3$ antibody, MAb 15 and 8053 rabbit serum were kindly provided by Dr. Mark Ginsberg (University of California, San Diego, La Jolla, Calif.); lipofectamine 2000, viraPower lentivirus expression system, Alexa Fluor 546-conjugated phalloidin, and Fluor 546-conjugated anti-mouse secondary antibody were from Invitrogen; Y-27632 is from Calbiochem.

Platelets Preparation and Spreading on Immobilized Fibrinogen

Studies using human platelets were approved by institutional review board of University of Illinois at Chicago. Human washed platelets were prepared from freshly drawn blood of healthy volunteers as previously described and resuspended in modified Tyrode's buffer (12 mM NaHCO$_3$, 138 mM NaCl, 5.5 mM glucose, 2.6 mM KCl, 1 mM MgCl$_2$, 0.42 mM NaH$_2$PO$_4$, 2.5 mM HEPES, 1 mM CaCl$_2$ pH 7.4, 0.1% BSA)[24]. Mice were anesthetized by isoflurane (Pharmaceutical, Inc) and platelets were prepared from freshly drawn blood from the inferior vena cava and washed using the previously described method[25]. For analyzing platelet spreading on integrin ligand fibrinogen, washed platelets were allowed to spread on 100 µg/ml fibrinogen-coated coverslips at 37° C. for different time points, fixed, permeabilized, stained and viewed with a Leica RMI RB microscope or Zeiss LSM510 META confocal microscope as previously described[8].

Fibrinogen Binding Assay

Washed human or mouse platelets resuspended in modified Tyrode's buffer (3×10$^8$/ml, 50 µl) were incubated with 10 µg/ml Oregon Green$^{488}$-conjugated fibrinogen (Molecular Probes) and 50 µM PAR4AP for 30 minutes at 22° C. as previously described[26]. The reaction was diluted with 0.5 ml of PBS and analyzed by flow cytometry using FACS Caliber (BD Biosciences, San Jose, Calif.).

Co-immunoprecipitation and In Vitro Binding Assays

Platelets or CHO-1b9 cells expressing recombinant integrin α$_{IIb}$β$_3$[14, 23] were solubilized in modified RIPA Buffer (50 mM Tris, pH 7.4, 150 mM NaCl, 1% NP-40, 1 mM sodium orthovanadate, 1 mM NaF) with complete protease inhibitor cocktail tablets. Cell lysates were incubated with rabbit anti-Gα$_{13}$ IgG (1.5 µg/ml), anti-integrin β$_3$ rabbit serum (5 µl/ml) or an equal amount of rabbit IgG or pre-immune serum at 4° C. overnight, and subsequently with protein A-conjugated Sepharose beads for 1 hour. For the integrin β$_3$ clustering experiment, human platelets (3×10$^8$) were stimulated with 0.025 U/ml α-thrombin for 2 minutes at room temperature (to avoid platelet aggregation) with or without 2 mM RGDS, then incubated with 5 µl anti-integrin β$_3$ 8053 rabbit serum at room temperature for 1 hour, and 5 µg goat anti-rabbit secondary antibody for another 1 hour. Platelets were then solubilized in modified RIPA Buffer. For the un-clustering control and pre-immune serum control, cells were solubilized in modified RIPA Buffer first, than incubated with 5 µl 8053 serum or pre-immune serum. After 3-6 washes with lysis buffer, immunoprecipitates were analyzed by SDS-polyacrylamide gel electrophoresis and Western blots using antibodies against β$_3$, talin, or Gα$_{13}$. In some experiments, 500 µM control or inhibitor peptides, mP$_5$, mP$_7$ and mP$_{13}$ were incubated with platelet lysates prior to immunoprecipitation, or 2 mM RGDS was added into washed human platelets before stimulation by 0.025 U/ml α-thrombin. GST bead pull down analysis was previously described[8]. Purified Gα$_{13}$ or MBP-talin head were incubated with glutathione beads-bound to GST or GST-β$_3$CD at 4° C. overnight. Bead-bound proteins were analyzed by immunoblotting.

RhoA Activity Assay

Platelets or α$_{IIb}$β$_3$-expressing CHO cells in modified Tyrode's buffer or adherent on immobilized fibrinogen were solubilized in 0.8 ml lysis buffer (50 mM Tris, pH 7.4, 10 mM MgCl$_2$, 500 mM Nacl, 1% Triton X-100, 0.1% SDS, 0.5% deoxycholate, 10 µg/ml each of aprotinin and leupeptin, 1 mM phenylmethylsulfonyl fluoride, and 200 µM sodium vanadate). Lysates were cleared at 14,000 rpm for 2 minutes at 4° C., and the supernatant was incubated for 1 hour with 30 µg purified GST-Rhotekin RhoA-binding domain fusion protein (GST-RBD) bound to glutathione-Sepharose beads as previously described[37]. Samples were washed three times with 50 mM Tris, pH 7.4, 10 mM MgCl$_2$, 150 mM NaCl, 1% Triton X-100, and then immunoblotted with an anti-RhoA monoclonal antibody. Cell lysates were also immunoblotted with anti-RhoA as loading control.

Bone Marrow Transplantation

Lenti-virus was prepared by co-transfection of pLenti6/V5-Dest vector inserted with integrin β$_3$ or AAA mutant β$_3$ cDNA with pLP1, pLP2 and pLP/VSVG plasmids (Invitrogen) into ~90% confluent 293FT cells using Lipofectamine 2000. 48-72 hours after transfection, cell culture medium containing virus was concentrated, titered and stored at −80° C. Bone marrow cells from 6-8 week old integrin β$_3$$^{-/-}$ mice (Jackson Laboratories) were isolated aseptically from femurs and tibias. Stem cells were negatively selected by MACS Lineage cell depletion kit (Miltenyi Biotech) and cultured in RPMI 1640 complete medium with 10 ng/ml interleukin-3, 10 ng/ml interleukin-6, 10 ng/ml granulocyte-macrophage colony stimulating factor (GM-CSF), and 100 ng/ml stem cell factor (SCF). 50 multiplicity of infection (MOI) lenti-virus was used to infect mice bone marrow stem cells twice with 6 µg/ml polybrene. 48 hours after infection, 5×10$^6$ stem cells resuspended in PBS were transplanted by retrobulbar injection into irradiated (5Gy) integrin β$_3$$^{-/-}$ mice one day after irradiation[s].

Immunofluorescence and Confocal Microscopy

Coverslides were pre-coated with 100 µg/ml fibrinogen and blocked with 5% BSA in PBS. 300 µl α$_{IIb}$β$_3$-expressing CHO cells (expressing WT or mutant integrins; $1\times10^5$/ml) or platelets ($1\times10^7$/ml) suspended in Tyrode's buffer were added to coverslides and incubated at 37° C. for various lengths of time. Cells were fixed with 4% paraformaldehyde (PFA) for 10 minutes and permeabilized with 0.1% Triton X-100 in PBS for 2 minutes. After blocking with 5% BSA for 10 minutes, coverslides were incubated with 0.2 μg/ml mAb 15, or Alexa Fluor-546 conjugated phalloidin. For mouse platelets re-express wild type $\beta_3$ or the AAA mutant of $\beta_3$, $\beta_3$ was immuno-stained with the anti-$\beta_3$ monoclonal antibody MAb 15 and Alexa Fluor-546 conjugated phalloidin. The slides were scanned with a Zeiss LSM510 META confocal microscope as previously described[11]

Quantitation and Statistics

Image J software was used for quantitation of uncalibrated optical density of Western blot bands. Paired t-test was used for statistic analysis (mean±SD).

Example 4

As shown in the preceding examples, a G protein subunit, $G\alpha_{13}$, directly binds to the cytoplasmic domain of $\beta_3$, and is required for integrin outside-in signaling leading to c-Src activation, RhoA inhibition, and cell spreading[8]. To map the $G\alpha_{13}$ binding sites, we characterized the binding of $G\alpha_{13}$ to a panel of $\beta_3$ C-terminal truncation mutants that are stably co-expressed with wild type $\alpha_{IIb}$ in Chinese hamster ovary (CHO) cells[14] (FIG. 11A). $G\alpha_{13}$ binds to $\beta_3$ deletion mutants Δ759 and Δ741 and wild type $\alpha_{IIb}\beta_3$. However, $G\alpha_{13}$ failed to bind to the deletion mutations Δ728 and Δ715 (FIG. 11B), indicating that the $\beta_3$ sequence between amino acid residues $K^{729}$ and $T^{741}$ is required for $G\alpha_{13}$ binding.

Figure 12A:
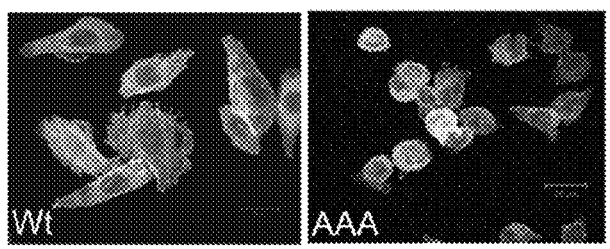
In FIG. 12A, CHO cells expressing wild type or AAA mutant $\alpha_{IIb}\beta_3$ were allowed to spread on fibrinogen surfaces.
Figure 12B:
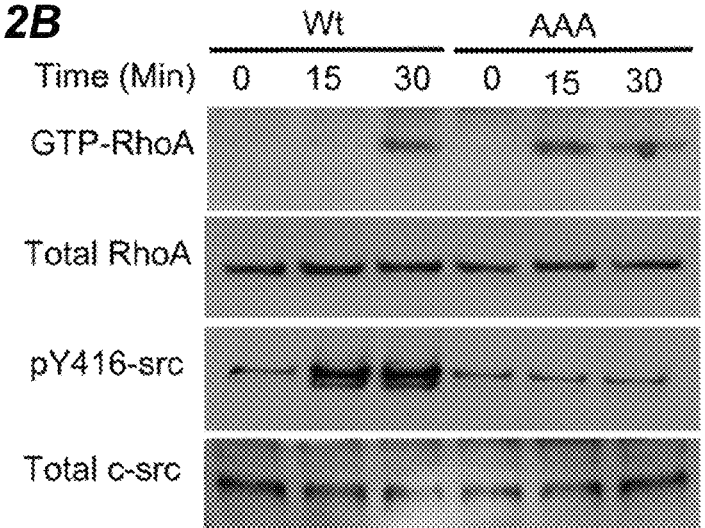
(FIG. 12B) Wild-type or AAA-mutant $\alpha_{IIb}\beta_3$-expressing CHO-1b9 cells were allowed to adhere to immobilized fibrinogen, solubilized and analyzed for RhoA activation and c-Src $Tyr^{416}$ phosphorylation.
Figure 12C:
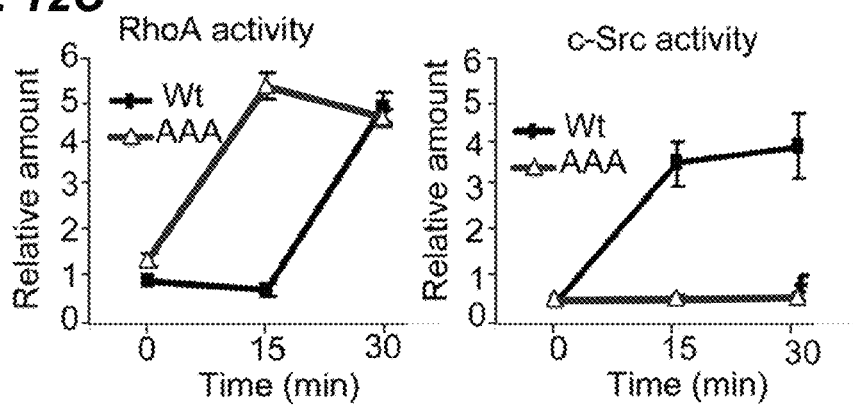
(FIG. 12C) Quantitation of RhoA activity and c-Src $Tyr^{416}$ phosphorylation as shown in (d) (mean±SD, 3 experiments).
Figure 12D:
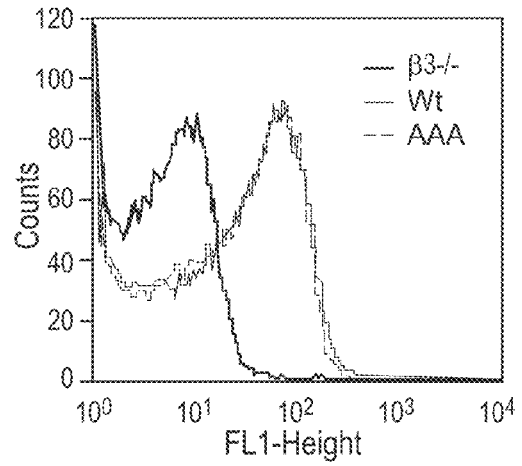
(FIG. 12D) Flow cytometry analysis of PAR4AP-induced Oregon-green-labeled fibrinogen binding to wild-type or AAA-mutant $\alpha_{IIb}\beta_3$-expressing platelets from bone marrow-transplanted $\beta_3^{-/-}$ mice. $\beta_3^{-/-}$ platelets served as negative control.

To determine the amino acid residues in this region in binding to $G\alpha_{13}$, we made $\beta_3$ mutants changing glutamic acid residues E731, E732 or E733 to alanine (E731A, E732A and E733A) (FIGS. 11 A and C). We also made a mutant in which all these three glutamic acid residues were changed to alanine residues (AAA). These mutants were co-expressed with $\alpha_{IIb}$ in CHO cells, and co-immunoprecipitated with $G\alpha_{13}$ (FIG. 11C). Wild-type integrin $\beta_3$, but not E731A, E733A, or AAA mutants, bind to $G\alpha_{13}$ (FIG. 11C), indicating that the E731 and E733 residues within the region are important for $G\alpha_{13}$ binding. Alignment of the sequences of different integrin $\beta$ subunits reveals an ExE motif conserved among most $\beta$ subunits ($\beta1$-$\beta7$, in $\beta5$, the first glutamic acid is replaced with a glutamine) (FIG. 11A). In our experiments, the $\beta$ subunits containing the ExE motif ($\beta_1$, $\beta_2$, and $\beta_3$) all interacted with $G\alpha_{13}$, indicating a conserved ExE motif in the cytoplasmic domains of most integrin $\beta$ subunits that is critical for $G\alpha_{13}$ binding. Interestingly, the $G\alpha_{13}$ binding-deficient mutant of $\beta_3$, AAA, did not negatively affect the binding of talin head domain. Thus, the ExE motif is not required for talin binding. Therefore, we further investigated the effect of AAA mutation on $G\alpha_{13}$-dependent outside-in signaling of $\beta_3$. Wild type $\beta_3$ and the AAA mutant $\beta_3$ in lenti-virus vectors were transfected into bone marrow stem cells isolated from $\beta_3^{-/-}$ mice. The transfected bone marrow stem cells were transplanted into $\beta_3^{-/-}$ mice following high dose irradiation. Flow cytometric analysis showed that platelets from the recipient mice express similar levels of wild type or AAA mutant $\beta_3$ (FIG. 11E). When the platelets were plated on the integrin ligand fibrinogen, most wild type $\beta_3$-expressing platelets spread, compared to the $\beta_3^{-/-}$ platelets that do not spread. In contrast to platelets expressing wild type $\beta_3$, the spreading of AAA mutant platelets on fibrinogen was diminished (FIG. 11D). Similarly, CHO cells expressing $\alpha_{IIb}$/AAA mutant $\beta_3$ were also defective in spreading on fibrinogen compared with wild type $\alpha_{IIb}\beta_3$ expressing cells (FIG. 12A). CHO cells expressing the $\beta_3$ AAA mutant also showed a defect in the integrin-dependent activation of c-Src, as shown by phosphorylation at $Tyr^{416}$, and abolished the integrin-dependent early-phase transient inhibition of RhoA during cell spreading (FIGS. 12B and C). These data indicate that the disruption of the $G\alpha_{13}$-binding ExE motif in $\beta_3$ caused defects in c-Src-dependent integrin outside-in signaling.

Figure 13A:
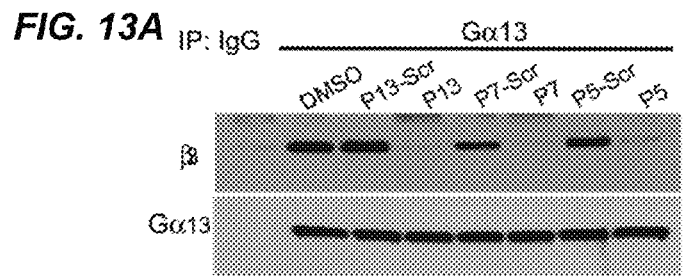
(FIG. 13A) Platelets were treated with 500 μM control peptide, $mP_{13}$, $mP_7$, or $mP_5$ peptides, then immunoprecipitated with anti-$G\alpha_{13}$ antibody or equal amount of control rabbit IgG. Lysates and immunoprecipitates were immunoblotted with anti-$G\alpha_{13}$ or anti-$\beta_3$ (MAb15) antibody.
Figure 13B:
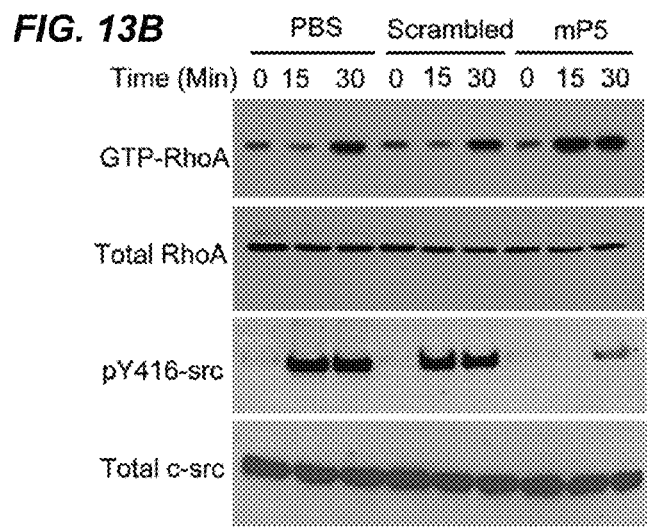
(FIG. 13B) Human platelets treated with DMSO, Myr-Scrambled peptide or $mP_5$ peptide were allowed to adhere to immobilized fibrinogen, solubilized and analyzed for RhoA activation and c-Src $Tyr^{416}$ phosphorylation.

To further develop the potential competitive inhibitors of $G\alpha13$ binding to $\beta_3$, we synthesized three myristoylated peptides mirroring sequences within the $K^{729}$-$T^{741}$ region of $\beta_3$: $mP_{13}$ (Myr-KFEEERARAKWDT), $mP_7$ (Myr-KFEEERA), and $mP_5$ (Myr-EEERA) (FIG. 11A). These peptides were incubated with platelet lysates before co-immunoprecipitation of $G\alpha_{13}$ with $\beta_3$. All 3 peptides inhibited co-immunoprecipitation between $G\alpha_{13}$ and $\beta_3$ (FIG. 13A), showing $mP_5$), indicating that the sequence EEERA is a critical $G\alpha_{13}$ binding site, and these synthetic peptides are novel inhibitors of $G\alpha13$-integrin interaction.

Figure 13D:
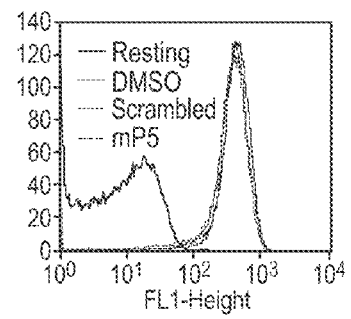
(FIG. 13D) Flow cytometry analysis of PAR4AP (50 μM)-induced Oregon-green labelled fibrinogen binding to human platelets pre-treated with DMSO, 250 μM Myr-Scrambled peptide or 250 μM mP$_5$ peptide.
Figure 13E:
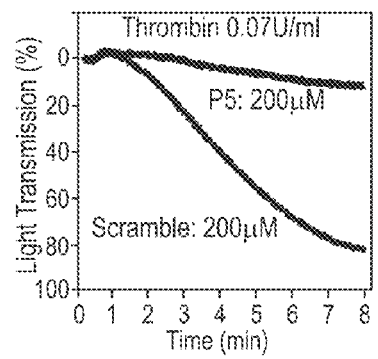
(FIG. 13E) Platelets were preincubated with mP5 or scrambled control peptides and then stimulated with thrombin in a platelet aggregometer at 37° C. Platelet aggregation traces were recorded.
Figure 13C:
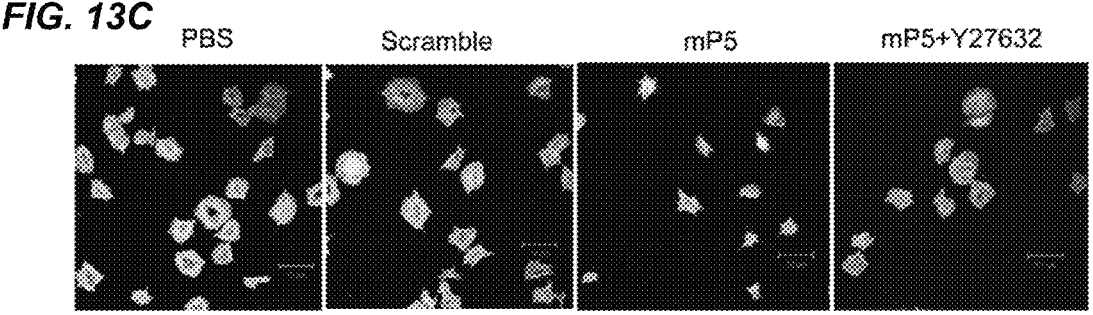
(FIG. 13C) Confocal microscopy images of platelets treated with DMSO, Myristoylated Scrambled peptides, and $mP_5$ peptide treated platelets adherent on fibrinogen for 30 minutes, without or with Rho kinase inhibitor Y27632. Merged integrin $\beta_3$ (green) fluorescence and Alexa Fluor 546-conjugated phalloidin (red) fluorescence.
Figure 14A:
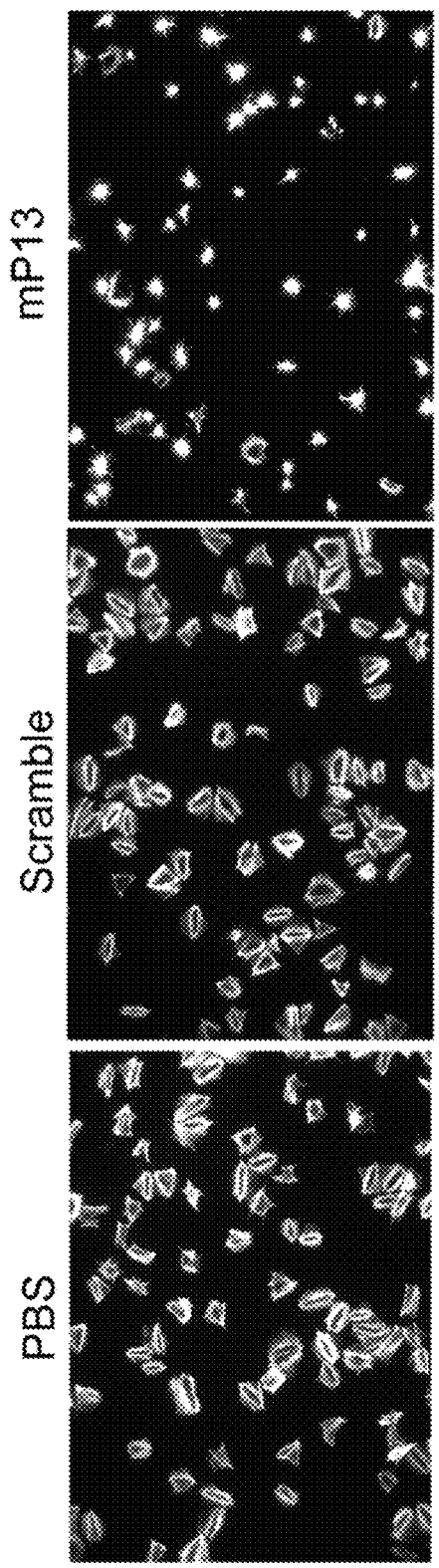
(FIG. 14A) Fluorescence microscopy images of human platelets adherent on fibrinogen that were pretreated with 250 μM myristoylated scrambled control peptide, 250 μM mP$_{13}$ peptide.
Figure 14B:
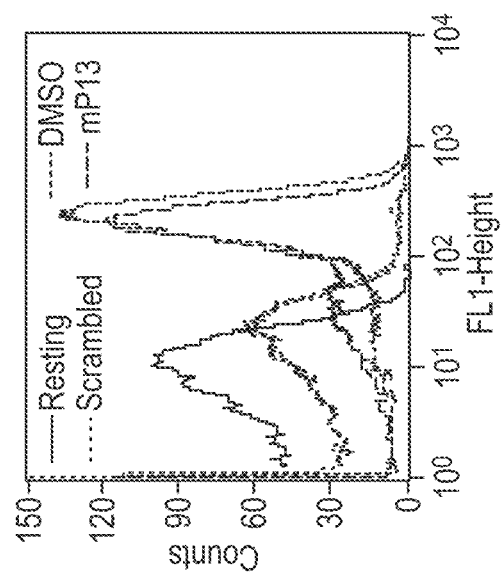
(FIG. 14B) Flow cytometry analysis of PAR4AP (50 μM)-induced Oregon-green labelled fibrinogen binding to human platelets pre-treated with DMSO, 150 μM Myr-Scrambled peptide or 150 μM mP$_{13}$ peptide.
Figure 19A:
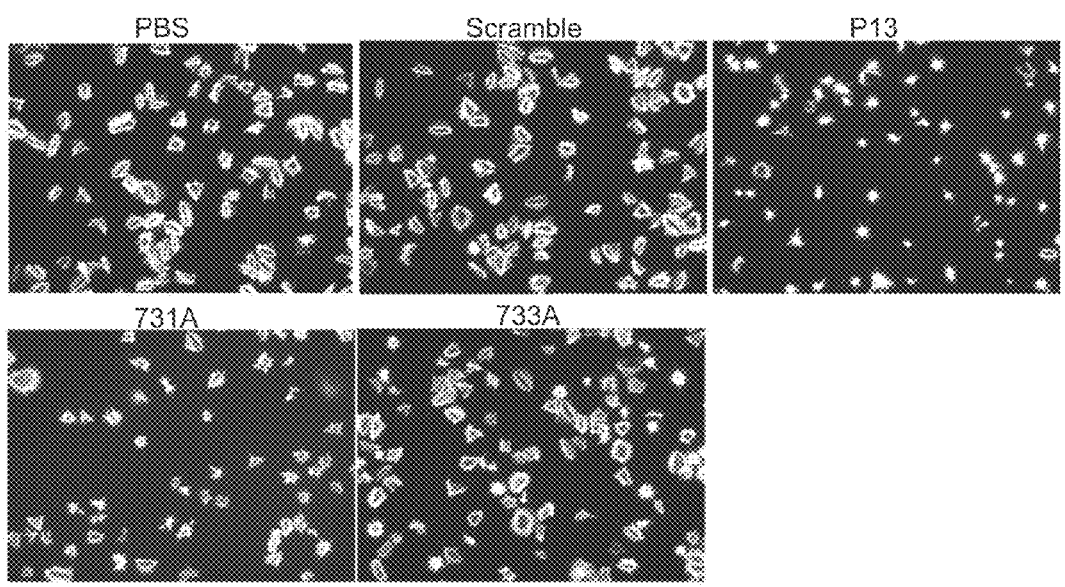
(FIG. 19A) Spreading of washed human platelets pre-treated with vehicle (PBS), scramble peptide or P13 peptide on immobilized fibrinogen for 1 hour. Platelets were stained with Alexa Fluor 546-conjugated phalloidin.
Figure 19B:
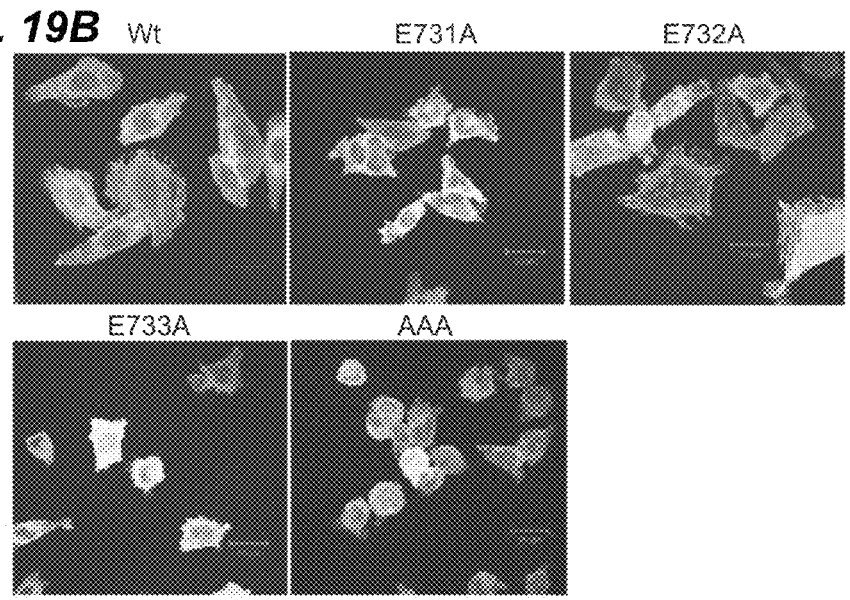
(FIG. 19B) Microscopy images of spreading 123 cells or E to A-mutant cells on fibrinogen for 1 hour. Merged integrin β3 (green) fluorescence and talin head (Red) fluorescence.

In order to determine whether these peptide inhibitors interfere with integrin outside-in signaling, we tested the effects of these myristoylated $\beta_3$ cytoplasmic domain peptide on integrin outside-in signaling. Treatment of platelets with $mP_5$ (and $mP_7$ and $mP_{13}$, similar data not shown) also inhibited integrin-dependent c-Src activation and c-Src-dependent transient RhoA inhibition (FIG. 13 B), and also abolished platelet spreading on fibrinogen (FIG. 13C). The inhibitory effect of $mP_5$ on platelet spreading was reversed by the Rho kinase inhibitor, Y27632 (FIG. 13C), suggesting that $mP_5$ inhibited platelet spreading mainly by blocking the $G\alpha_{13}$- and c-Src-dependent RhoA inhibitory signaling pathway, as characterized in our recent study[8]. Furthermore, $mP_5$ inhibited platelet aggregation induced by thrombin (FIG. 13E). In contrast, $mP_5$ had no effect on agonist (thrombin receptor PAR4 agonist)-induced fibrinogen binding to platelets (FIG. 13D). Thus, the inhibitor peptide $mP_5$ inhibited $G\alpha_{13}$-dependent integrin outside-in signaling without affecting inside-out signaling. The peptide $mP_{13}$ also inhibited integrin outside-in signaling (FIG. 14A), but also significantly affected inside-out signaling as indicated by reduced fibrinogen binding (FIG. 14B), which is consistent with the previous observations that some residues (particularly $F^{730}$, and $W^{739}$) in this peptide are critical for talin interaction. These results demonstrate the selectively inhibition of integrin outside-in signaling by the membrane-permeable peptide inhibitors of $G\alpha13$-integrin interaction. These data also demonstrate that these inhibitors also inhibit platelet spreading and aggregation and therefore useful in treating thrombosis. Such selective inhibitors may allow platelet adhesion without dramatic amplification effect of outside-in signaling, and thus are potentially useful as anti-thrombotics without profound bleeding side effect, compared to currently used integrin inhibitors.

Example 5

Platelet aggregation assays were carried out as follows: Platelet aggregation and secretion was measured in a turbidometric platelet aggregometer (Chronolog) at 37° C. with stirring (1000 rpm). Washed platelets ($3\times10^8$/ml) in modified Tyrode's buffer were stimulated with thrombin (Enzyme Research Laboratories). For talin knockdown platelet aggregation assay stimulated with manganese and ADP, manganese and ADP was mixed prior to experiment to achieve final concentration of 1 mM manganese and 5 μM ADP in reaction tube. Aggregation traces shown are representative of at least three independent experiments.

Example 6

Platelet Adhesion Assays were carried out as follows: As described before (6), microtiter wells were coated with 30 μg/ml fibrinogen in PBS overnight. Washed human platelets in modified Tyrode's buffer in the absence or presence of 1 mM $MnCl_2$ were incubated in the microtiter wells for one hour at 37° C. in a $CO_2$ incubator. After 3 washes, 50 μl of reaction buffer (0.3% p-nitrophenyl phosphate (Sigma) in 1% Triton-X-100, 50 mM sodium acetate, pH 5.0) was added into each microtiter well and incubated at 37° C. for one hour. The reaction was stopped by adding 50 μl of 1 M NaOH. Results were determined by reading OD at 405 nm wave length. The percentage of platelet adhesion was estimated from the ratio of the readings of adherent platelets to that of total platelets. Statistic significance was determined using t test (n=3).

Example 7

Clot Retraction Assays were carried out as follows: Similar as described before (2, 3), freshly prepared human whole blood was citrated with 1/10 volume of 3.8% sodium citrate. After centrifugation at 1300 rpm for 22 min with break, platelet rich plasm (PRP) was collected. Pre-incubated of PRP with 0.05% DMSO (vehicle), 250 μM mP5 peptide, 250 μM mP13 peptide, or their corresponding scrambled control peptides mP5Scr or mP13Scr for 5 minutes at room temperature. After that, 0.5 U/ml thrombin was added into PRP and mixed gently. The clots were formed and allowed to retract at 37° C. incubator with $CO_2$ and were photographed at various times. The two-dimensional sizes of retracted clots on photographs were quantified using Image J software and were expressed as clot size. Statistical significance was determined using a t test (n=3).

Example 8

Figure 21A:
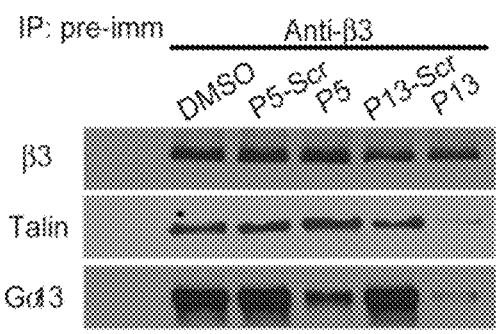
FIG. 21A represents a set of Western blots using β3, talin or Gα13 specific antibodies. Platelets treated with DMSO, 500 μM mP13, mP5, or corresponding control peptides were stimulated with 0.025 U/ml thrombin at 22° C., solubilized and immunoprecipitated with anti-β$_3$ or preimmune rabbit serum. Lysates and immunoprecipitates were immunoblotted with anti-Gα$_{13}$, anti-talin or anti-β$_3$ antibody

Myristoylated peptides were synthesized: $mP_5$ (Myr-EEERA) and $mP_{13}$ (Myr-KFEEERARAKWDT). Control peptides comprising the scrambled sequence mP5 and mP13 were also made. The peptides were tested for inhibiting binding between in $G\alpha_{13}$ and $\beta_3$ and for inhibiting binding between talin and $\beta_3$. Both peptides inhibited co-immunoprecipitation between $G\alpha_{13}$ and $\beta_3$ (FIG. 21A), indicating that the minimal sequence EEERA, which includes the ExE motif, is sufficient to bind $G\alpha_{13}$. In contrast, only $mP_{13}$, but not $mP_5$, inhibited talin association with $\beta_3$, which is consistent with the previously data that the sequence in $mP_{13}$ contains important talin-interacting residues (4, 17, 18, 21), and indicate that the EEERA sequence is not sufficient to interact with talin.

Figure 21B:
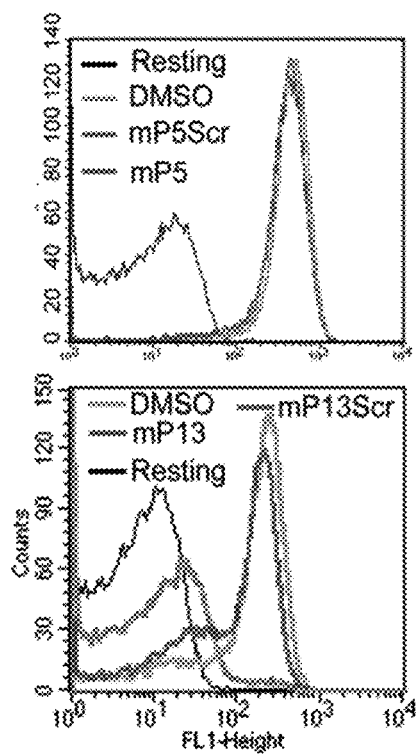
FIG. 21B represents a set of graphs of a flow cytometrical analysis of PAR4AP (50 μM)-induced Oregon-Green labelled fibrinogen binding to human platelets pre-treated with DMSO, 250 μM Myr-Scrambled peptide or 250 μM mP5 (upper panel), or pre-treated with DMSO, 150 μM Myr-Scrambled peptide or 150 μM mP13 (lower panel).
Figure 21C:
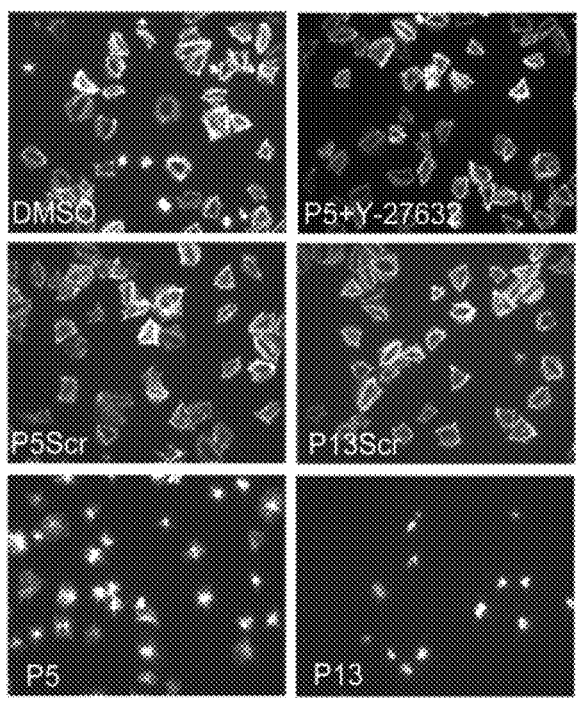
FIG. 21C represent as a set of fluorescence microscopy images of phalloidin-stained human platelets spreading on fibrinogen for 1 hr. Platelets were pre-treated with 0.05% DMSO, 250 μM myristoylated mP5, mP13, or the corresponding control peptides for 5 min at room temperature.
Figure 21D:
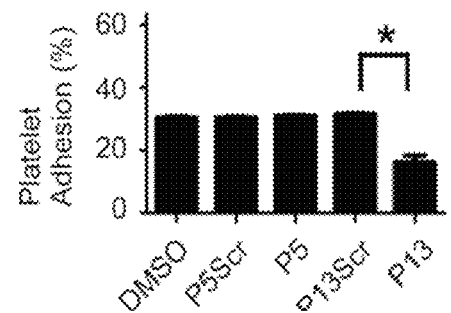
FIG. 21D represents a graph of % resting platelet adhesion to immobilized fibrinogen of platelets treated with $mP_5$ or $mP_{13}$ (250 μM) or their respective scrambled peptide (mean±SD, n=3, *p<0.001).
Figure 22:
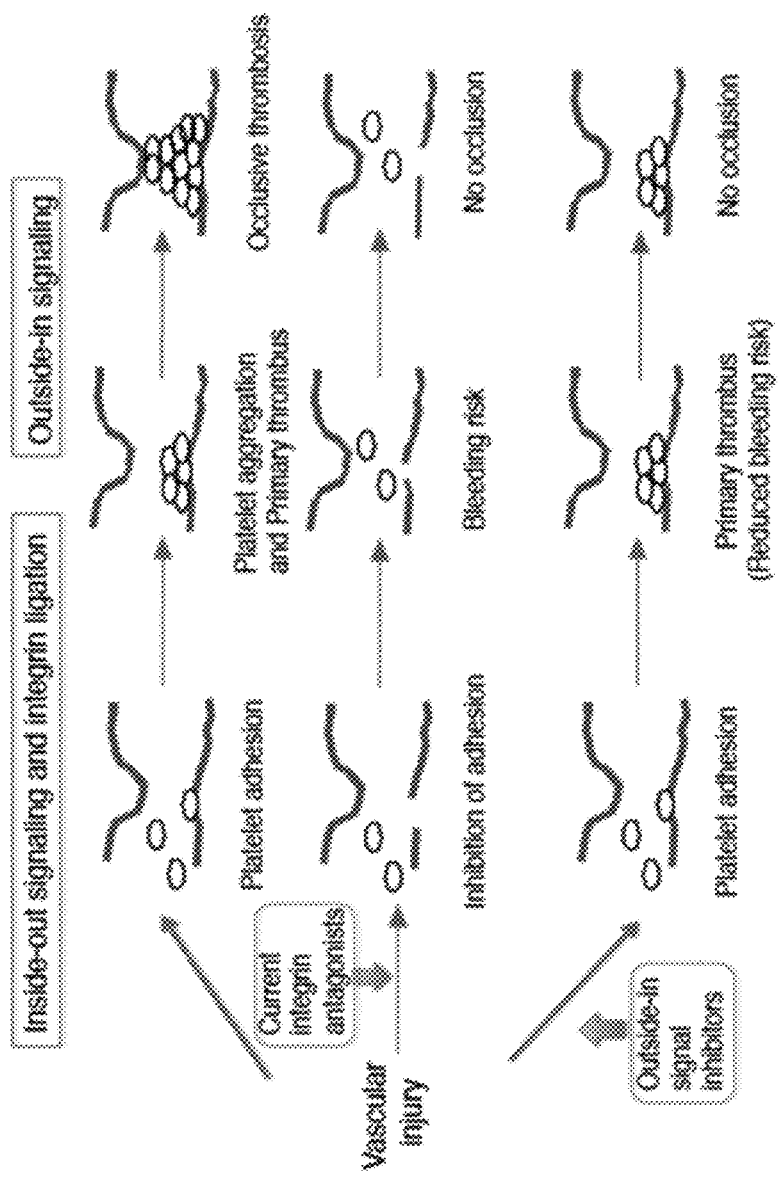
FIG. 22 is an illustration depicting the differences in inside-out and outside-in signaling upon vascular injury treated with a current integrin antagonist vs. an outside-in signal inhibitor.
Figure 23:
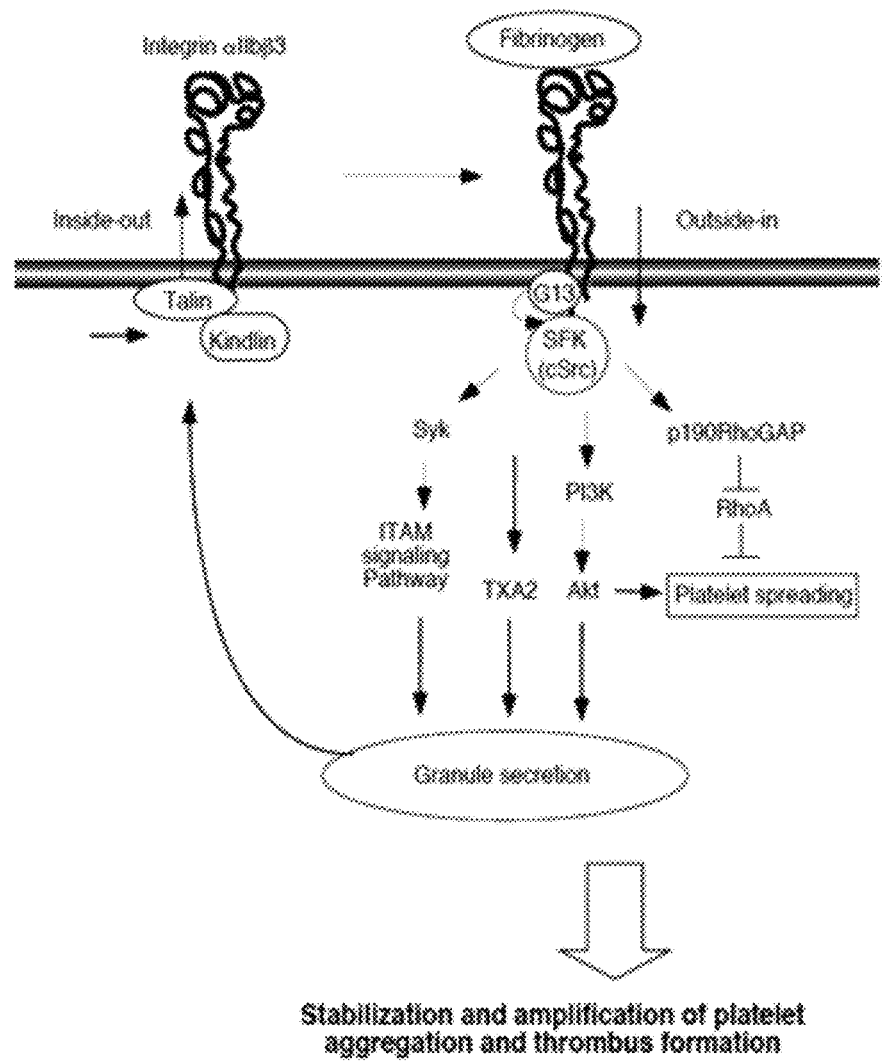
FIG. 23 is an illustration depicting signal transduction pathways of integrins.

The peptides were also tested for inhibition of platelet spreading on fibrinogen and for inhibition of platelet adhesion to immobilized fibrinogen. The $mP_5$ peptide inhibited platelet spreading on fibrinogen (FIG. 21C). The inhibitory effect of $mP_5$ on platelet spreading was reversed by the Rho kinase inhibitor, Y27632 (FIG. 21C), suggesting that $mP_5$ inhibited platelet spreading mainly by blocking the $G\alpha_{13}$- and c-Src-dependent RhoA inhibitory signaling pathway as characterized in our recent study (8). In contrast, $mP_5$ had no effect on agonist-induced fibrinogen binding to platelets (FIG. 21B) nor does it affect platelet adhesion to immobilized fibrinogen (FIG. 21D).

The peptides were furthermore analyzed for their ability to inhibit clot retraction mediated by platelets. mP5 did not inhibit but rather accelerated integrin-dependent clot retraction mediated by platelets, which requires late phase outside-in signaling.

These data indicate that the $\beta_3$-based $G\alpha_{13}$ inhibitor peptide $mP_5$ selectively inhibited the early phase of outside-in signaling without affecting talin-dependent inside-out signaling or ligand-induced integrin activation. Nor did it inhibit the late phase outside-in signaling associated with the second wave of talin binding. Thus, $G\alpha_{13}$ plays a selective role in the early phase of outside-in signaling during which it binds to $\beta_3$. In contrast to $mP_5$, $mP_{13}$ not only inhibited early phase outside-in signaling (FIG. 21C), but also inhibited inside-out signaling as indicated by diminished fibrinogen binding (FIG. 21B). This peptide also inhibited platelet adhesion to immobilized fibrinogen (FIG. 21D). Furthermore, mP13 inhibited clot retraction and this inhibition was not reversed by manganese.

Example 9

Figure 24:
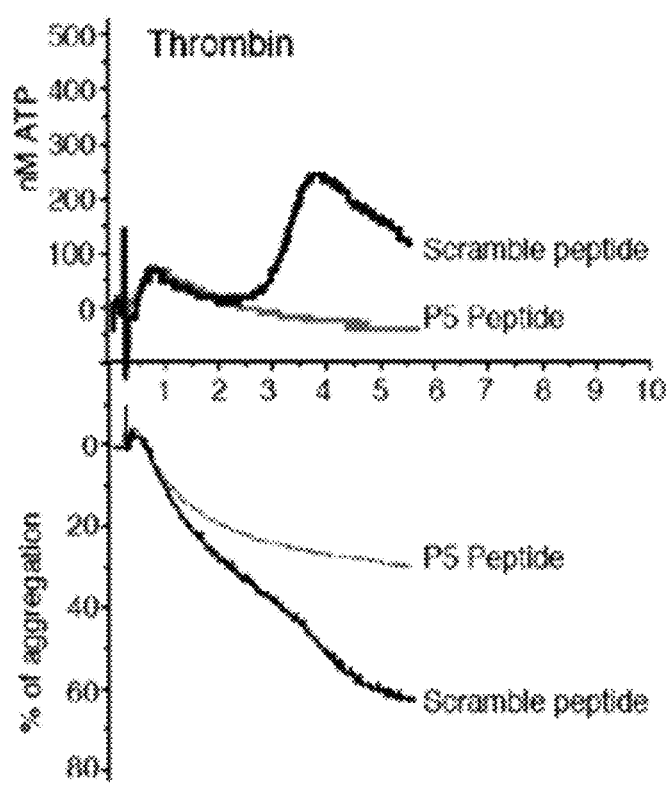
FIG. 24 represents a set of graphs depicting the differences in platelet ATP secretion (top) and % platelet aggregation (bottom) upon treatment with mP5 peptide or a scambled control peptide thereof.

The effect of mP5 (Myr-EEERA) on platelet aggregation and secretion was tested. As shown in FIG. 24, mP5 inhibited platelet granule secretion and the second wave of platelet aggregation. These results support the notion that mP5 selectively inhibits outside-in signaling.

Example 10

This example demonstrates the design of modified forms of the mP5 peptide (Myr-EEERA). A first set of modified forms of the mP5 peptide are made wherein each peptide of the set retains the EEE motif, but adds 1, 2, 3, 4, 5, or more flanking residues N-terminal to the EEE motif or C-terminal to the EEE motif. The flanking residues are based on the flanking sequences that naturally occur in the β3 integrin sequence, or other beta integrin sequences. The modified peptides include, for example, KFEEE, FEEER, AKFEEE, KFEEER, FEEERA, EEERAR, EEERARA, and EEER-ARAK. For each modified peptide synthesized, two control peptides are synthesized: (1) a scrambled peptide having the same amino acid composition but having a different amino acid sequence, and (2) a loss of function peptide in which the sequence is identical except for each of the ExE residues are changed to alanine. Each peptide is tested for the ability to inhibit talin binding or until the affinity of the peptide peaks.

In a second set of peptides, the peptides of the first set are modified to contain the second glutamic acid in the EEE motif to another amino acid. Some will be changed to EAE or EKE. These peptides are subsequently tested for their affinity for Gα13.

A third set of modified forms of the mP5 peptide are made wherein the peptide is cyclized. Cyclization can increase the efficiency of delivery and minimize extracellular cleavage of the peptide. In an exemplary instance, the peptides are made with a Cys at each termini (N- and C-termini) and reacted under conditions to form a disulfide bridge. The cyclic peptides are subsequently tested for inhibitory effect on Gα13-integrin interaction, biochemical markers of integrin outside-in signaling, platelet adhesion, platelet aggregation, and thrombus formation in vitro.

The above sets of peptides are tested for their ability to inhibit Gα13-integrin interaction by an in vitro binding assay using purified Gα13 and purified integrin β3 cytoplasmic domain[14]. The recombinant β3 cytoplasmic domain-GST fusion protein and control GST protein are immobilized to glutathione-beads. The beads are mixed with recombinant Gα13 in the presence or absence of GTPγS. After washes, bound Gα13 is analyzed by western blot. The modified peptides as well as each of the control peptides are added to the reaction in order to determine the inhibitory effects of these peptides.

Modified forms of mP5 are additionally screened by an assay in which modified or control peptides are added to microtiter wells to which the recombinant β3 cytoplasmic domain is immobilized. After addition of the peptide to each well, biotinylated Gα13 is added to each well. HRP-labeled streptoavidin in an ELISA assay is used to determine which peptides inhibited the interaction between Gα13 and the immobilized β3 cytoplasmic domain, as those wells containing HRP-labeled streptoavidin bound to biotinylated Gα13 indicates that the peptide successfully inhibited the binding between Gα13 and the immobilized β3 cytoplasmic domain.

Screening of ExE peptides are additionally tested by constructing a phage library expressing the ExE motif peptides with random flanking amino acid residues, and screen for high affinity binding using microtiter wells coated with Gα13 protein. The phage clones with high affinity binding sequences are sequenced and the corresponding peptide are synthesized for further testing, as described herein.

Top performing peptides are selected and used for in vivo studies, as described in the following examples.

Example 11

Figure 25:
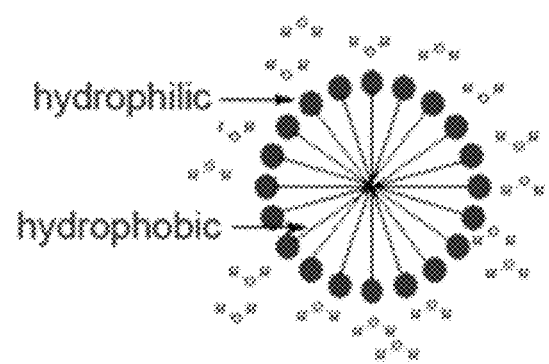
FIG. 25 is an illustration of a micelle.

Micelles are nano-sized particles formed by aggregation of amphiphilic molecules in water (FIG. 25). Peptides of the invention attached to a fatty acid may be used to formulate the peptides into micelles. The ExE motif peptide of SEQ ID NO: 87 was made into a micellar formulation, as follows: 1,2-distearoyl-sn-glycero-3-phosphoethanolamine-N-[amino (polyethylene glycol)-2000] (PEG$_{2000}$-DSPE; Northern Lipids Inc., Vancouver, BC), L-α-phosphatidylcholine (egg PC, Type XI-E, Sigma-Aldrich, St. Louis, Mo.) and peptide was mixed at a molar ratio of 45:5:1. Micelles were prepared using a film rehydration method, as previously described[21]. The lipid film was rehydrated with 10 mM isotonic HEPES buffer (HEPES 10 mM, NaCl 135 mM, pH 7.4) to form the micelle colloid. The mixture of the lipids and peptides was dissolved in methanol and chloroform, followed by evaporation using a rotary-evaporator R-215 (40 mbar, 45° C., Buchi, New Castle, Del.) to form a thin lipid layer. The lipid film was desiccated under vacuum (in the dark) overnight and then rehydrated with 10 mM isotonic HEPES buffer (HEPES 10 mM, NaCl 135 mM, pH 7.4) to form micelle colloid.

In a preliminary dose-dependent study, the micellar formulation of FEEERA (SEQ ID NO: 87) was compared to the same peptide dissolved in DMSO. Whereas 250 μM of this peptide dissolved in DMSO was required for the maximal effect on in vitro platelet aggregation, only 4 μM of this peptide was required for the maximal effect when made into a micellar formulation (FIG. 29).

Example 12

The following experiments are performed ex vivo using isolated platelets, platelet rich plasma (PRP), or whole blood from human donors and animals.

Platelet Aggregation and Granule Secretion

Blood is drawn from either human donors or from the vena cava of anethetized mice. For preparation of washed platelets, acid citrate dextrose (ACD; 85 mM trisodium citrate, 83 mM dextrose, and 21 mM citric acid) is used as anti-coagulant. For PRP, 3.2% sodium citrate is used as anti-coagulant. Either isolated platelets or PRP is preincubated with increasing concentrations of micellar ExE motif peptides or control scrambled peptides, and, after adding luciferase/luciferin reagents, the peptides are tested for platelet aggregation and simultaneously recorded for secretion of ATP from dense granules using a Lumi-aggregometer (Chronolog). Adenosine triphosphate (ADP), thrombin, PAR4AP, PAR1AP, U46619, ristocetin/botrocetin and collagen are used to stimulate platelets. P-selectin exposure, which is an indicator of α-granule secretion, is measured using flow cytometry using anti-p-selectin antibodies[22].

Figure 27:
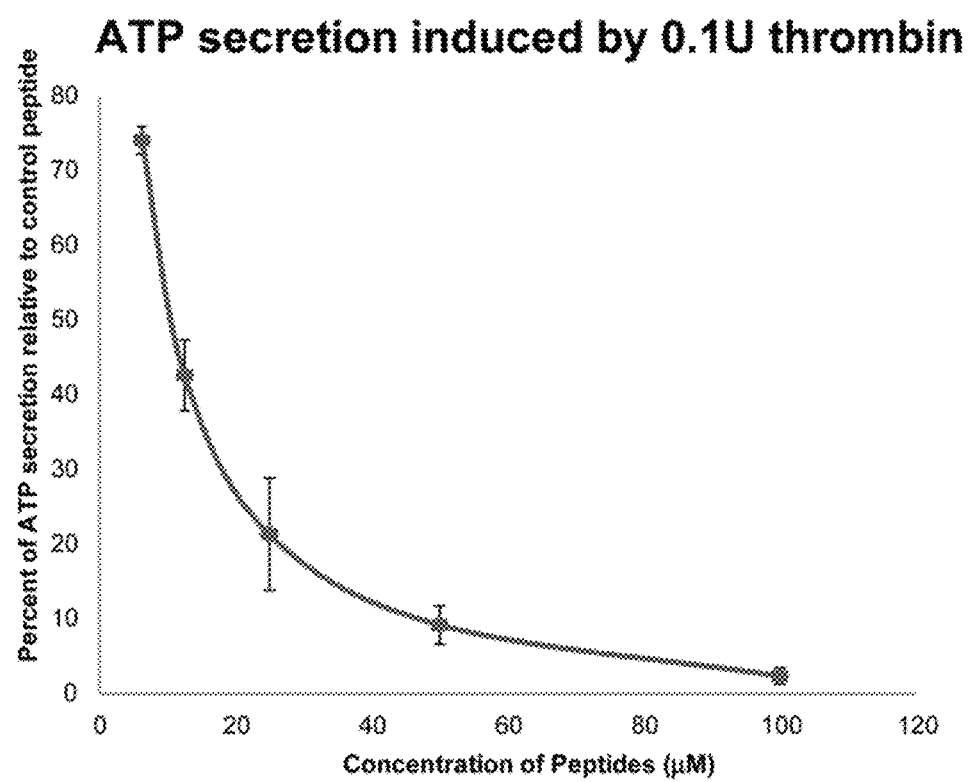
FIG. 27 represents a graph of ATP secretion by platelets stimulated with 0.1 U thrombin and pre-incubated with FEEERA peptide dissolved in DMSO or the control scrambled peptide thereof.

Isolated platelets or PRP were pre-incubated with various concentrations of either a peptide of FEEERA (SEQ ID NO: 87), or a scrambled control thereof, dissolved in DMSO. 0.1 U thrombin was then added to the cells to stimulate ATP secretion. ATP secretion by the cells was then measured using a lumi-aggregometer. % secretion relative to the scrambled control peptide is shown in FIG. 27.

Example 13

Platelet Adhesion and Thrombus Formation Under Flow Conditions

The effect of micellar ExE motif peptides, such as mP5 and the peptide of FEEERA (SEQ ID NO: 87), on platelet adhesion and thrombus formation are tested under flow conditions ex vivo under flow conditions that mimic arterial blood flow. Two different types of flow adhesion assays are set up in the laboratory using: (1) a laminar flow chamber and (2) a cone-plate rheometer. Laminar flow chambers are coated with sub-endothelial matrix proteins, such as collagen, von Willebrand Factor (VWF) or both. Platelets are labeled with a fluorescent dye (mepacrine or 5-chloromethylfluorescein diacetate (CM-FDA)), and anti-coagulated blood, PRP or isolated platelets are infused into the chamber at defined flow shear rates with a syringe pump. Adhesion and the formation of platelet-rich thrombi are monitored using an inverted fluorescence microscope and charge coupled device (CCD) camera. In some experiments, the thrombus size is quantitated using a confocal microscope (similar to that described below). When using the cone-plate rheometer, glass slides are coated with VWF or collagen, and placed on the stage of a Thermo-Haake rheometer with constant temperature control. Mepacrine-labeled platelets, treated with ExE peptide micelles or control micelles, are added to the glass plate and subjected to constant shear stress. Stable platelet adhesion and the formation of platelet aggregates are photographed and analyzed under a fluorescence microscope. Different doses of ExE motif peptides or control peptides are incubated with platelets to obtain an inhibition constant ($K_i$).

Example 14

PFA-100 Analysis of ExE Motif Peptides

PFA-100 is a clinically used test of platelet function that allows passage of blood through a cartridge coated with platelet agonists/adhesive proteins (such as epinephrine/collagen) until the time of thrombotic occlusion occurs in the cartridge[27]. ExE motif peptides like mP5 and the peptide of FEEERA SEQ ID NO: 87) on thrombosis are tested in this apparatus. Blood from healthy donors who have not taken platelet inhibitors for two weeks is anticoagulated with 3.2% sodium citrate, and micellar ExE motif peptides or control peptides are added. The blood samples are then analyzed by PFA-100 assay as essentially described in [27].

Example 15

In Vivo Bleeding Time Analysis for Hemostatic Function

Figure 26:
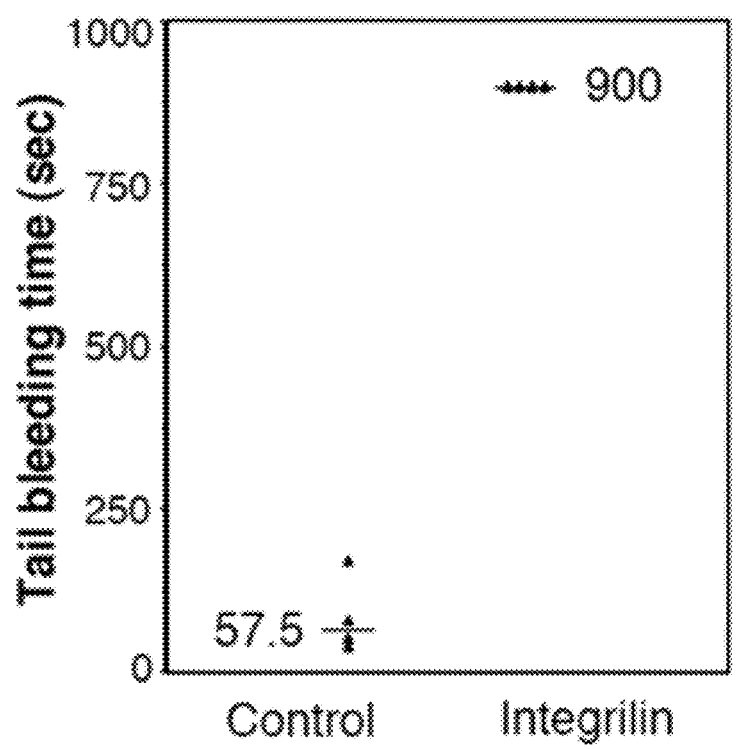
FIG. 26 represents a graph of tail bleeding time in mice treated with Integrillin or a saline control. Median value indicated.

Bleeding time analysis is an indicator of overall in vivo hemostatic function. The ligand-binding function of integrin is critical for primary platelet adhesion and aggregation and thus important for hemostasis. Bleeding time analysis is carried out as follows: C57BL/6 mice are retro-orbitally injected with micelle formulated ExE motif peptides (such as mP5) and scrambled controls. Distal portions of the mouse tail (5 mm) are amputated with a scalpel and the tail immersed in 0.15 M NaCl at 37° C. as previously described[28]. Time to cessation of bleeding is recorded. If the bleeding fails to stop after 900 seconds, the assay is stopped and pressure is applied to the tail to prevent excessive loss of blood. The assay is performed in a double-blinded fashion. Similarly, bleeding time of wild type mice treated with current integrin antagonists, reopro and integrillin, are also tested in comparison with the ExE motif peptides. Integrillin was tested in this fashion (with a saline control and 4 mice per group). The results are shown in FIG. 26 with the median value indicated. Bleeding time for mice treated with integrillin exceeded the upper limit of the assay (900 s). Consequently, the assay was terminated and bleeding was stopped via pressure application.

Because the ExE motif peptides do not affect the ligand binding function of integrin $\alpha IIb\beta 3$, it is expected that the effect of these peptides on bleeding time should be significantly reduced as compared to current integrin antagonists, which abolish ligand binding to integrins.

Example 16

Safety of the Micellar ExE Motif Peptides for In Vivo Use

The maximal tolerated doses (MTD) in C57BL mice are determined in order to assess acute toxicity of the ExE motif peptide. An initial dose of 5× the maximal effective dose (as determined by ex vivo study) is injected into 2 mice via tail vein. A lower dose is administered if mice die or show clinical sign of intolerance. Conversely, if none die or show sign of intolerance, a higher dose is administrated. This process is repeated until the MTD is approached. MTD is tested in additional mice for two weeks (5 mice of each gender). It is possible that mice tolerate these micellar peptides well even at high doses well above the effective dose. If this is the case, the peptides are considered safe for in vivo use.

Example 17

The effects of varying doses of the ExE motif peptides (e.g., mP5, the peptide of FEEERA (SEQ ID NO: 87) on in vivo thrombosis are tested using the $FeCl_3$- and laser-induced injury models. Existing integrin antagonists and other anti-platelet drugs (cyclooxygenase inhibitors and P2Y12 inhibitors) are run so that the effects of the EXE motif peptides can be compared to the effects induced by the existing drugs. Negative controls include vehicle controls. Additional tests are performed to see if the use of the ExE motif peptides in combination with one or more existing integrin antagonists or anti-platelet drugs produce an additive or synergistic effect on thrombosis.

Ferric Chloride-Induced Thrombosis Model

The ferric chloride injury-induced carotid artery thrombosis model has been carried out in C57BL/6 mice[29, 30]. $FeCl_3$-induced thrombosis is widely used to reflect the role of platelets in the formation of occlusive arterial thrombosis[31]. In this study, adult mice are anesthetized by intraperitoneal injection of pentobarbital (120 mg/kg). The left common carotid artery is surgically exposed and a miniature Doppler flow probe (Model 0.5VB; Transonic Systems, Ithaca, N.Y.) is placed on the surface of the artery. After adding 0.9% sodium chloride solution in the surgical wound to allow Doppler monitoring, baseline blood flow is recorded using a Transonic flowmeter. Thereafter, sodium chloride solution is removed and filter paper (round, 1.0 mm in diameter) saturated with 10% $FeCl_3$ is applied to the surface of the carotid artery immediately proximal to the flow probe. After 3 minutes, the filter paper is removed, saline solution is again administered to the wound, and carotid blood flow is monitored. If occlusive thrombosis occurs to the injured carotid artery, blood flow is reduced to zero. ExE motif peptide micelles and controls are injected i.v. via the tail vein in C57BL/6 mice, then tested for occlusive thrombosis using this model.

Figure 28:
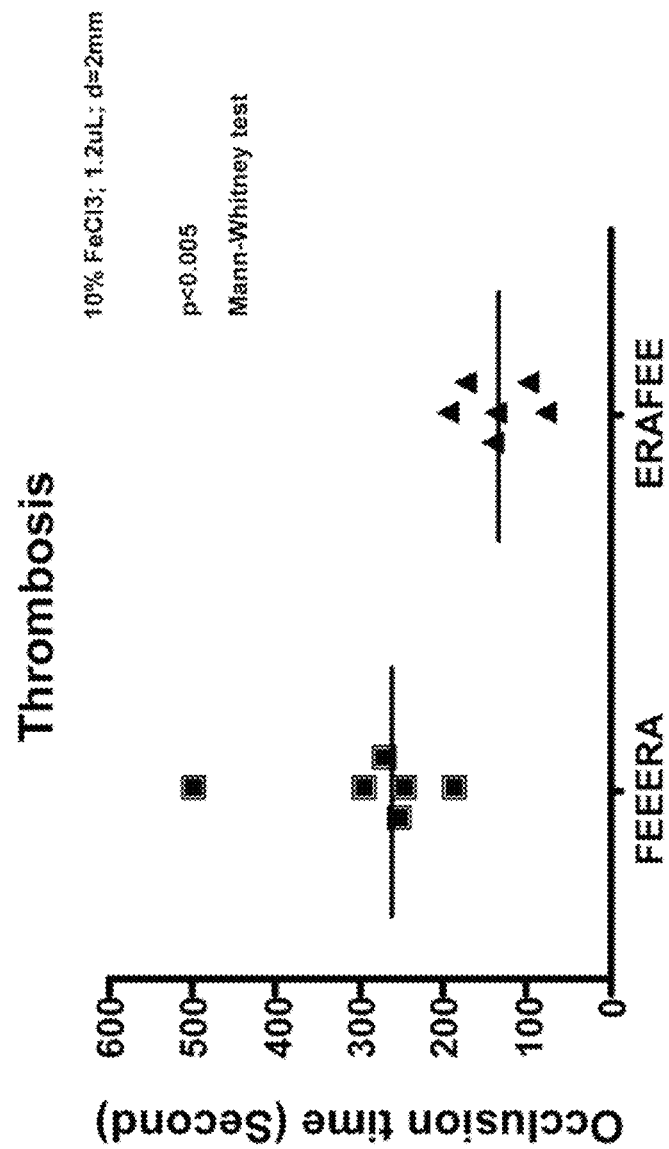
FIG. 28 represents a graph of the occlusion time of mice treated with an EXE motif peptide or the scrambled peptide control.

This assay was carried out with two EXE peptides: FEEERA and the scrambled control thereof (ERAFEE). As shown in FIG. 28, the time to occlusion was increased when the mice were given FEEERA as compared to its scrambled control.

Laser-Induced Injury Model of In Vivo Thrombosis Using Intravital Microscopy The effects of the ExE motif peptides on in vivo thrombosis are examined using a laser-ablation wide-field confocal microscope system[32]. Using this system, in vivo thrombosis in small blood vessels are observed in real time. Using video photography, the kinetics of thrombosis are recorded and analyzed. Fluorescently labeled platelet-specific antibodies are injected to monitor the incorporation of platelets in thrombi. Control or ExE motif peptide-injected mice (male, 6-8 weeks) are anesthetized via intraperitoneal injection of ketamine and xylazine. A cannula is placed in the jugular vein for injection of drugs. The cremaster muscle is exteriorized by removing connective tissues. The muscle is fixed as a single sheet on a glass slide on an intravital microscopy tray. Rat anti-mouse CD42b antibody conjugated with Dylight 649 is infused through the jugular cannula in mice for 5 minutes. Platelet thrombus formation is visualized using an Olympus fluorescence microscope with a 60× water immersion objective lens and recorded using a high speed digital camera. Vaso-occlusive state is determined by monitoring red cell flow velocity. It is expected that the ExE motif peptide-treated mice show a significant reduction in occlusive thrombus formation, but minimally affect initial platelet adhesion in response to laser-induced injury.

Example 18

The Effect of In Vivo Injection of Micellar ExE Motif Peptides on Ex Vivo Platelet Function Micelles containing the ExE motif peptides are injected through the tail vein of mice, and after a defined time (such as 5 min, 10 min and 30 min), the mice are anesthetized and their blood drawn. Platelet function is tested in vitro as described herein. These experiments allow the determination of whether injection of ExE motif peptides have an effect on overall platelet function.

Example 19

Figures 30, 30A, 30B:
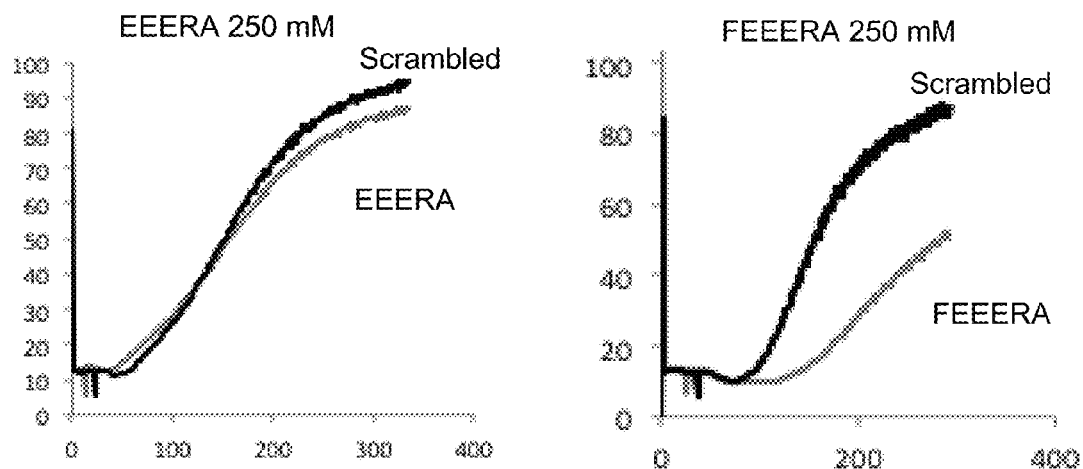
FIG. 30A represents a table including scores of ability to inhibit platelet aggregation for varying doses of mP5 or the peptide of SEQ ID NO: 87.
FIG. 30B represents a set of graphs depicting platelet aggregation traces for the mP5 peptide, the scambled control of mP5, the peptide of SEQ ID NO: 87 or its scrambled control.

Platelet aggregation assays were performed with myristoylated peptide mP5, myristoylated peptide of SEQ: ID NO: 87, or their respective scrambled control peptides, as essentially described herein. Briefly, washed human platelets were preincubated with 25, 50, 100, 250, or 500 µM peptide solubilized in DMSO. The platelets were subsequently induced with 0.09 U/ml thrombin and platelet aggregation was measured in a turbidometric platelet aggregometer. FIG. 30A provides a table of scores for each test peptide (mP5, myristoylated peptide of SEQ ID NO: 87) at the indicated dose, wherein the score indicates how well the peptide inhibited platelet aggregation. As shown in FIG. 30A, the myristoylated peptide of SEQ ID NO: 87 was able to inhibit platelet aggregation at lower doses, as compared to the mP5 peptide. The aggregation traces for each test peptide at 250 µM are shown in FIG. 30B.

REFERENCES

The following represents a listing of the references cited in EXAMPLES 1 and 2.
1. R. O. Hynes, *Cell* 110, 673 (2002).
2. M. H. Ginsberg, A. Partridge, S. J. Shattil, *Curr Opin Cell Biol* 17, 509 (2005).
3. Y. Ma, J. Qin, E. Plow, *J Thromb Haemost* 5, 1345 (2007).
4. S. J. Shattil, *Trends Cell Biol* 15, 399 (2005).
5. A. Obergfell et al., *J Cell Biol* 157, 265 (2002).
6. E. G. Arias-Salgado et al., *Proc Natl Acad Sci USA* 100, 13298 (2003).
7. P. Flevaris et al., *J Cell Biol* 179, 553 (2007).
8. P. Flevaris et al., *Blood* 113, 893 (2009).
9. N. A. Riobo, D. R. Manning, *Trends Pharmacol Sci* 26, 146 (2005).
10. L. F. Brass, D. R. Manning, S. J. Shattil, *Prog Hemost Thromb* 10, 127 (1991).
11. A. Moers et al., *Nat Med* 9, 1418 (2003).
12. T. Kozasa et al., *Science* 280, 2109 (1998).
13. M. J. Hart et al., *Science* 280, 2112 (1998).
14. B. Klages, U. Brandt, M. I. Simon, G. Schultz, S. Offermanns, *J Cell Biol* 144, 745 (1999).
15. V. Senyuk et al., *Cancer Res* 69, 262 (2009).
16. B. S. Coller, *Blood* 55, 169 (1980).
17. Z. Li, G. Zhang, R. Feil, J. Han, X. Du, *Blood* 107, 965 (2006).
18. M. Gu, X. Xi, G. D. Englund, M. C. Berndt, X. Du, *J. Cell. Biol.* 147, 1085 (1999).
19. W. T. Arthur, L. A. Petch, K. Burridge, *Curr Biol* 10, 719 (2000).
20. S. Tanabe, B. Kreutz, N. Suzuki, T. Kozasa, *Methods Enzymol* 390, 285 (2004).
21. J. S. Huang, L. Dong, T. Kozasa, G. C. Le Breton, *J Biol Chem* 282, 10210 (2007).
22. C. Vidal, B. Geny, J. Melle, M. Jandrot-Perrus, M. Fontenay-Roupie, *Blood* 100, 4462 (2002).
23. K. Moissoglu, M. A. Schwartz, *Biol Cell* 98, 547 (2006).
24. X. P. Du et al., *Cell* 65, 409 (1991).
25. X. D. Ren, M. A. Schwartz, *Methods Enzymol* 325, 264 (2000).
S1. J. S. Huang, L. Dong, T. Kozasa, G. C. Le Breton, J Biol Chem 282, 10210 (2007).
S2. S. Tanabe, B. Kreutz, N. Suzuki, T. Kozasa, Methods Enzymol 390, 285 (2004).
S3. X. P. Du et al., Cell 65, 409 (1991).
S4. H. Yin, A. Stojanovic, N. Hay, X. Du, Blood 111, 658 (2008).
S5. H. Yin et al., Blood 112, 1139 (2008).
S6. P. Flevaris et al., Blood 113, 893 (2009).
S7. P. Flevaris et al., J Cell Biol 179, 553 (2007).
S8. X. Du, J. E. Fox, S. Pei, J Biol Chem 271, 7362 (1996).
S9. J. Niu, J. Profirovic, H. Pan, R. Vaiskunaite, T. Voyno-Yasenetskaya, Circ Res 93, 848 (2003).
S10. X. D. Ren, M. A. Schwartz, Methods Enzymol 325, 264 (2000).
S11. V. Senyuk et al., Cancer Res 69, 262 (2009).

The following represents a listing of the references cited in EXAMPLES 3 and 4.
1. Hynes, R. O. Integrins: bidirectional, allosteric signaling machines. *Cell* 110, 673-687 (2002).
2. Moissoglu, K. & Schwartz, M. A. Integrin signalling in directed cell migration. *Biol Cell* 98, 547-555 (2006).
3. Tadokoro, S. et al. Talin binding to integrin beta tails: a final common step in integrin activation. *Science* 302, 103-106 (2003).
4. Ginsberg, M. H., Partridge, A. & Shattil, S. J. Integrin regulation. *Curr Opin Cell Biol* 17, 509-516 (2005).
5. Moser, M., Nieswandt, B., Ussar, S., Pozgajova, M. & Fassler, R. Kindlin-3 is essential for integrin activation and platelet aggregation. *Nat Med* 14, 325-330 (2008).
6. Montanez, E. et al. Kindlin-2 controls bidirectional signaling of integrins. *Genes Dev* 22, 1325-1330 (2008).
7. Ma, Y. Q., Qin, J., Wu, C. & Plow, E. F. Kindlin-2 (Mig-2): a co-activator of beta3 integrins. *J Cell Biol* 181, 439-446 (2008).
8. Gong, H. et al. G protein subunit Galpha13 binds to integrin alphaIIbbeta3 and mediates integrin "outside-in" signaling. *Science* 327, 340-343 (2010).
9. Arias-Salgado, E. G. et al. Src kinase activation by direct interaction with the integrin beta cytoplasmic domain. *Proc Natl Acad Sci USA* 100, 13298-13302 (2003).
10. Obergfell, A. et al. Coordinate interactions of Csk, Src, and Syk kinases with [alpha]IIb[beta]3 initiate integrin signaling to the cytoskeleton. *J Cell Biol* 157, 265-275 (2002).
11. Flevaris, P. et al. A molecular switch that controls cell spreading and retraction. *J Cell Biol* 179, 553-565 (2007).
12. Wegener, K. L. et al. Structural basis of integrin activation by talin. *Cell* 128, 171-182 (2007).
13. Patil, S. et al. Identification of a talin-binding site in the integrin beta(3) subunit distinct from the NPLY regulatory motif of post-ligand binding functions. The talin n-terminal head domain interacts with the membrane-proximal region of the beta(3) cytoplasmic tail. *J Biol Chem* 274, 28575-28583 (1999).
14. Gu, M., Xi, X., Englund, G. D., Berndt, M. C. & Du, X. Analysis of the roles of 14-3-3 in the platelet glycoprotein Ib-IX-mediated activation of integrin alpha(IIb)beta(3) using a reconstituted mammalian cell expression model. *J Cell Biol* 147, 1085-1096 (1999).
15. Arias-Salgado, E. G., Lizano, S., Shattil, S. J. & Ginsberg, M. H. Specification of the direction of adhesive signaling by the integrin beta cytoplasmic domain. *J Biol Chem* 280, 29699-29707 (2005).
16. Zhang, X. et al. Talin depletion reveals independence of initial cell spreading from integrin activation and traction. *Nat Cell Biol* 10, 1062-1068 (2008).

17. Law, D. A. et al. Integrin cytoplasmic tyrosine motif is required for outside-in alphaIIbbeta3 signalling and platelet function. *Nature* 401, 808-811. (1999).
18. Anthis, N. J. et al. Beta integrin tyrosine phosphorylation is a conserved mechanism for regulating talin-induced integrin activation. *J Biol Chem* 284, 36700-36710 (2009).
19. Nayal, A., Webb, D. J. & Horwitz, A. F. Talin: an emerging focal point of adhesion dynamics. *Curr Opin Cell Biol* 16, 94-98 (2004).
20. Wang, R., Shattil, S. J., Ambruso, D. R. & Newman, P. J. Truncation of the cytoplasmic domain of beta3 in a variant form of Glanzmann thrombasthenia abrogates signaling through the integrin alpha(IIb)beta3 complex. *J Clin Invest* 100, 2393-2403 (1997).
21. Petrich, B. G. et al. Talin is required for integrin-mediated platelet function in hemostasis and thrombosis. *J Exp Med* 204, 3103-3111 (2007).
22. Goksoy, E. et al. Structural basis for the autoinhibition of talin in regulating integrin activation. *Mol Cell* 31, 124-133 (2008).
23. Xi, X., Bodnar, R. J., Li, Z., Lam, S. C. & Du, X. Critical roles for the COOH-terminal NITY and RGT sequences of the integrin beta3 cytoplasmic domain in inside-out and outside-in signaling. *J Cell Biol* 162, 329-339 (2003).
24. Flevaris, P. et al. Two distinct roles of mitogen-activated protein kinases in platelets and a novel Rac1-MAPK-dependent integrin outside-in retractile signaling pathway. *Blood* 113, 893-901 (2009).
25. Yin, H. et al. Src family tyrosine kinase Lyn mediates VWF/GPIb-IX-induced platelet activation via the cGMP signaling pathway. *Blood* 112, 1139-1146 (2008).
26. Su, X. et al. RGT, a synthetic peptide corresponding to the integrin beta 3 cytoplasmic C-terminal sequence, selectively inhibits outside-in signaling in human platelets by disrupting the interaction of integrin alpha IIb beta 3 with Src kinase. *Blood* 112, 592-602 (2008).
27. Ren, X. D. & Schwartz, M. A. Determination of GTP loading on Rho. *Methods Enzymol* 325, 264-272 (2000).

The following represents a listing of the references cited in EXAMPLE 5-7.
1. Xi et al., *Journal of Cell Biology* 162, 329 (Jul. 21, 2003);
2. Gong et al., *Science* 327, 340 (2010);
3. Flevaris et al., *J Cell Biol* 179, 553 (Nov. 5, 2007);
4. Yin et al., *Blood* 111, 658 (Jan. 15, 2008);
5. Su et al., *Blood* 112, 592 (Aug. 1, 2008);
6. Gu, et al., *J Cell Biol* 147, 1085 (Nov. 29, 1999);
7. Ren and Schwartz, *Methods Enzymol* 325, 264 (2000); and
8. Edelstein et al., *Curr Protoc Mol Biol* Chapter 14, Unit 14 20 (October 2010).

The following represents a listing of the references cited in EXAMPLE 8.
1. R. O. Hynes, *Cell* 110, 673 (Sep. 20, 2002).
2. S. J. Shattil, P. J. Newman, *Blood* 104, 1606 (Sep. 15, 2004).
3. K. Moissoglu, M. A. Schwartz, *Biol Cell* 98, 547 (September 2006).
4. S. Tadokoro et al., *Science* 302, 103 (Oct. 3, 2003).
5. M. Moser, B. Nieswandt, S. Ussar, M. Pozgajova, R. Fassler, *Nat Med* 14, 325 (March 2008).
6. F. Ye, C. Kim, M. H. Ginsberg, *J Thromb Haemost* 9 Suppl 1, 20 (July 2011).
7. X. P. Du et al., *Cell* 65, 409 (May 3, 1991).
8. H. Gong et al., *Science* 327, 340 (2010, 2010).
9. A. Obergfell et al., *J Cell Biol* 157, 265 (Apr. 15, 2002).
10. E. G. Arias-Salgado et al., *Proc Natl Acad Sci USA* 100, 13298 (Nov. 11, 2003).
11. P. Flevaris et al., *J Cell Biol* 179, 553 (Nov. 5, 2007).
12. G. Giannone, G. Jiang, D. H. Sutton, D. R. Critchley, M. P. Sheetz, *Journal of Cell Biology* 163, 409 (Oct. 27, 2003).
13. J. D. Humphries et al., *Journal of Cell Biology* 179, 1043 (Dec. 3, 2007).
14. B. Nieves et al., *J Cell Sci* 123, 1216 (Apr. 15, 2010).
15. X. D. Xi, R. J. Bodnar, Z. Y. Li, S. C. T. Lam, X. P. Du, *Journal of Cell Biology* 162, 329 (Jul. 21, 2003).
16. S. Patil et al., *J Biol Chem* 274, 28575 (Oct. 1, 1999).
17. K. L. Wegener et al., *Cell* 128, 171 (Jan. 12, 2007).
18. B. G. Petrich et al., *Journal of Experimental Medicine* 204, 3103 (Dec. 24, 2007).
19. B. S. Coller, *Blood* 55, 169 (1980).
20. T. P. Ugarova et al., *J Biol Chem* 268, 21080 (Oct. 5, 1993).
21. E. Goksoy et al., *Molecular Cell* 31, 124 (Jul. 11, 2008).
22. J. R. Haling, S. J. Monkley, D. R. Critchley, B. G. Petrich, *Blood* 117, 1719 (Feb. 3, 2011).

The following represents a listing of the references cited in EXAMPLES 9-18.
1. Roger et al., *Circulation* 125(1):188-197 (2012);
2. Ruggeri, *Nat. Med.* 8(11):1227-1234 (2002);
3. Shattil and Newman, *Blood* 104(6):1606-1615 (2004);
4. Li et al., *Arterioscler Thromb Vasc Biol.* 30(12):2341-2349 (2010);
5. Coller, *Thromb Haemost.* 86(1):427-443 (2001);
6. Dyke, *American heart journal* 138(4 Pt 2):307-316 (1999);
7. Saab et al., *Expert opinion on drug safety* 11(2):315-324 (2012);
8. Shattil et al., *Blood* 91(8):2645-2657 (1998);
9. Calderwood et al., *J Biol Chem.* 274(40):28071-28074 (1999);
10. Tadokoro et al., *Science* 302(5642):103-106 (2003);
11. Moser et al., *Nat Med.* 14(3):325-330 (2008);
12. Ginsberg et al., *Curr Opin Cell Biol.* 17(5):509-516 (2005);
13. Ma et al., *J Thromb Haemost.* 5(7):1345-1352 (2007);
14. Gong et al., *Science* 327(5963):340-343 (2010);
15. Wegener et al., *Cell* 128(1):171-182 (2007);
16. Goksoy et al., *Molecular Cell* 31(1):124-133 (2008);
17. Petrich et al., *J Clin Invest* 117(8):2250-2259 (2007);
18. Ren et al., *Curr Opin Hematol* 15(5):537-541 (2008);
19. Kataoka et al, *Advanced drug delivery reviews* 47(1):113-131 (2001);
20. Dai et al., *Blood* 106(6):1975-1981 (2005);
21. Krishnadas et al., *Pharm Res.* 20(2):297-302 (2003);
22. Li et al., *J Biol Chem* 279(41):42469-42475 (2004);
23. Coller et al., *Blood* 55:169-178 (1980);
24. Flevaris et al., *J Cell Biol.* 179(3):553-565 (2007);
25. Yin et al., *Blood* 112(4):1139-1146 (2008);
26. Yin et al., *Blood* 111(2):658-665 (2008);
27. Hayward et al., J Thromb Haemost 4(2):312-319 (2006);
28. Li et al., *Cell* 12:77-86 (2003);
29. Marjanovic et al., *J Biol Chem.* 280(45):37430-37438 (2005);
30. O'Brien et al., *Blood* 118(15):4215-4223 (2011);
31. Day et al., *Thromb Haemost* 92(3):486-494 (2004);
32. Falati et al., *Nat Med.* 8(10):1175-1181 (2002); and
33. Cho et al., *J Clin Invest* 118(3):1123-1131 (2008).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A peptide comprising FEEERA (SEQ ID NO: 87) wherein the peptide is a 6-mer, 7-mer, 8-mer, or 9-mer.

2. A peptide consisting essentially of or consisting of FEEERA (SEQ ID NO: 87).

3. The peptide of claim 1, comprising a fatty acid.

4. The peptide of claim 3, wherein the fatty acid is a C4 to C30 fatty acid.

5. The peptide of claim 4, wherein the fatty acid is covalently attached to the N-terminus of the peptide.

6. The peptide of claim 5, wherein the N-terminus of the peptide is the Phe of SEQ ID NO:87 and is covalently attached to a fatty acid.

7. A micelle comprising a peptide of claim 3 and at least one lipid.

8. The micelle of claim 7, comprising a lipid covalently attached to a water soluble polymer and a lipid free of a water soluble polymer.

9. The micelle of claim 8, wherein the lipid covalently attached to a water soluble polymer is 1,2-distearoyl-sn-glycero-3-phosphoethanolamine-N-[amino(polyethylene glycol)-2000], the lipid free of a water soluble polymer is phophatidylcholine.

10. The micelle of claim 9, wherein the N-terminus of the peptide is the Phe of SEQ ID NO:87 and is covalently attached to a C14 fatty acid or a C16 fatty acid.

11. A composition comprising the micelle of claim 7 and an aqueous solution.

12. A pharmaceutical composition comprising the peptide of claim 1, or a micelle comprising the peptide of claim 1, and a pharmaceutically acceptable carrier, diluent, or excipient.

13. The pharmaceutical composition of claim 12, wherein the N-terminus of the peptide is the Phe of SEQ ID NO:87 and is covalently attached to a C14 fatty acid or a C16 fatty acid.

14. A conjugate comprising a peptide and a fatty acid, wherein the peptide consists of FEEERA (SEQ ID NO: 87).

15. The conjugate of claim 14, wherein the fatty acid is a C4 to C30 fatty acid.

16. The conjugate of claim 15, wherein the fatty acid is covalently attached to the N-terminus of the peptide.

17. A micelle comprising a conjugate of claim 14 and at least one lipid.

18. A composition comprising the micelle of claim 17 and an aqueous solution.

19. A pharmaceutical composition comprising the conjugate of claim 14, or a micelle comprising the conjugate of claim 14, and a pharmaceutically acceptable carrier, diluent, or excipient.

20. The pharmaceutical composition of claim 19, wherein the Phe at position 1 of the peptide is covalently attached to a C14 fatty acid or a C16 fatty acid.

21. The peptide of claim 1, wherein the fatty acid is a C12 to C20 fatty acid.

22. The peptide of claim 21, wherein the fatty acid is a C14 fatty acid, C16 fatty acid, or C18 fatty acid.

23. The peptide of claim 22, wherein the fatty acid is a C14 fatty acid.

24. The conjugate of claim 15, wherein the fatty acid is a C12 to C20 fatty acid.

25. The conjugate of claim 21, wherein the fatty acid is a C14 fatty acid, C16 fatty acid, or C18 fatty acid.

26. The conjugate of claim 25, wherein the fatty acid is a C14 fatty acid.

* * * * *

UNITED STATES PATENT AND TRADEMARK OFFICE
CERTIFICATE OF CORRECTION

PATENT NO. : 8,685,921 B2
APPLICATION NO. : 13/621064
DATED : April 1, 2014
INVENTOR(S) : Xiaoping Du It is certified that error appears in the above-identified patent and that said Letters Patent is hereby corrected as shown below:

In the Specification

Column 1, delete lines 18-21 and insert the following

--This invention was made with government support under Grant Nos. HL080264, HL062350, HL068819, awarded by the National Institutes of Health. The government has certain rights in this invention.--

Signed and Sealed this
Fifteenth Day of March, 2016

Michelle K. Lee
*Director of the United States Patent and Trademark Office*